US012758786B2

(12) United States Patent
Lampe et al.

(10) Patent No.: US 12,758,786 B2

(45) Date of Patent: Oct. 13, 2026

(54) SYSTEMS AND METHODS OF USE FOR A WEARABLE ULTRASOUND BLOOD FLOW SENSOR

(71) Applicant: ZOLL Medical Corporation, Chelmsford, MA (US)

(72) Inventors: Joshua W Lampe, Groton, MA (US); Gary A Freeman, Waltham, MA (US); Paolo Giacometti, North Grafton, MA (US); Jeffrey R Gould, Salem, MA (US); Joshua R Harvey, Ayer, MA (US); Brian L Robey, Nashua, NH (US)

(73) Assignee: ZOLL Medical Corporation, Chelmsford, MA (US)

( * ) Notice: Subject to any disclaimer, the term of this patent is extended or adjusted under 35 U.S.C. 154(b) by 1105 days.

(21) Appl. No.: 17/817,689

(22) Filed: Aug. 5, 2022

(65) Prior Publication Data

US 2023/0048327 A1 Feb. 16, 2023

Related U.S. Application Data

(60) Provisional application No. 63/203,995, filed on Aug. 6, 2021.

(51) Int. Cl.

*A61H 31/00* (2006.01)
*A61N 1/39* (2006.01)

(52) U.S. Cl.

CPC ....... *A61N 1/39044* (2017.08); *A61H 31/005* (2013.01); *A61N 1/3987* (2013.01); *A61H 2230/065* (2013.01); *A61H 2230/255* (2013.01)

(58) Field of Classification Search

CPC .... A61H 31/00; A61H 31/004; A61H 31/005; A61H 31/006; A61H 31/007

See application file for complete search history.

(56) References Cited

U.S. PATENT DOCUMENTS 4,905,206 A 2/1990 Nishiyama et al.
7,565,194 B2 7/2009 Tan et al.
(Continued)

FOREIGN PATENT DOCUMENTS

CN 102895002 1/2013
EP 1963884 9/2008
(Continued)

OTHER PUBLICATIONS

Kenny, Jon-Emile S. et al., "A Novel Index From A Wearable Continuous Wave Doppler Ultrasound Patch Instantly Detects Fall In Cardiac Output", Flosonnics Medical, 1 page.
(Continued)

*Primary Examiner* — Timothy A Stanis
*Assistant Examiner* — Christopher E Miller
(74) *Attorney, Agent, or Firm* — The Webb Law Firm

(57) ABSTRACT

An example of a system for providing patient care guidance to a caregiver based on ultrasound detection of blood flow includes a defibrillator including an electrode assembly and an output device, a portable computing device communicatively coupled to the defibrillator and including an output device, a Doppler shift waveform evaluation engine disposed at the defibrillator and/or the portable computing device, and a wearable ultrasound blood flow sensor configured to couple to a patient and the defibrillator and/or the portable computing device and to generate data signals representing a Doppler shift waveform. The engine is configured to receive the data signals representing the waveform, generate caregiver instructions according to a cardiac arrest protocol, analyze the waveform based on the received data signals, identify heart-induced blood flow based on the waveform analysis, and generate and provide caregiver instructions according to a non-cardiac arrest protocol based on the identified heart-induced blood flow.

28 Claims, 49 Drawing Sheets

(56) References Cited

U.S. PATENT DOCUMENTS

| | | | | |
|---|---|---|---|---|
| 7,650,181 | B2 | 1/2010 | Freeman et al. | |
| 8,463,364 | B2 | 6/2013 | Wood et al. | |
| 8,758,249 | B2 | 6/2014 | Zhang et al. | |
| 10,661,009 | B2 | 5/2020 | Eibl et al. | |
| 10,987,085 | B2 | 4/2021 | Eibl et al. | |
| 11,266,566 | B2 | 3/2022 | Quan | |
| 12,004,870 | B2 * | 6/2024 | Walker | A61B 5/486 |
| 2007/0060785 | A1 * | 3/2007 | Freeman | G16H 20/40 600/16 |
| 2008/0015439 | A1 * | 1/2008 | Raju | A61B 8/488 600/455 |
| 2008/0077010 | A1 * | 3/2008 | Cohen-Solal | A61B 8/06 600/441 |
| 2009/0306525 | A1 * | 12/2009 | Pinter | A61B 5/6822 600/500 |
| 2010/0022886 | A1 * | 1/2010 | Ayati | A61B 5/6822 600/454 |
| 2011/0301513 | A1 | 12/2011 | Freeman | |
| 2012/0010543 | A1 * | 1/2012 | Johnson | G16H 20/40 601/41 |
| 2012/0016179 | A1 * | 1/2012 | Paradis | A61N 1/3987 601/41 |
| 2012/0184854 | A1 * | 7/2012 | Raju | A61B 8/4236 600/459 |
| 2015/0164417 | A1 * | 6/2015 | Tupin, Jr. | A61N 1/3925 600/407 |
| 2015/0265497 | A1 * | 9/2015 | Kaufman | A61H 31/005 601/41 |
| 2015/0289838 | A1 | 10/2015 | Nichol et al. | |
| 2016/0143805 | A1 | 5/2016 | Aelen | |
| 2017/0000688 | A1 * | 1/2017 | Kaufman | A61H 31/005 |
| 2017/0049413 | A1 | 2/2017 | Nichol et al. | |
| 2017/0231600 | A1 | 8/2017 | Piraino | |
| 2018/0153506 | A1 * | 6/2018 | Rodriquez | A61H 31/00 |
| 2018/0369065 | A1 * | 12/2018 | Siedenburg | A61B 8/04 |
| 2019/0328354 | A1 | 10/2019 | Xu et al. | |
| 2019/0343412 | A1 * | 11/2019 | Sullivan | A61B 5/316 |
| 2019/0366384 | A1 | 12/2019 | Pang et al. | |
| 2019/0374428 | A1 * | 12/2019 | Kaufman | A61N 1/39044 |
| 2020/0022670 | A1 | 1/2020 | Eibl et al. | |
| 2020/0034567 | A1 | 1/2020 | Besperstov | |
| 2020/0100705 | A1 | 4/2020 | Dellimore et al. | |
| 2020/0107989 | A1 * | 4/2020 | Adedipe | A61B 8/5215 |
| 2021/0015446 | A1 * | 1/2021 | Ritchie | A61B 5/021 |
| 2021/0045967 | A1 * | 2/2021 | Lampe | A61H 31/007 |

FOREIGN PATENT DOCUMENTS

| | | | | |
|---|---|---|---|---|
| EP | 3672493 | | 3/2021 | |
| KR | 1020180031991 | | 3/2018 | |
| WO | 2007069155 | | 6/2007 | |
| WO | 2008137030 | | 11/2008 | |
| WO | WO-2015074015 | A1 * | 5/2015 | A61B 8/488 |
| WO | WO-2015121114 | A1 * | 8/2015 | A61N 1/3925 |
| WO | WO-2017096487 | A1 * | 6/2017 | G16H 50/30 |

OTHER PUBLICATIONS

Adedipe, Adeyinka A. et al., "Carotid Doppler Blood Flow Measurement During Cardiopulmonary Resuscitation Is Feasible: A First In Man Study" Resuscitation, 2015, pp. 121-125, vol. 96.

AccuVein, "AccuVein AV500 User Manual", 16 pages.

* cited by examiner

Heartbeat-induced blood flow
and
automated mechanical compression-induced blood flow = blood flow peaks due to heart activity "C" = blood flow peaks due to compressions Automated mechanical compression-induced blood flow "C" = blood flow peaks due to compressions 799a

2110

2120

2130

SYSTEMS AND METHODS OF USE FOR A WEARABLE ULTRASOUND BLOOD FLOW SENSOR

CROSS-REFERENCE TO RELATED APPLICATIONS

This application claims the benefit under 35 U.S.C. § 119(e) of U.S. Provisional Application No. 63/203,995 filed Aug. 6, 2021. All subject matter set forth in the above referenced application is hereby incorporated by reference in its entirety into the present application as if fully set forth herein.

BACKGROUND

Resuscitative care for a victim of cardiac arrest entails interventions directed at restoring heart-induced blood flow and at treating weakened blood flow and other physiologic effects the cardiac arrest along with the etiology of the cardiac arrest. Hemodynamic monitoring, and specifically a monitoring of blood flow, enables a rescuer to select between and determine the efficacy of various therapeutic interventions. Additionally, blood flow monitoring provides physiologic data that may enable a caregiver to more efficiently and accurately identify and quantify weakened blood flow and other physiologic effects and diagnose etiology. The blood flow data may supplement other hemodynamic treatment data such as electrocardiograms (ECG) and chest compression metrics.

SUMMARY

The foregoing general description of the illustrative implementations and the following detailed description thereof are merely exemplary aspects of the teachings of this disclosure and are not restrictive.

An example of a system for providing patient care guidance to a caregiver based on ultrasound detection of blood flow includes a defibrillator including an electrode assembly and a first output device, a portable computing device communicatively coupled to the defibrillator and including a second output device, and at least one wearable ultrasound blood flow sensor configured to couple to a patient and one of the defibrillator and the portable computing device and to generate data signals representing at least one Doppler shift waveform, wherein the portable computing device is configured to receive the data signals representing the at least one Doppler shift waveform, generate caregiver instructions according to a cardiac arrest protocol, analyze the at least one Doppler shift waveform based on the received data signals, identify heart-induced blood flow based on the analysis of the at least one Doppler shift waveform, and generate caregiver instructions according to a non-cardiac arrest protocol in response to the identified heart-induced blood flow, wherein at least one of the first output device and the second output device is configured to provide the caregiver instructions.

Implementations of such a system may include one or more of the following features. The portable computing device may be configured to analyze the at least one Doppler shift waveform during ongoing chest compression and ventilation cycles according to the cardiac arrest protocol. The portable computing device may be configured to analyze the data signals representing the at least one Doppler shift waveform during an administration of chest compressions, wherein the ongoing chest compression and ventilation cycles alternate between chest compressions and ventilations according to a predetermined X:Y ratio of X chest compressions and Y ventilations. The portable computing device may be configured to identify return of spontaneous circulation (ROSC) based at least in part on the analysis of the at least one Doppler shift waveform. The portable computing device may be configured to identify re-arrest subsequent to ROSC based at least in part on the analysis of the at least one Doppler shift waveform. The portable computing device may be configured to identify pseudo-pulseless electrical activity (pseudo-PEA) based at least in part on the analysis the at least one Doppler shift waveform. The portable computing device may be configured to detect heart-induced blood flow associated with a manually impalpable pulse based on the at least one Doppler shift waveform. The portable computing device may be configured to detect the heart-induced blood flow at a blood pressure below approximately 60-80 systolic. The portable computing device may be configured to distinguish between PEA and pseudo-PEA based at least in part on the analysis of the at least one Doppler shift waveform. The portable computing device may be configured to distinguish between ROSC and pseudo-PEA based at least in part on the analysis of the at least one Doppler shift waveform. The portable computing device may be configured to identify pseudo-PEA as distinguished from ROSC based on an absence of an indication of positive blood flow between peaks in the at least one Doppler shift waveform. The portable computing device may be configured to analyze the data signals representing the at least one Doppler shift waveform during an administration of ventilations, wherein the ongoing chest compression and ventilation cycles alternate between chest compressions and ventilations according to a predetermined X:Y ratio of X chest compressions and Y ventilations. The portable computing device may be configured to analyze the at least one Doppler shift waveform during a pause in an administration of chest compressions. The portable computing device may be configured to analyze the at least one Doppler shift waveform to identify the heart-induced blood flow in a presence of compression-induced blood flow. The portable computing device may be configured to identify the heart-induced blood flow based on an analysis of peaks in the at least one Doppler shift waveform, wherein the at least one Doppler shift waveform indicates blood flow volume per unit time as a function of time. The portable computing device may be configured to distinguish between peaks due to compression-induced blood flow and the heart-induced blood flow based on one or more of a peak shape, a period or frequency associated with the peaks, and a phase shift between the peaks due to the compression-induced blood flow and the heart-induced blood flow. The portable computing device may be configured to calculate a first phase shift at a first time, calculate a second phase shift at a second time, and verify the heart-induced blood flow identification based on the second phase shift exceeding the first phase shift due to an increase in blood flow velocity from the first time to the second time. The portable computing device may be configured to perform a spectral analysis of the at least one Doppler shift waveform to identify the heart-induced blood flow in the presence of compression-induced blood flow. The spectral analysis may include an analysis of frequency and amplitude of the at least one Doppler shift waveform as a function of time. The defibrillator may be configured to receive an ECG waveform from the electrode assembly, and analyze the ECG waveform to identify the ECG waveform as representing a shockable heart rhythm or a non-shockable heart rhythm. The at least one of the first output device and the second output device may be configured to provide the instructions according to the cardiac arrest protocol based on the ECG waveform analysis and on the at least one Doppler shift waveform analysis. The defibrillator may be configured to analyze the ECG waveform to identify the shockable heart rhythm, control a defibrillation shock circuit to deliver at least one defibrillation shock, analyze the data signals representing the at least one Doppler shift waveform during ongoing chest compressions after the at least one defibrillation shock, and identify heart-induced blood flow corresponding to ROSC. The portable computing device may be configured to generate the caregiver instructions according to the non-cardiac arrest protocol, wherein the non-cardiac arrest protocol may include ROSC interventions. The defibrillator may be configured to analyze the ECG waveform to identify a non-shockable rhythm, analyze the data signals representing the at least one Doppler shift waveform during ongoing chest compressions, identify heart-induced blood flow corresponding to pseudo-PEA. The portable computing device may be configured to generate the caregiver instructions according to the non-cardiac arrest protocol, wherein the non-cardiac arrest protocol may include pseudo-PEA interventions. The defibrillator may include a chest compression waveform evaluation engine configured to receive data signals representing a chest compression waveform, and identify chest compression frequency components of the chest compression waveform. The portable computing device may include a Doppler shift waveform evaluation engine configured to analyze the at least one Doppler shift waveform to identify blood flow frequency components, receive the chest compression frequency components from the chest compression waveform evaluation engine, isolate a subset of the blood flow frequency components that may be absent from the chest compression frequency components, and identify the isolated subset of the blood flow frequency components as frequency components associated with heart-induced blood flow. The chest compression waveform evaluation engine may be configured to receive the data signals representing the chest compression waveform from a chest compression monitor configured for use during manual chest compressions. The chest compression waveform evaluation engine may be configured to receive the data signals representing the chest compression waveform from an automated chest compression device. The portable computing device may be configured to remove motion artifacts from the at least one Doppler shift waveform. The system may include plurality of wearable ultrasound blood flow sensors located at different locations on the patient relative to a pulse point, wherein the portable computing device may be configured to remove the motion artifacts from the at least one Doppler shift waveform based on at least a first Doppler shift waveform from a first wearable ultrasound blood flow sensor and a second Doppler shift waveform from a second wearable ultrasound blood flow sensor. The portable computing device may be configured to remove the motion artifacts in the first Doppler shift waveform based on a comparison between a first frequency content of the first Doppler shift waveform and a second frequency content of the second Doppler shift waveform. The first wearable ultrasound blood flow sensor may be disposed at a location on the patient proximate to the pulse point and the second wearable ultrasound blood flow sensor may be disposed at a location on the patient distant from the pulse point. The first wearable ultrasound blood flow sensor may be disposed at a location on the patient proximate to a first pulse point and the second wearable ultrasound blood flow sensor may be disposed at a location on the patient proximate to a second and different pulse point. The pulse point may correspond to a carotid, femoral, or brachial artery. The portable computing device may be configured to generate a caregiver instruction to pause chest compressions in response to the identification of the heart-induced blood flow based on the at least one Doppler shift waveform analysis, verify the heart-induced blood flow identification during the paused chest compressions, and generate a caregiver instruction to cease the chest compressions in response to the verification. The system may include a plurality of wearable ultrasound blood flow sensors located at different locations on the patient relative to a pulse point, wherein the portable computing device may be configured to receive data signals representing a first Doppler shift waveform from a first wearable ultrasound blood flow sensor at a first location, receive data signals representing additional Doppler shift waveforms from one or more additional wearable ultrasound blood flow sensors located at one or more second and different locations, analyze a first frequency content of the first Doppler shift waveform, analyze at least one additional frequency content of the additional Doppler shift waveforms, and calculate a pulse transmit time between the first location and the one or more second and different locations based on the first frequency content and the at least one additional frequency content of the at least one Doppler shift waveform. The portable computing device may be configured to calculate an estimated vascular stiffness based on the pulse transmit time. The portable computing device may be configured to calculate an estimated blood pressure time trend based on the pulse transmit time. The system may include a plurality of wearable ultrasound blood flow sensors located at different locations on the patient relative to a pulse point, wherein the portable computing device may be configured to receive data signals representing a first Doppler shift waveform from a first wearable ultrasound blood flow sensor, receive data signals representing additional Doppler shift waveforms from one or more additional wearable ultrasound blood flow sensors, analyze a first frequency content of the first Doppler shift waveform, analyze at least one additional frequency content of the additional Doppler shift waveforms, identify correlated frequency content and uncorrelated frequency content between the first Doppler shift waveform and the additional Doppler shift waveforms, and identify the heart-induced blood flow based on the uncorrelated frequency content, wherein the correlated frequency content may correspond to chest compressions. The data signals representing the at least one Doppler shift waveform may indicate a blood flow velocity per unit time and the portable computing device may be configured to calculate a blood volume per unit time from the blood flow velocity per unit time, and identify heart-induced blood flow based on the analysis of the blood flow velocity per unit time calculated at the defibrillator. The data signals representing the at least one Doppler shift waveform may indicate a blood volume per unit time and the portable computing device may be configured to identify heart-induced blood flow based on a blood flow velocity per unit time received from the at least one wearable ultrasound blood flow sensor. The at least one Doppler shift waveform may be first physiologic data and the system may include one or more physiologic sensors configured to provide one or more types of second physiologic data other than blood flow data based on the at least one Doppler shift waveform. The portable computing device may be configured to analyze the second physiologic data together with the at least one Doppler shift waveform to generate a cumulative blood flow score, and automatically detect heart-induced blood flow based on the cumulative blood flow score. The portable computing device may be configured to calculate a confidence score associated with the cumulative blood flow score. The portable computing device may be configured to automatically generate the caregiver instructions according to the non-cardiac arrest protocol based on the cumulative blood flow score. The automatically generated caregiver instructions include an instruction to stop chest compressions. The second physiologic data may include one or more of ECG data, continuous non-invasive blood pressure (NIBP) data, NIBP data, near-infrared spectroscopy (NIRS) data, heart sound data, and photo-plethysmography data. The second physiologic data may include one or more of pulse oximetry data, capnography data, and spirometry data. The first output device may include one or more of a display screen integrated with the defibrillator, an audio device integrated with the defibrillator, a haptic device integrated with the defibrillator, a display screen external to the defibrillator, an audio device external to the defibrillator, a haptic device external to the defibrillator, and a wearable device including one or more of a watch and glasses. The second output device may include one or more of a display screen integrated with the portable computing device, an audio device integrated with the portable computing device, a haptic device integrated with the portable computing device, a display screen external to the portable computing device, an audio device external to the portable computing device, a haptic device external to the portable computing device, and the wearable device including one or more of a watch and glasses.

An example of a system for positioning a wearable ultrasound blood flow sensor to detect blood flow of a patient includes a medical device for monitoring and/or providing therapy to the patient and comprising a first output device, a portable computing device communicatively coupled to the medical device and comprising a second output device and configured to generate data signals representing at least one Doppler shift waveform, and at least one wearable ultrasound blood flow sensor configured to couple to the medical device and to the patient and one of the medical device and the portable computing device, wherein the portable computing device is configured to receive the data signals representing the at least one Doppler shift waveform, receive data signals representing a chest compression waveform, analyze the at least one Doppler shift waveform for periodic features indicative of compression-induced blood flow based on the chest compression waveform, identify a location of the wearable ultrasound blood flow sensor relative to at least one blood vessel of the patient based on the periodic features in the at least one Doppler shift waveform, and generate caregiver instructions for positioning the wearable ultrasound blood flow sensor based on the identified location, wherein at least one of the first output device and the second output device is configured to provide the caregiver instructions for positioning.

Implementations of such a system may include one or more of the following features. The portable computing device may be configured to identify the location of the wearable ultrasound blood flow sensor as corresponding to a location of the at least one blood vessel in a presence of the periodic features indicative of a chest compression rate, and identify the location of the wearable ultrasound blood flow sensor as a location with insufficient proximity to the at least one blood vessel to detect the blood flow of the patient in an absence of the periodic features indicative of the chest compression rate. The location of the at least one blood vessel may be at least one of a location of a carotid artery, a location of a brachial artery, or a location of a femoral artery. The portable computing device may be configured to generate caregiver instructions to adjust the wearable ultrasound blood flow sensor in response to the identification of the location of the wearable ultrasound blood flow sensor as the location with insufficient proximity to the at least one blood vessel to detect the blood flow of the patient, and wherein the at least one of the first output device and the second output device may be configured to provide the caregiver instructions to adjust the wearable ultrasound blood flow sensor. The caregiver instructions to adjust the wearable ultrasound blood flow sensor may include an instruction to remove the wearable ultrasound blood flow sensor from the patient, and reapply the wearable ultrasound blood flow sensor. The caregiver instruction to remove and reapply the wearable ultrasound blood flow sensor may include an instruction to reapply the wearable ultrasound blood flow sensor in approximately a same location on the patient as originally applied. The caregiver instruction to remove and reapply the wearable ultrasound blood flow sensor may include an instruction to reapply the wearable ultrasound blood flow sensor in a different location on the patient than as originally applied. The different location may correspond to a location proximate to a same blood vessel on an opposite side of the patient than as originally applied relative to a sagittal plane. The caregiver instructions to adjust the wearable ultrasound blood flow sensor may include an instruction to replace the wearable ultrasound blood flow sensor with a new wearable ultrasound blood flow sensor. The portable computing device may be configured to receive the data signals representing the chest compression waveform from a chest compression monitor coupled to the medical device and configured for use during manual chest compressions, analyze the at least one Doppler shift waveform for periodic features indicative of compression-induced blood flow from manual chest compressions. The chest compression waveform may be an acceleration waveform. The medical device may be configured to evaluate the chest compression waveform for indications that the manual chest compressions meet threshold compression requirements, and the portable computing device may be configured to, if the manual chest compressions meet the threshold compression requirements, then analyze the at least one Doppler shift waveform for the periodic features indicative of compression-induced blood flow, else provide caregiver instructions to modify an administration of the manual chest compressions to meet the threshold compression requirements. The threshold compression requirements may include a target compression depth, a target compression rate, and a target number of administered chest compressions. The portable computing device may be configured to instruct an automated compression device to provide a series of chest compressions according to a patterned compression rate variation, receive the data signals representing the chest compression waveform from the automated compression device, and analyze the at least one Doppler shift waveform for the periodic features corresponding to the patterned compression rate variation and indicative of compression-induced blood flow. The patterned compression rate variation may include two or more compression rates applied alternately for two or more groups of three or more compressions. The portable computing device may be configured to generate caregiver instructions to couple the wearable ultrasound blood flow sensor to the patient. The at least one of the first output device and the second output device may be configured to provide the caregiver instructions to couple the wearable ultrasound blood flow sensor to the patient as one or more of displayed instructions and audible instructions. One or more of a housing for the wearable ultrasound blood flow sensor and a packaging for the wearable ultrasound blood flow sensor may include placement instructions for coupling the wearable ultrasound blood flow sensor to the patient. The placement instructions may include graphic representations of anatomical reference points for placement of the wearable ultrasound blood flow sensor. The anatomical reference points may include a laryngeal prominence, an anterior triangle, and a transverse neck midline. The system may include at least one anatomically contoured frame with at least one opening configured to accept the wearable ultrasound blood flow sensor and enable the wearable ultrasound blood flow sensor to couple to the patient. The at least one anatomically contoured frame may be configured for use on one of (a) a neck wherein the at least one opening may correspond to a location of a carotid artery, (b) an upper arm wherein the at least one opening may correspond to a location of a brachial artery, or (c) a thigh wherein the at least one opening may correspond to a location of a femoral artery. The system may include a plurality of anatomically contoured frames configured for use with a plurality of patient sizes. The at least one anatomically contoured frame may be adjustable for use with a plurality of patient sizes. The at least one anatomically contoured frame may include two openings, each opening corresponding to one of two bilaterally located blood vessels. The at least one anatomically contoured frame may be reusable and the wearable ultrasound blood flow sensor may be disposable. The at least one of the first output device and the second output device may include augmented reality glasses configured to provide placement instructions for the wearable ultrasound blood flow sensor. The placement instructions may include audible and/or visible instructions describing placement steps and augmented reality images of blood vessels superimposed upon a real-time view of the patient. The portable computing device may be configured to determine that the received data signals representing at least one Doppler shift waveform fails to meet a threshold signal strength, and generate caregiver instructions for adjusting the wearable ultrasound blood flow sensor, wherein the at least one of the first output device and the second output device may be configured to provide the caregiver instructions for adjusting the wearable ultrasound blood flow sensor. The threshold signal strength may be a signal-to-noise ratio threshold indicative of acoustic coupling between the wearable ultrasound blood flow sensor and the patient. The caregiver instructions may include at least one of an instruction to remove and replace the wearable ultrasound blood flow sensor, an instruction to confirm liner removal for the wearable ultrasound blood flow sensor, and an instruction to confirm placement of the wearable ultrasound blood flow sensor according to placement instructions provided at one or more of a housing for the wearable ultrasound blood flow sensor, a packaging for the wearable ultrasound blood flow sensor, and at least one of the first output device and the second output device. The first output device may include one or more of a display screen integrated with the medical device, an audio device integrated with the medical device, a haptic device integrated with the medical device, a display screen external to the medical device, an audio device external to the medical device, a haptic device external to the medical device, and a wearable device including one or more of a watch and glasses. The second output device may include one or more of a display screen integrated with the portable computing device, an audio device integrated with the portable computing device, a haptic device integrated with the portable computing device, a display screen external to the portable computing device, an audio device external to the portable computing device, a haptic device external to the portable computing device, and the wearable device including one or more of a watch and glasses. The medical device may be an automated external defibrillator (AED). The medical device may be an advanced life support defibrillator.

An example of a method of positioning a wearable ultrasound blood flow sensor to detect blood flow of a patient includes receiving data signals representing at least one Doppler shift waveform from at least one wearable ultrasound blood flow sensor, receiving data signals representing a chest compression waveform, analyzing the at least one Doppler shift waveform for periodic features indicative of compression-induced blood flow based on the chest compression waveform, identifying a location of the wearable ultrasound blood flow sensor relative to at least one blood vessel of the patient based on the periodic features in the at least one Doppler shift waveform, generating caregiver instructions for positioning the wearable ultrasound blood flow sensor based on the identified location, and providing the caregiver instructions for positioning at an output device.

Implementation of such a method may include one or more of the following features. The method may include identifying the location of the wearable ultrasound blood flow sensor as corresponding to a location of the at least one blood vessel in a presence of the periodic features indicative of a chest compression rate, and identifying the location of the wearable ultrasound blood flow sensor as a location with insufficient proximity to the at least one blood vessel to detect the blood flow of the patient in an absence of the periodic features indicative of the chest compression rate. The location of the at least one blood vessel may be at least one of a location of a carotid artery, a location of a brachial artery, or a location of a femoral artery. The method may include generating caregiver instructions to adjust the wearable ultrasound blood flow sensor in response to the identification of the location of the wearable ultrasound blood flow sensor as the location with insufficient proximity to the at least one blood vessel to detect the blood flow of the patient, and providing the caregiver instructions to adjust the wearable ultrasound blood flow sensor at the output device. The method may include generating the caregiver instructions including an instruction to remove the wearable ultrasound blood flow sensor from the patient and reapply the wearable ultrasound blood flow sensor. The instruction to remove and reapply the wearable ultrasound blood flow sensor may include an instruction to reapply the wearable ultrasound blood flow sensor in approximately a same location on the patient as originally applied. The caregiver instruction to remove and reapply the wearable ultrasound blood flow sensor may include an instruction to reapply the wearable ultrasound blood flow sensor in a different location on the patient than as originally applied. The different location may correspond to a location proximate to a same blood vessel on an opposite side of the patient than as originally applied relative to a sagittal plane. The method may include generating the caregiver instructions including an instruction to replace the wearable ultrasound blood flow sensor with a new wearable ultrasound blood flow sensor. The method may include receiving the data signals representing the chest compression waveform from a chest compression monitor and configured for use during manual chest compressions, analyzing the at least one Doppler shift waveform for periodic features indicative of compression-induced blood flow from manual chest compressions. The chest compression waveform may be an acceleration waveform. The method may include evaluating the chest compression waveform for indications that the manual chest compressions meet threshold compression requirements, and if the manual chest compressions meet the threshold compression requirements, then analyzing the at least one Doppler shift waveform for the periodic features indicative of compression-induced blood flow, else providing caregiver instructions to modify an administration of the manual chest compressions to meet the threshold compression requirements. The threshold compression requirements may include a target compression depth, a target compression rate, and a target number of administered chest compressions. The method may include instructing an automated compression device to provide a series of chest compressions according to a patterned compression rate variation, receiving the data signals representing the chest compression waveform from the automated compression device, and analyzing the at least one Doppler shift waveform for the periodic features corresponding to the patterned compression rate variation and indicative of compression-induced blood flow. The patterned compression rate variation may include two or more compression rates applied alternately for two or more groups of three or more compressions. The method may include generating caregiver instructions to couple the wearable ultrasound blood flow sensor to the patient. The method may include providing the caregiver instructions to couple the wearable ultrasound blood flow sensor to the patient at the output device as one or more of displayed instructions and audible instructions. The method may include providing placement instructions for coupling the wearable ultrasound blood flow sensor to the patient on one or more of a housing for the wearable ultrasound blood flow sensor and a packaging for the wearable ultrasound blood flow sensor. The placement instructions may include graphic representations of anatomical reference points for placement of the wearable ultrasound blood flow sensor. The anatomical reference points may include a laryngeal prominence, an anterior triangle, and a transverse neck midline. The method may include providing instructions for positioning the wearable ultrasound blood flow sensor using at least one anatomically contoured frame with at least one opening configured to accept the wearable ultrasound blood flow sensor and enable the wearable ultrasound blood flow sensor to couple to the patient. The at least one anatomically contoured frame may be configured for use on one of: (a) a neck wherein the at least one opening may correspond to a location of a carotid artery, (b) an upper arm wherein the at least one opening may correspond to a location of a brachial artery, or (c) a thigh wherein the at least one opening may correspond to a location of a femoral artery. The at least one anatomically contoured frame may be adjustable for use with a plurality of patient sizes. The at least one anatomically contoured frame may include two openings, each opening corresponding to one of two bilaterally located blood vessels. The at least one anatomically contoured frame may be reusable and the wearable ultrasound blood flow sensor may be disposable. The method may include providing the caregiver instructions for positioning the output device at augmented reality glasses. The caregiver instructions for positioning may include audible and/or visible instructions describing placement steps and augmented reality images of blood vessels superimposed upon a real-time view of the patient. The method may include determining that the received data signals representing at least one Doppler shift waveform fails to meet a threshold signal strength, generating caregiver instructions for adjusting the wearable ultrasound blood flow sensor, and providing the caregiver instructions for adjusting the wearable ultrasound blood flow sensor at the output device. The threshold signal strength may be a signal-to-noise ratio threshold indicative of acoustic coupling between the wearable ultrasound blood flow sensor and the patient. The method may include providing one or more of an instruction to remove and replace the wearable ultrasound blood flow sensor, an instruction to confirm liner removal for the wearable ultrasound blood flow sensor, and an instruction to confirm placement of the wearable ultrasound blood flow sensor according to placement instructions provided at one or more of a housing for the wearable ultrasound blood flow sensor, a packaging for the wearable ultrasound blood flow sensor, and the output device. The method may include providing the caregiver instructions for positioning as one or more of audible, visible, and haptic instructions.

An example of a system for providing patient care guidance to a caregiver based on ultrasound detection of blood flow includes a defibrillator including an electrode assembly and an output device; and at least one wearable ultrasound blood flow sensor configured to couple to the defibrillator and to a patient, wherein the defibrillator is configured to receive data signals representing at least one Doppler shift waveform from the at least one wearable ultrasound blood flow sensor, generate caregiver instructions according to a cardiac arrest protocol, analyze the at least one Doppler shift waveform based on the received data signals, identify heart-induced blood flow based on the analysis of the at least one Doppler shift waveform, and generate caregiver instructions according to a non-cardiac arrest protocol in response to the identified heart-induced blood flow, wherein the output device may be configured to provide the caregiver instructions according to the cardiac arrest protocol and the non-cardiac arrest protocol.

Implementation of such a system may include one or more of the following features. The defibrillator may be configured to analyze the at least one Doppler shift waveform during ongoing chest compression and ventilation cycles according to the cardiac arrest protocol. The defibrillator may be configured to analyze the data signals representing the at least one Doppler shift waveform during an administration of chest compressions, wherein the ongoing chest compression and ventilation cycles alternate between chest compressions and ventilations according to a predetermined X:Y ratio of X chest compressions and Y ventilations. The defibrillator may be configured to identify return of spontaneous circulation (ROSC) based at least in part on the analysis of the at least one Doppler shift waveform. The defibrillator may be configured to identify re-arrest subsequent to ROSC based at least in part on the analysis of the at least one Doppler shift waveform. The defibrillator may be configured to identify pseudo-pulseless electrical activity (pseudo-PEA) based at least in part on the analysis the at least one Doppler shift waveform. The defibrillator may be configured to detect heart-induced blood flow associated with a manually impalpable pulse based on the at least one Doppler shift waveform. The defibrillator may be configured to detect the heart-induced blood flow at a blood pressure below approximately 60-80 systolic. The defibrillator may be configured to distinguish between PEA and pseudo-PEA based at least in part on the analysis of the at least one Doppler shift waveform. The defibrillator may be configured to distinguish between ROSC and pseudo-PEA based at least in part on the analysis of the at least one Doppler shift waveform. The defibrillator may be configured to identify pseudo-PEA as distinguished from ROSC based on an absence of an indication of positive blood flow between peaks in the at least one Doppler shift waveform. The defibrillator may be configured to analyze the data signals representing the at least one Doppler shift waveform during an administration of ventilations, wherein the ongoing chest compression and ventilation cycles alternate between chest compressions and ventilations according to a predetermined X:Y ratio of X chest compressions and Y ventilations. The defibrillator may be configured to analyze the at least one Doppler shift waveform during a pause in an administration of chest compressions. The defibrillator may be configured to analyze the at least one Doppler shift waveform to identify the heart-induced blood flow in a presence of compression-induced blood flow. The defibrillator may be configured to identify the heart-induced blood flow based on an analysis of peaks in the at least one Doppler shift waveform, wherein the at least one Doppler shift waveform indicates blood flow volume per unit time as a function of time. The defibrillator may be configured to distinguish between peaks due to compression-induced blood flow and the heart-induced blood flow based on one or more of a peak shape, a period or frequency associated with the peaks, and a phase shift between the peaks due to the compression-induced blood flow and the heart-induced blood flow. The defibrillator may be configured to calculate a first phase shift at a first time, calculate a second phase shift at a second time, and verify the heart-induced blood flow identification based on the second phase shift exceeding the first phase shift due to an increase in blood flow velocity from the first time to the second time. The defibrillator may be configured to perform a spectral analysis of the at least one Doppler shift waveform to identify the heart-induced blood flow in the presence of compression-induced blood flow. The spectral analysis may include an analysis of frequency and amplitude of the at least one Doppler shift waveform as a function of time. The defibrillator may be configured to receive an ECG waveform from the electrode assembly, analyze the ECG waveform to identify the ECG waveform as representing a shockable heart rhythm or a non-shockable heart rhythm, and provide the instructions according to the cardiac arrest protocol based on the ECG waveform analysis and on the at least one Doppler shift waveform analysis. The defibrillator may be configured to analyze the ECG waveform to identify the shockable heart rhythm, control a defibrillation shock circuit to deliver at least one defibrillation shock, analyze the data signals representing the at least one Doppler shift waveform during ongoing chest compressions after the at least one defibrillation shock, identify heart-induced blood flow corresponding to ROSC, and generate the caregiver instructions according to the non-cardiac arrest protocol, wherein the non-cardiac arrest protocol may include ROSC interventions. The defibrillator may be configured to analyze the ECG waveform to identify a non-shockable rhythm, analyze the data signals representing the at least one Doppler shift waveform during ongoing chest compressions, identify heart-induced blood flow corresponding to pseudo-PEA, and generate the caregiver instructions according to the non-cardiac arrest protocol, wherein the non-cardiac arrest protocol may include pseudo-PEA interventions. The defibrillator may include a chest compression waveform evaluation engine configured to receive data signals representing a chest compression waveform, and identify chest compression frequency components of the chest compression waveform; and a Doppler shift waveform evaluation engine configured to analyze the at least one Doppler shift waveform to identify blood flow frequency components, receive the chest compression frequency components from the chest compression waveform evaluation engine, isolate a subset of the blood flow frequency components that may be absent from the chest compression frequency components, and identify the isolated subset of the blood flow frequency components as frequency components associated with heart-induced blood flow. The chest compression waveform evaluation engine may be configured to receive the data signals representing the chest compression waveform from a chest compression monitor configured for use during manual chest compressions. The chest compression waveform evaluation engine may be configured to receive the data signals representing the chest compression waveform from an automated chest compression device. The defibrillator may be configured to remove motion artifacts from the at least one Doppler shift waveform. The system may include a plurality of wearable ultrasound blood flow sensors located at different locations on the patient relative to a pulse point, wherein the defibrillator may be configured to remove the motion artifacts from the at least one Doppler shift waveform based on at least a first Doppler shift waveform from a first wearable ultrasound blood flow sensor and a second Doppler shift waveform from a second wearable ultrasound blood flow sensor. The defibrillator may be configured to remove the motion artifacts in the first Doppler shift waveform based on a comparison between a first frequency content of the first Doppler shift waveform and a second frequency content of the second Doppler shift waveform. The first wearable ultrasound blood flow sensor may be disposed at a location on the patient proximate to the pulse point and the second wearable ultrasound blood flow sensor may be disposed at a location on the patient distant from the pulse point. The first wearable ultrasound blood flow sensor may be disposed at a location on the patient proximate to a first pulse point and the second wearable ultrasound blood flow sensor may be disposed at a location-on the patient proximate to a second and different pulse point. The pulse point may correspond to a carotid, femoral, or brachial artery. The defibrillator may be configured to generate a caregiver instruction to pause chest compressions in response to the identification of the heart-induced blood flow based on the at least one Doppler shift waveform analysis, verify the heart-induced blood flow identification during the paused chest compressions, and generate a caregiver instruction to cease the chest compressions in response to the verification. The system may include a plurality of wearable ultrasound blood flow sensors located at different locations on the patient relative to a pulse point, wherein the defibrillator may be configured to receive data signals representing a first Doppler shift waveform from a first wearable ultrasound blood flow sensor at a first location, receive data signals representing additional Doppler shift waveforms from one or more additional wearable ultrasound blood flow sensors located at one or more second and different locations, analyze a first frequency content of the first Doppler shift waveform, analyze at least one additional frequency content of the additional Doppler shift waveforms, and calculate a pulse transmit time between the first location and the one or more second and different locations based on the first frequency content and the at least one additional frequency content of the at least one Doppler shift waveform. The defibrillator may be configured to calculate an estimated vascular stiffness based on the pulse transmit time. The defibrillator may be configured to calculate an estimated blood pressure time trend based on the pulse transmit time. The system may include a plurality of wearable ultrasound blood flow sensors located at different locations on the patient relative to a pulse point, wherein the defibrillator may be configured to receive data signals representing a first Doppler shift waveform from a first wearable ultrasound blood flow sensor, receive data signals representing additional Doppler shift waveforms from one or more additional wearable ultrasound blood flow sensors, analyze a first frequency content of the first Doppler shift waveform, analyze at least one additional frequency content of the additional Doppler shift waveforms, identify correlated frequency content and uncorrelated frequency content between the first Doppler shift waveform and the additional Doppler shift waveforms, and identify the heart-induced blood flow based on the uncorrelated frequency content, wherein the correlated frequency content may correspond to chest compressions. The data signals representing the at least one Doppler shift waveform may indicate a blood flow velocity per unit time and the defibrillator may be configured to calculate a blood volume per unit time from the blood flow velocity per unit time, and identify heart-induced blood flow based on the analysis of the blood flow velocity per unit time calculated at the defibrillator. The data signals representing the at least one Doppler shift waveform may indicate a blood volume per unit time and the defibrillator may be configured to identify heart-induced blood flow based on a blood flow velocity per unit time received from the at least one wearable ultrasound blood flow sensor. The at least one Doppler shift waveform may be first physiologic data and the system may include one or more physiologic sensors configured to provide one or more types of second physiologic data other than blood flow data based on the at least one Doppler shift waveform. The defibrillator may be configured to analyze the second physiologic data together with the at least one Doppler shift waveform to generate a cumulative blood flow score, and automatically detect heart-induced blood flow based on the cumulative blood flow score. The defibrillator may be configured to calculate a confidence score associated with the cumulative blood flow score. The defibrillator may be configured to automatically generate the caregiver instructions according to the non-cardiac arrest protocol based on the cumulative blood flow score. The automatically generated caregiver instructions may include an instruction to stop chest compressions. The second physiologic data may include one or more of ECG data, continuous non-invasive blood pressure (NIBP) data, NIBP data, near-infrared spectroscopy (NIRS) data, heart sound data, and photo-plethysmography data. The second physiologic data may include one or more of pulse oximetry data, capnography data, and spirometry data. The output device may include one or more of a display screen on the defibrillator, a display screen of a computing device communicatively coupled to the defibrillator, an audio device, a haptic device, and a wearable device including one or more of a watch and glasses.

An example of a system for positioning a wearable ultrasound blood flow sensor to detect blood flow of a patient includes a medical device for monitoring and/or providing therapy to the patient and including an output device and at least one wearable ultrasound blood flow sensor configured to couple to the medical device and to the patient, wherein the medical device may be configured to receive data signals representing at least one Doppler shift waveform from the at least one wearable ultrasound blood flow sensor, receive data signals representing a chest compression waveform, analyze the at least one Doppler shift waveform for periodic features indicative of compression-induced blood flow based on the chest compression waveform, identify a location of the wearable ultrasound blood flow sensor relative to at least one blood vessel of the patient based on the periodic features in the at least one Doppler shift waveform, and generate caregiver instructions for positioning the wearable ultrasound blood flow sensor based on the identified location, wherein the output device may be configured to provide the caregiver instructions for positioning.

Implementation of such a system may include one or more of the following features. The medical device may be configured to identify the location of the wearable ultrasound blood flow sensor as corresponding to a location of the at least one blood vessel in a presence of the periodic features indicative of a chest compression rate, and identify the location of the wearable ultrasound blood flow sensor as a location with insufficient proximity to the at least one blood vessel to detect the blood flow of the patient in an absence of the periodic features indicative of the chest compression rate. The location of the at least one blood vessel may be at least one of a location of a carotid artery, a location of a brachial artery, or a location of a femoral artery. The medical device may be configured to generate caregiver instructions to adjust the wearable ultrasound blood flow sensor in response to the identification of the location of the wearable ultrasound blood flow sensor as the location with insufficient proximity to the at least one blood vessel to detect the blood flow of the patient, and wherein the output device may be configured to provide the caregiver instructions to adjust the wearable ultrasound blood flow sensor. The caregiver instructions to adjust the wearable ultrasound blood flow sensor may include an instruction to remove the wearable ultrasound blood flow sensor from the patient, and reapply the wearable ultrasound blood flow sensor. The caregiver instruction to remove and reapply the wearable ultrasound blood flow sensor may include an instruction to reapply the wearable ultrasound blood flow sensor in approximately a same location on the patient as originally applied. The caregiver instruction to remove and reapply the wearable ultrasound blood flow sensor may include an instruction to reapply the wearable ultrasound blood flow sensor in a different location on the patient than as originally applied. The different location may correspond to a location proximate to a same blood vessel on an opposite side of the patient than as originally applied relative to a sagittal plane. The caregiver instructions to adjust the wearable ultrasound blood flow sensor may include an instruction to replace the wearable ultrasound blood flow sensor with a new wearable ultrasound blood flow sensor. The medical device may be configured to receive the data signals representing the chest compression waveform from a chest compression monitor coupled to the medical device and configured for use during manual chest compressions, and analyze the at least one Doppler shift waveform for periodic features indicative of compression-induced blood flow from manual chest compressions. The chest compression waveform may be an acceleration waveform. The medical device may be configured to evaluate the chest compression waveform for indications that the manual chest compressions meet threshold compression requirements, and if the manual chest compressions meet the threshold compression requirements, then analyze the at least one Doppler shift waveform for the periodic features indicative of compression-induced blood flow, else provide caregiver instructions to modify an administration of the manual chest compressions to meet the threshold compression requirements. The threshold compression requirements may include a target compression depth, a target compression rate, and a target number of administered chest compressions. The medical device may be configured to instruct an automated compression device to provide a series of chest compressions according to a patterned compression rate variation, receive the data signals representing the chest compression waveform from the automated compression device, and analyze the at least one Doppler shift waveform for the periodic features corresponding to the patterned compression rate variation and indicative of compression-induced blood flow. The patterned compression rate variation may include two or more compression rates applied alternately for two or more groups of three or more compressions. The medical device may be configured to generate caregiver instructions to couple the wearable ultrasound blood flow sensor to the patient. The output device may be configured to provide the caregiver instructions to couple the wearable ultrasound blood flow sensor to the patient as one or more of displayed instructions and audible instructions. One or more of a housing for the wearable ultrasound blood flow sensor and a packaging for the wearable ultrasound blood flow sensor may include placement instructions for coupling the wearable ultrasound blood flow sensor to the patient. The placement instructions may include graphic representations of anatomical reference points for placement of the wearable ultrasound blood flow sensor. The anatomical reference points may include a laryngeal prominence, an anterior triangle, and a transverse neck midline. The system may include at least one anatomically contoured frame with at least one opening configured to accept the wearable ultrasound blood flow sensor and enable the wearable ultrasound blood flow sensor to couple to the patient. The at least one anatomically contoured frame may be configured for use on one of (a) a neck wherein the at least one opening may correspond to a location of a carotid artery, (b) an upper arm wherein the at least one opening may correspond to a location of a brachial artery, or (c) a thigh wherein the at least one opening may correspond to a location of a femoral artery. The system may include a plurality of anatomically contoured frames configured for use with a plurality of patient sizes. At least one anatomically contoured frame may be adjustable for use with a plurality of patient sizes. The at least one anatomically contoured frame may include two openings, each opening corresponding to one of two bilaterally located blood vessels. The at least one anatomically contoured frame may be reusable and the wearable ultrasound blood flow sensor may be disposable. The output device may include augmented reality glasses configured to provide placement instructions for the wearable ultrasound blood flow sensor. The placement instructions may include audible and/or visible instructions describing placement steps and augmented reality images of blood vessels superimposed upon a real-time view of the patient. The medical device may be configured to determine that the received data signals representing at least one Doppler shift waveform fails to meet a threshold signal strength, and generate caregiver instructions for adjusting the wearable ultrasound blood flow sensor, wherein the output device may be configured to provide the caregiver instructions for adjusting the wearable ultrasound blood flow sensor. The threshold signal strength may be a signal-to-noise ratio threshold indicative of acoustic coupling between the wearable ultrasound blood flow sensor and the patient. The caregiver instructions may include at least one of an instruction to remove and replace the wearable ultrasound blood flow sensor, an instruction to confirm liner removal for the wearable ultrasound blood flow sensor, and an instruction to confirm placement of the wearable ultrasound blood flow sensor according to placement instructions provided at one or more of a housing for the wearable ultrasound blood flow sensor, a packaging for the wearable ultrasound blood flow sensor, and the output device. The output device may include one or more of a display screen on the medical device, a display screen of a computing device communicatively coupled to the medical device, an audio device, a haptic device, and a wearable device including one or more of a watch and glasses. The medical device may be an automated external defibrillator (AED). The medical device may be an advanced life support defibrillator.

An example of a system for providing patient care guidance to a caregiver based on ultrasound detection of blood flow includes a defibrillator including an electrode assembly and an output device, at least one wearable ultrasound blood flow sensor configured to couple to the defibrillator and to a patient, and at least one automated compression device communicatively coupled to the defibrillator and the defibrillator is configured to receive data signals representing at least one Doppler shift waveform from the at least one wearable ultrasound blood flow sensor, generate caregiver instructions according to a cardiac arrest protocol, analyze the at least one Doppler shift waveform based on the received data signals, identify heart-induced blood flow based on the analysis of the at least one Doppler shift waveform, and generate caregiver instructions according to a non-cardiac arrest protocol in response to the identified heart-induced blood flow and the output device is configured to provide the caregiver instructions.

Implementations of such a system may include one or more of the following features. The defibrillator may be configured to receive a chest compression driving frequency from the automated compression device, identify automated chest compression frequency components represented in the at least one Doppler shift waveform, analyze the at least one Doppler shift waveform to identify blood flow frequency components, receive the identified automated chest compression frequency components from the chest compression waveform evaluation engine, remove the automated chest compression frequency components from the at least one Doppler shift waveform, and identify remaining blood flow frequency components as indicators of heart-induced blood flow. The defibrillator may be configured to decompose the at least one Doppler shift waveform into chest compression frequency components, and identify provided chest compressions as automated chest compressions based on the chest compression frequency components. The defibrillator may be configured to provide a control signal to the automated compression device based on the blood flow frequency components. The control signal and the at least one Doppler shift waveform may enable closed loop control of the automated chest compression device by the defibrillator. The control signal controls one or more compression delivery parameters for the automated compression device based on the blood flow frequency components of the at least one Doppler shift waveform. The one or more compression delivery parameters may be one of more of compression rate, compression depth, compression driving frequency, and a compression waveform envelope. The defibrillator may be configured to receive an ECG waveform from the electrode assembly, determine a phase of automated compressions delivered by the automated compression device that may be synchronous with a repetitive feature of the ECG waveform, and control the automated compression device to deliver compressions according to the determined phase via the control signal. The defibrillator may be configured to analyze the at least one Doppler shift waveform during a pause in an administration of chest compressions.

The system may include a ventilation device communicatively coupled to the defibrillator and the defibrillator may be configured to receive start and stop indications for a ventilation cycle from the ventilation device during the pause in the administration of chest compressions, analyze the at least one Doppler shift waveform during the ventilation cycle in response to the start and stop indications. The defibrillator may be configured to analyze the at least one Doppler shift waveform during ongoing chest compression and ventilation cycles according to the cardiac arrest protocol. The defibrillator may be configured to analyze the data signals representing the at least one Doppler shift waveform during an administration of chest compressions and the ongoing chest compression and ventilation cycles may alternate between chest compressions and ventilations according to a predetermined XY ratio of X chest compressions and Y ventilations. The defibrillator may be configured to identify return of spontaneous circulation (ROSC) based at least in part on the analysis of the at least one Doppler shift waveform. The defibrillator may be configured to identify re-arrest subsequent to ROSC based at least in part on the analysis of the at least one Doppler shift waveform. The defibrillator may be configured to identify pseudo-pulseless electrical activity (pseudo-PEA) based at least in part on the analysis the at least one Doppler shift waveform. The defibrillator may be configured to detect heart-induced blood flow associated with a manually impalpable pulse based on the at least one Doppler shift waveform. The defibrillator may be configured to detect the heart-induced blood flow at a blood pressure below approximately 60-80 systolic. The defibrillator may be configured to distinguish between PEA and pseudo-PEA based at least in part on the analysis of the at least one Doppler shift waveform. The defibrillator may be configured to distinguish between ROSC and pseudo-PEA based at least in part on the analysis of the at least one Doppler shift waveform. The defibrillator may be configured to identify pseudo-PEA as distinguished from ROSC based on an absence of an indication of positive blood flow between peaks in the at least one Doppler shift waveform. The defibrillator may be configured to analyze the data signals representing the at least one Doppler shift waveform during an administration of ventilations and the ongoing chest compression and ventilation cycles may alternate between chest compressions and ventilations according to a predetermined XY ratio of X chest compressions and Y ventilations. The defibrillator may be configured to analyze the at least one Doppler shift waveform to identify the heart-induced blood flow in a presence of compression-induced blood flow. The defibrillator may be configured to identify the heart-induced blood flow based on an analysis of peaks in the at least one Doppler shift waveform and the at least one Doppler shift waveform indicates blood flow volume per unit time as a function of time. The defibrillator may be configured to distinguish between peaks due to compression-induced blood flow and the heart-induced blood flow based on one or more of a peak shape, a period or frequency associated with the peaks, and a phase shift between the peaks due to the compression-induced blood flow and the heart-induced blood flow. The defibrillator may be configured to calculate a first phase shift at a first time, calculate a second phase shift at a second time, and verify the heart-induced blood flow identification based on the second phase shift exceeding the first phase shift due to an increase in blood flow velocity from the first time to the second time. The defibrillator may be configured to perform a spectral analysis of the at least one Doppler shift waveform to identify the heart-induced blood flow in the presence of compression-induced blood flow. The spectral analysis may include an analysis of frequency and amplitude of the at least one Doppler shift waveform as a function of time. The defibrillator may be configured to receive an ECG waveform from the electrode assembly, analyze the ECG waveform to identify the ECG waveform as representing a shockable heart rhythm or a non-shockable heart rhythm, and provide the instructions according to the cardiac arrest protocol based on the ECG waveform analysis and on the at least one Doppler shift waveform analysis. The defibrillator may be configured to analyze the ECG waveform to identify the shockable heart rhythm, control a defibrillation shock circuit to deliver at least one defibrillation shock, analyze the data signals representing the at least one Doppler shift waveform during ongoing chest compressions after the at least one defibrillation shock, identify heart-induced blood flow corresponding to ROSC, and generate the caregiver instructions according to the non-cardiac arrest protocol and the non-cardiac arrest protocol may include ROSC interventions. The defibrillator may be configured to analyze the ECG waveform to identify a non-shockable rhythm, analyze the data signals representing the at least one Doppler shift waveform during ongoing chest compressions, identify heart-induced blood flow corresponding to pseudo-PEA, and generate the caregiver instructions according to the non-cardiac arrest protocol and the non-cardiac arrest protocol may include pseudo-PEA interventions.

An example of a system for providing patient care guidance to a caregiver based on ultrasound detection of blood flow includes at least one wearable ultrasound blood flow sensor configured to adhesively couple to a patient, an automated compression device, and a Doppler shift waveform evaluation engine communicatively coupled to the at least one wearable ultrasound blood flow sensor and the automated compression device and configured to receive data signals representing at least one Doppler shift waveform from the at least one wearable ultrasound blood flow sensor, analyze the at least one Doppler shift waveform based on the received data signals, identify heart-induced blood flow based on the analysis of the at least one Doppler shift waveform, and provide a control signal to the automated compression device based on the blood flow frequency components. The control signal controls one or more compression delivery parameters for the automated compression device based on the blood flow frequency components of the at least one Doppler shift waveform.

Implementations of such a system may include one or more of the following features. The control signal and the at least one Doppler shift waveform may be part of a closed loop control system for the automated compression device. The automated compression device may be a belt-based device. The automated compression device may be a piston-based device. The one or more compression delivery parameters may include one of more of compression rate, compression depth, compression driving frequency, and a compression waveform envelope. The Doppler shift waveform evaluation engine may be disposed at the automated compression device. The system may include a defibrillator communicatively coupled to the Doppler shift waveform evaluation engine and configured to receive an ECG waveform from a defibrillator electrode assembly, and provide the ECG waveform to the Doppler shift waveform evaluation engine. The Doppler shift waveform evaluation engine may be configured to determine a phase of automated compressions delivered by the automated compression device that may be synchronous with a repetitive feature of the ECG waveform, and control the automated compression device to deliver compressions according to the determined phase via the control signal. The Doppler shift evaluation engine may be disposed at the defibrillator. The system may include a chest compression waveform evaluation engine configured to receive a chest compression driving frequency from the automated compression device, and identify automated chest compression frequency components represented in the at least one Doppler shift waveform. The Doppler shift waveform evaluation engine may be configured to analyze the at least one Doppler shift waveform to identify blood flow frequency components, receive the identified automated chest compression frequency components from the chest compression waveform evaluation engine, remove the automated chest compression frequency components from the at least one Doppler shift waveform, and identify remaining blood flow frequency components as indicators of heart-induced blood flow. The Doppler shift waveform evaluation engine may be configured to identify return of spontaneous circulation (ROSC) based at least in part on the analysis of the at least one Doppler shift waveform. The Doppler shift waveform evaluation engine may be configured to identify re-arrest subsequent to ROSC based at least in part on the analysis of the at least one Doppler shift waveform. The Doppler shift waveform evaluation engine may be configured to identify pseudo-pulseless electrical activity (pseudo-PEA) based at least in part on the analysis the at least one Doppler shift waveform. The Doppler shift waveform evaluation engine may be configured to detect heart-induced blood flow associated with a manually impalpable pulse based on the at least one Doppler shift waveform. The Doppler shift waveform evaluation engine may be configured to detect the heart-induced blood flow at a blood pressure below approximately 60-80 systolic. The Doppler shift waveform evaluation engine may be configured to distinguish between PEA and pseudo-PEA based at least in part on the analysis of the at least one Doppler shift waveform. The Doppler shift waveform evaluation engine may be configured to distinguish between ROSC and pseudo-PEA based at least in part on the analysis of the at least one Doppler shift waveform. The Doppler shift waveform evaluation engine may be configured to identify pseudo-PEA as distinguished from ROSC based on an absence of an indication of positive blood flow between peaks in the at least one Doppler shift waveform. The Doppler shift waveform evaluation engine may be configured to analyze the at least one Doppler shift waveform during ongoing chest compression and ventilation cycles and the chest compression cycles provided by the automated compression device. The Doppler shift waveform evaluation engine may be configured to analyze the data signals representing the at least one Doppler shift waveform during an administration of chest compressions and the ongoing chest compression and ventilation cycles may alternate between chest compressions and ventilations according to a predetermined XY ratio of X chest compressions and Y ventilations. The Doppler shift waveform evaluation engine may be configured to analyze the data signals representing the at least one Doppler shift waveform during an administration of ventilations and the ongoing chest compression and ventilation cycles may alternate between chest compressions and ventilations according to a predetermined XY ratio of X chest compressions and Y ventilations. The system may include a ventilation device communicatively coupled to the Doppler shift waveform evaluation engine. The Doppler shift waveform may be configured to analyze the at least one Doppler shift waveform during the administration of ventilations from the ventilation device. The Doppler shift waveform evaluation engine may be configured to receive start and stop indications for the administration of ventilations during a ventilation cycle from the ventilation device. The system may include at least one display and the Doppler shift waveform evaluation engine may be configured to generate caregiver instructions based on the Doppler shift waveform analysis, and provide the caregiver instructions at the at least one display.

An example of a system for providing patient care guidance to a caregiver based on ultrasound detection of blood flow includes a defibrillator including an electrode assembly and a first output device, and a portable computing device communicatively coupled to the defibrillator and including a second output device, a Doppler shift waveform evaluation engine disposed at one or more of the defibrillator and the portable computing device, and at least one wearable ultrasound blood flow sensor configured to couple to the Doppler shift waveform evaluation engine and to a patient. The Doppler shift waveform evaluation engine is configured to receive data signals representing at least one Doppler shift waveform from the at least one wearable ultrasound blood flow sensor, generate caregiver instructions according to a cardiac arrest protocol, analyze the at least one Doppler shift waveform based on the received data signals, identify heart-induced blood flow based on the analysis of the at least one Doppler shift waveform, and generate caregiver instructions according to a non-cardiac arrest protocol in response to the identified heart-induced blood flow. The at least one of the first output device and the second output device is configured to provide the caregiver instructions.

Implementations of such a system may include one or more of the following features. The Doppler shift waveform evaluation engine may be configured to analyze the at least one Doppler shift waveform during ongoing chest compression and ventilation cycles according to the cardiac arrest protocol. The Doppler shift waveform evaluation engine may be configured to analyze the data signals representing the at least one Doppler shift waveform during an administration of chest compressions and the ongoing chest compression and ventilation cycles may alternate between chest compressions and ventilations according to a predetermined XY ratio of X chest compressions and Y ventilations. The Doppler shift waveform evaluation engine may be configured to identify return of spontaneous circulation (ROSC) based at least in part on the analysis of the at least one Doppler shift waveform. The Doppler shift waveform evaluation engine may be configured to identify re-arrest subsequent to ROSC based at least in part on the analysis of the at least one Doppler shift waveform. The Doppler shift waveform evaluation engine may be configured to identify pseudo-pulseless electrical activity (pseudo-PEA) based at least in part on the analysis the at least one Doppler shift waveform. The Doppler shift waveform evaluation engine may be configured to detect heart-induced blood flow associated with a manually impalpable pulse based on the at least one Doppler shift waveform. The Doppler shift waveform evaluation engine may be configured to detect the heart-induced blood flow at a blood pressure below approximately 60-80 systolic. The Doppler shift waveform evaluation engine may be configured to distinguish between PEA and pseudo-PEA based at least in part on the analysis of the at least one Doppler shift waveform. The Doppler shift waveform evaluation engine may be configured to distinguish between ROSC and pseudo-PEA based at least in part on the analysis of the at least one Doppler shift waveform. The Doppler shift waveform evaluation engine may be configured to identify pseudo-PEA as distinguished from ROSC based on an absence of an indication of positive blood flow between peaks in the at least one Doppler shift waveform. The Doppler shift waveform evaluation engine may be configured to analyze the data signals representing the at least one Doppler shift waveform during an administration of ventilations and the ongoing chest compression and ventilation cycles may alternate between chest compressions and ventilations according to a predetermined XY ratio of X chest compressions and Y ventilations. The Doppler shift waveform evaluation engine may be configured to analyze the at least one Doppler shift waveform to identify the heart-induced blood flow in a presence of compression-induced blood flow based on an analysis of peaks in the at least one Doppler shift waveform and the at least one Doppler shift waveform indicates blood flow volume per unit time as a function of time. The Doppler shift waveform evaluation engine may be configured to distinguish between peaks due to compression-induced blood flow and the heart-induced blood flow based on one or more of a peak shape, a period or frequency associated with the peaks, and a phase shift between the peaks due to the compression-induced blood flow and the heart-induced blood flow. The Doppler shift waveform evaluation engine may be configured to perform a spectral analysis of the at least one Doppler shift waveform to identify the heart-induced blood flow in the presence of compression-induced blood flow. The spectral analysis may include an analysis of frequency and amplitude of the at least one Doppler shift waveform as a function of time. The defibrillator may be configured to receive an ECG waveform from the electrode assembly. The Doppler shift waveform evaluation engine may be configured to analyze the ECG waveform to identify the ECG waveform as representing a shockable heart rhythm or a non-shockable heart rhythm, and provide the caregiver instructions according to the cardiac arrest protocol based on the ECG waveform analysis and on the at least one Doppler shift waveform analysis. The defibrillator may be configured to analyze the ECG waveform to identify the shockable heart rhythm, and control a defibrillation shock circuit to deliver at least one defibrillation shock. The Doppler shift waveform evaluation engine may be configured to analyze the data signals representing the at least one Doppler shift waveform during ongoing chest compressions after the at least one defibrillation shock, identify heart-induced blood flow corresponding to ROSC, and generate the caregiver instructions according to the non-cardiac arrest protocol and the non-cardiac arrest protocol may include ROSC interventions. The defibrillator may be configured to analyze the ECG waveform to identify a non-shockable rhythm. The Doppler shift waveform evaluation engine may be configured to analyze the data signals representing the at least one Doppler shift waveform during ongoing chest compressions, identify heart-induced blood flow corresponding to pseudo-PEA, and generate the caregiver instructions according to the non-cardiac arrest protocol and the non-cardiac arrest protocol may include pseudo-PEA interventions. The system may include a chest compression evaluation engine communicatively coupled to the Doppler shift waveform evaluation engine. The chest compression evaluation engine may be configured to receive data signals representing a chest compression waveform, and identify chest compression frequency components of the chest compression waveform. The Doppler shift waveform evaluation engine may be configured to analyze the at least one Doppler shift waveform to identify blood flow frequency components, receive the chest compression frequency components from the chest compression waveform evaluation engine, isolate a subset of the blood flow frequency components that may be absent from the chest compression frequency components, and identify the isolated subset of the blood flow frequency components as frequency components associated with heart-induced blood flow. The chest compression evaluation engine may be configured to receive the data signals representing the chest compression waveform from a chest compression monitor configured for use during manual chest compressions. The Doppler shift waveform evaluation engine may be configured to generate a caregiver instruction to pause chest compressions in response to the identification of the heart-induced blood flow based on the at least one Doppler shift waveform analysis, verify the heart-induced blood flow identification during the paused chest compressions, and generate a caregiver instruction to cease the chest compressions in response to the verification. The at least one Doppler shift waveform may be first physiologic data and the system may include one or more physiologic sensors configured to provide one or more types of second physiologic data other than blood flow data based on the at least one Doppler shift waveform, and the Doppler shift waveform evaluation engine may be configured to analyze the one or more types of second physiologic data together with the at least one Doppler shift waveform to generate a cumulative blood flow score, and automatically detect heart-induced blood flow based on the cumulative blood flow score. The system may include an automated chest compression device communicatively coupled to the at least one of the defibrillator and the portable computing device. The Doppler shift waveform evaluation engine may be configured to receive a chest compression driving frequency from the automated compression device, identify automated chest compression frequency components represented in the at least one Doppler shift waveform, analyze the at least one Doppler shift waveform to identify blood flow frequency components, receive the identified automated chest compression frequency components from the chest compression waveform evaluation engine, remove the automated chest compression frequency components from the at least one Doppler shift waveform, and identify remaining blood flow frequency components as indicators of heart-induced blood flow. The Doppler shift waveform evaluation engine may be configured to provide a control signal to the automated compression device based on the blood flow frequency components. The control signal and the at least one Doppler shift waveform enable closed loop control of the automated chest compression device by the defibrillator. The control signal may control one or more compression delivery parameters for the automated compression device based on the blood flow frequency components of the at least one Doppler shift waveform. The one or more compression delivery parameters may include one of more of compression rate, compression depth, compression driving frequency, and a compression waveform envelope. The defibrillator may be configured to receive an ECG waveform from a defibrillator electrode assembly and provide the ECG waveform to the Doppler shift waveform evaluation engine. The Doppler shift waveform evaluation engine may be configured to determine a phase of automated compressions delivered by the automated compression device that may be synchronous with a repetitive feature of the ECG waveform, and control the automated compression device to deliver compressions according to the determined phase via the control signal. The first and second output devices may include one or more of a touchscreen, an audio device, a haptic device, and a wearable device including one or more of a watch and glasses.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values and/or dimensions illustrated in the accompanying graphs and figures are for illustration purposes only and may or may not represent actual or preferred values or dimensions. Where applicable, some or all features may not be illustrated to assist in the description of underlying features.

FIG. 7B-1 shows an example of a Doppler shift waveform that indicates heart-induced blood flow and compression-induced blood flow for automated compressions.

FIG. 7B-2 shows and example of a Doppler shift waveform that indicates heart-induced blood flow and compression induced blood flow for manual compressions.

FIG. 7E-1 shows an example of a Doppler shift waveform that indicates compression-induced blood flow for automated compressions.

FIG. 7E-2 shows an example of a Doppler shift waveform that indicates compression-induced blood flow for manual compressions.

FIGS. 7G-1 and 7G-2 show examples of spectrograms representative of a frequency domain analysis of the Doppler shift waveforms for automated compressions.

FIGS. 7H-1 and 7H-2 show examples of spectrograms representative of a frequency domain analysis of the Doppler shift waveforms for manual compressions.

DETAILED DESCRIPTION

Figure 1:
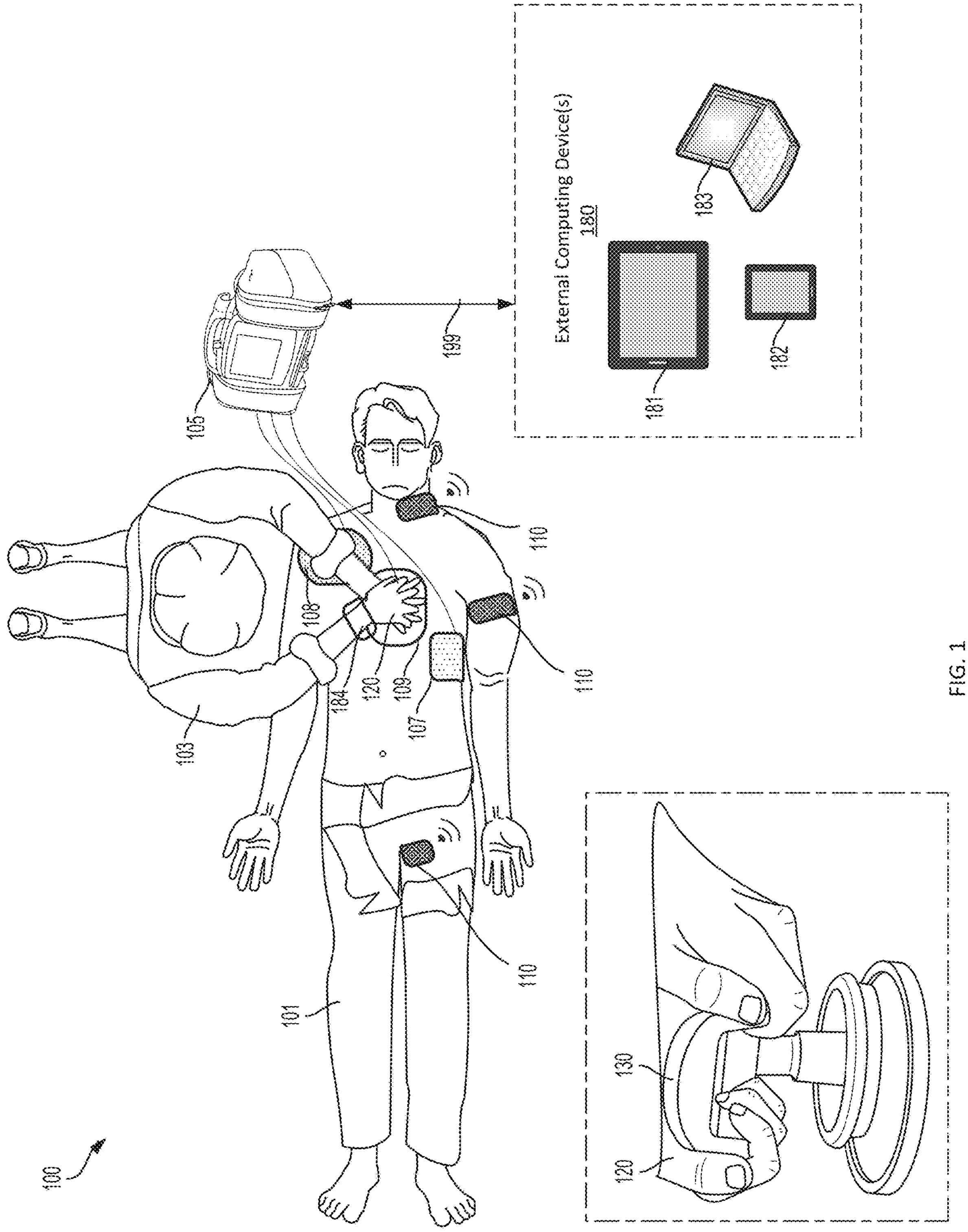
FIG. 1 shows an example of a manual compression patient care system that includes at least one wearable ultrasound blood flow sensor.

The description set forth below in connection with the appended drawings is intended to be a description of various, illustrative embodiments or implementations of the disclosed subject matter. Specific features and functionalities are described in connection with each illustrative embodiment or implementation; however, it will be apparent to those skilled in the art that the disclosed embodiments and implementations may be practiced without each of those specific features and functionalities.

Reference throughout the specification to "one embodiment," "an embodiment," or "an implementation" means that a particular feature, structure, or characteristic described in connection with an embodiment or implementation is included in at least one embodiment or implementation of the subject matter disclosed. Thus, the appearance of the phrases "in one embodiment" or "in an embodiment" or "in an implementation" in various places throughout the specification is not necessarily referring to the same embodiment or implementation. Further, the particular features, structures or characteristics may be combined in any suitable manner in one or more embodiments or implementations. Further, it is intended that embodiments and implementations of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values in between.

All of the functionalities described in connection with one embodiment or implementation are intended to be applicable to the additional embodiments and implementations described below except where expressly stated or where the feature or function is incompatible with the additional embodiments and implementations. For example, where a given feature or function is expressly described in connection with one embodiment or implementation but not expressly mentioned in connection with an alternative embodiment or implementation, it should be understood that that feature or function may be deployed, utilized or implemented in connection with the alternative embodiment or implementation unless the feature or function is incompatible with the alternative embodiment or implementation.

Emergency medical care focuses, at least initially, on timely and efficient evaluation and treatment of a patient's presenting conditions. Such medical care occurs, for example, in response to a 911 call, in a military triage, or in an emergency room of a hospital. A presenting condition commonly encountered in emergency medical care is cardiac arrest. Upon encountering a patient in cardiac arrest, chest compressions and ventilations must be given to the patient as soon as possible because a patient in cardiac arrest has no heart-induced blood flow. Generally speaking, a patient's chance of survival from a cardiac arrest decreases by 10% for every minute delay in the administration of chest compressions. In addition, five seconds of interruption in chest compression can drop a victim's survival rate by about 18%. Chest compressions and ventilations are one portion of cardiopulmonary resuscitation (CPR). For cardiac arrest in which the patient presents with a shockable heart rhythm, such as ventricular fibrillation (VF) or ventricular tachycardia (VT), another component of CPR is administration of a defibrillation shock. However, for cardiac arrest in which the patient presents with a non-shockable rhythm, such as pulseless electrical activity (PEA), CPR does not include the administration of the defibrillation shock. For a non-shockable rhythm, the caregiver must continue to administer chest compressions and ventilation until heart-induced blood flow resumes (or until the patient is no longer able to be resuscitated). A patient in cardiac arrest may also be treated pharmacologically as an aid to the chest compressions, ventilation, and, if appropriate, defibrillation shock. For any cardiac arrest, it is critical to continue chest compressions until the heart is no longer in cardiac arrest and is generating heart-induced blood flow.

The goal of defibrillation shock is to restore a heart rhythm that generates blood circulation. Thus, if the defibrillation shock is successful, then the blood circulation post-shock is a return of spontaneous circulation (ROSC). In many cardiac arrest cases, ROSC does not occur within 1-3 second of the defibrillation shock but rather with a significant delay post-shock of 5-50 seconds, for example. This delay can be large enough that chest compressions are necessarily resumed post-shock because the first few seconds of monitoring the patient does not indicate ROSC. Additionally, pauses in chest compressions for manual palpation to identify ROSC decrease the patient's chances of survival. However, in these cases, unbeknownst to the rescuer, ROSC may occur during the chest compressions. Chest compressions on a beating heart may cause the patient to go into ventricular fibrillation again in what is known as re-arrest. It is therefore desirable to detect ROSC during ongoing chest compressions with a monitoring system other than ECG.

In PEA, the heart retains electrical activity but lacks contractility and thus does not induce blood flow. Chest compressions may successfully restore contractility to the heart but the heart may still exhibit the ECG characteristics of PEA. During PEA, there is electrical activity in the heart that does not result in a pulse while during pseudo-PEA, the same electrical activity in the heart does result in a very small pulse that is hard to ascertain. This restored pumping function with ECG characteristics of PEA is known as pseudo-PEA; PEA is cardiac arrest but pseudo-PEA is not cardiac arrest. Although both ROSC and pseudo-PEA refer to a resumption of heart-induced, or spontaneous circulation, pseudo-PEA designates a specific sub-category of heart-induced blood flow in which the ECG is indistinguishable from the cardiac arrest state of PEA. Discrimination between PEA and pseudo-PEA is difficult because the ECG's for the two states are the same and the pulse produced by pseudo-PEA is too weak to ascertain by manual radial or carotid palpation. Furthermore, during the ongoing chest compressions necessary for a patient's survival, manual palpation cannot distinguish between heart-induced blood flow and compression induced blood flow. As long as the rescuer considers the patient to be in cardiac arrest and considering the survival statistics discussed above in the absence of chest compressions, it is crucial to continue chest compressions. However, once the patient is no longer in cardiac arrest, it is crucial to stop chest compressions, transport the patient, and commence a non-cardiac arrest protocol that includes interventions directed at the underlying heart malfunction causing pseudo-PEA. This malfunction stems from either an issue with the available blood flow such as, for example, loss of blood due to trauma, dehydration or internal bleeding or from a mechanical heart issue in which the heart muscle is unable to respond to the electrical impulses manifested in the ECG. This type of rhythm is not repairable by a delivery of energy to the heart via a defibrillation shock. Instead, resuscitative treatment includes chest compressions and medications and/or other interventions directed at relieving blood loss. A patient exhibiting pseudo-PEA may require treatment for shock as well.

The contractility of the heart during pseudo-PEA is non-zero but it is not full contractility that provides life-sustaining flow without any further medical interventions. The QRS-width is less and the heart rate is higher in full life-sustaining flow than in pseudo-PEA (e.g., an ECG may show sharper peaks and a higher heart rate in full life-sustaining flow than in pseudo-PEA). Transport is often delayed during cardiac arrest due to the significant difficulty of providing continuous chest compressions while loading a patient into an ambulance. Additionally, even weak heart-induced blood flow is more effective and efficient in terms of cardiac output than compression-induced blood flow. Thus chest compressions are continued on-scene. It is therefore desirable to detect pseudo-PEA during ongoing chest compressions.

A wearable ultrasound blood flow sensor provides portable, sensitive, and non-invasive hemodynamic monitoring. Such monitoring is well-suited to for use in the mobile emergency care environment that is often the first and most critical point of care for a cardiac arrest victim. In contrast to a handheld transducer, the wearable ultrasound blood flow sensor enables continuous or frequent periodic blood flow monitoring while freeing the hands of the caregiver for other resuscitative tasks. In the emergency care environment where the number of available caregivers is limited, this hands-free advantage is particularly significant. An ultrasound system that requires the caregiver to use one hand to control a transducer and another hand to control an imaging system fully occupies the caregiver.

The wearable ultrasound blood flow sensor enables the detection of ROSC and pseudo-PEA along with other advantages described below. This sensor is a portable device that may be affordable and disposable and provides non-invasive blood flow monitoring with a sensitivity suited to the weak blood flow associated with recovery from cardiac arrest. This device aids in the provisioning of care of critically-ill individuals, (e.g., cardiac arrest victims) by providing functional and instantaneous, or near instantaneous, hemodynamic assessments. As a non-invasive device, use of the wearable ultrasound blood flow sensor eliminates the risk of infection from an invasive device (such as an invasive blood pressure sensor) and eliminates the need for the rescuer to devote time to the extra surgical steps necessary for use of such a device. The non-invasive device also reduces the time needed for healing and tissue repair. Further, the non-invasive approaches, in the context of emergency situations, the non-invasive device requires less in the way of sterilization and specialized skillsets and equipment. The portability of the wearable ultrasound blood flow sensor enables the sensor to be easily transported to the patient, instead of transporting the patients to a sensor location such as a hospital. Thus, the easily transported sensor is well-suited to the on-scene care typical of initial interventions for cardiac arrest.

The wearable ultrasound blood flow sensor provides a number of advantages over other blood flow sensing techniques. As one advantage, the wearable ultrasound blood flow sensor described herein enables detection of heart-induced blood flow in a manner that minimizes or eliminates chest compression pauses during CPR. This detection may occur during ongoing chest compressions. Such detection enables real-time and rapid detection of ROSC in a manner that minimizes or eliminates the risk of re-arrest. Additionally, such detection enables discrimination between PEA and pseudo-PEA with minimal or no pauses in chest compressions. Because manual palpation cannot distinguish between heart-induced blood flow and compression induced blood flow, compressions must be paused in order to discern via manual palpation that heart-induced blood flow exists. Therefore, even if a rescue team included a person dedicated to keeping their fingers in place to monitor for heart-induced blood flow, there must be a pause in compressions, either by an automated compression device or by another rescuer providing manual compressions in order to identify a palpated pulse as the product of heart-induced flow. Additionally, in practice palpation loses accuracy over time because a typical rescuer loses sensitivity in their touch perception over time and, particularly in trying to detect a weak pulse from the victim, detects their own blood pressure as felt in their fingers pressing against the victim. Generally, the rescuer has to pause and restart in order to separate the perception of their own blood pressure from that of the victim or patient. Therefore, unlike continuous blood flow monitoring available from a wearable ultrasound blood flow sensor, manual palpation does not provide continuous monitoring or monitoring during ongoing compressions.

Timely and accurate detection of ROSC and pseudo-PEA enable expedited post-cardiac arrest care. Such care eliminates protracted interventions for cardiac arrest beyond the time when the patient is no longer in cardiac arrest. These protracted interventions not only reduce patient survival rates and outcomes, but in some cases, like re-arrest, may actually worsen the condition of the patient. Detecting the heart-induced blood flow associated with ROSC and pseudo-PEA during ongoing chest compressions enables the patient to receive these life-saving compressions for a longer time period without unnecessary interruptions.

As another advantage, the wearable ultrasound blood flow sensor described herein may provide the above benefits in conjunction with caregiver guidance from a medical device used in conjunction with the blood flow sensor. The medical device, for example, defibrillator, and/or an external computing device communicatively coupled to the medical device, may receive data signals from the wearable ultrasound blood flow sensor that represent blood velocity in a patient's blood vessels due to chest compression induced blood flow and due to heart-induced blood flow. Further, the medical device may receive data signals that represent other patient care and cardiac indicators such as chest compression motion parameters, ECG, and respiration data. With the analysis of the blood flow data together with the patient care and cardiac indicators, the medical device or the communicatively coupled external computing device may provide positioning guidance to the caregiver for proper positioning of the wearable ultrasound blood flow sensor on the cardiac arrest victim. Additionally, the medical device may provide patient care guidance that enables a caregiver to move from cardiac arrest interventions to post-cardiac arrest interventions based on an accurate and prompt detection of heart-induced blood flow (e.g., ROSC or pseudo-PEA).

The systems and methods described herein enable the advantages described above to be realized in the extremely time sensitive situation of medical care for cardiac arrest. With the data analysis and caregiver guidance provided by the medical device with the wearable ultrasound blood sensor, the benefits of this type of blood flow analysis may be available for lay rescuers using an AED and first responders, like emergency medical technicians or firefighters using a basic life support defibrillator and is not limited to paramedics or hospital medical professionals. This benefits the victims of cardiac arrest by making highly efficacious care available from first moment of a response. Additionally, the wearable nature of the ultrasound blood flow sensor allows the sensor to remain in place to provide blood flow analysis continuously from as early as the initial moments of rescue, through on-scene CPR, patient transport, and transition to a medical facility. This continuity of care improves the efficacy of interventions all along the patient care path thus improving the overall outcome for the victim of cardiac arrest. The rescue scene for a cardiac arrest victim is an unstructured environment and the rescuers and the variance in experience and training among individuals responsible for assessing functional hemodynamics may have a wide range of experience and training. With these variations and the need to monitor the patient over protracted period of time, a sensor that is attached to and remains in place on the patient provides data with better precision and reproducibility than a sensor that must continuously be applied and reapplied.

Furthermore, the wearable nature and guidance from the medical device enable efficient and efficacious care by one rescuer or a small team of rescuers. The wearable ultrasound blood flow sensor enables hands-free pulse monitoring and does not require a rescuer to be devoted to the single task of monitoring for a pulse. The guidance from the medical device provided with the wearable ultrasound blood flow sensor enables the rescuer or rescue team to concentrate on life-saving interventions requiring their hands and attention without losing sight of blood flow, that critical parameter indicating the end of cardiac arrest.

Other methods of sensing heart-induced blood flow lack the advantages provided by the wearable ultrasound blood flow sensor used in conjunction with the medical device as described herein. Methods of detecting heart-induce blood flow include manual palpation, ECG, manual palpation, invasive blood pressure (IBP), and ultrasound imaging.

In the absence of a patient regaining consciousness, for example, it is not obvious that heart-induced blood flow has resumed during a resuscitation effort and rescuers do not rely on ECG as a sole indicator of blood flow. Rather, for an unconscious patient, rescuers need to determine if blood flow, particularly to the brain, has resumed. ECG provides insight into the electrical behavior of the heart, but ECG it does not provide a direct measure of the heart's mechanical activity or the resulting blood flow. It is this blood flow resulting from the mechanical pumping action of the heart that is the critical goal of resuscitation because the blood flow provides the necessary perfusion of blood to the brain and other organs to keep the cells in these organs alive. In the case of an arrhythmogenic cardiac arrest, the defibrillation shock may end the fibrillation activity but the ECG generally exhibits nonspecific changes in response to the shock and typically does not return, at least over a time frame of minutes, to a normal sinus rhythm (where a normal sinus rhythm is one associated with a healthy heart). Furthermore, for non-arrhythmogenic cardiac arrest, or PEA, the ECG rhythm mimics the behavior of a repeating and perfusing ECG rhythm but without actual blood flow. Although there is ongoing research into using ECG to detect the resumption of spontaneous blood flow, such detection mechanisms are not commercially available and not of general practice as part of standard resuscitation protocols. Thus, particularly in non-hospital settings, the primary mechanism for detecting heart-induced blood flow is manual palpation.

Manual palpation cannot distinguish between heart-induced and compression-induced blood flows, the rescuer has to pause the manual compressions to palpate. Manual palpation cannot distinguish between heart-induced blood flow and compression induced blood flow and, therefore, compressions must be paused in order to discern via manual palpation that heart-induced blood flow exists. Additionally, in practice, a typical rescuer palpating loses sensitivity over time and, particularly in trying to detect a weak pulse from the victim, detects their own blood pressure as felt in their fingers pressing against the victim. Generally, the rescuer has to pause and restart in order to separate the perception of their own blood pressure from that of the victim or patient. Additionally, with manual palpation, weak heartbeats typical ROSC and pseudo-PEA are easily missed by the rescuer. The pulse detected at, for example, the carotid artery, the brachial artery, the femoral artery, etc. is a peripheral pulse caused by a high-pressure wave of blood moving away from the heart following a systolic ejection and reaching vessels in these extremities. In a controlled clinical environment with a healthy heart providing strong systolic blood pressure, the reliability of manual pulse palpation is better than the reliability in the context of cardiac arrest. The reliability in the controlled clinical environment ranges from approximately 47-91% with the highest accuracy ascribable to acute care doctors and nurses. In the context of cardiac arrest, the presence of a pathology, time and environmental pressures, and likely lack of experience of a lay responder or inexperience of a first responder makes manual pulse palpation even less reliable. During CPR, manual palpation is done quickly to minimize pause times in compressions and the heart is in a severely weakened condition. Furthermore, CPR is often administered in a non-clinical environment at the site of a cardiac arrest. With regard to the effect of pathology, as an example, for a blood pressure below 60-80 mm/Hg systolic, radial, femoral, and/or carotid pulses are generally manually impalpable. With the wearable ultrasound sensor, the defibrillator 105 described herein may detect heart-induced blood flow associated with a manually impalpable pulse (e.g., heart-induced blood flow at a blood pressure below approximately 60-80 mm/Hg systolic).

A method of providing continuous and sensitive blood flow monitoring during chest compressions is invasive blood pressure (IBP). However, an invasive device requires sterilization and specialized skillsets and equipment. For example, lay rescuers using an AED or emergency medical technicians do not have the requisite skillset and equipment for such a procedure. Additionally, an invasive method such as IBP creates a risk of infection and requires a caregiver to devote time to the extra surgical steps necessary for use of such a device. The invasive device also increases the time needed for healing and tissue repair.

A further method of providing blood flow monitoring during chest compressions is ultrasound imaging with a hand-held transducer. The data collection for a complete ultrasound image takes about 6-10 seconds and therefore ultrasound imaging cannot detect changes in blood flow that occur within a 6-10 second window. Additionally, using a hand-held ultrasound imaging transducer is difficult in terms of finding a proper probe placement for pulse detection and requires a dedicated rescuer to hold and manipulate the transducer. Practically speaking, this hand-held transducer cannot stay in place on a patient for the duration of a rescue to provide continuous monitoring. For example, a patient may be moved from the ground to a gurney, transported on a stretcher over rough terrain, transported to an ambulance, helicopter, or other transport vehicle, monitored in the tight confines and turbulent environment of the transport vehicle, and transferred again to a medical facility.

Often the patient is moved from the ground and transported after heart-induced blood flow has resumed in response to a defibrillation shock and/or chest compressions. However, the patient is still in a precarious situation physiologically and it is possible for cardiac arrest to re-occur during transport (e.g., on route from the site of the cardiac arrest to a medical facility). Approximately 15-35% of patients resuscitated from cardiac arrest undergo rearrest during transport. Blood flow monitoring is the fastest and most direct indicator of a cessation of flow due to cardiac arrest. Other measures like ECG, blood pressure, EtCO2, pulse oximetry, NIRS, etc. measure the effects of heart-induced blood flow or physiologic behavior that typically accompanies heart-induced blood flow. Therefore, a direct measure of blood flow may be more sensitive to deterioration of the heart such as that which precedes re-arrest. Therefore, during this transport, unlike a handheld transducer, a fixed wearable ultrasound device can continuously monitor blood flow and immediately alert rescuers to the lack of flow that indicates cardiac arrest, re-arrest, or other emerging or re-emerging hemodynamic pathology.

Referring to FIG. 1, an example of a manual compression patient care system that includes at least one wearable ultrasound blood flow sensor is shown. A quantity of each component in FIG. 1 is an example only and other quantities of each, or any, component could be used.

As shown in FIG. 1, at patient care scene 100, a rescuer or caregiver 103 attends to a victim or patient 101 (the terms are used interchangeably here to indicate a person who is the subject of intended or actual medical treatment(s) and/or interventions), such as an individual who has suffered a cardiac arrest. The emergency care scene 100 can be, for instance, at the scene of an accident or health emergency, in an ambulance, in an emergency room or hospital, or another location in which a rescuer may provide resuscitative care. The rescuer 103 may be, for instance, a civilian responder with limited or no training in lifesaving techniques, a first responder with limited training (e.g., an emergency medical technician (EMT), a police officer, a firefighter, etc.), and/or a medical professional with advanced resuscitative care training (e.g., a paramedic, a physician, a nurse, etc.). The rescuer 103 may be acting alone or may be acting with assistance from one or more other rescuers.

The rescuer 103 may employ various devices and sensors to deliver resuscitative care to the victim 101. These devices may include a medical device. The medical device may be, for example, a defibrillator 105 (e.g., a basic life support device such as an automated external defibrillator or an advanced life support device such as an external defibrillator designed for use by a trained medical caregiver). The defibrillator 105 may be configured to provide therapeutic care to the victim 101, including, for example, delivery of a defibrillation shock. The defibrillator 105 may also be configured to couple to one or more sensors and monitor a physiologic status of the victim 101 based on data signals from the one or more sensors. As shown for example in FIG. 1, the one or more sensors may include at least two electrodes 107 and 108, a compression monitor 109, and at least one wearable ultrasound blood flow sensor 110.

Figure 26A:
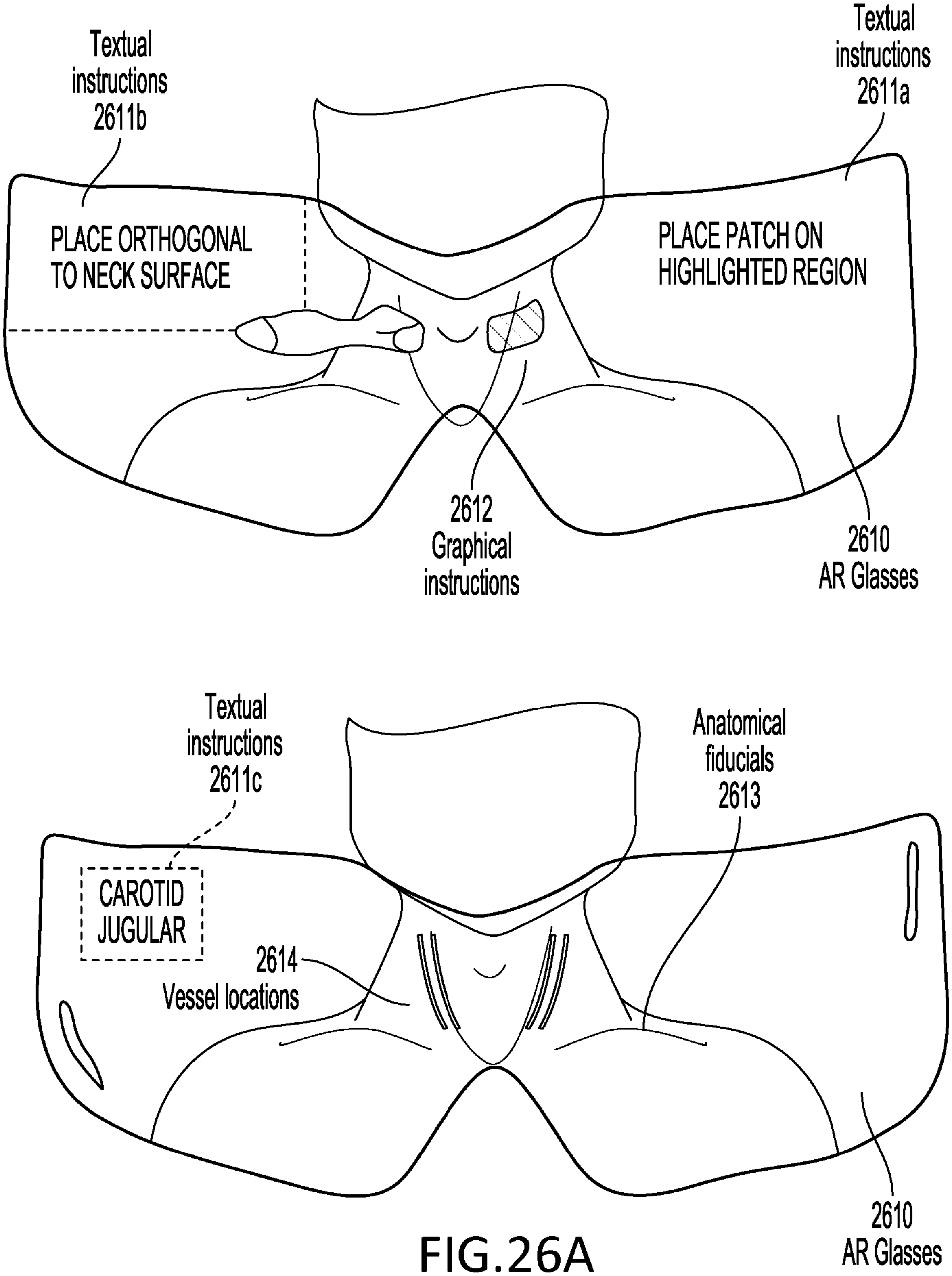
FIGS. 26A and 26B show an example of augmented reality (AR) glasses used as an output device for placement instructions for the wearable ultrasound blood flow sensor.
Figure 26B:
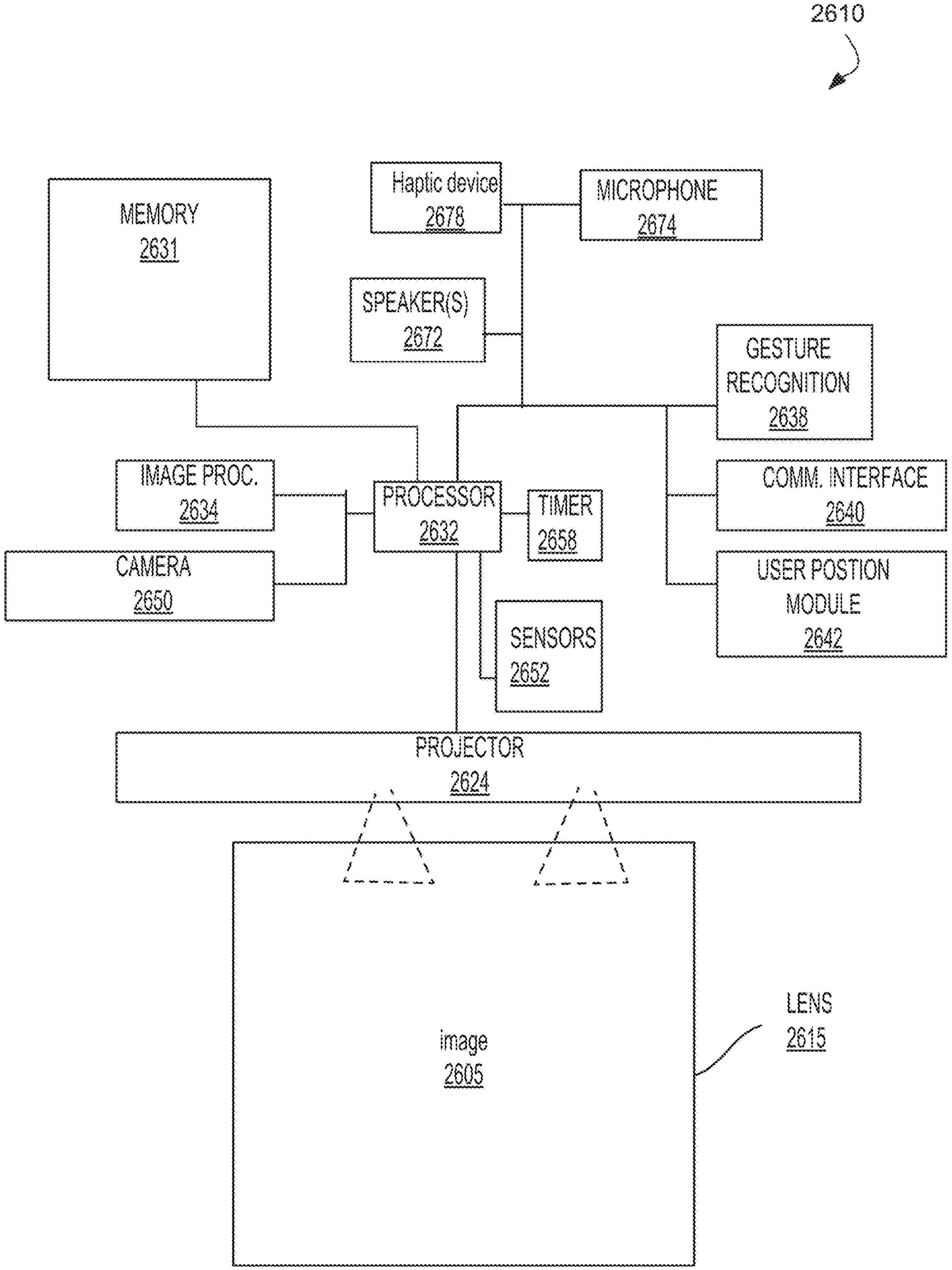

In an implementation, the defibrillator 105 may be communicatively coupled (e.g., via a wired or wireless connection 199) to one or more external computing devices 180. For example, the one or more external computing devices may include a one or more of computer tablet 181, a smartphone 182, a laptop 183, or other portable computing device. The one or more external computing devices 180 may further include wearable computing devices such as a watch 184 and/or augmented reality (AR) glasses (e.g., the AR glasses 2610 as shown in FIGS. 26A and 26B). The various external computing devices are examples only and not limiting of the disclosure.

In an implementation with multiple external computing devices, two or more of these may be communicatively coupled with one another and various communication paths are contemplated by the disclosure. For example, the defibrillator 105 may be communicatively coupled to one or more of the tablet 181, the smartphone 182, and the laptop 183 and the one or more of the tablet 181, the smartphone 182, and the laptop 183 may be communicatively coupled to one or more of the watch 184, the AR glasses 2610, and another wearable computing device. However, the one or more of the watch 184, the AR glasses 2610, and another wearable computing device may or may not be communicatively coupled to the defibrillator 105. Without the communicative coupling to the defibrillator 105, the one or more of the watch 184, the AR glasses 2610, and the another wearable computing device may only receive defibrillator information via the intermediary device, e.g., the one or more of the tablet 181, the smartphone 182, and the laptop 183. Additionally or alternatively, the defibrillator 105 and one or more of the external computing devices 180 may communicate via a long range communicative coupling, for example via an Internet Wi-Fi connection and/or via a cloud computing device.

The compression monitor 109 is shown with a wired coupling to the defibrillator 105 and the wearable ultrasound blood flow sensor 110 is shown with a wireless coupling to the defibrillator 105 as examples only. In various implementations, the compression monitor 109 and the wearable ultrasound blood flow sensor 110 may transmit and/or receive data from the defibrillator 105 via wired and/or wireless communicative couplings. Additionally, the electrodes 107 and 108 and the compression monitor 109 are shown as individual components as an example only. In an implementation, the electrodes 107 and 108 may be components of a unitary electrode pad applied to the victim's chest. In an implementation, the electrodes 107 and 108 and the compression monitor 109 may be components of a unitary pad applied to the victim's chest. The chest compression monitor 109 may be a motion sensor configured for use during manual chest compressions or may be a motion sensor communicatively coupled to the automated chest compression device and configured to detect the compressions delivered by this device. In this case, the chest compression monitor 109 may be disposed on the belt or piston of the automated compression device. The chest compression sensor 109 may include one or more motion sensors including, for example, one or more accelerometers, one or more force sensors, one or more magnetic sensors, one or more velocity sensors, one or more displacement sensors, etc. The chest compression sensor 109 may be, for example, but not limited to, a compression puck, a smart-phone, a hand-held device, a wearable device, etc. The chest compression sensor 109 may be configured to detect chest motion imparted by a rescuer and/or an automated chest compression device (e.g., a belt system, a piston system, etc.). The chest compression sensor 109 may provide data signals indicative of chest compression data including displacement data, velocity data, release velocity data, acceleration data, force data, compression rate data, dwell time data, hold time data, blood flow data, blood pressure data, etc. In an implementation, the defibrillation and/or pacing electrodes may include or be configured to couple to the chest compression sensor 109.

In various implementations, the rescuer 103 may employ one or more of the wearable ultrasound blood flow sensor 110. For example, the rescuer may use only one sensor 110, two sensors 110, or three or more sensors 110. With sensors 110, the rescuer 103 may attach each sensor 110 to a different location on the victim's body. Each location corresponds to an artery located relatively close to the skin surface of the victim, for example, an artery at which a rescuer might palpate for a pulse. The sensors 110 in FIG. 1 are shown, for example, at a neck location of the carotid artery, at an upper arm location of the brachial artery, and at a leg location of the femoral artery (e.g., the thigh proximate to the groin). These locations are examples only and other arterial locations are within the scope of the disclosure. Although most of the examples herein refer to the neck location, the rescuer 103 may attach a single sensor 110 at any other arterial location. Furthermore, when used in combination, the multiple transducer arrays may be applied to any combination of two or more arterial locations that may or may not include the neck location. In an implementation, the rescuer 103 may attach two transducer arrays on either side of the midline but on the same artery (e.g., on the left carotid artery and on the right carotid artery).

In the example of FIG. 1, the rescuer 103 is shown administering manual chest compressions to the victim 101. In manual chest compressions, also referred to as two-hand chest compressions, the source of the chest compressions is the body of the rescuer 103 pushing on the hands 120. The manual compressions are mechanically unassisted. The compression monitor 109 functions merely as a measurement tool without enhancing and with negligible modification of the compressions and of the forces exerted by the rescuer's body.

In an implementation, the rescuer 103 may use a hand-held compression device (e.g., the device 130 as shown in the inset of FIG. 1) to mechanically assist, i.e., enhance and modify the compressions. The rescuer's hands 120 grasps the hand-held compression device and the hand-held compression device enhances and modifies the forces exerted by the rescuer's body on the victim. For example, the hand-held compression device may be an active compression-active decompression device (ACD device) configured to compress the chest and then actively decompress the chest by pulling the chest up past a natural recoil position of the ribcage. The ACD device includes an adhesive surface and/or one or more suction cups that enable the active decompression.

Figure 2:
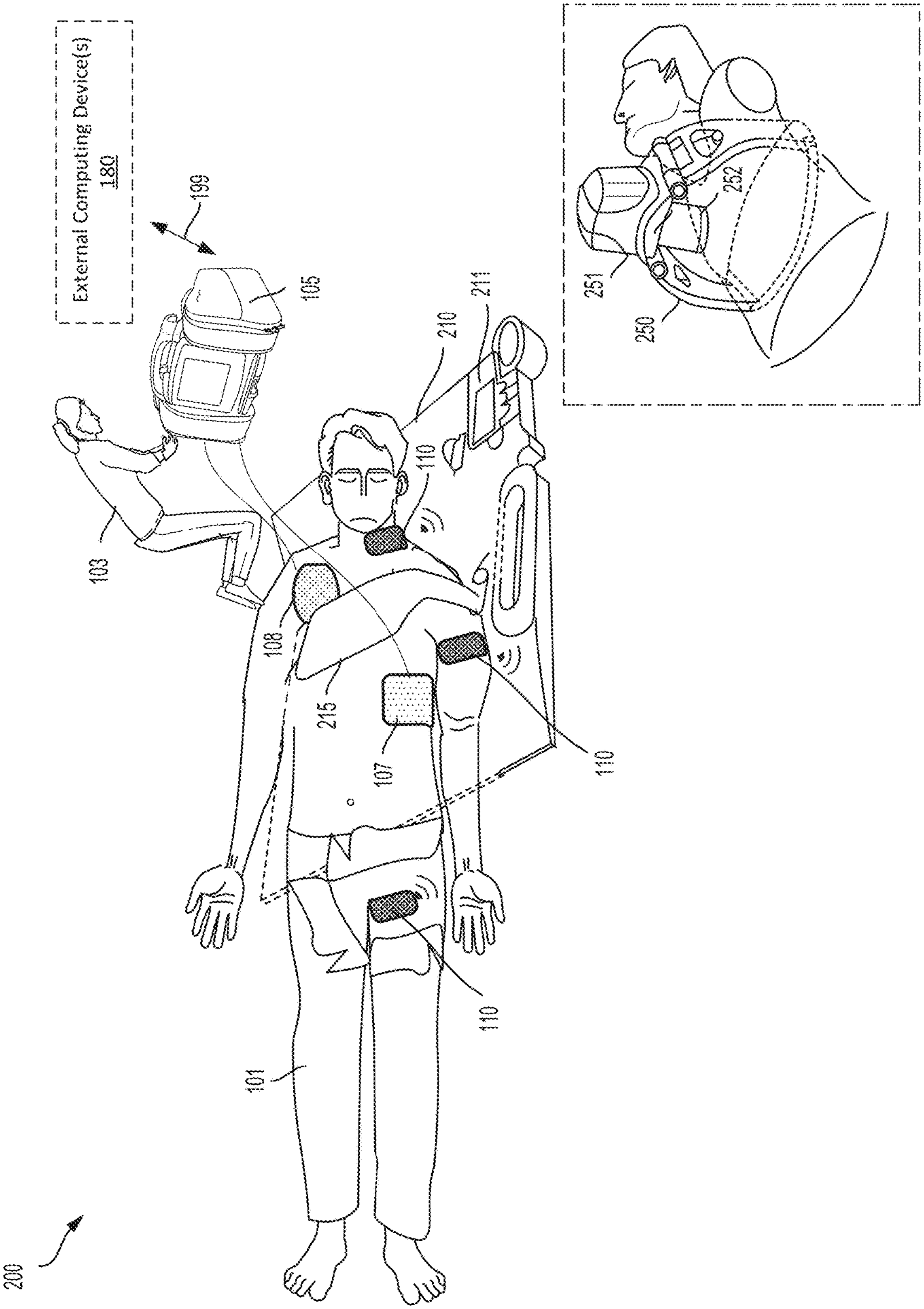
FIG. 2 shows an example of an automated compression patient care system that includes at least one wearable ultrasound blood flow sensor

Referring to FIG. 2, an example of an automated compression patient care system that includes at least one wearable ultrasound blood flow sensor is shown. A quantity of each component in FIG. 2 is an example only and other quantities of each, or any, component could be used.

The patient care scene 200 in FIG. 2 is substantially similar to the scene 100 in FIG. 1 with the exception of the compression delivery system. The compression delivery system in FIG. 2 is an automated chest compression device 210 or 250. The automated chest compression device 210 is a belt-based device. An automatic controller of the device 210 controls a motor to tighten and loosen a belt 215 around the chest of the victim at a preprogrammed compression rate and depth. The inset shows an alternative automated chest compression device 250, a piston-based device, in which an automatic controller controls a piston 252 to impact the chest of the victim at a preprogrammed compression rate and depth. In an implementation, the automated piston device may be an ACD device configured to provide active decompressions. As shown in FIG. 2, with an automated compression device, the rescuer 103 attends to resuscitative activities for the victim but does not administer the chest compressions.

Generally, rescuer controlled chest compressions (e.g., mechanically unassisted manual chest compressions or mechanically assisted ACD compressions) are subject to variability in compression parameters (e.g., compression rate, periodicity, compression depth, release velocity, and other compression waveform characteristics) due to variations in human performance (e.g., due to rescuer inconsistencies, fatigue, etc.). For example, the rate and/or the depth of compressions may vary by 15%-50%. In these types of compressions, the rescuer is able to respond to feedback and effect a change in the chest compression parameters. The measurements from the compression monitor 109 may enable this feedback. For example, the compression monitor 109 may provide a signal to the defibrillator 105 and the defibrillator 105 may provide feedback at a defibrillator display screen. The feedback may be to compress faster, slower, deeper, less deep, etc.

Unlike the rescuer controlled chest compressions, the automated chest compression exhibit significantly lower variation in rate and depth. For example, the variability of the compression rate may be within +/−2-6% of a target compression rate. The automated chest compression systems generally utilize pre-programmed target values for various chest compression parameters including rate and depth. For example, the manufacturer may determine these pre-programmed values and/or a user may determine or adjust these pre-programmed values prior to usage of the system.

Figure 3A:
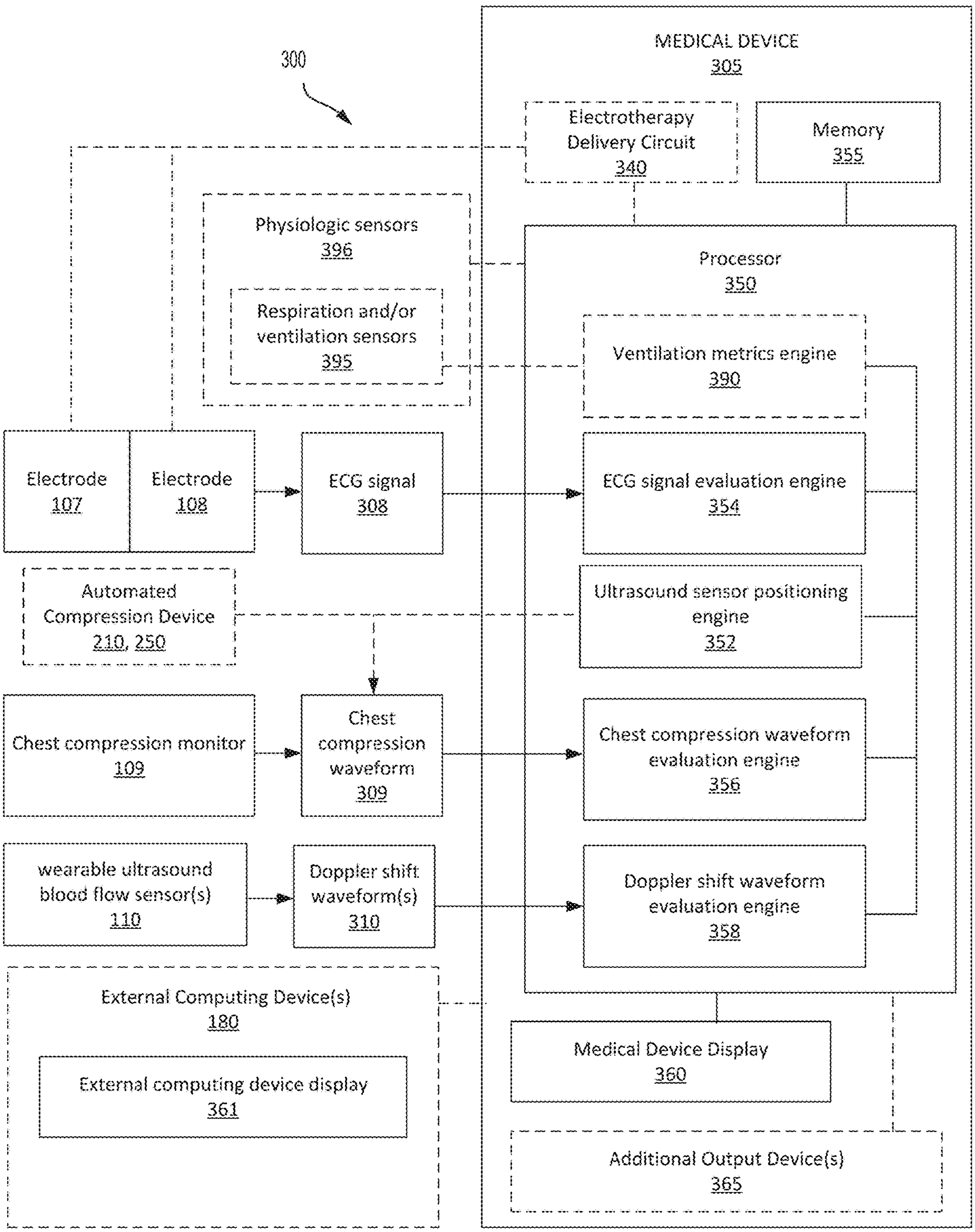
FIG. 3A is a schematic diagram of a medical device configured for detection of blood flow with a wearable ultrasound blood flow sensor.

Referring to FIG. 3A, with further reference to FIGS. 1 and 2, a schematic diagram of a medical device configured for detection of blood flow with a wearable ultrasound blood flow sensor is shown. A quantity of each component in the hardware system 300 of FIG. 3A is an example only and other quantities of each, or any, component could be used. The electrodes 107 and 108, the chest compression monitor 109, and at least one wearable ultrasound blood flow sensor 110 may generate data signals and provide those data signals to a medical device 305. The medical device 305 includes at least one memory 355 and at least one processor 350. The processor 350 may execute instructions stored in the memory 355 to process and analyze the provided data signals. The electrodes 107 and 108 are cardiac sensing electrodes that are conductive and/or capacitive electrodes configured to measure changes in a patient's electrophysiology to measure the patient's ECG information. The electrodes 107 and 108 may further be configured to deliver a defibrillation shock. Additionally, the electrodes may measure the transthoracic impedance of the patient. Although shown in FIGS. 1, 2, and 3A as a pair of electrodes, the electrodes may be 12-lead ECG electrodes and/or a set of electrodes configured to generate impedance cardiography data and to provide that data to the processor 350.

The medical device 305 may include a medical device display 360. Additionally or alternatively the medical device 305 may provide information for a user via one or more additional output devices 365 that may include, for example, one or more of a speaker and a haptic device.

One or more of the additional output devices may be integrated with the medical device 305 or may be external to and communicatively coupled with (e.g., via a wired or wireless coupling) the medical device 305. Output device(s) 360 and 365 are shown as integrated with the medical device 305 in FIG. 3A by way of example only. In various implementations, the output device(s) 360 and 365 may be integrated into the medical device and/or communicatively coupled to the medical device 305 via a wired or wireless connection. Further the output device(s) 360 and 365 may include one or more physical devices such as, for example, one or more displays, speakers, haptic devices, and/or wearable devices (e.g., watch, glasses, heads-up display, etc.). The output device(s) 360 and 365 may be a visual display on the medical device 305 and/or a display on another computing device or medical device that is communicatively coupled to the defibrillator (e.g., as shown, for example, in FIGS. 3B and 3C).

The signal processing and analysis may be functionally organized according to various engines, namely, the ECG signal evaluation engine 354, the chest compression waveform evaluation engine 356, and the Doppler shift waveform evaluation engine 358. Each engine includes hardware logic and/or software logic configured to process and analyze a respective type of signal. During operation, the electrodes 107 and 108 generate an ECG signal 308 and provide this signal to the ECG signal evaluation engine 354 for processing and analysis. Additionally, the chest compression monitor 109 generates a chest compression waveform 309 and provides this signal to the chest compression waveform evaluation engine 356 for processing and analysis. Further, at least one wearable ultrasound blood flow sensor 110 generates at least one Doppler shift waveform and provides this signal to the Doppler shift waveform evaluation engine 358 for processing and analysis.

The system 300 may include additional physiologic sensors 396. For example, the sensors 396 may include a vascular illumination device, a continuous non-invasive blood pressure (NIBP) sensor, a NIBP sensor, a near-infrared spectroscopy (NIRS) sensor (e.g., cerebral NIRS and/or muscular NIRS), a heart sound sensor, a photoplethysmography (PPG) sensor, etc. The physiologic sensors 396 may include one or more ventilation and/or ventilation and/or respiration sensors 395. The processor 350 may receive data signals from the additional physiologic sensors 396.

Optionally, the processor 350 may include a ventilation metrics engine 390 coupled to the ventilation and/or respiration sensors 395. The ventilation metrics engine 390 may monitor and/or record ventilation treatment data for ventilation treatment of a patient. The ventilation treatment data may include one or more of ventilation rate data and end-tidal carbon dioxide data. For example, the ventilation metrics device may monitor and/or record the time(s) when ventilation begins, the time(s) when ventilation ends, the occurrence of each inhale and/or exhale cycle, patient breathing, the timing of ventilation activity, various pressures during the inhale/exhale cycle, and volumes and volume flow rates. The ventilation metrics engine 390 may receive ventilation data from the sensors 395. The sensors 395 may include, for example, but not limited to, a pulse oximeter, a blood oxygen monitor, an air flow sensor, a spirometer, a lung function monitor, and/or a capnography device.

In an implementation, the system 300 may include ventilation devices such as a nasal cannula, an endotracheal tube, an oxygen mask, a bag valve mask, a mechanical ventilator, an abdominal and/or chest compressor (e.g., a belt, a cuirass, etc.), etc. and combinations thereof. One or more of these devices may be coupled to the sensors 395 and/or the ventilation metrics engine 390. In an implementation, the ventilation devices may be coupled to, incorporate, and/or function as ventilation and/or respiration sensors 395, e.g., flow sensors, gas species sensors (e.g., oxygen sensor, carbon dioxide sensor, etc.), etc. The sensors 395 may include spirometry sensors, flow sensors, pressure sensors, oxygen and/or carbon dioxide sensors such as, for example, one or more of pulse oximetry sensors, oxygenation sensors (e.g., muscle oxygenation/pH), 02 gas sensors and capnography sensors, impedance sensors, and combinations thereof.

The processor 350 may further include an ultrasound sensor positioning engine 352. The ultrasound sensor positioning engine 352 includes hardware logic and/or software logic configured to use signal analysis output from one or more of the engines 354, 356, and 358 to identify a location of the wearable ultrasound blood flow sensor(s) 110 relative to at least one blood vessel of the patient 101. In other words, the positioning engine 352 may determine if the wearable ultrasound blood flow sensor is placed close enough to a blood vessel to generate a measurable Doppler shift waveform 310 due to blood flow in the vessel. An improper position of the sensor(s) 110 is one that is not sufficiently proximate to a blood vessel so as to detect blood flow in the vessel.

Additionally or alternatively, the positioning engine 352 may determine if there is an improper acoustic connection between the sensor 110 and the patient 101, a malfunction of the sensor 110 and/or an improper connection with the medical device 305. An improper connection to the patient may indicate an acoustic impedance interface between the sensor(s) 110 and the patient's skin that is causing an attenuation of the transmitted and reflected ultrasound waves. For example, an air gap, an improper gel distribution, or another irregularity in the patient pad, adhesive, or other component of the sensor 110 that affects the sensor-patient interface may produce an interface between high and low acoustic impedance causing reflection of the transmitted and reflected waves at this interface. Such reflection attenuates the data signals from the sensor(s) 110 to the engine 358. In the absence of this acoustic impedance interface, there is acoustic coupling between the sensor(s) 110 and the patient 101. A communications and/or electrical link malfunction may cause an improper connection to the medical device 305

The positioning engine 352 may generate user feedback to guide the user in positioning, re-positioning, or replacing the wearable ultrasound blood flow sensor(s) in order to generate the measurable Doppler shift waveform 310. The positioning engine 352 may provide the generated user feedback to the output device(s) 360.

In an implementation, the ultrasound sensor positioning engine 352 includes hardware logic and/or software logic configured to control compression delivery parameters of an automated compression device (e.g., the device 210 or 250). For example, as described in further detail below the ultrasound sensor positioning engine 352 may cause the automated compression device to provide a series of chest compression according to a patterned compression rate variation. The patterned compression rate variation may cause variations in detected blood flow corresponding to the patterned compression rate variation. The Doppler shift waveform evaluation engine 358 may identify detected blood flow as compression-induced blood flow based on the patterned variation. For example, the positioning engine 352 may select the patterned compression rate variation and provide that selected compression rate variation to the Doppler shift waveform evaluation engine 358. Additionally, the positioning engine 352 may instruct or control the automated compression device so that the device provides compression according to the pattern for an initial period of compressions. The patterned compression rate variation may cause variations in detected blood flow corresponding to the patterned compression rate variation. The patterned compression rate may include two or more different compression rates applied alternately for two or more groups of three or more compressions. For example, the positioning engine 352 may cause or instruct the automated compression device to provide three compressions at 80 compressions per minute (cpm) followed by three compressions at 100 cpm followed by a return to 80 cpm. As another example, the positioning engine 352 may cause or instruct the automated compression device to provide five compressions at 100 cpm followed by three compressions at 80 cpm followed by six compressions at 100 cpm and a return to 80 cpm. In general, the patterned compression rate may be J compressions at R cpm followed by K compressions at S cpm followed by a return to T cpm or one or more additional cycles of a number of compressions at a particular compression rate. J, K, R, S, and T are all integers and R, S, and T are all compression rates consistent with recognized cardiac arrest protocol compression rates.

In an implementation, the medical device 305 may be a defibrillator (e.g., the defibrillator 105). The defibrillator includes an electrotherapy delivery circuit 340 electrically coupled to the electrodes 107 and 108 and configured to deliver electrotherapy to a patient via the electrodes 107 and 108. The electrotherapy delivery circuit 340 includes one or more high-voltage capacitors configured to store electrical energy for a pacing pulse or a defibrillating pulse. The electrotherapy delivery circuit 340 may further include resistors, additional capacitors, relays and/or switches, electrical bridges such as an H-bridge (e.g., including a plurality of insulated gate bipolar transistors or IGBTs), voltage measuring components, and/or current measuring components. Alternatively, the medical device 305 may be a patient monitor that is not configured to deliver electrotherapy but is configured to monitor an ECG via ECG electrodes, for example, twelve-lead electrodes. In an implementation, the medical device 305 may be communicatively coupled to the one or more external computing devices 180 and/or physiologic sensors 396.

In various implementations, the medical device 305 may include and/or be coupled to one or more sensor devices configured to provide sensor data that includes, for example, but not limited to blood flow, electrocardiogram (ECG), blood pressure, heart rate, respiration rate, heart sounds, lung sounds, respiration sounds, end tidal $CO_2$, saturation of muscle oxygen ($SMO_2$), oxygen saturation (e.g., $SpO_2$ and/or $PaO_2$), cerebral blood flow, point of care laboratory measurements (e.g., lactate, glucose, etc.), temperature, electroencephalogram (EEG) signals, brain oxygen level, tissue pH, tissue fluid levels, images and/or videos via ultrasound, laryngoscopy, and/or other medical imaging techniques, near-infrared spectroscopy, pneumography, cardiography, and/or patient movement. Images and/or videos may be two-dimensional or three-dimensional, such a various forms of ultrasound imaging.

The external computing device 180 may be a portable computing device such as a tablet, laptop, or smart-phone. The external computing device 180 may provide an additional display screen for data provided at the medical device 300. In an implementation, the external computing device 180 may receive patient monitoring data from the medical device 305. The external computing device 180 may provide data and/or receive user input at one or more display screens and/or may control one or more of the functional operations of the medical device 300, as described in the embodiments herein. The external computing device 180 may provide a working view of patient data that provides the same data shown on a display of the medical device 305 and in real-time. The external computing device 180 may also provide one or more user-customized data displays including, for example, data trends, historical data, data playback, disease specific data, protocol information, clinical decision support information, etc. In some implementations, the information obtained from the ventilation and/or respiration sensors 395, the physiologic sensors 396, the automated compression device 210 or 250, the electrodes 107, 108, the chest compression monitor 109, the wearable ultrasound blood flow sensor(s) 110, and/or the AR glasses 2610 (discussed below in regard to FIGS. 26A and 26B) can be used to generate information displayed at the medical device 305 and simultaneously at the display views at external computing device 180.

Figure 3B:
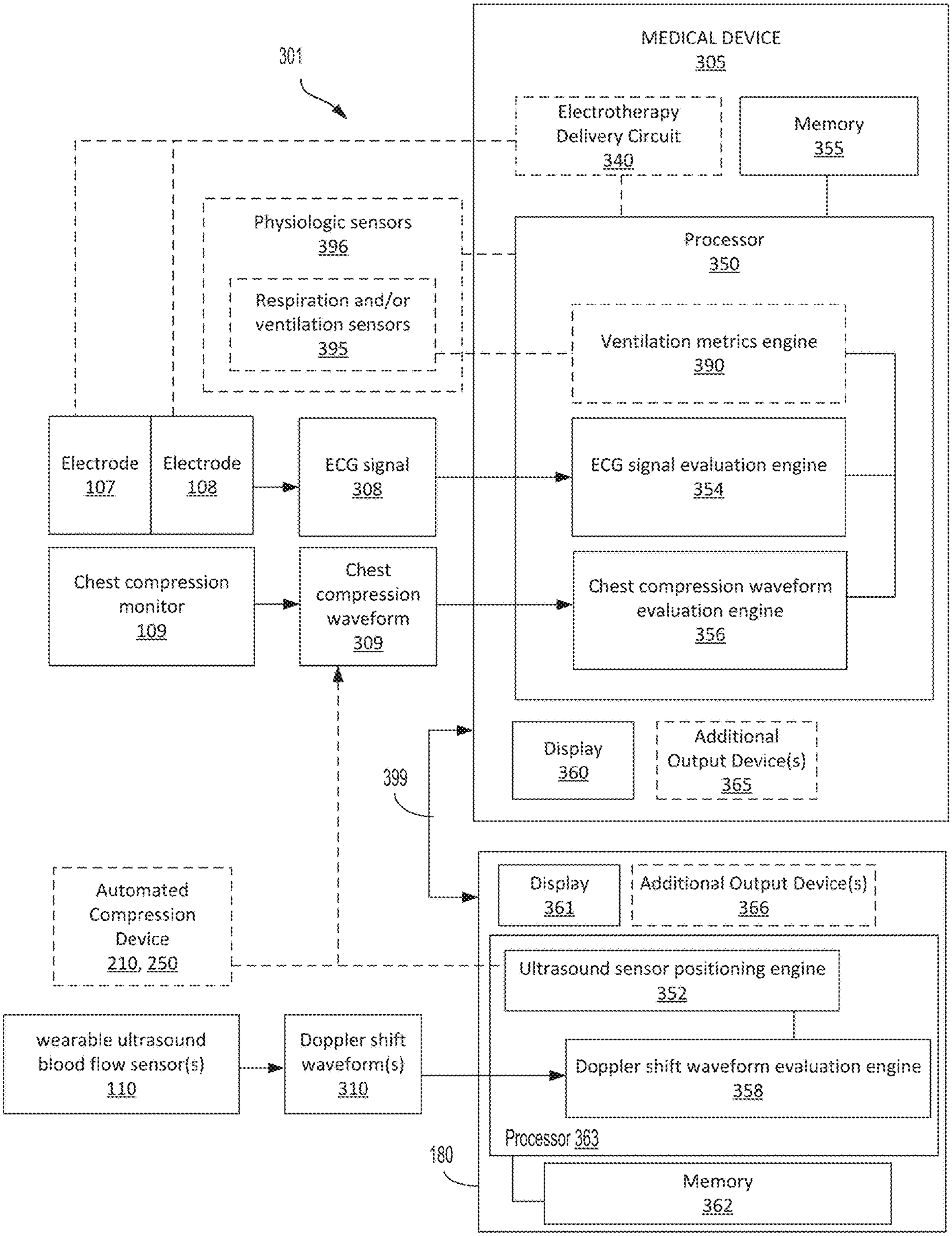
FIGS. 3B and 3C are schematic diagrams of a combination medical device-external computing device system configured for detection of blood flow with a wearable ultrasound blood flow sensor.
Figure 3C:
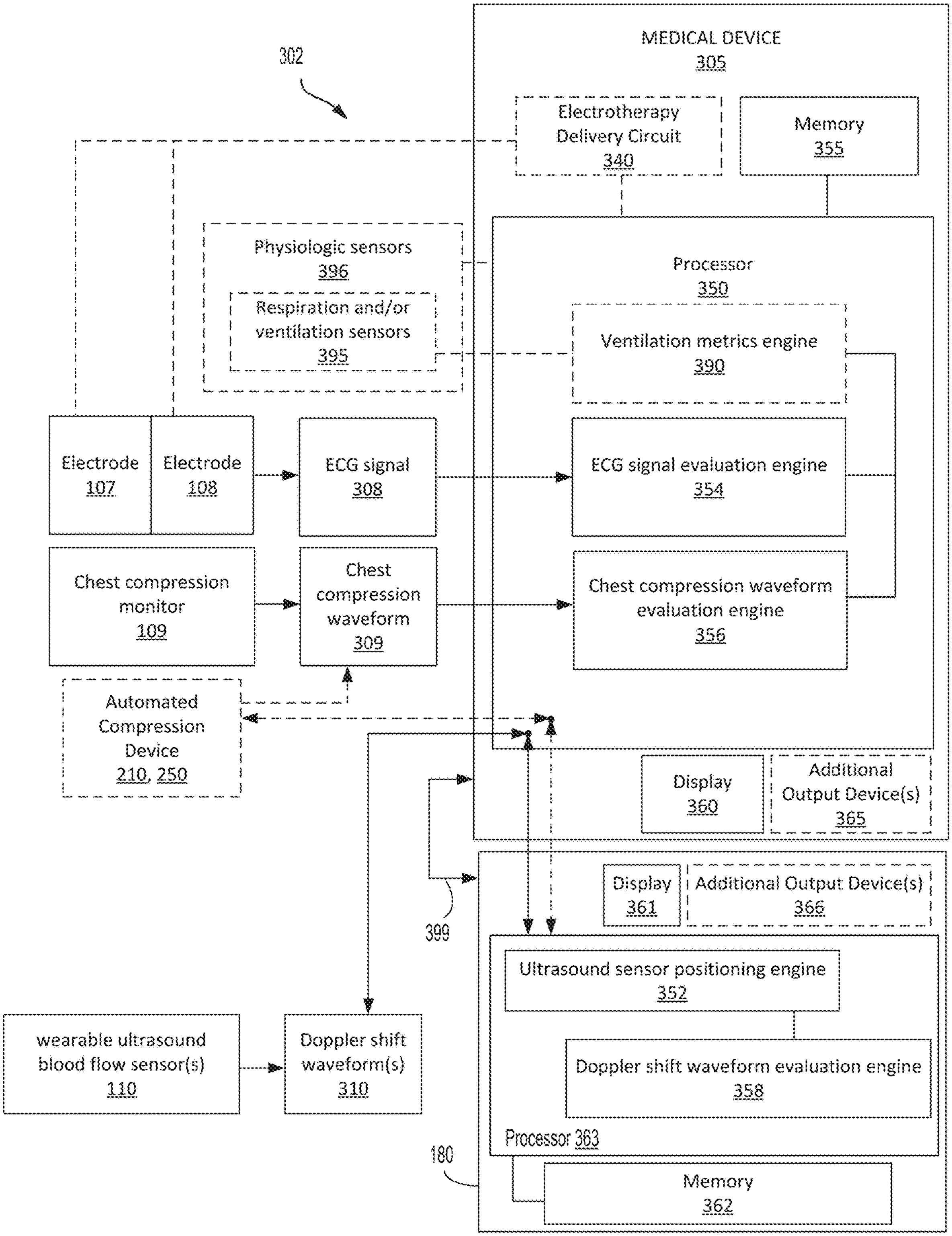

Referring to FIGS. 3B and 3C, with further reference to FIGS. 1 and 2, schematic diagrams of a combination medical device-external computing device system configured for detection of blood flow with a wearable ultrasound blood flow sensor is shown. A quantity of each component in the hardware systems 301 and 302 of FIGS. 3B and 3C, respectively, is an example only and other quantities of each, or any, component could be used. As similarly described in regard to FIG. 3A, the electrodes 107 and 108 and the chest compression monitor 109 may generate data signals (e.g., the chest compression waveform 309) and provide those data signals to the medical device 305 for processing and analysis by the at least one processor 350. The medical device 305 may be a defibrillator (e.g., the defibrillator 105) that includes the electrotherapy delivery circuit 340 electrically coupled to the electrodes 107 and 108 and configured to deliver electrotherapy to a patient via the electrodes 107 and 108. In further similarity to FIG. 3A, the medical device 305 may include the ECG signal evaluation engine 354 and the chest compression waveform evaluation engine 356. During operation, the electrodes 107 and 108 generate an ECG signal 308 and provide this signal to the ECG signal evaluation engine 354 for processing and analysis. Additionally, the chest compression monitor 109 generates a chest compression waveform 309 and provides this signal to the chest compression waveform evaluation engine 356 for processing and analysis. Optionally, as similarly described above in regard to FIG. 3A, the processor 350 may include the ventilation metrics engine 390 coupled to the ventilation and/or respiration sensors 395. The systems 301 and 302 may include the one or more physiologic sensors 396 and these sensors may be communicatively coupled with one or more of the medical device 305 and the external computing device 180.

In an implementation, the external computing device 180 may include one or more of the ultrasound positioning engine 352 and the Doppler shift waveform evaluation engine 358. The medical device 305 and the external computing device 180 may exchange data via the communicative coupling 399 (e.g., via USB, Bluetooth®, Wi-Fi, etc.).

The external computing device 180 may be a portable computing device such as a tablet, laptop, or smart-phone. The external computing device 180 may include a display 361. Additionally or alternatively the external computing device 180 may provide information for a user via one or more additional output devices 366 that may include, for example, one or more of a speaker and a haptic device. The external computing device 180 includes at least one memory 362 and at least one processor 363. The processor 363 may execute instructions stored in the memory 362 to process and analyze the provided data signals. The processor 363 may include the ultrasound positioning engine 352 and the Doppler shift waveform evaluation engine 358. In various implementations, the processor 363 may generate caregiver instructions according to a cardiac arrest protocol, generate caregiver instructions according to a non-cardiac arrest protocol in response to identified heart-induced blood flow, and may provide caregiver instructions at a display.

As shown for example in FIG. 3B, in an implementation, the at least one wearable ultrasound blood flow sensor 110 may generate data signal representative of the Doppler shift waveform and provide the data signal to the Doppler shift waveform evaluation engine 358 at the external computing device 180. Alternatively, as shown for example in FIG. 3C, the at least one wearable ultrasound blood flow sensor 110 may generate data signals and provide those data signals to the medical device 305. The medical device 305 may provide data signals representative of the received data signals from the sensor 110 to the Doppler shift waveform evaluation engine 358 at the external computing device 180. Similarly, the ultrasound sensor positioning engine 352 may control compression delivery parameters of the automated compression device (e.g., the device 210 or 250) directly (e.g., as shown for example in FIG. 3B) or via the medical device 305 (e.g., as shown for example in FIG. 3C).

As similarly described above in regard to FIG. 3A, the ultrasound sensor positioning engine 352 includes hardware logic and/or software logic configured to use signal analysis output from one or more of the engines 354, 356, and 358 to identify a location of the wearable ultrasound blood flow sensor(s) 110 relative to at least one blood vessel of the patient 101. The medical device 305 may provide the signal analysis output from one or more of the engines 354, 356, and 358 to the external computing device 180 via the communicative coupling 399. In an implementation, this data exchange between the medical device 305 and the external computing device 180 may occur automatically in response to a detected connection between the wearable ultrasound blood flow sensor(s) 110 and one of the medical device 105 or the external computing device 180. Alternatively, this data exchange may occur in response to a user request provided at one or more of the medical device 305 and the external computing device 180.

As similarly described above, the positioning engine 352 may determine if there is an improper acoustic connection between the sensor 110 and the patient 101, a malfunction of the sensor 110 and/or an improper connection with the external computing device 180. The positioning engine 352 may generate user feedback to guide the user in positioning, re-positioning, or replacing the wearable ultrasound blood flow sensor(s) in order to generate the measurable Doppler shift waveform 310. The positioning engine 352 may provide the generated user feedback to the display 361 and/or the additional output device(s) 366.

As similarly described above in regard to FIG. 3A, in an implementation, the external computing device 180 may receive patient monitoring data from the medical device 305. The external computing device 180 may provide data and/or receive user input at the display 361 and/or via one or more of the additional output device(s) 365. The external computing device 180 may control one or more of the functional operations of the medical device 300, as described in the embodiments herein. The external computing device 180 may provide a working view of patient data that provides the same data shown on a display of the medical device 305 and in real-time. The external computing device 180 may also provide one or more user-customized data displays including, for example, data trends, historical data, data playback, disease specific data, protocol information, clinical decision support information, etc. In some implementations, the information obtained from the ventilation and/or respiration sensors 395, the physiologic sensors 396, the automated compression device 210 or 250, the electrodes 107, 108, the chest compression monitor 109, the wearable ultrasound blood flow sensor(s) 110, and/or the AR glasses 2610 (discussed below in regard to FIGS. 26A and 26B) can be used to generate information displayed at the medical device 305 and simultaneously at the display views at external computing device 180.

As similarly described in regard to FIG. 3A, the medical device 305 may include the medical device display 360. Additionally or alternatively the medical device 305 may provide information for a user via one or more additional output devices 365 that may include, for example, one or more of a speaker and a haptic device.

In an implementation, the systems 301 and 302 may include ventilation devices such as a nasal cannula, an endotracheal tube, an oxygen mask, a bag valve mask, a mechanical ventilator, an abdominal and/or chest compressor (e.g., a belt, a cuirass, etc.), etc. and combinations thereof. One or more of these devices may be coupled to the sensors 395 and/or the ventilation metrics engine 390. In an implementation, the ventilation devices may be coupled to, incorporate, and/or function as ventilation and/or respiration sensors 395, e.g., flow sensors, gas species sensors (e.g., oxygen sensor, carbon dioxide sensor, etc.), etc. The sensors 395 may include spirometry sensors, flow sensors, pressure sensors, oxygen and/or carbon dioxide sensors such as, for example, one or more of pulse oximetry sensors, oxygenation sensors (e.g., muscle oxygenation/pH), 02 gas sensors and capnography sensors, impedance sensors, and combinations thereof.

One or more of the additional output devices may be integrated with the external computing device 180 or may be external to and communicatively coupled with (e.g., via a wired or wireless coupling) the external computing device 180. Output device(s) 362 and 366 are shown as integrated with the external computing device 180 in FIGS. 3B and 3C by way of example only. In various implementations, the output device(s) 362 and 366 may be integrated into the external computing device 180 and/or communicatively coupled to the external computing device 180 via a wired or wireless connection. Further the output device(s) 362 and 366 may include one or more physical devices such as, for example, one or more displays, speakers, haptic devices, and/or wearable devices (e.g., watch, glasses, heads-up display, etc.). The output device(s) 362 and 366 may be a visual display on the external computing device 180 and/or a display on another computing device or medical device that is communicatively coupled to the external computing device 180.

Figure 3D:
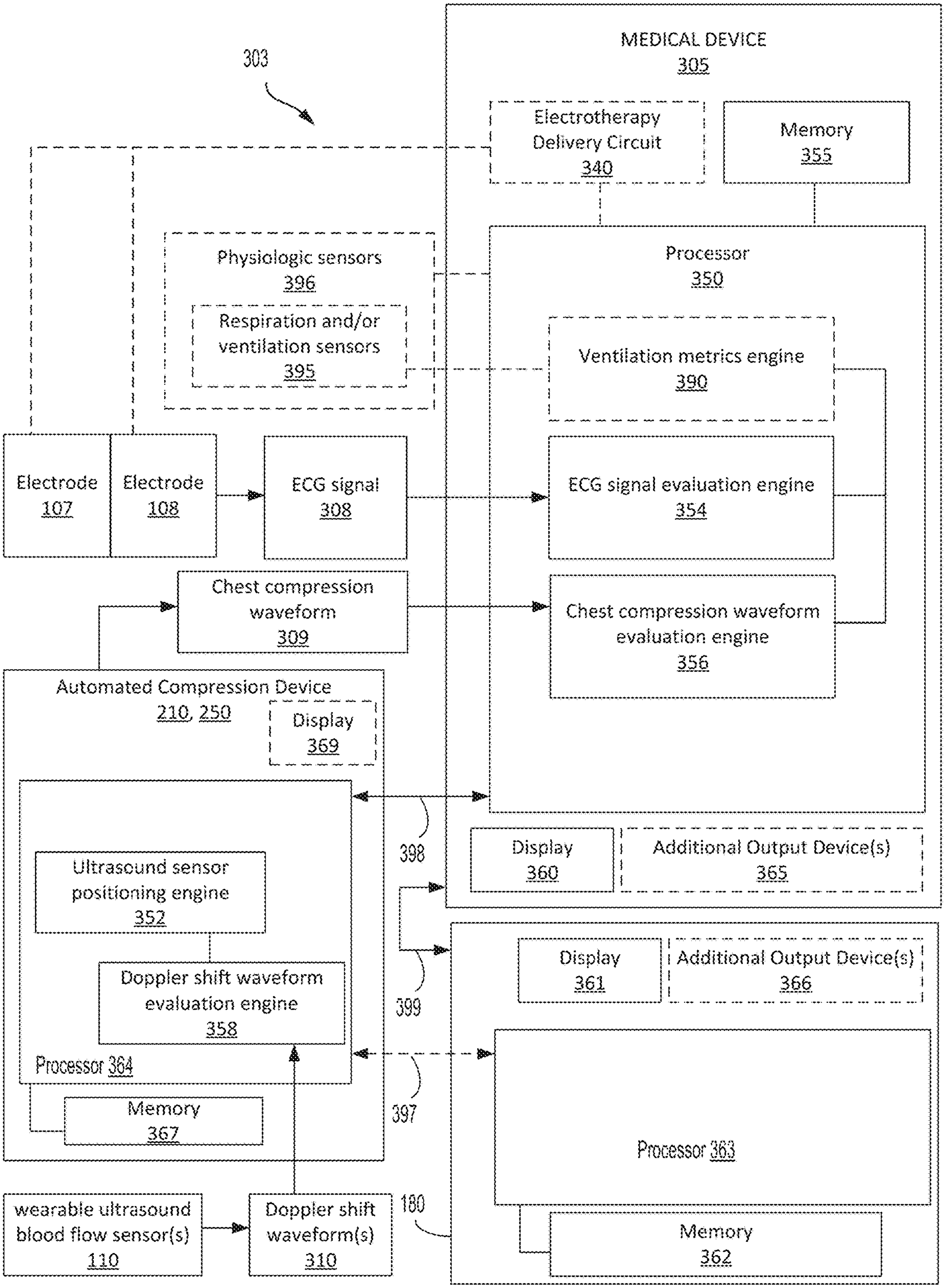
FIG. 3D is a schematic diagram of an automated compression device configured for detection of blood flow with a wearable ultrasound blood flow sensor.

Referring to FIG. 3D, with further reference to FIGS. 1-3C, a schematic diagram of an automated mechanical compression device configured for detection of blood flow with a wearable ultrasound blood flow sensor is shown. A quantity of each component in the hardware system 303 of FIG. 3D, respectively, is an example only and other quantities of each, or any, component could be used.

As similarly described in regard to FIG. 3A, the electrodes 107 and 108 may generate data signals and provide those data signals to the medical device 305 for processing and analysis by the at least one processor 350. The medical device 305 may be a defibrillator (e.g., the defibrillator 105) that includes the electrotherapy delivery circuit 340 electrically coupled to the electrodes 107 and 108 and configured to deliver electrotherapy to a patient via the electrodes 107 and 108. In further similarity to FIG. 3A, the medical device 305 may include the ECG signal evaluation engine 354 and the chest compression waveform evaluation engine 356. During operation, the electrodes 107 and 108 generate an ECG signal 308 and provide this signal to the ECG signal evaluation engine 354 for processing and analysis. Additionally, the processor 364 of the automated compression device (e.g., 210 and/or 250) may control compressions and provide a compression waveform 309 to the chest compression waveform evaluation engine 356 for processing and analysis. Optionally, as similarly described above in regard to FIG. 3A, the processor 350 may include the ventilation metrics engine 390 coupled to the ventilation and/or respiration sensors 395. The system 303 may include the one or more physiologic sensors 396 and these sensors may be communicatively coupled with one or more of the medical device 305 and the external computing device 180.

The medical device 305 and the external computing device 180 may exchange data via the communicative coupling 399 (e.g., via USB, Bluetooth®, Wi-Fi, etc.). Similarly, the automated compression device (e.g., 210 and/or 250) may exchange data with the medical device 305 via the communicative coupling 398 and optionally with the external computing device 180 via the communicative coupling 397.

The external computing device 180 may be a portable computing device such as a tablet, laptop, or smart-phone. The external computing device 180 may include a display 361. Additionally or alternatively the external computing device 180 may provide information for a user via one or more additional output devices 366 that may include, for example, one or more of a speaker and a haptic device. The external computing device 180 includes at least one memory 362 and at least one processor 363. The processor 363 may execute instructions stored in the memory 362 to process and analyze the provided data signals. The processor 363 may include the ultrasound positioning engine 352 and the Doppler shift waveform evaluation engine 358.

In an implementation, the processor 364 of the automated compression device (e.g., 210 and/or 250) may include one or more of the ultrasound positioning engine 352 and the Doppler shift waveform evaluation engine 358. The wearable ultrasound blood flow sensor 110 may provide the Doppler shift waveform(s) 310 to the Doppler shift waveform evaluation engine disposed at the automated compression device (e.g., 210 and/or 250). The processor 364 is coupled to a memory 367 and associated circuitry. In an implementation, the automated compression device (e.g., 210 and/or 250) may include a display 369. In various implementations, the processor 364 may generate caregiver instructions according to a cardiac arrest protocol, generate caregiver instructions according to a non-cardiac arrest protocol in response to identified heart-induced blood flow, and may provide caregiver instructions at a display.

As shown for example in FIG. 3D, in an implementation, the at least one wearable ultrasound blood flow sensor 110 may generate data signal representative of the Doppler shift waveform and provide the data signal to the Doppler shift waveform evaluation engine 358 at the automated compression device (e.g., 210 and/or 250). In an implementation, the ultrasound sensor positioning engine 352 may control compression delivery parameters of the automated compression device (e.g., 210 and/or 250).

As similarly described above in regard to FIG. 3A, the ultrasound sensor positioning engine 352 includes hardware logic and/or software logic configured to use signal analysis output from one or more of the engines 354, 356, and 358 to identify a location of the wearable ultrasound blood flow sensor(s) 110 relative to at least one blood vessel of the patient 101. The medical device 305 may provide the signal analysis output from one or more of the engines 354, 356, and 358 to the processor 364 via the communicative coupling 398. In an implementation, this data exchange between the medical device 305 and the automated compression device (e.g., 210 and/or 250) may occur automatically in response to a detected connection between the wearable ultrasound blood flow sensor(s) 110 and the automated compression device (e.g., 210 and/or 250). Alternatively, this data exchange may occur in response to a user request provided at one or more of the medical device 305, the external computing device 180, and/or the automated compression device (e.g., 210 and/or 250).

As similarly described above, the positioning engine 352 may determine if there is an improper acoustic connection between the sensor 110 and the patient 101, a malfunction of the sensor 110 and/or an improper connection with the external computing device 180. The positioning engine 352 may generate user feedback to guide the user in positioning, re-positioning, or replacing the wearable ultrasound blood flow sensor(s) in order to generate the measurable Doppler shift waveform 310. The positioning engine 352 may provide the generated user feedback to one or more of the display 369, the display 361, the display 360, and/or the additional output device(s) 366 or 365.

As similarly described above in regard to FIG. 3A, in an implementation, the external computing device 180 may receive, patient monitoring data from the medical device

305. The external computing device 180 may provide data and/or receive user input at the display 361 and/or via one or more of the additional output device(s) 365. The external computing device 180 may control one or more of the functional operations of the medical device 300, as described in the embodiments herein. The external computing device 180 may provide a working view of patient data that provides the same data shown on a display of the medical device 305 and in real-time. The external computing device 180 may also provide one or more user-customized data displays including, for example, data trends, historical data, data playback, disease specific data, protocol information, clinical decision support information, etc. In some implementations, the information obtained from the ventilation and/or respiration sensors 395, the physiologic sensors 396, the automated compression device 210 or 250, the electrodes 107, 108, the chest compression monitor 109, the wearable ultrasound blood flow sensor(s) 110, and/or the AR glasses 2610 (discussed below in regard to FIGS. 26A and 26B) can be used to generate information displayed at the medical device 305 and simultaneously at the display views at external computing device 180.

As similarly described in regard to FIG. 3A, the medical device 305 may include the medical device display 360. Additionally or alternatively the medical device 305 may provide information for a user via one or more additional output devices 365 that may include, for example, one or more of a speaker and a haptic device.

In an implementation, the system 303 may include ventilation devices such as a nasal cannula, an endotracheal tube, an oxygen mask, a bag valve mask, a mechanical ventilator, an abdominal and/or chest compressor (e.g., a belt, a cuirass, etc.), etc. and combinations thereof. One or more of these devices may be coupled to the sensors 395 and/or the ventilation metrics engine 390. In an implementation, the ventilation devices may be coupled to, incorporate, and/or function as ventilation and/or respiration sensors 395, e.g., flow sensors, gas species sensors (e.g., oxygen sensor, carbon dioxide sensor, etc.), etc. The sensors 395 may include spirometry sensors, flow sensors, pressure sensors, oxygen and/or carbon dioxide sensors such as, for example, one or more of pulse oximetry sensors, oxygenation sensors (e.g., muscle oxygenation/pH), 02 gas sensors and capnography sensors, impedance sensors, and combinations thereof.

As shown schematically in FIGS. 3A-3D, the automated compression device (e.g., 210 and/or 250) may include or be communicatively coupled to a processor that includes the Doppler shift waveform evaluation engine 358. The communication between the automated compression device and the Doppler shift waveform evaluation engine 358 may enable closed loop control of the automated compression device.

Figure 3E:
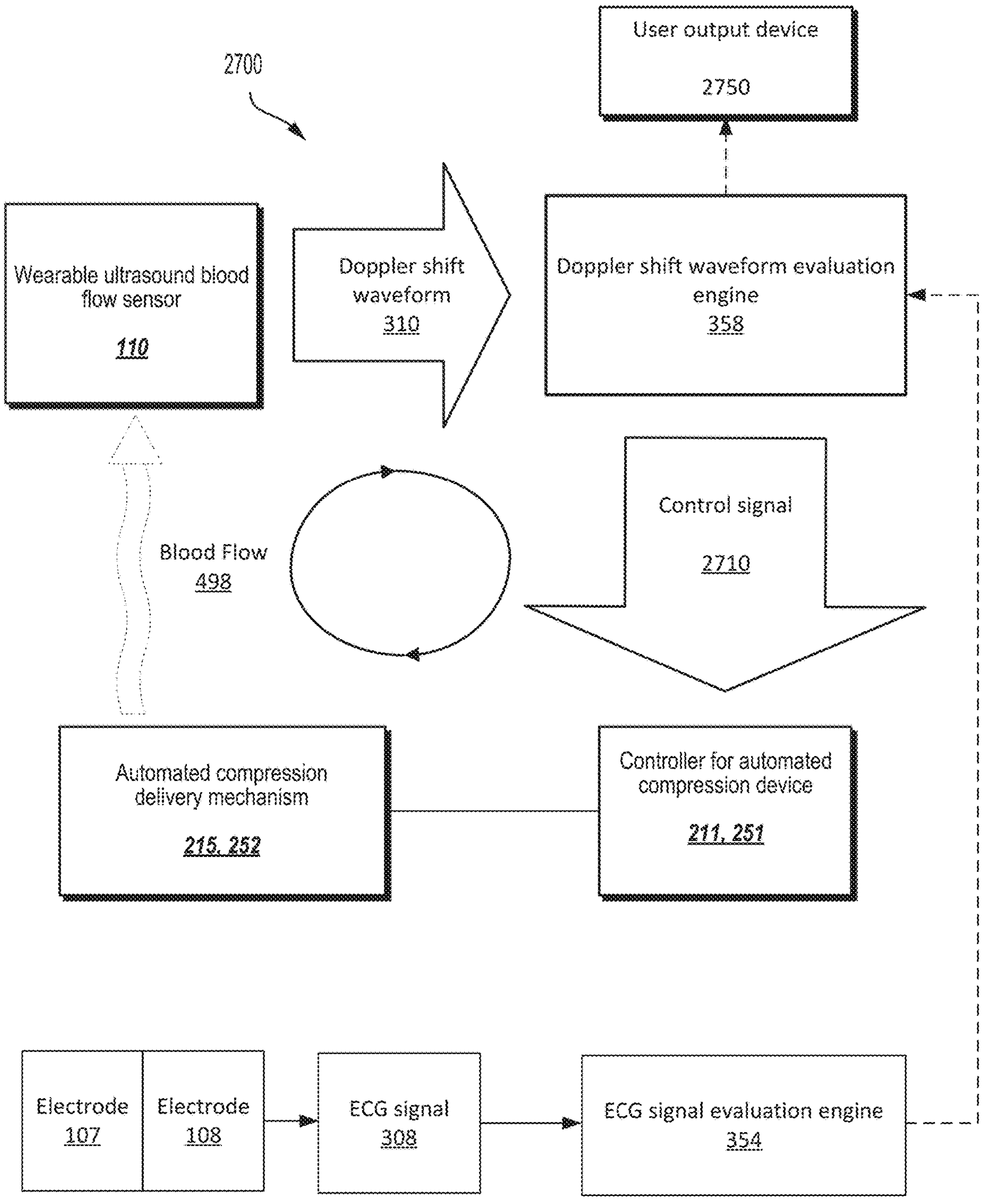
FIG. 3E shows a schematic diagram of an example of closed loop control of an automated compression device using Doppler shift waveform analysis.

Referring to FIG. 3E, a schematic diagram of an example of closed loop control of an automated compression device using Doppler shift waveform analysis is shown. A quantity of each component in FIG. 3E is an example only and other quantities of each, or any, component could be used. In an implementation, an evaluation of a Doppler shift waveform 310 generated by the wearable ultrasound blood flow sensor 110 may enable closed loop control of an automated compression device (e.g., 210 and/or 250). In the case of a wearable ultrasound blood flow sensor 110 placed above the carotid artery, the blood flow measured by the sensor 110 is indicative of blood perfusion to the brain. Blood perfusion to the brain is a critical determining factor for a patient outcome following an adverse cardiac event. For example, an automated compression delivery mechanism, e.g., the belt 215 of the automated compression device 210 or the piston 252 of the automated compression device 250, may provide automated compressions that generate blood flow 498 in response to the compressions. The wearable ultrasound blood flow sensor 110 may provide a Doppler shift waveform 310 as a measurement of the blood flow 498 induced by the compressions. The Doppler shift waveform evaluation engine 358 may receive and analyze the Doppler shift waveform to evaluate the efficacy of the automated compressions with regard to blood flow. The efficacy of the compressions may depend on the compression rate, compression depth, and compression waveform envelope (e.g., a shape of the waveform such as the trapezoidal shape discussed in regard to FIG. 7E-1) provided by the automated compression device. Based on the evaluation, the Doppler shift waveform evaluation engine 358 may provide a control signal 2710 to the controller 211 of the automated compression device 210 or to the controller 251 of the automated compression device 250. The control signal may control and/or adjust one or more compression delivery parameters for the automated compression device (e.g., 210 and/or 250). For example, the automated compression device (e.g., 210 and/or 250) may adjust one or more of compression rate, compression depth, driving frequency, or compression waveform envelope based on the blood flow measured by the wearable ultrasound blood flow sensor 110. The controller 211 or 251 may then control a respective automated compression delivery mechanism, e.g., the belt 215 of the automated compression device 210 or the piston 252 of the automated compression device 250, according to the control signal 2710. The blood flow 498 generated in response to the adjusted automated compressions is sensed by the wearable ultrasound blood flow sensor 110 to complete the control loop.

The Doppler shift waveform evaluation engine 358 may distinguish between PEA and pseudo-PEA based at least in part on the analysis of the at least one Doppler shift waveform. Additionally, The Doppler shift waveform evaluation engine 358 may distinguish between ROSC and pseudo-PEA based at least in part on the analysis of the at least one Doppler shift waveform. In either case, in an implementation, the Doppler shift waveform evaluation-engine 358 may provide an indication of the state of heart activity (e.g., ROSC, PEA, or, pseudo-PEA) to a user output device 2750 as shown in FIG. 3E with reference to FIGS. 3A-3D. For example, the user output device 2750 may be one or more of the display 369, the display 360, the display 361, and/or additional output device(s) 365 and/or 366.

In an implementation, the Doppler shift waveform evaluation engine 358 may receive an input from the ECG signal evaluation engine 354. This input may include an ECG waveform that enables the Doppler shift waveform evaluation engine 358 to include phase control of the automated compressions in the control signal 2710. The Doppler shift waveform evaluation engine 358 may determine a phase of automated compressions delivered by the automated compression device that is synchronous with a repetitive feature of the ECG waveform (e.g., the R wave) and control the automated compression device to deliver compressions according to the determined phase via the control signal 2710. The control signal 2710 may include a driving frequency for the automated compression delivery mechanism 215 and/or 252. This enables the automated compression device (e.g., 210 and/or 250) to synchronize delivered compressions with heart electrical activity indicated by the ECG waveform.

Synchronization of compressions with heart electrical activity may improve perfusion as compared with asynchronous compressions. For example, when the heart is in the early stages of recovery after a defibrillation shock, often with rhythmic electrical activity but degraded mechanical output, cardiac recovery is enhanced if chest compressions are synchronized with the normal, if low level, mechanical activity of the recovering heart, as may occur during pseudo-PEA. Asynchronous chest compressions that occur during ventricular filling are less effective because the volume of blood in the heart is small and little or no blood is ejected in to the aorta and coronary arteries. A compression during this time may increase intrathoracic and/or diastolic pressures and further slow ventricular filling.

The measurement of blood flow with the wearable ultrasound blood flow sensor 110 and the frequency analysis enabled by the Doppler shift waveform evaluation engine 358 allow the engine 358 to confirm that the blood flow resulting from electrical heart activity that causes mechanical pumping activity of the heart and the blood flow resulting from compressions are time synchronized. In the absence of synchronization, the compressions and heart induced flow will go in and out of phase and there will be more blood flow peaks than compressions (some due to heart induced flow and some due to compressions). This also helps to refine the distinction between pseudo-PEA and PEA. The detection of pseudo-PEA requires a detection of blood flow correlated with an ECG. The ECG indicates electrical heart activity that does not necessarily result in mechanical heart activity, i.e., pumping. This is the case in PEA where there is rhythmic electrical heart activity but no mechanical heart activity. Thus, for example, R-wave peaks in an ECG during PEA will not be correlated with blood flow peaks in a Doppler shift waveform because the R-wave peaks are ineffective at producing mechanical pumping of the heart during PEA. Thus the name "pulseless" electrical activity.

A combination of blood flow and electrical activity is indicative of pseudo-PEA. The ECG will indicate the frequency components of the electrical activity that can correlate with frequency components in the Doppler shift waveform attributable to heart-induced flow. Other frequency components corresponding to peaks in the blood flow waveform may be attributable to compressions. However, compression frequency components that are not aligned with and additive with the heart induced frequency components represent compressions that are asynchronous with the heart's activity, i.e., asynchronous with the ECG. The R-wave is a strong peak in the ECG and thus provides a useful tool for identifying the frequency components of heart-induced blood flow, particularly in a damaged heart where other ECG features may be more difficult to identify.

Figure 3F:
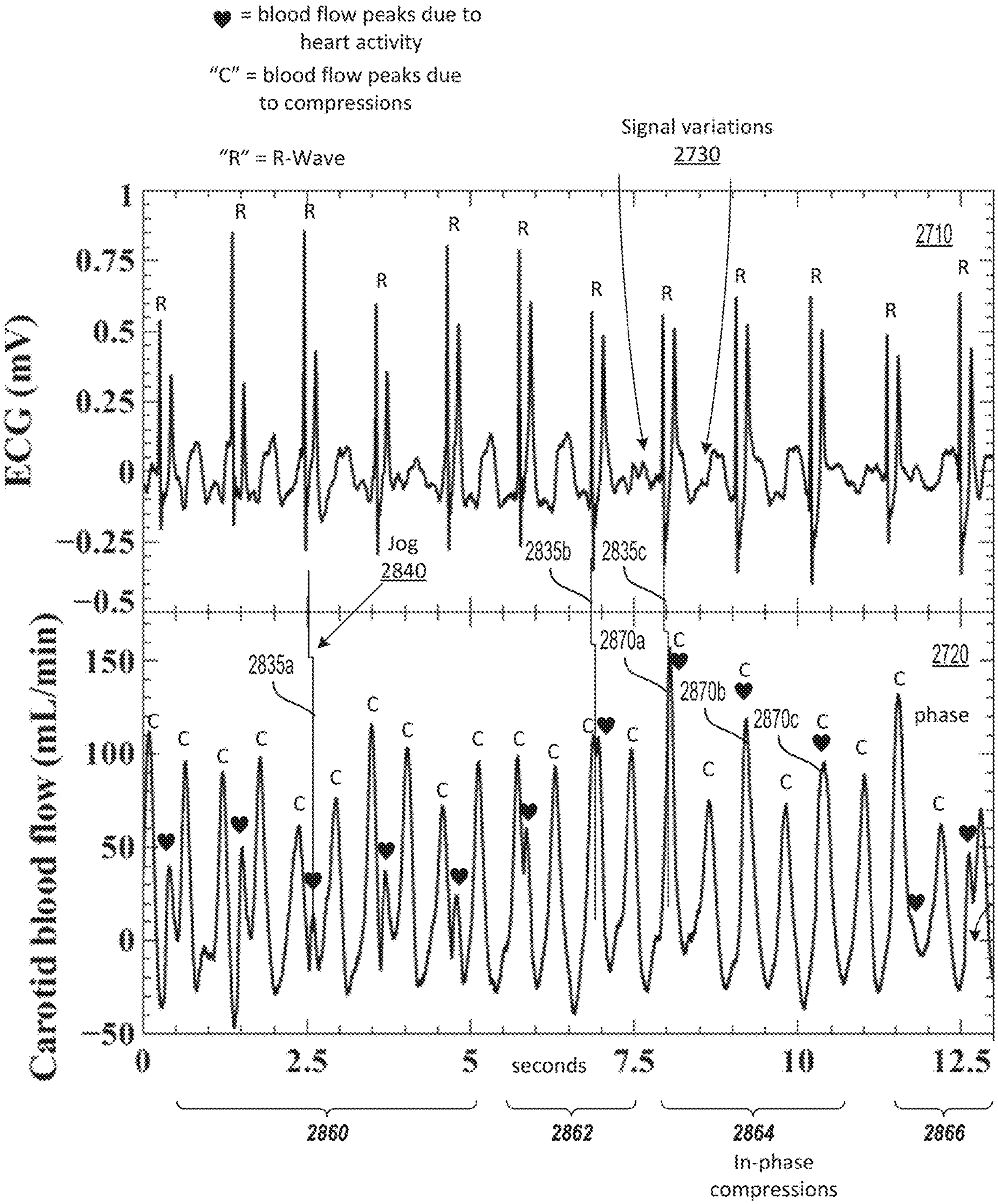
FIG. 3F shows an example of carotid blood flow measured during chest compressions provided synchronously and asynchronously with heart electrical activity.

Referring to FIG. 3F, an example of carotid blood flow measured during chest compressions provided synchronously and asynchronously with heart electrical activity is shown. The waveforms shown in FIG. 3F show measurements of ECG 2710 and carotid blood flow 2720 during animal studies using a swine model of cardiac arrest.

The ECG 2710 is measuring heart electrical activity in a damaged heart where compressions are still beneficial in maintaining sufficient blood perfusion. The repetitive R-wave in the ECG trace 2710 is labeled as "R." The R-wave reflects depolarization of the main mass of the ventricles. Ventricular depolarization leads to ventricular contraction causing blood to move into the pulmonary artery and aorta and one to the carotid artery. The areas of the ECG trace 2710 between the R-waves show signal variations 2730 typical of motion-induced artifacts in the electrical signal. For example, patient motion during an ECG measurement due to a moving gurney, stretcher, and/or ambulance may contribute to the motion-induced artifacts in an ECG trace.

The carotid artery is physically at a distance from the heart and, therefore, there is a slight delay between the electrical impulse of the R-wave and a resulting surge of blood flow in the carotid artery. Therefore, each line in FIG. 3F includes a horizontal jog 2840 representing this delay. This approximately 90 msec delay is consistent over time because the physical distance between the wearable blood flow sensor 110 measuring carotid blood flow is fixed with respect to the heart. A carotid blood flow measurement from a sensor on the femoral artery, for example, will show a different delay in the R-wave induced flow than the carotid blood flow measurement from a sensor on the carotid artery.

The carotid blood flow trace 2720 exemplifies both synchronous and asynchronous compressions. In this trace, the compressions move in and out of phase with the heart electrical activity. Section 2860 corresponds to asynchronous compressions. Here, peaks in the carotid blood flow measurement due to heart activity appear between and separate from the peaks in the carotid blood flow measurement due to compressions. Sections 2862 and 2866 corresponds to compressions with less asynchrony than section 2860 and moving into phase. Here, peaks in the carotid blood flow measurement due to heart activity appear between the peaks in the carotid blood flow measurement due to compressions. However, the peaks due to heart activity increasingly overlap with the peaks due to compressions as the trace moves into and then out of the in-phase compression section 2864.

Section 2864 corresponds to compressions that are in phase with the heart electrical activity. Here, the peaks due to compressions and heart activity are additive and indistinguishable in the trace 2720. The average amplitude of the blood flow peaks 2870*a*, 2870*b*, and 2970*c* that are in phase with the R-wave is approximately 125 mL/min. The average amplitude of the remaining blood flow peaks asynchronous with the R-wave is approximately 90 mL/min. Thus, the compressions synchronized with heart electrical activity increase the average carotid blood blow. As a result, perfusion of blood to the heart is maximized when the compressions are synchronized with the heart electrical activity to the benefit of the patient.

The closed loop system 2700 may monitor an ECG signal and the blood flow measurements determined from the Doppler shift waveform. The Doppler shift waveform evaluation engine 358 may determine whether or not the compressions are in phase or out of phase with the heart electrical activity based on a peak and frequency analysis as exemplified in FIG. 3F. The Doppler shift waveform evaluation engine 358 may additionally determine the phase difference. Based on this analysis, the Doppler shift waveform evaluation engine 358 may provide the control signal 2710 to the controller for the automated compression device to adjust the compression delivery to maintain compressions that are in phase with any measured electrical activity shown in the ECG signal from the ECG signal evaluation engine 354.

Figure 4A:
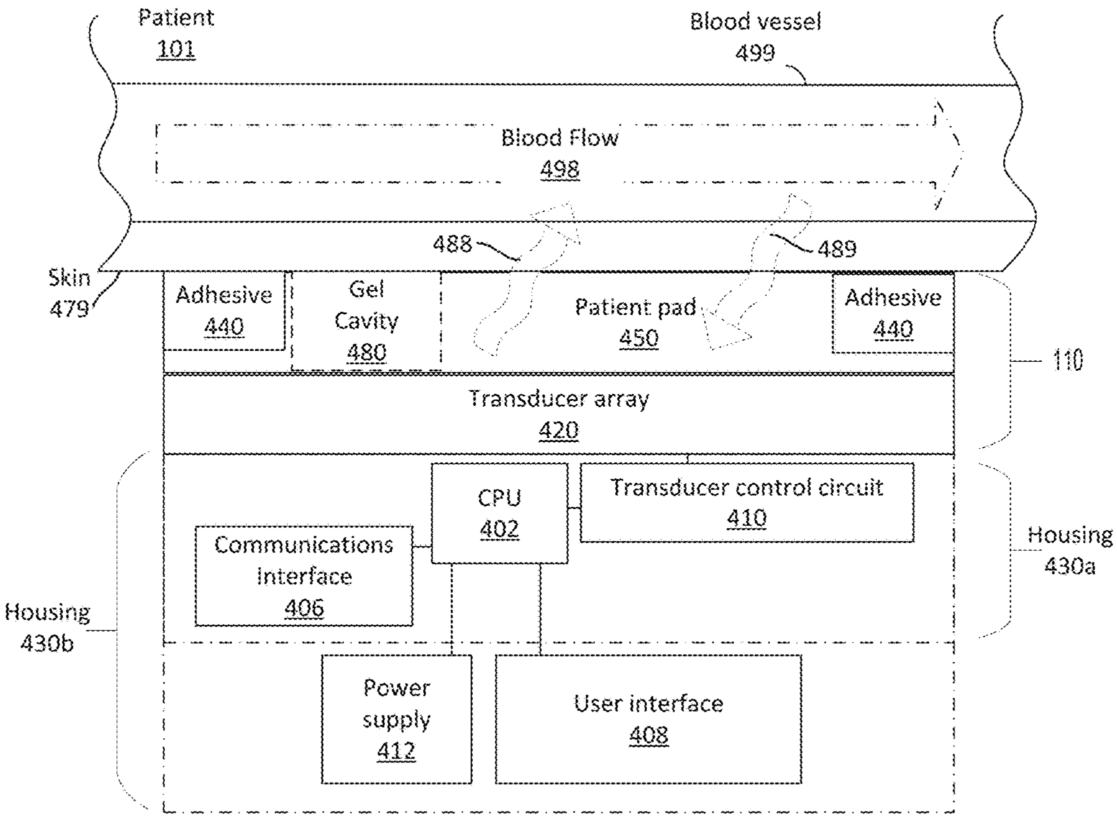
FIG. 4A is a schematic block diagram of an example of a wearable ultrasound blood flow sensor.

Referring to FIG. 4A, a schematic block diagram of an example of a wearable ultrasound blood flow sensor is shown. A quantity of each component in FIG. 4A is an example only and other quantities of each, or any, component could be used. A rescuer may attach the wearable ultrasound blood flow sensor 110 to the skin 479 of the patient 101 to detect blood flow 498 in a blood vessel 499.

The sensor 110 and an associated housing provide a portable and non-invasive device for hemodynamic monitoring. In various implementations, all or a portion of the sensor 110 may be in the form of a bandage or patch that couples to the patient. The bandage or patch may couple to the patient in a variety of ways, not limiting of the disclosure, such as, for example, as a wrap around a body part, with a self-adhesive, with a wrap that contains the sensor 110 and holds it against the patient, with a frame that couples to the sensor 110, etc.

The wearable ultrasound blood flow sensor 110 may include a transducer array 420 and adhesive 440 and/or a patient pad 450. The sensor 110 may optionally include a gel dispenser, or gel cavity, 480. The sensor 110 may be flexible and/or stretchable in order to conform to contours on the patient's body. To enable flexibility, the transducer array 420 may include multiple piezoelectric elements joined by a flexible adhesive and/or springs and may be mounted to a flexible circuit board. With an adhesive, the sensor 110 may self-adhere to the skin 479 of the patient 101. Without an adhesive, the sensor 110 may include an external bandage that wraps around the sensor 110 to attach the sensor 110 to the patient. Additionally or alternatively, the sensor 110 may couple with a positioning frame (e.g., the positioning frame 2510 as discussed below with regard to FIG. 25). The positioning frame may include an adhesive or an external bandage to secure the frame and the sensor 110 to the patient. In an implementation, the sensor 110 may be disposable.

In addition to features that enable mechanically coupling to the patient 101, the sensor 110 includes features that enable acoustical coupling to the patient 101. In an implementation, the adhesive 440 may be an acoustically transmissive adhesive and cover the entire interface between the transducer array 420 and the skin 479. Such an adhesive may eliminate the need for ultrasound gel. Alternatively, the sensor 110 may include one or more gel cavities 480. In an implementation, a peel-back cover could expose the gel and make it ready for application. Alternatively, the gel cavities 480 may function as gel dispensers. Each gel cavity 480 may include a volume of ultrasound gel and be positioned substantially adjacent to an adhesive seal. The adhesive seal may be configured to release the ultrasound gel from the cavity 480 when pressure is applied about a perimeter of the adhesive seal. As a further alternative, the acoustic and mechanical requirements may be separated with a first material providing the acoustic coupling and second material providing the mechanical coupling. An example design may include utilizing an adhesive 440 in a ring shape with a central patient pad 450. The patient pad 450 may comprise a solid or liquid gel. In such a design, the adhesive 440 mechanically connects the sensor 110 to the patient 101 and the patient pad 450 provides the acoustic connection. In an implementation, the patient pad 450 may include a silicone layer for acoustic coupling at the sensor/skin interface that may be used in lieu of or in conjunction with ultrasound gel.

The sensor 110 is coupled to a housing. The housing may include a CPU 402, a communications interface 406, and a transducer control circuit 410 as shown, for example, with the housing 430*a*. The housing 430*a* may be coupled to an external power supply and/or user interface 408. As shown for example with the housing 430*b*, the housing may further include one or more of the power supply 412 and the user interface 408.

In an implementation, the transmitter elements (TX) and the receiver elements (RX) of the transducer array 420 may all be individually wired (e.g., not wired in parallel). This enables the CPU 402 to separately analyze the signal in separate channels and select the TX/RX pair that produces the strongest signal. The CPU 402 may evaluate the signal strength based on a threshold signal-to-noise ratio. With multiple elements in the transducer array, the TX/RX pair producing the strongest signal may be those elements best positioned over the desired vessel to generate a stronger reflected ultrasound signal. In an implementation, the CPU 402 may poll the various channels to determine the pair(s) of TX/RX elements generating signals above a threshold signal-to-noise ratio. From these candidate TX/RX pair(s), the CPU 402 may further select the one or more TX/RX pairs generating the strongest signals above the signal-to-noise ratio. The CPU 402 may use these strongest TX and/or RX signals to generate the data signals representing the Doppler shift waveforms 310 that are transmitted from the sensor 110 to the Doppler shift waveform evaluation engine 358.

Figure 4E:
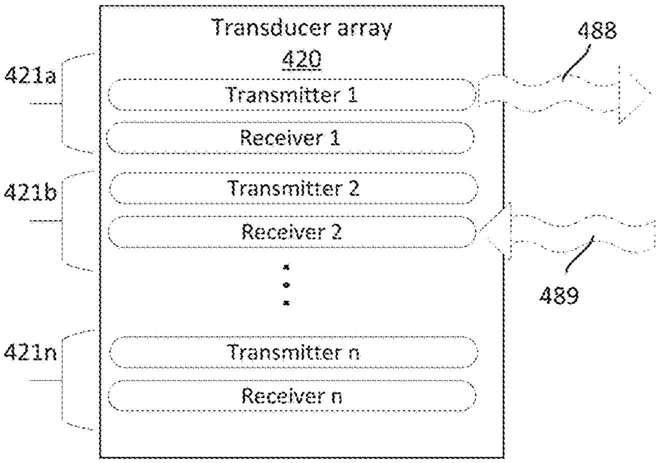
FIG. 4E shows a schematic block diagram of an example of a transducer array.
Figure 4B:
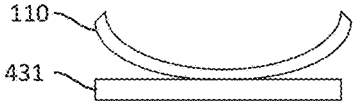
FIGS. 4B-4D show examples of a flexible and/or stretchable wearable ultrasound sensor coupled to various types of housings.
Figure 4C:
Figure 4D:
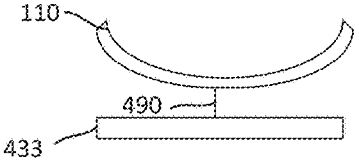

Referring to FIGS. 4B, 4C, and 4D, examples of a flexible and/or stretchable wearable ultrasound sensor coupled to various types of housings is shown. A quantity of each component in each of FIGS. 4B, 4C, and 4D is an example only and other quantities of each, or any, component could be used. As shown in FIG. 4B, the flexible and/or stretchable sensor 110 is mechanically and electrically coupled to a relatively less flexible or substantially rigid housing 431. As shown in FIG. 4C, the sensor 110 is mechanically and electrically coupled to a flexible and/or stretchable housing 432. As shown in FIG. 4D, the sensor 110 is electrically coupled (e.g., via an electrical coupling 490) to a housing 433 but is physically separate from the housing 433. Each of the housings 431, 432, and 433 may include the components of housing 430*a* or 430*b*. Further, one or more of the housings 431, 432, and 433 may be configured to mechanically and/or electrically couple to and decouple from the sensor 110.

Referring to FIG. 4E, with further reference to FIG. 4A, a schematic block diagram of an example of a transducer array is shown. A quantity of each component in FIG. 4E is an example only and other quantities of each, or any, component could be used. The transducer array 420 may include one or more transmitter-receiver pairs (e.g., 421*a*, 421*b*, . . . , 421*n*). Each transmitter is configured to generate a transmitted ultrasound wave 488 and each receiver is configured to receive a reflected ultrasound wave 489. Each of the transducers 421*a*, 421*b*, . . . , 421*n* is an approximately rectangular shaped piezoelectric transducer (e.g., PZT metallic oxide or another piezoelectric material) secured to a circuit board, for example, with a non-conductive epoxy. The top and bottom surfaces of the transducers include an area of metallic coating that provides a conductive electrode contact for the transducer. The transducers 421*a*, 421*b*, . . . , 421*n* are arranged in an array. Although shown arranged in parallel and of uniform size in FIG. 4E, this is an example only and not limiting of the disclosure. In various implementations, the transducers 421*a*, 421*b*, . . . , 421*n* may be of various sizes. The array may include transducers oriented in various geometric patterns, randomly oriented transducers, and combinations thereof. In an implementation, the transducers 421*a*, 421*b*, . . . , 421*n* may be parallel to a surface of the sensor 110 or may be arranged at one or more angles such that the transducers 421*a*, 421*b*, . . . , 421*n* are not orthogonal to the direction of blood flow in the blood vessel. In an implementation, the transducers 421*a*, 421*b*, . . . , 421*n* may be oriented to lie parallel to the surface of the patient's skin and the sensor 110 may include one or more lenses configured to steer transmitted and received signals away from an orthogonal beam direction. The transducers 421*a*, 421*b*, . . . , 421*n* may be disposed on a flexible and/or stretchable circuit board that includes and/or enables electrical coupling of the piezoelectric elements to the transducer control circuit 410.

In operation, the plurality of transducer pairs are configured to transmit unfocused ultrasound beams and detect overlapping ultrasonic waves reflected by body tissues. Specifically, when the sensor 110 is placed on the patient 101 in proximity to a blood vessel 499 in which there is blood flow 498, the ultrasound waves reflected from red blood cells are indicative of hemodynamic properties of blood flow from the patient's heart through the blood vessel 499. Due to the movement of the blood in the vessel, the reflected signals undergo a frequency shift relative to the transmitted signals due to the Doppler effect. The magnitude of this frequency shift, referred to as a Doppler shift, is determined by the velocity of the red blood cells in blood through an artery or vein. The movement over time of the red blood cells relative to the stationary sensor 110 produces the Doppler shift.

In an implementation, the CPU 402 may process raw frequency shift data to calculate velocity. Over time, the CPU 402 may generate the Doppler shift waveform as a flow waveform that indicates velocity per unit time. In various implementations, the CPU 402 may provide this data for display at the user interface 408 and/or control the transducer array 420 via the transducer control circuit 410 based on this data. The transducer control circuit 410 and/or the CPU 402 may be configured to perform digital signal processing that may be utilized to both send and receive data signals, including beam-forming and Doppler shift computations. The CPU 402 may also host an operating system of the sensor 110. The memory 404 may store data (e.g., raw data, pre-processed data, processed data, and post-processed data).

In an implementation, the CPU 402 and/or the Doppler shift waveform evaluation engine 358 may calculate a velocity time integral that is indicative of the amount of blood passing through a cross section over the span of time from the Doppler shift waveform. Calculating the area under the velocity-time curve (i.e., the calculus integral), the CPU 402 and/or the engine 358 may utilize the data to determine the velocity-time integral ("VTI"), and the VTI may be multiplied by the cross-sectional surface area of the vessel over the time of one cardiac cycle (heart beat). The velocity time integral is proportional to the volume of blood that flows through a vessel per unit time. Therefore, it is a surrogate for cardiac output, which is an important hemodynamic parameter (e.g., a proxy that can be obtained based on measured physiological indicators). The resulting waveform (e.g., as shown, for example, in FIGS. 7B-1-7E-2) may be data that indicates blood volume per unit time (e.g., milliliters per minute) as a function of time (e.g., seconds).

The CPU 402 may transmit data to the medical device 305 (e.g., the Doppler shift waveform evaluation engine 358) via the communications interface 406. In an implementation, the CPU 402 may transmit data signals representing the flow waveform (velocity per unit time) to the medical device 305 or the external computing device 180. In an implementation, the CPU 402 may calculate the velocity time integral waveform and transmit data signals representing the velocity time integral to the engine 358 for analysis. In an implementation, the engine 358 may receive the data signals representing the flow waveform and calculate the velocity time integral waveform. The engine 358 may perform a spectral analysis on data received from the CPU 402 and/or data calculated at the engine 358. The engine 358 may analyze blood flow to guide patient treatment based on one or more of the flow waveforms, the velocity time integral waveform, and the spectral analysis.

The power supply 412 (e.g., a battery) may supply power to the sensor components. The power supply 412 may be rechargeable or replaceable. As size is a consideration, lithium-ion technology may, in some embodiments, be selected as an option for compact power density. Operating under the assumption that these batteries typically can store 77,000 Ah/cm3 (amp-hours per cubic centimeter), the battery in the device may have to be, for example, 125 cm3 for 1 hour of continuous active use. A Li-ion battery of this size typically weighs about 250 g. Additional lifetime can be achieved by adding a larger (and heavier) battery, which may be suitable for a larger embodiment.

The transducer control circuit 410 may control an ultrasound transducer array 420. The control circuit 410 and/or the CPU 402 may include an analog-to-digital converter along with circuit elements to amplify and filter received data signals. An ultrasound emitter (not shown) may be utilized to produce the high-voltage signal needed to drive the ultrasound transducers in the transducer array 420. The emitter may be provided a positive voltage supply and a negative voltage supply that is controlled by low-voltage logic data signals from the transducer control circuit 410. The transducer control circuit 410 may be configured to control the emitter and receive logic data signals from the transducer array.

The communications interface 406 may communicatively couple the sensor 110 to the medical device 305 or the external computing device 180. The interface 406 may send sensor data, including the Doppler shift waveform, and/or receive data to and/or from the medical device 305 (e.g., USB, Bluetooth®, Wi-Fi, etc.). Although shown in FIGS. 1 and 2 with a wireless connection to the defibrillator 105, this is an example only and the sensor 110 may communicate with an external medical device and/or computing device via a wired connection, a wireless connection, or a combination thereof.

The user interface 408 may enable various input-output functionality, including the ability to receive parameters, etc. from users (e.g., the rescuer 103) and/or provide a graphical interface. In some implementations, the user interface 408 may be provided on a separate computing device, such as, for example, the medical device 305, the external computing device(s) 180, or a combination thereof. The user interface 408 may be provided on the separate computing device in combination with or in lieu of a user interface provided with the sensor 110. In various implementations, the user interface 408 may include LED indicators, an LCD touchscreen, and/or mechanical buttons. Other types of displays may be contemplated. The user interface 408 may further include a speaker and/or a haptic device configured to generate sounds and/or vibrations, for example, to provide rescuer feedback. In some embodiments, visual, audible, and/or haptic feedback may correspond to operating conditions of the sensor 110 include positioning. The feedback may direct the rescuer 103 to orient and/or position the sensor 110 on a desirable and/or acceptable local site on the patient 101. The purpose of this direction may be to permit full operability of the device with a minimum of training or experience. In various implementations, the components 402, 404, and 408 of the wearable ultrasound sensor(s) 110 may be combined into one or more discrete components and component 408 may be part of the CPU 402.

Figure 5:
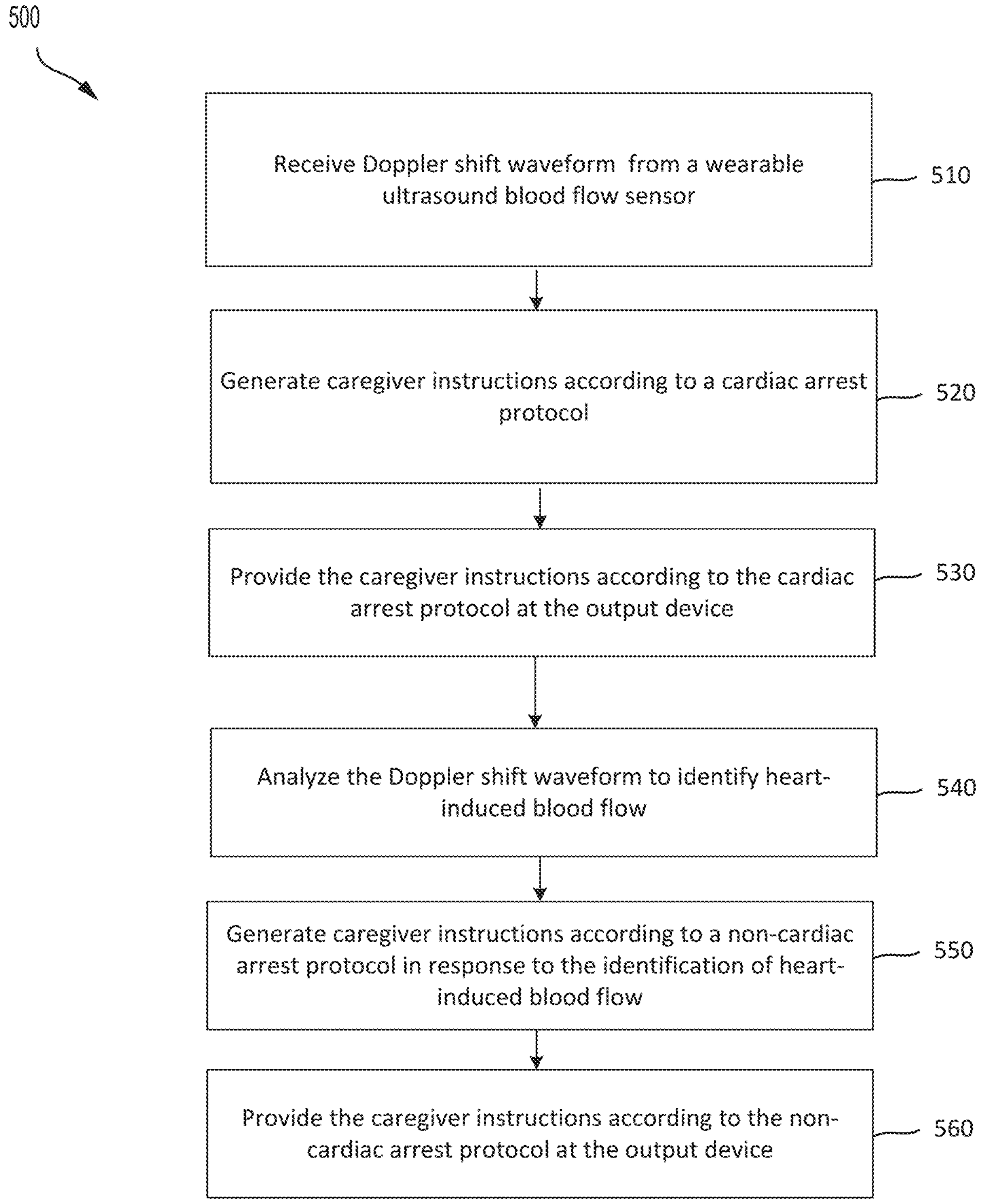
FIG. 5 shows an example of processor implemented steps for heart-induced blood flow detection using a Doppler shift waveform.

Referring to FIG. 5, an example of processor implemented steps for heart-induced blood flow detection using a Doppler shift waveform is shown. FIG. 5 provides an overview of these steps with further detail provided in regard to subsequent figures. The steps shown is FIG. 5 are examples only and not limiting of the disclosure. Additionally, the sequence of steps can be altered, e.g., by having stages added, removed, rearranged, combined, and/or performed concurrently.

In an implementation, the system shown, for example, in FIG. 3A may implement the process 500 as shown in FIG. 5 to provide patient care guidance to a caregiver based on ultrasound detection of blood flow using at least one wearable ultrasound blood flow sensor 110. The medical device 305, which may be a defibrillator, includes the processor 350 and the memory 355. The memory 355 is a non-transitory storage medium having stored thereon processor-executable instructions. The at least one wearable ultrasound blood flow sensor 110 is configured to couple to the medical device 305 and to the patient 101. The sensor 110 may generate at least one Doppler shift waveform 310. At the stage 510, the Doppler shift waveform evaluation engine 358 of the processor 350 may receive the at least one Doppler shift waveform 310 from the sensor 110.

At the stage 520, the processor 350 may generate caregiver instructions according to a cardiac arrest protocol. At the stage 530, the output device(s) 360 may provide these generated instructions.

Details of a cardiac arrest protocol are described below with regard to FIGS. 6 and 7A. In brief, when a rescuer or other caregiver encounters a person that is unresponsive and not breathing, the person is likely a victim of a cardiac arrest. Therefore, the rescuer would provide interventions according to a cardiac arrest protocol. For example, the cardiac arrest protocol may include administering chest compressions and ventilation breath according to a procedure commonly referred to as cardiopulmonary resuscitation (CPR). Depending on the training level of the rescuer, CPR may also include interventions with a ventilator and/or other respiratory resuscitation and monitoring equipment, automated chest compression devices, medications, fluid delivery, etc.

The purpose of the chest compressions is to generate blood flow through the victim's body during a time in which the victim is in cardiac arrest. During this time, the heart is not effectively pumping blood. Effective heart-induced blood flow creates a pulsatile rhythm of flow due to organized electrical activity of the heart. Administering chest compressions to the victim according to the cardiac arrest protocol is appropriate and beneficial as long as the victim remains in cardiac arrest. The victim remains in cardiac arrest as long as there is no effective heart-induced blood flow. However, once there is heart-induced blood flow, the victim is no longer in cardiac arrest and the interventions and treatments may differ from those administered for cardiac arrest. As will be discussed in further detail below, in some cases, prolonging interventions and treatments appropriate for cardiac arrest past a point where heart-induced blood flow has resumed may reduce patient health and possibly create life-threatening complications.

At the stage 540, the Doppler shift waveform evaluation engine 358 of the processor 350 may analyze the at least one Doppler shift waveform 310 to identify the heart-induced blood flow. After a cardiac arrest, heart-induced blood flow may resume in response, at least partially, to the chest compressions and/or to electrotherapy such as defibrillation. Chest compressions generate blood flow according to the rhythm of the chest compressions. The rhythm of the chest compressions may manifest itself in the Doppler shift waveform 310 as a substantially periodic surge in blood velocity. The heart-induced blood flow may occur as a periodic contribution to the Doppler shift waveform at a different frequency than that contribution from the chest compressions. Therefore, the signal analysis performed by the Doppler shift waveform evaluation engine 358 may sort, filter, and identify these contributions in order to identify the heart-induced blood flow that has resumed post-cardiac arrest. As discussed in further detail below, the Doppler shift waveform evaluation engine 358 may also implement noise filtering instructions and/or instructions to correlate the Doppler shift waveform with ECG data in order to identify the heart-induced blood flow.

In an implementation, the Doppler shift waveform evaluation engine 358 may evaluate the Doppler shift waveform in conjunction with other data that can detect heart-induced blood flow in order to partially or fully automate a determination that the victim is no longer in cardiac arrest. In this manner, the engine 358 may integrate Doppler shift waveform analysis into context-sensitive guidance and decision support provided to a caregiver by the medical device 305. Combining the Doppler shift waveform analysis with these other indicators available to a patient monitor or a defibrillator may improve the confidence of this determination sufficiently to rely on this automated determination. Because the decision to stop chest compressions is a critical clinical decision with regard to the patient's health and recovery, a high confidence level may be required for such an automated determination. For example, in conjunction with the Doppler shift waveform analysis for identifying heart-induced blood flow, the rescuer 103 and/or the processor may evaluate ventilation and/or respiration data. The system may include the respiration and/or ventilation sensors 395 (e.g., capnography sensors, pulse oximetry sensors, spirometry sensors, air flow sensors, etc.). The ventilation metrics engine 390 may receive, evaluate, and monitor data from one or more of these sensors and may provide SpO2, EtCO2, and/or other ventilation and/or respiratory data to the Doppler shift waveform evaluation engine 358. As additional examples, the engine 358 may receive data such as, but not limited to, ECG data, continuous NIBP data, NIRS data, impedance cardiography data, PPG data, and/or heart sound data. The engine 358 may receive this data from one or more of the electrodes 107,108 and the physiologic sensors 396. These types of data do not directly measure blood flow but rather measure physiologic effects or conditions that vary with blood flow and may be indicative of blood-flow when considered as part of a larger diagnostic inquiry. For example, arterial blood pressure, SpO2, EtCO2, and tissue oxygenation as detected with NIRS all increase in the presence of heart-induced blood flow. The efficiency of this type of blood flow exceeds that of compression-induced blood flow. However, these parameters, inclusive of ECG, can be affected by factors other than cardiac output and also may not provide as immediate an indication of blood flow (e.g., there may be associated time delays) as the Doppler shift waveform. ECG measures the electrical function of the heart rather than the mechanical function. As evidenced by PEA, electrical function may exist in the absence of mechanical function (i.e., the heart may not pump blood despite the existence of a rhythmic electrical signal). Therefore, practitioners or an automated diagnostic or guidance system may use these as confirmation tools to increase the confidence in a determination that heart-induced blood flow has resumed and, therefore, that the patient is no longer in cardiac arrest and in need of treatments for resuscitation from cardiac arrest.

In an implementation, the engine 358 may analyze one or more types of data along with the Doppler shift waveform data to generate a cumulative blood flow score based on multiple indicators of heart-induced blood flow. The engine 358 may analyze these multiple indicators statistically, e.g., according to a logistic regression, or according to other decision logic and/or machine learning in order to automate the identification of heart-induced blood flow with increase accuracy due to multiple physiologic measures. The cumulative score may be associated with a confidence level and/or may be compared to a threshold at which the patient is automatically determined to no longer be in cardiac arrest. In response to this automatic determination, the engine 358 may generate caregiver prompts to stop chest compressions and generate caregiver prompts and guidance for post-cardiac arrest care. In an implementation, the engine 358 may utilize the cumulative score to evaluate priorities and/or expected efficacies of various post-cardiac arrest care interventions (e.g., the interventions listed in Table 1 and Table 2).

As shown in FIGS. 1 and 2, the systems described herein may include multiple sensors 110 disposed on the victim. In an implementation, the Doppler shift waveform evaluation engine 358 may receive Doppler shift waveforms 310 from multiple sensors 110 in order to isolate motion artifacts. Upon isolation of the motion artifacts, the engine 358 may generate a corrected Doppler shift waveform by removing motion artifact contributions and identify heart-induced blood flow based on the corrected Doppler shift waveforms. The engine 358 may receive data signals representing the Doppler shift waveform 310 from a first sensor 110 in a first location and receive at least one additional waveform 310 from one or more additional sensors 110 in one or more additional locations that are at different positions on the victim than the first location.

For example, the first location may be proximate to at least one blood vessel of the patient and the additional locations may be distant from (i.e., not proximate to) a blood vessel. The location distant from any blood vessel is a location at which the wearable ultrasound sensor would not detect existing blood flow in an artery or vein due to the artery or vein being too far from the skin's surface for blood flow in the vessel to provide a detectable reflected ultrasound wave. For example, the first location may be proximate to a pulse point such as that provided by a carotid, femoral, or brachial artery and the second location may be at another location on the patient that is distant from a pulse point such as that provided by the carotid, femoral, or brachial artery. By isolating a sensor 110 from the blood vessels, the sensor 110 collects Doppler shift waveform contributions from motion of the patient and/or fluctuations in the patient's tissues that are neither attributable to compression-induced or heart-induced blood flow. In an implementation, the engine 358 may analyze a frequency content of the Doppler shift waveforms from each of the sensors and isolate the motion artifacts in the waveforms based on a comparison between these frequency contents. The spectrogram or frequency power spectrum of the Doppler shift waveform indicates the energy associated with each frequency present in the waveform. By looking at the salient frequencies, those associated with each of the main contributors to the signal can be isolated. For example, the main contributors may be motion artifacts along with compression-induced flow and/or heart-induced flow. When a first sensor is placed proximate to a vessel (e.g., directly above or on top of the vessel) and a second sensor is placed away from a vessel, the differences between the main contributors to the each signal can be assigned, and therefore isolated. The first sensor data signals will include the signal contributions from motion artifacts and from blood flow (compression-induced and/or heart-induced). However the second sensor data signals will not include a contribution from blood flow. Therefore, the processor 350 may filter the data signals from the first sensor based on the data signals from the second sensor to isolate the signal contributions from blood flow.

As another example, the first location may be proximate to at least one blood vessel in the neck of the patient and the additional locations may be proximate to at least one blood vessel in an arm, leg, and/or groin of the patient. When the multiple sensors are all located proximately to vessels (e.g., directly above or on top of the vessel) but in different locations, such as the groin and the neck, they both will include substantially similar contributions from heart-induced and/or compression-induced flow. For example, these data signals may exhibit the same frequency components but with a phase difference between the two. Both sensor data signals will include motion artifact contributions but the motion artifacts may be substantially different at the two location. For example, the mechanical response of a neck to motion from compressions, gurney or stretcher motion, vehicle motion, etc. may be different that the mechanical response of a leg or other extremity. The processor 350 may isolate the frequencies associated with flow by filtering out frequency contributions that differ between the data signals from the two sensor locations.

Use of multiple sensors 110 at different locations on the victim may provide benefits in addition to or other than noise or motion artifact removal. For example, based on a frequency content of a Doppler shift waveform from a first sensor 110 at a first location on the victim and a frequency content of a Doppler shift waveform from a second sensor 110 at a second and different location on the victim, the engine 358 may calculate a pulse transit time between the first location and the second and different location. Further, the engine 358 may calculate an estimated vascular stiffness and/or calculate a blood pressure time trend based on the pulse transit time.

At the stage 550, in response to the identification of the heart-induced blood flow, the processor 350 may generate caregiver instructions according to a non-cardiac arrest protocol. At the stage 560, the output device(s) 360 may provide these generated instructions.

Once the victim exhibits heart-induced blood flow, the victim is no longer in cardiac arrest and the interventions and treatments may differ from those administered for cardiac arrest. For example, as described with regard to FIGS. 10A-14B, the non-cardiac arrest protocol may include interventions and treatments appropriate for return of spontaneous circulation (ROSC) subsequent to defibrillation or for pseudo-pulseless electrical activity (pseudo-PEA). Additionally, the victim will likely require advanced circulatory care to address weakened blood flow that is typically exhibited post-cardiac arrest. The advanced circulatory care may also address any other deleterious physiologic effects of the cardiac arrest, the etiology of the cardiac arrest, and/or any co-occurring conditions. The rescuer may fully provide that advanced circulatory care or may initiate such care at the emergency scene and continue this care during patient transport to a medical facility. The wearable ultrasound blood flow sensor may remain in place on the victim during this time period to substantially continuously monitor the patient's blood flow.

Figure 6:
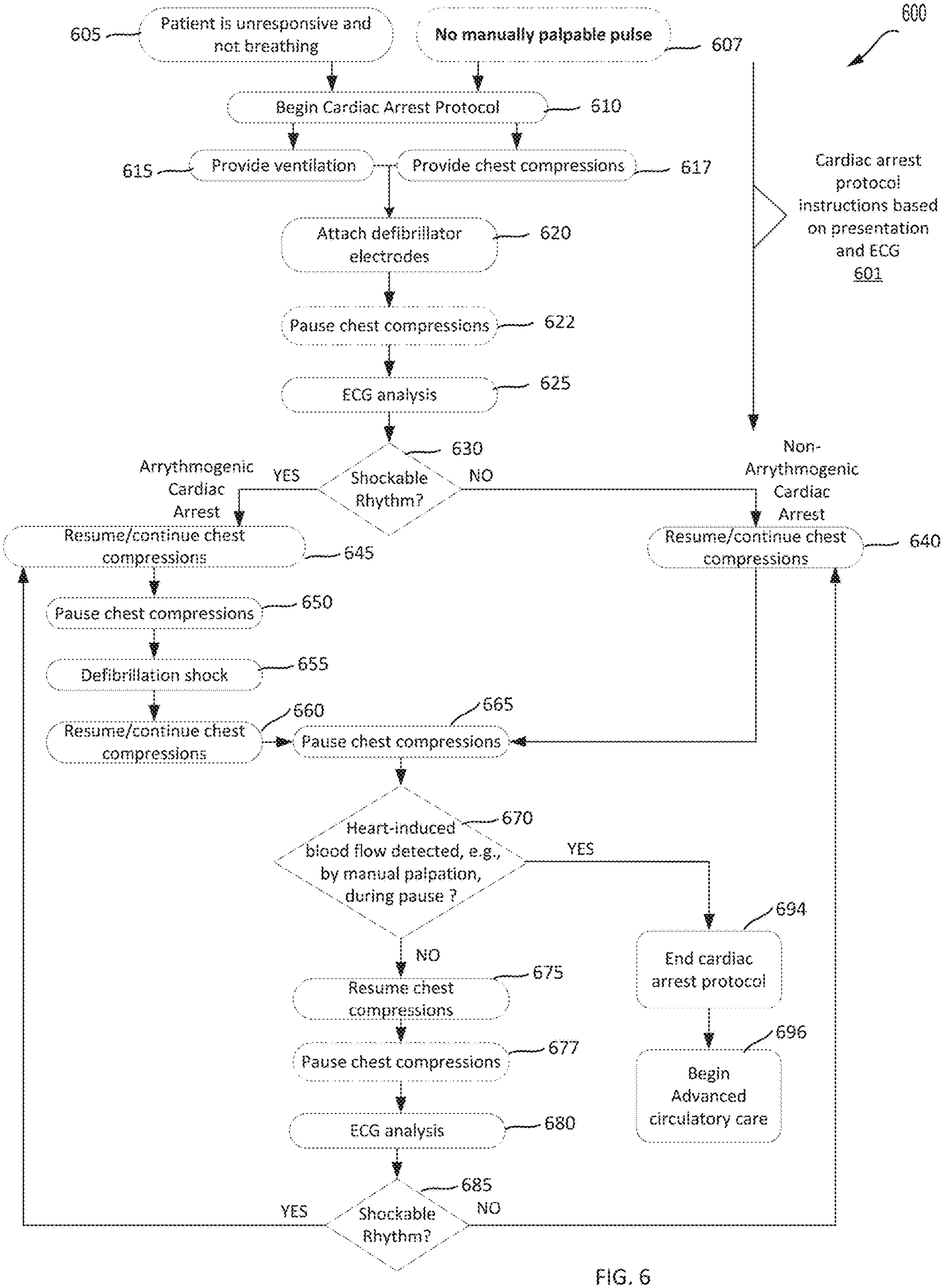
FIG. 6 provides an example of a cardiac arrest protocol without the use of a wearable ultrasound blood flow sensor.
Figure 7A:
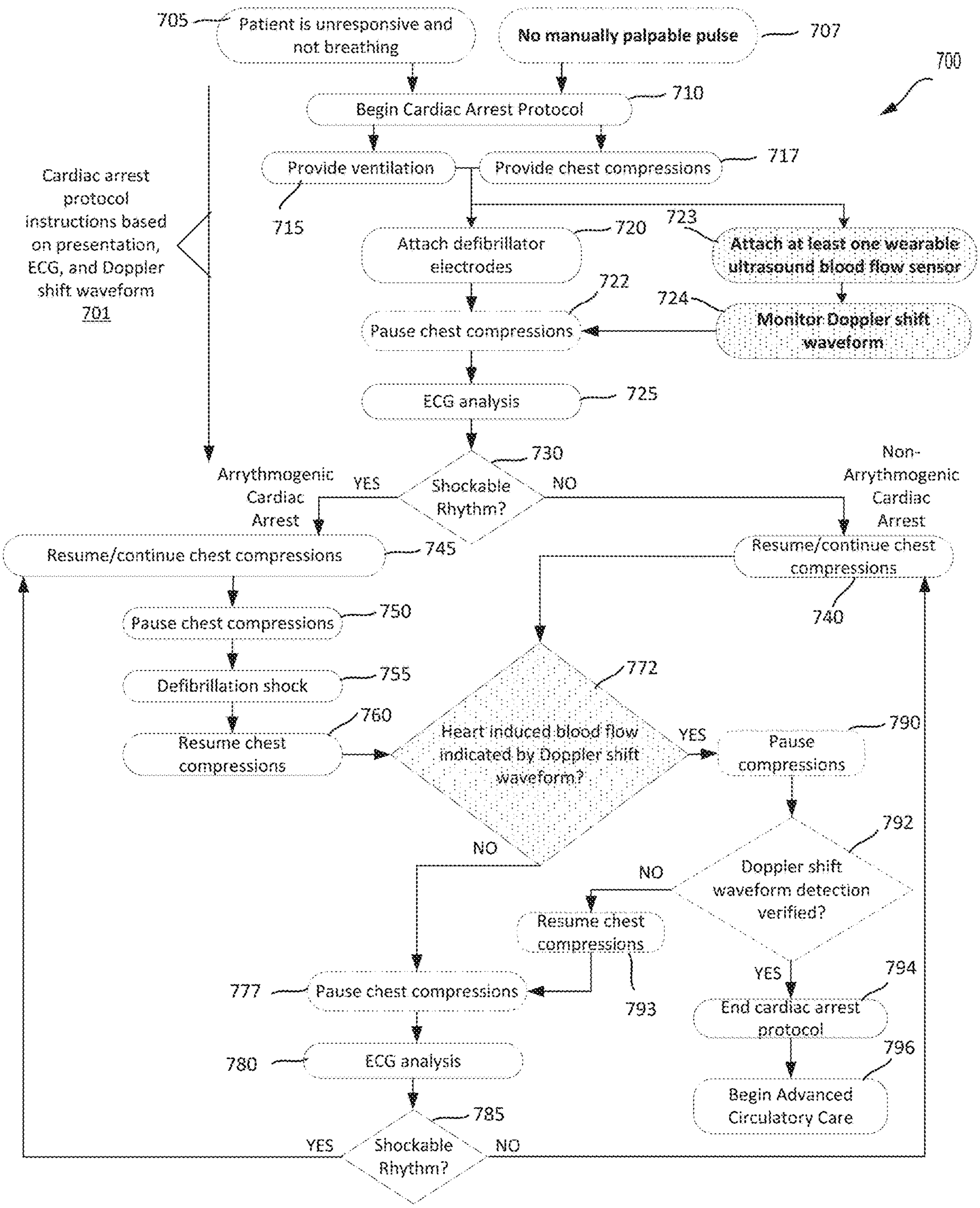
FIG. 7A provides an example of a cardiac arrest protocol with the use of a wearable ultrasound blood flow sensor.

Referring to FIGS. 6 and 7A, examples of a cardiac arrest protocol without the use of a wearable ultrasound blood flow sensor and with the use of the wearable ultrasound blood flow sensor are provided. Comparison of these two protocols highlights the capabilities of the sensor 110 and the patient care advantages derived from use of the sensor 110. The steps shown in the protocols 600 and 700 are examples only and not limiting of the disclosure. Additionally, the sequence of steps can be altered, e.g., by having stages added, removed, rearranged, combined, and/or performed concurrently.

The initial steps for identifying a victim of cardiac arrest are a check of a patient's breathing and responsiveness (605, 705) and a check for a manually palpable pulse (607, 707). When a rescuer or other caregiver encounters a person that is unresponsive and not breathing, the person is likely a victim of a cardiac arrest. The lay rescuer may look for a pulse of the victim although general CPR training for lay rescuers may not include instructions regarding manually palpating for a pulse. If the rescuer is a trained rescuer, for example, an emergency medical technician (EMT), a paramedic, a physician, a nurse, etc., the training of such a rescuer would include looking for a manually palpable pulse in order to identify cardiac arrest.

Upon recognizing that the rescuer has encountered the victim of a cardiac arrest, the rescuer may begin a cardiac arrest protocol (610, 710). The cardiac arrest protocol typically includes an administration of chest compressions (617, 717) and an administration of ventilation breaths (615, 715). These procedures are commonly referred to as cardiopulmonary resuscitation (CPR).

The rescuer may employ a defibrillator (e.g., the defibrillator 105 in FIGS. 1 and 2) as part of CPR to analyze a heart rhythm and provide electrotherapy, when appropriate, to the cardiac arrest victim. The lay rescuer may employ an automated external defibrillator (AED). A rescuer with more advanced training (e.g., an EMT, paramedic, doctor, nurse, etc.) may employ an AED, a basic life support (BLS) defibrillator, or an advanced life support (ALS) defibrillator. Thus, in conjunction with the chest compressions and ventilation breaths, the rescuer may attach (620, 720) defibrillator electrodes to the victim. The defibrillator electrodes (e.g., the electrodes 107 and 108 in FIGS. 1 and 2) provide an electrocardiogram (ECG) signal to the defibrillator (e.g., the ECG signal 308 as provided to the ECG signal evaluation engine 354 in FIG. 3A).

In the cardiac arrest protocol 700, which includes the use a wearable ultrasound blood flow sensor 110, the rescuer may attach at least one wearable ultrasound blood flow sensor (723) in conjunction with attaching the defibrillator electrodes (720). In a rescue situation involving more than one rescuer, a first rescuer may attach the defibrillation electrodes and a second rescuer may attach the at least one wearable blood flow sensor 110. As shown in FIG. 3A, the wearable ultrasound blood flow sensor 110 may generate a Doppler shift waveform 310 and the Doppler shift waveform evaluation engine 358 of the medical device 305, which may be the defibrillator 105, may monitor this this waveform in order to monitor the victim's blood flow or lack thereof. Thus, the protocol 700 includes monitoring the Doppler shift waveform (724) once the wearable sensor 110 is attached to the victim.

In response to receiving the ECG signal, the defibrillator analyzes the ECG (625, 725) and makes a determination as to whether the victim's ECG rhythm is a shockable rhythm or a non-shockable rhythm (630, 730). Depending on the particular defibrillator employed, the defibrillator may instruct the rescuer to pause chest compressions (622, 722) during the ECG analysis. Some ECG analysis algorithms rely on an absence of chest compressions during the ECG analysis in order to provide an accurate analysis of the ECG.

From the stage 605 or 705, through the ECG analysis at the stage 625 or 725, the defibrillator 105 may generate and provide caregiver instructions and/or prompts based on a cardiac arrest protocol as indicated by the instructions 601 and 701. Once the patient is found to be unresponsive (e.g., unconscious) and not breathing, the patient is assumed to be in cardiac arrest and a caregiver is instructed to provide ventilations and chest compressions according to the cardiac arrest protocol. A more experience caregiver may also palpate for a pulse, the lack of which confirms the assumption of cardiac arrest. The ECG analysis at the stage 625 or 725 further confirms the cardiac arrest assumption and identifies the type of cardiac arrest as either arrhythmogenic or non-arrhythmogenic. As discussed herein, the ECG indicates the electrical status of the heart but is not a direct measure of blood flow and the direct measure of blood flow, the Doppler shift waveform, enables a more specific understanding of the patient's condition (as described below with regard to detection of ROSC and pseudo-PEA) and more efficacious and timely care based on this specific understanding. Thus, while the instructions 601 in FIG. 6 are based only on patient presentation and ECG, the instruction 701 in FIG. 7A are additionally based on the Doppler shift waveform data. These instructions may include placement instructions for the wearable ultrasound sensor and/or feedback and/or instructions for the rescuer based on blood flow (e.g., compression feedback, ventilation feedback, medication instructions, differential diagnosis instructions, etc.). The instructions 701 may be responsive directly to the detection, or lack thereof, of blood flow and modified accordingly (e.g., transitioned to post-cardiac arrest protocol instructions) based on the Doppler shift waveform analysis to provide the advantages described herein with regard to patient care.

In the protocol 700, the defibrillator 105 may substantially continuously receive and analyze the Doppler shift waveform from the sensor 110 as the protocol 700 proceeds. Thus, the defibrillator may receive and analyze the Doppler shift waveform during the ECG analysis (725) and shockable rhythm determination (730).

If the ECG analysis indicates a shockable rhythm, then the cardiac arrest is an arrhythmogenic cardiac arrest. If the ECG analysis indicates a non-shockable rhythm, then the cardiac arrest is a non-arrhythmogenic cardiac arrest. In both of the protocols 600 and 700, the arrhythmogenic cardiac arrest protocol steps differ from the non-arrhythmogenic cardiac arrest protocol steps.

For the non-arrhythmogenic cardiac arrest, if the rescuer paused the chest compressions (622, 722) during the ECG analysis, then the rescuer resumes chest compressions (640, 740) subsequent to the ECG analysis. If there was no pause in chest compressions during the ECG analysis, then the rescuer continues the uninterrupted chest compressions (640, 740).

Similarly, for the arrhythmogenic cardiac arrest, if the rescuer paused the chest compressions (622, 722) during the ECG analysis, then the rescuer resumes chest compressions (645, 745) subsequent to the ECG analysis. If there was no pause in chest compressions during the ECG analysis, then the rescuer continues the uninterrupted chest compressions (645, 745) subsequent to the ECG analysis. However, for the arrhythmogenic cardiac arrest, the defibrillator will charge and prepare to deliver a defibrillation shock. When the defibrillator is ready to apply the shock, the defibrillator will instruct the rescuer to pause chest compressions (650, 750) and stand clear of the victim. The defibrillator may instruct the rescuer to push a shock button or otherwise initiate the shock or may automatically deliver the shock without requiring the rescuer to push a button or otherwise initiate the shock. Once the shock is administered (655, 755), the rescuer may resume the chest compressions (660, 760).

The two protocols 600 and 700 have proceeded similarly up to this point, albeit with the additional steps 723 and 724 involving application of the sensor 110 in protocol 700. However, at the stages 665 in FIGS. 6 and 772 in FIG. 7A, a significant difference in the two protocols arises due to the use of the sensor 110 in the protocol 700. Following the post-shock resumption of chest compressions for the arrhythmogenic cardiac arrest or following a pre-determined number of compressions or pre-determined timed duration of chest compressions for the non-arrhythmogenic cardiac arrest, the protocols 600 and 700 both require and include a check for heart-induced blood flow. This check is critical to a determination as to whether or not the victim remains in cardiac arrest after the administration of chest compressions or the administration of chest compressions with defibrillation shock. However, the manner of this check differs as seen by comparing the stages 665, 670, and 675 in protocol 600 with the stage 772 in protocol 700.

As shown in FIG. 6, in the absence of the wearable ultrasound blood flow sensor 110, the protocol 600 includes a pause in chest compressions (665), a check for heart-induced blood flow as indicated by manual pulse palpation (670), and resumption of chest compressions (675) following the check for heart-induced blood flow. The chest compression pause (665) is necessary in order for the rescuer to ascertain that any pulse found via manual palpation is due to heart-induced blood flow as opposed to compression-induced blood flow.

In contrast, with the wearable ultrasound blood flow sensor 110, the chest compressions resumed or continued at either of the stages 740 or 760 in FIG. 7A may continue without a pause during the check (772) for heart-induced blood flow as indicated by the Doppler shift waveform. Therefore, in an implementation, use of the wearable ultrasound blood flow sensor 110 in the protocol 700 may eliminate the need for a pause in chest compressions prior to and during the check for heart-induced blood flow. In such an implementation, the Doppler shift waveform evaluation engine 358 is configured through hardware, software, firmware, or combinations thereof to analyze the at least one Doppler shift waveform during chest compressions administered as an intervention in response to cardiac arrest (i.e., chest compressions administered according to and as a part of a cardiac arrest treatment protocol).

The chest compressions at the time of the check (772) for heart-induced blood flow may be chest compressions administered in response to either of the arrhythmogenic cardiac arrest (e.g., compressions resumed at the stage 760) or the non-arrhythmogenic cardiac arrest (e.g., compressions resumed or continued at the stage 740). The heart-induced blood flow that may be detected in the Doppler shift waveform at the stage 772 may be ROSC following a defibrillation shock for the arrhythmogenic cardiac arrest or may be pseudo-PEA following chest compressions for the non-arrhythmogenic cardiac arrest.

Figures 1, 7B:
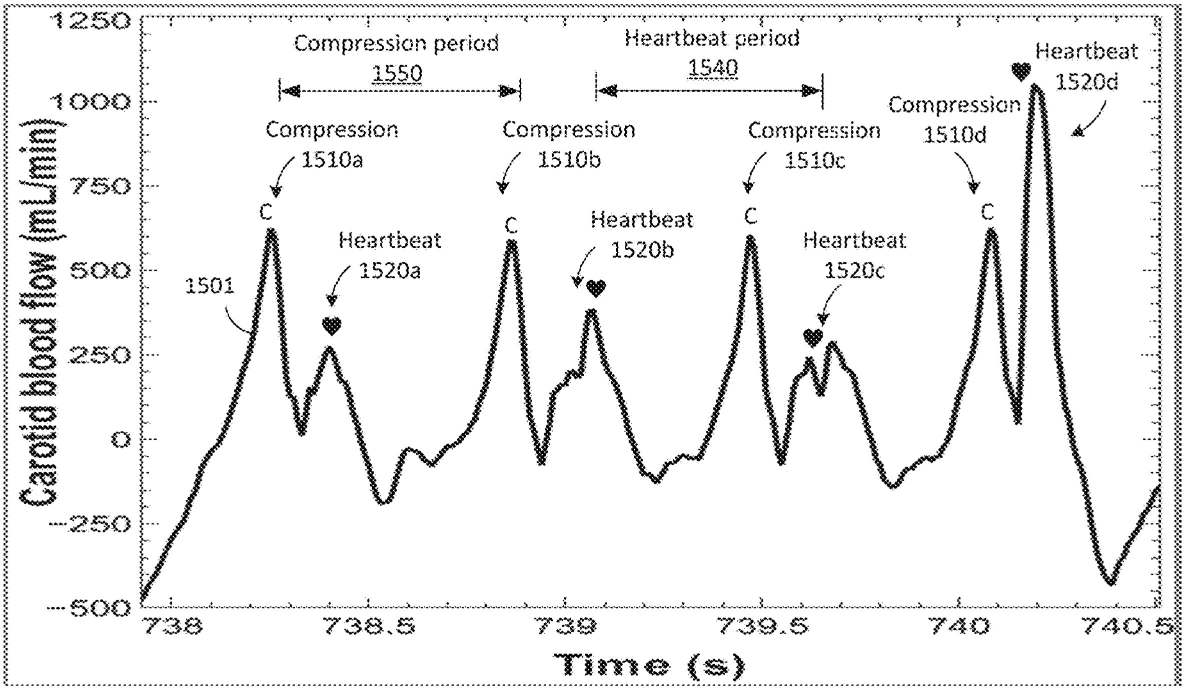
Figures 2, 7B:
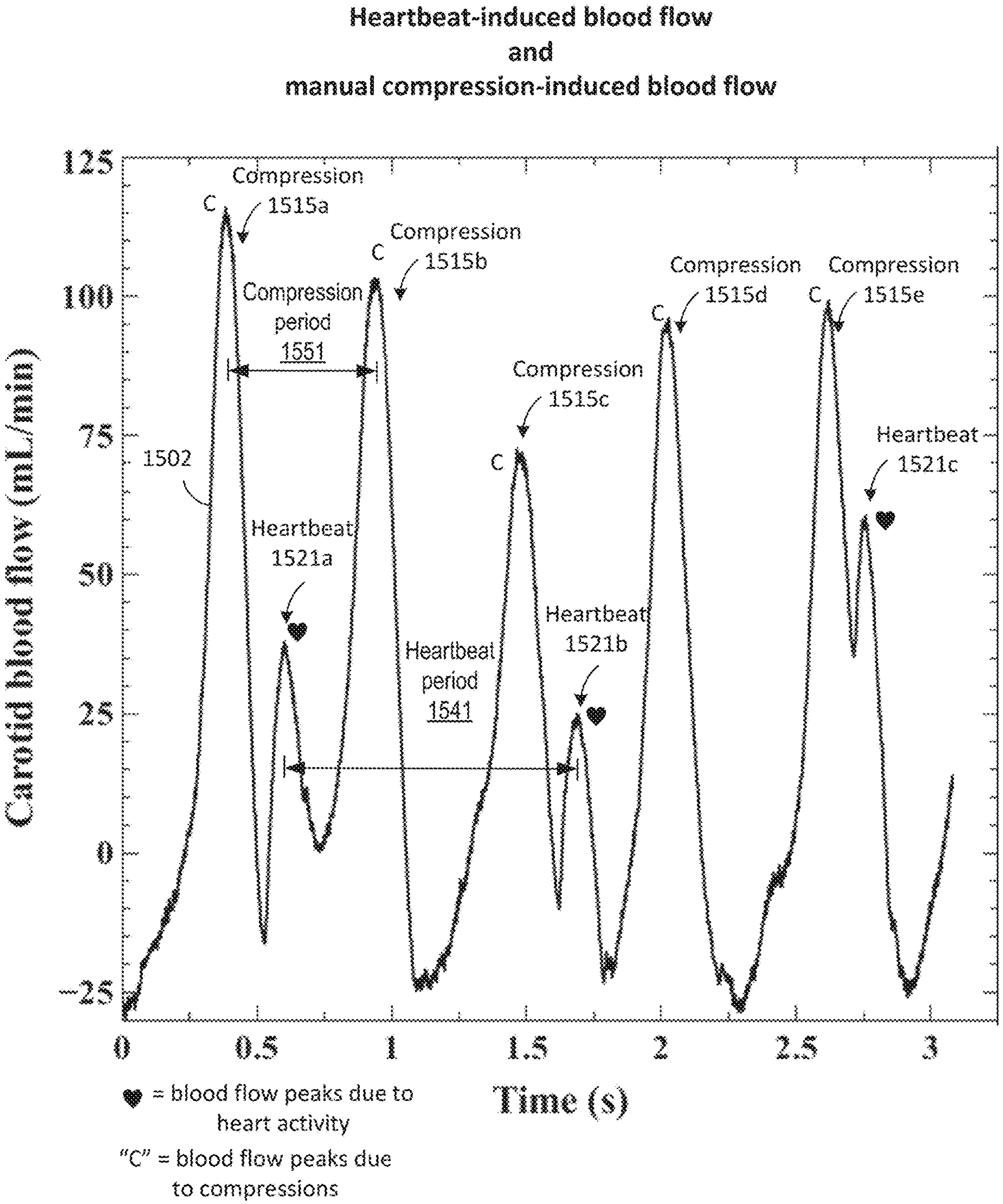
Figure 7C:
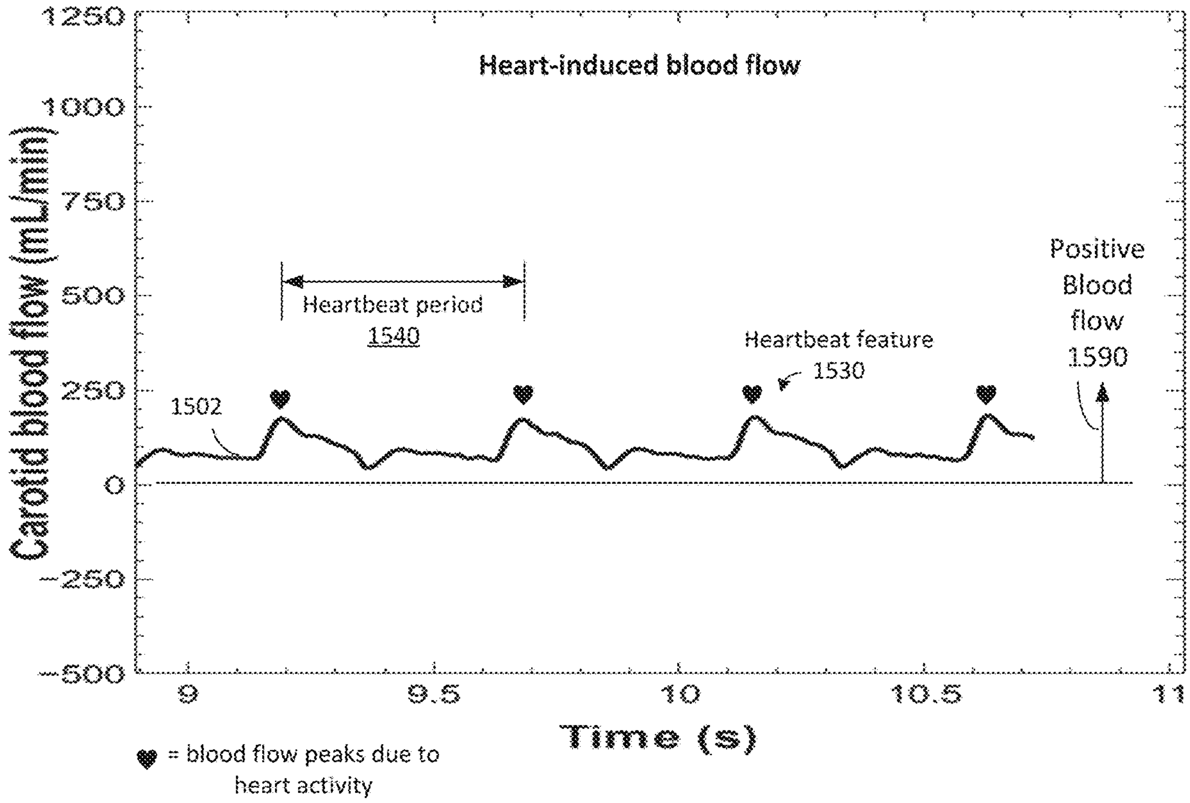
FIG. 7C shows an example of a Doppler shift waveform that indicates heart-induced blood flow.
Figure 7D:
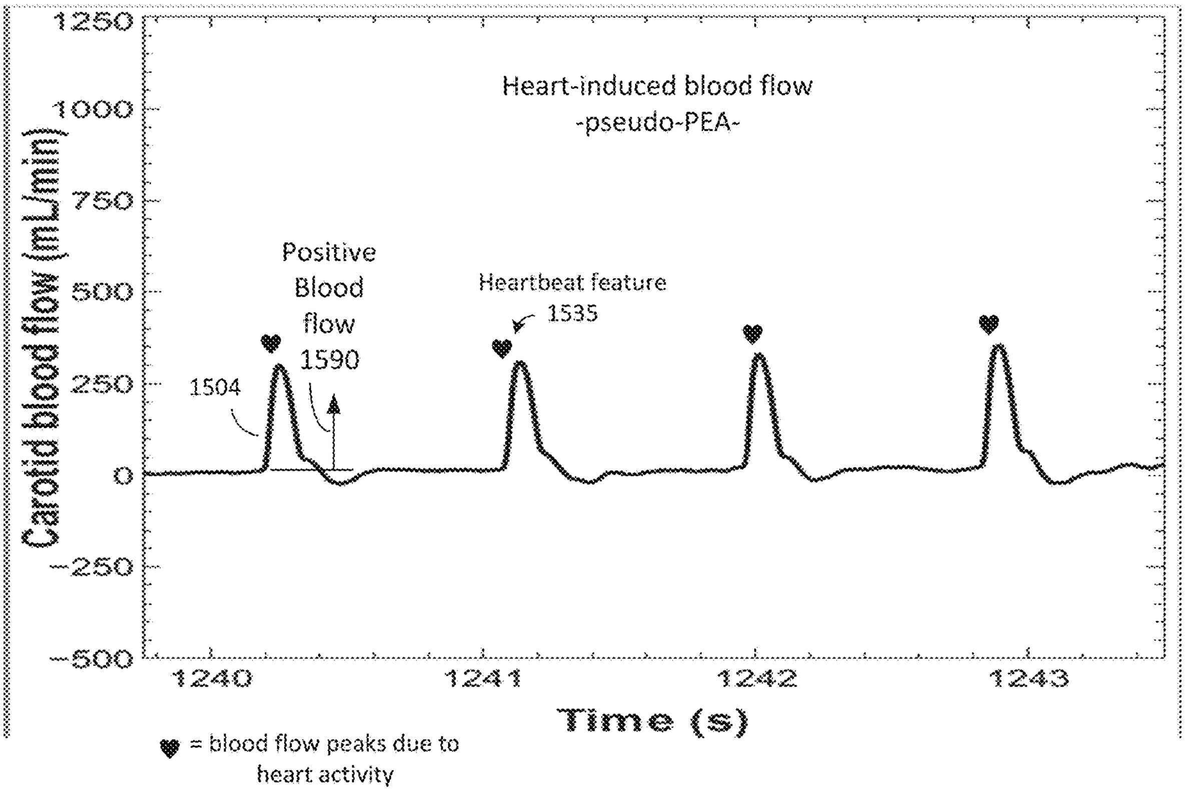
FIG. 7D shows an example of a Doppler shift waveform that indicates heart-induced blood flow corresponding to pseudo-PEA.
Figures 1, 7E:
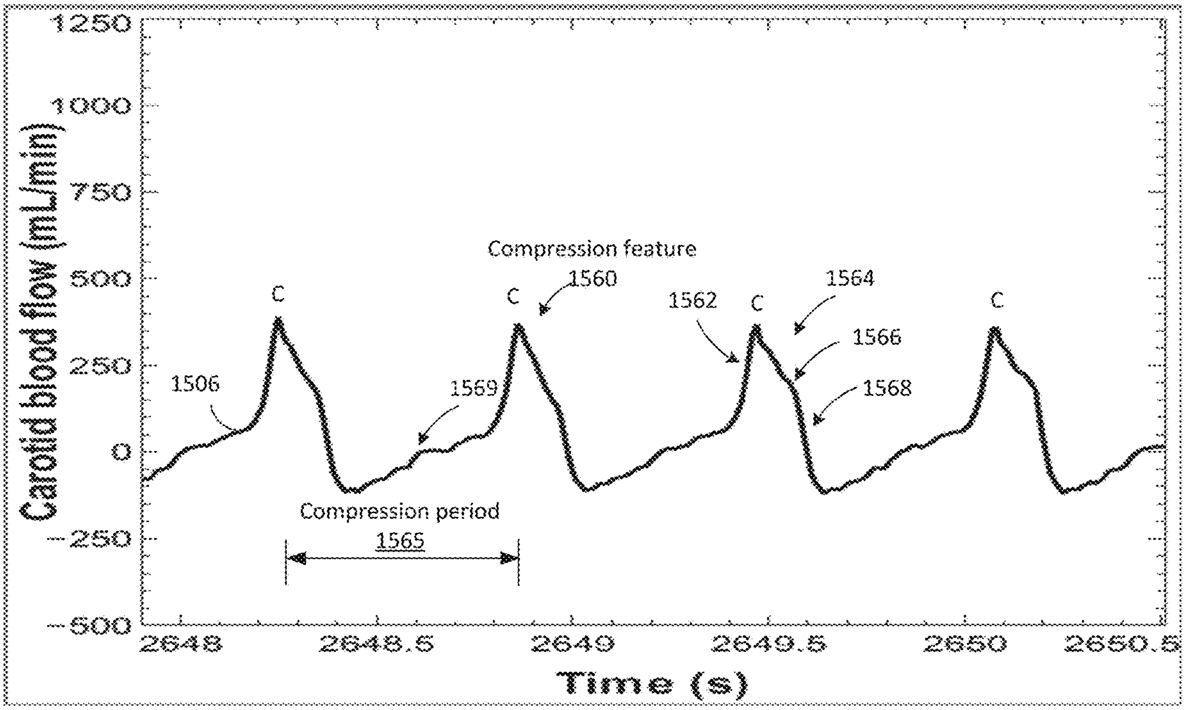
Figures 2, 7E:
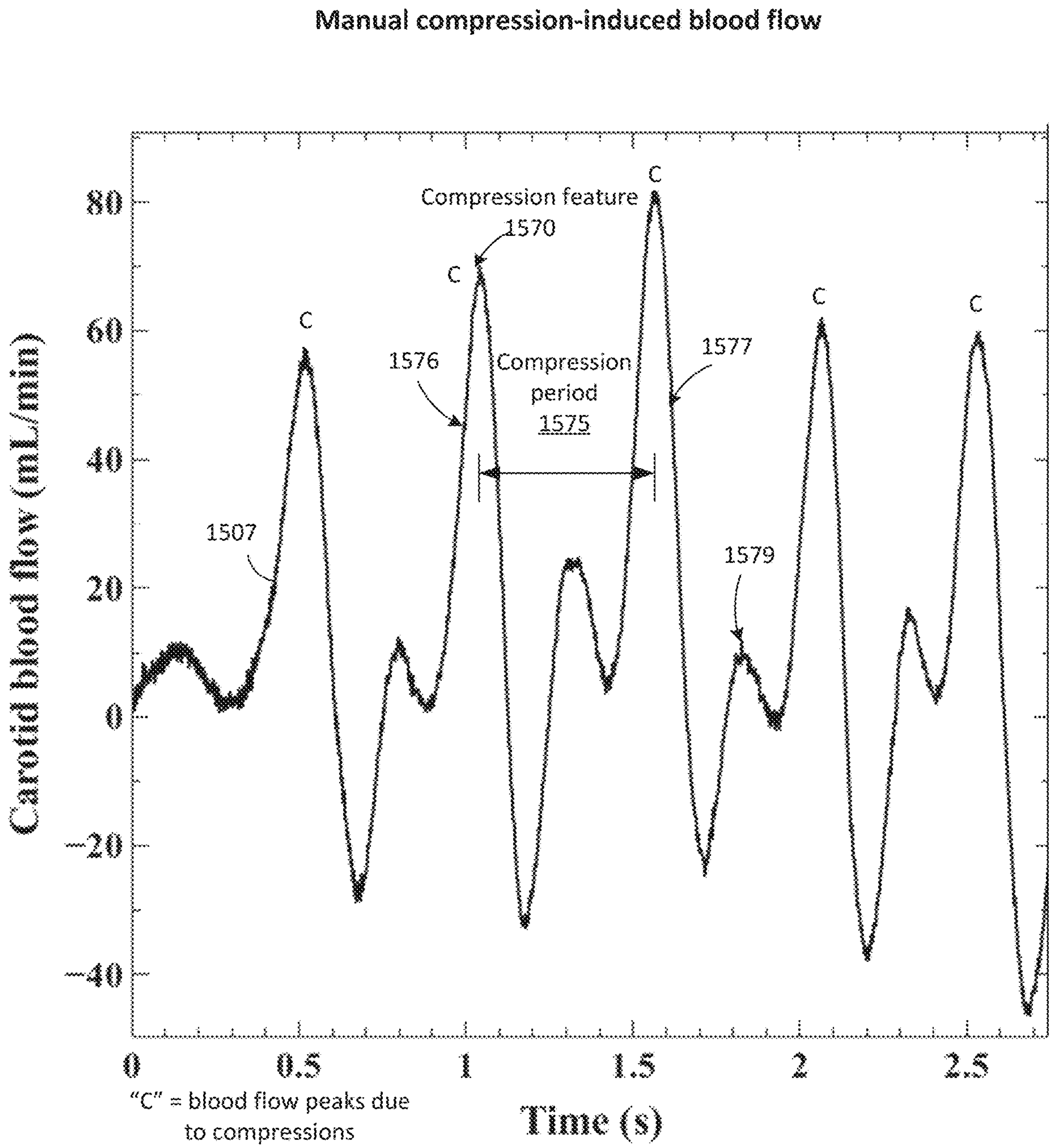
Figure 7F:
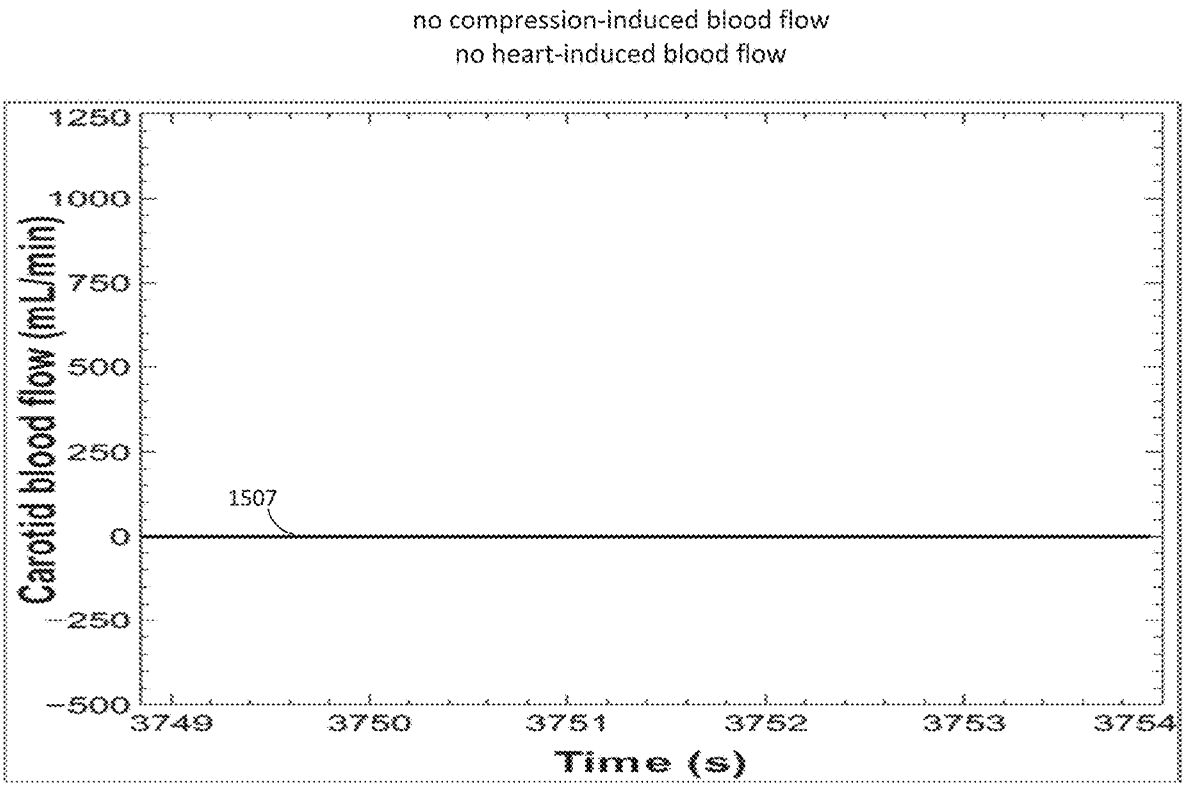
FIG. 7F shows examples of Doppler shift waveforms that indicate an absence of heart-induced blood flow and an absence of compression-induced blood flow.
Figures 1, 7G:
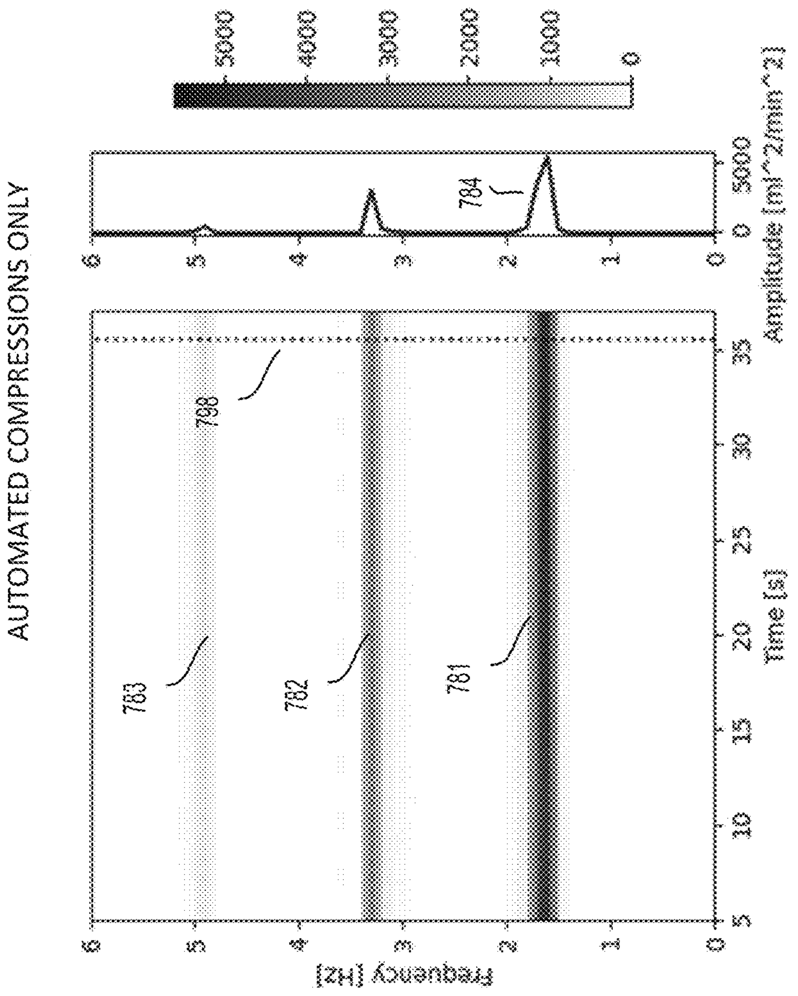
Figures 2, 7G:
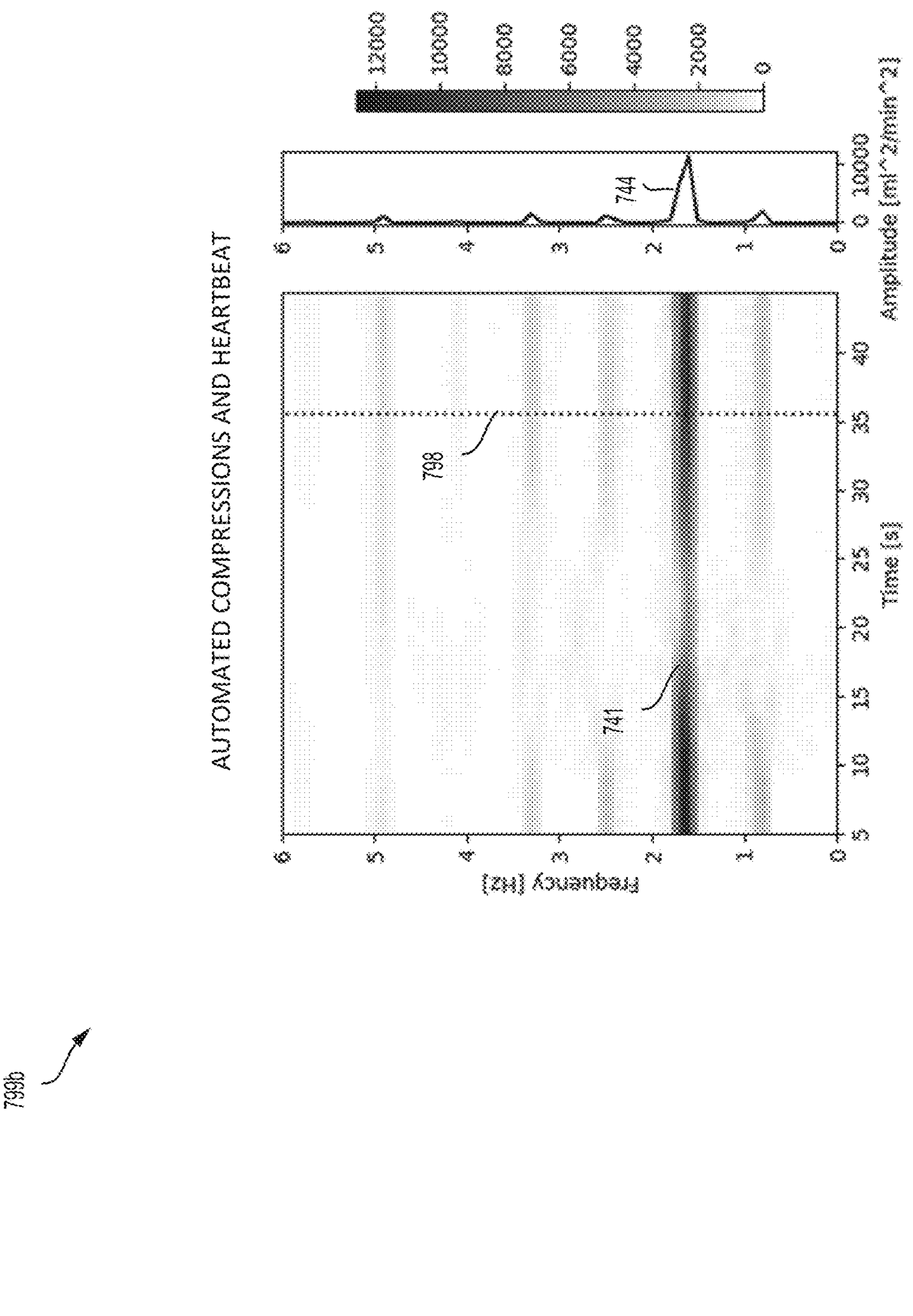
Figures 1, 7H:
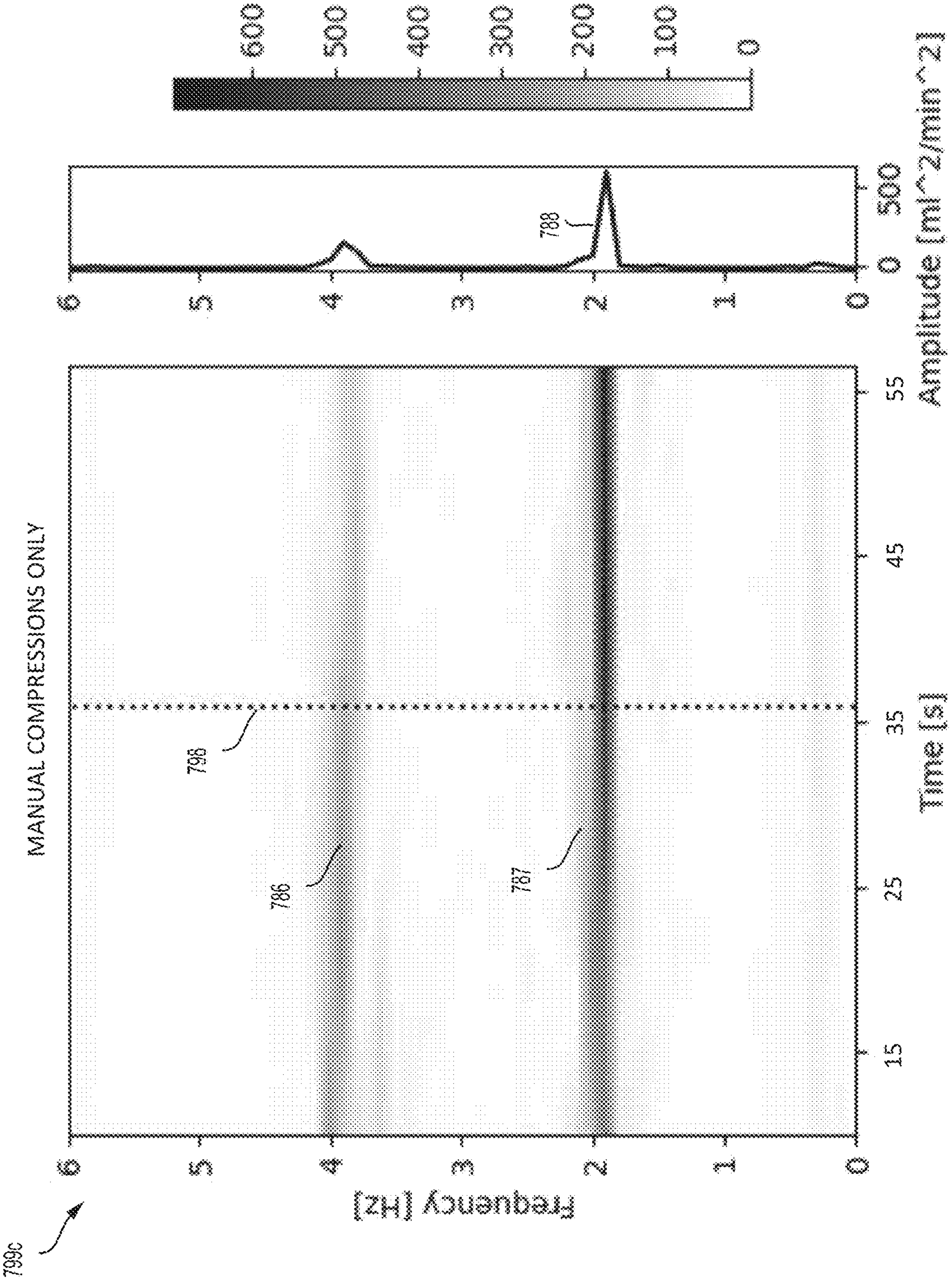
Figures 2, 7H:
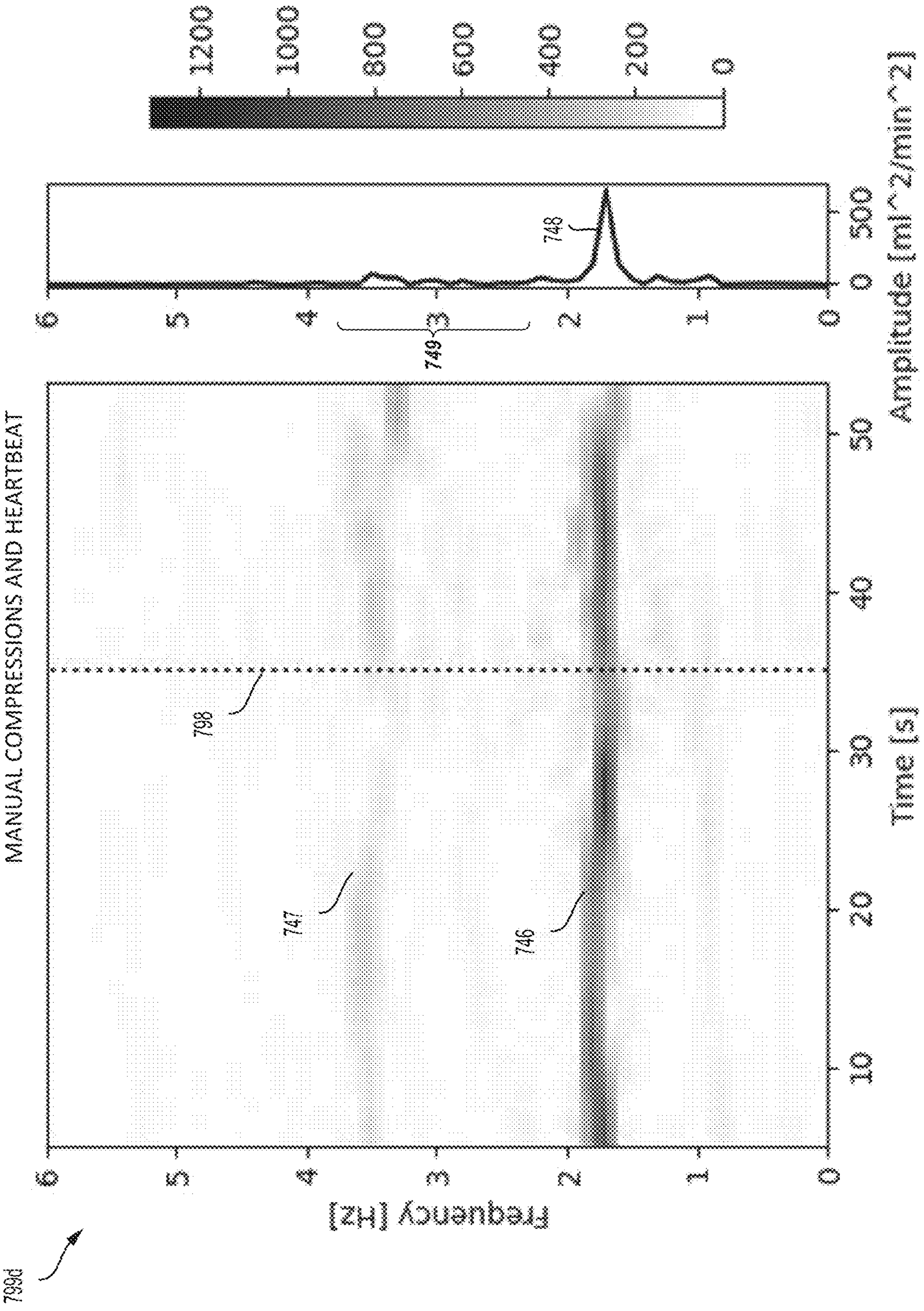
Figure 7I:
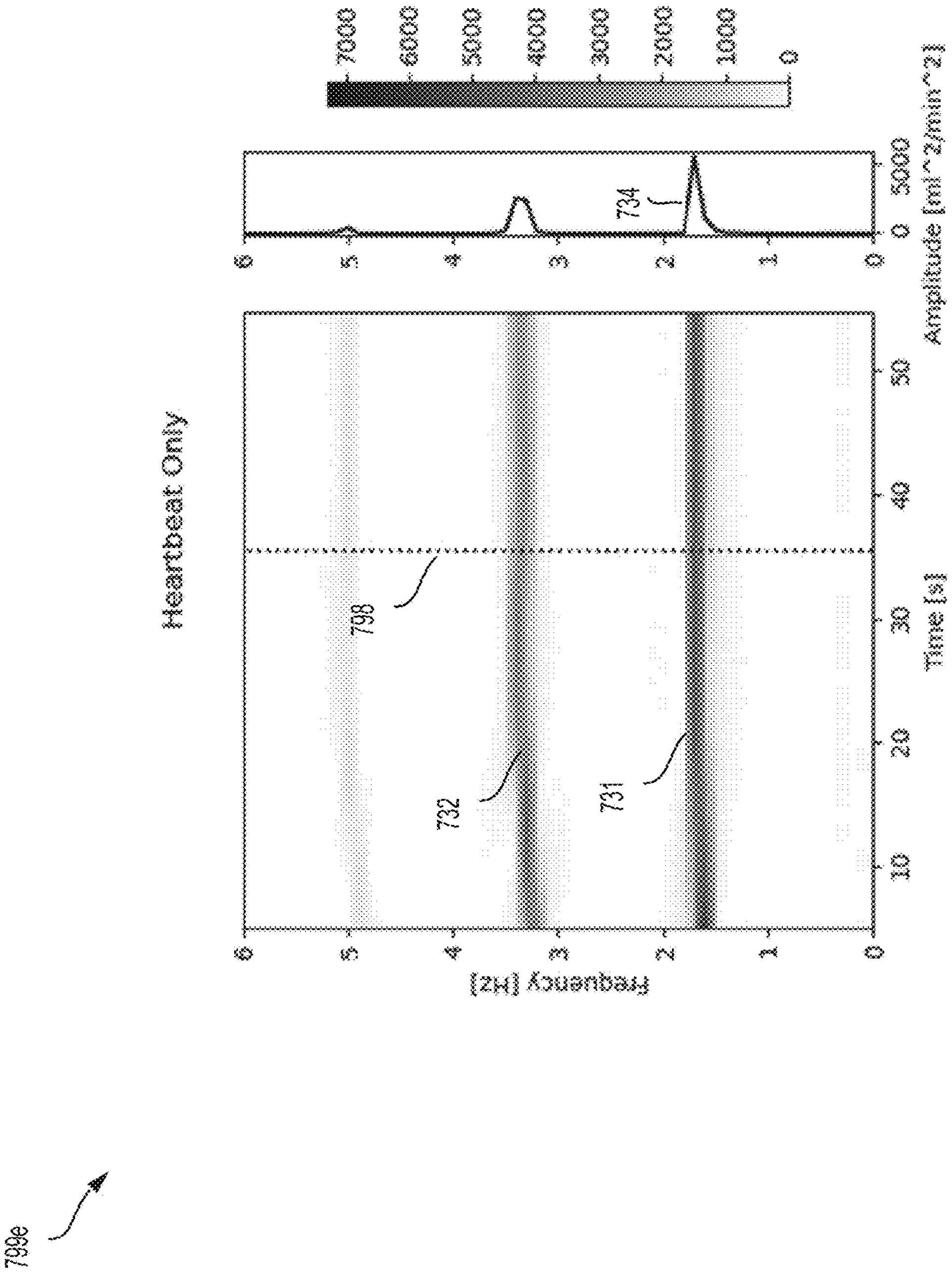
FIG. 7I shows an example of a heartbeat spectrogram used for a frequency domain analysis of the Doppler shift waveforms for automated compressions or manual compressions.

Referring to FIGS. 7B-1-7I, examples of Doppler shift waveforms are shown. The waveforms shown in FIGS. 7B-1-7I show measurements of carotid blood flow during animal studies using a swine model of cardiac arrest. VF was electrically induced by applying a brief 60 Hz current to the left ventricle using an invasive pacing catheter electrode. PEA and pseudo-PEA were induced by reducing the fraction of inspired oxygen (FiO2) delivered by a mechanical ventilator to cause hypoxia. In these figures, the "C" labels indicate peak features on the carotid blood flow trace attributable to compressions. The heart-shaped icon indicates peak features on the carotid blood flow trace attributable to mechanical pumping of the heart.

FIG. 7B-1 is an example of data showing the presence of an intrinsic heart beat producing heart-induced blood flow in the presence of automated chest compressions and automated compression-induced blood flow. The engine 358 may be configured to distinguish between the peaks due to compression-induced blood flow and the heart-induced blood flow based on one or more of a peak shape, a period or frequency associated with the peaks, and a phase shift between peaks.

The waveform 1501 includes peaks 1510*a*, 1510*b*, 1510*c*, and 1510*d* due to compression-induced blood flow and peaks 1520*a*, 1520*b*, 1520*c*, and 1520*d* due to heart-induced blood flow. The peaks 1520*a*-1520*d* occur at a pulse period 1540 that corresponds to an intrinsic pulsatile blood flow as generated by the heart. The compression peaks 1510*a*-1510*d* occur at a compression period 1550 that corresponds to an automated chest compression rate. The compression period 1550 for automated compressions is typically consistent within approximately 2-6% of a target compression rate. The peaks due to heart-induced flow and the peaks due to automated compression-induced flow are out of phase with one another. This phase difference contributes to changes in the amplitude of the peak envelopes (e.g., as exemplified most dramatically by the difference in amplitude between peaks 1510*a*, 1520*a* and peaks 1510*d*, 1520*d*). The phase difference and the resultant variation in peak amplitudes and in separations between the automated compression-induced flow peaks and heart-induced flow peaks indicate the existence of two periodic waveforms associated with blood flow.

FIG. 7B-2 is an example of data showing the presence of an intrinsic heart beat producing heart-induced blood flow in the presence of manual chest compressions and manual compression-induced blood flow. The engine 358 may be configured to distinguish between the peaks due to compression-induced blood flow and the heart-induced blood flow based on one or more of a peak shape, a period or frequency associated with the peaks, and a phase shift between peaks.

The waveform 1502 includes peaks 1515*a*, 1515*b*, 1515*c*, 1515*d*, and 1515*e* due to manual compression-induced blood flow and peaks 1521*a*, 1521*b*, and 1521*c* due to heart-induced blood flow. The peaks 1521*a*-1521*c* occur at a pulse period 1541 that corresponds to an intrinsic pulsatile blood flow as generated by the heart. The compression peaks 1515*a*-1515*e* occur at a compression period 1551 that corresponds to a manual chest compression rate. The compression period 1551 for automated compressions is typically consistent within approximately 15-50% of a target compression rate depending at least in part on the skill and/or fatigue state of the person delivering the manual compressions. The peaks due to heart-induced flow and the peaks due to manual compression-induced flow are out of phase with one another. This phase difference contributes to changes in the amplitude of the peak envelopes (e.g., as exemplified most dramatically by the difference in amplitude between peaks 1515*a* and 1521*a*). The phase difference and the resultant variation in peak amplitudes and in separations between the manual compression-induced flow peaks and heart-induced flow peaks indicate the existence of two periodic waveforms associated with blood flow.

FIGS. 7C and 7D are examples of data showing heart-induced blood flow in the absence of chest compressions. For example, a patient experiencing ROSC following a defibrillation shock for an arrhythmogenic cardiac arrest may exhibit blood flow characterized by the waveform 1502 in FIG. 7C. The waveform 1502 includes periodic feature 1530 corresponding to heart-induced blood flow. The blood flow produced during ROSC may not be that of a normal healthy heart, however, the blood flow is positive (indicating forward blood flow), even between pulses. Positive blood flow is indicated by the arrow 1590 in FIG. 7C.

As another example, a patient experiencing pseudo-PEA may exhibit blood flow characterized by the waveform 1504 in FIG. 7D. The waveform 1504 includes periodic feature 1560 1535 corresponding to heart-induced blood flow. In pseudo-PEA, the heart is generating positive (forward) blood flow (e.g., as indicated by the arrow 1590 in FIG. 7D) during pulses, but not between pulses, indicating a weak heart that is not generating life-sustaining flow. The engine 358 may distinguish between ROSC and pseudo-PEA based at least in part on the difference in positive blood flow as illustrated in FIGS. 7C and 7D. As discussed above, although both ROSC and pseudo-PEA refer to a resumption of heart-induced, or spontaneous circulation, pseudo-PEA designates a specific sub-category of heart-induced blood flow in which the ECG is indistinguishable from the cardiac arrest state of PEA. Discrimination between PEA and pseudo-PEA is difficult because the ECG's for the two states are the same and the pulse produced by pseudo-PEA is too weak to ascertain by manual radial or carotid palpation. The weakness of the pseudo-PEA pulse is illustrated in part by the lack of positive blood flow between pulses as shown in FIG. 7D. FIGS. 15A, 15B, and 15C (discussed in more detail with regard to FIGS. 14A and 14B) show examples, respectively, of ECG's for ROSC (e.g., following an arrhythmogenic cardiac arrest), for ventricular fibrillation, and for pseudo-PEA and PEA. The engine 358 may identify pseudo-PEA as distinguished from ROSC (i.e., identify pseudo-PEA as a particular sub-category of spontaneous circulation) based on the absence of positive blood flow between the peaks due to heart-induced blood flow in the Doppler shift waveform. Additionally, the engine 358 may identify ROSC that is not within the specific category of pseudo-PEA based on the presence of positive blood flow between the peaks due to heart-induced blood flow in the Doppler shift waveform.

FIG. 7E-1 is an example of automated compression induced flow during cardiac arrest. Both VF and PEA are conditions where the heart is not producing any blood flow. As such, FIG. 7E-1 shows representative data of carotid blood flow during automated compressions where blood flow is generated exclusively by chest compressions and not by the heart. The waveform 1506 includes a peak feature 1560 due to automated compression-induced blood flow. This compression peak 1560 occurs at a compression period 1565 that corresponds to a automated chest compression rate. When chest compressions are not being performed during cardiac arrest, there is substantially zero blood flow, as shown, for example, by the waveform 1507 in FIG. 7F. This waveform is substantially flat and devoid of features indicative of blood flow.

FIG. 7E-2 is an example of manual compression induced flow during cardiac arrest. Both VF and PEA are conditions where the heart is not producing any blood flow. As such, FIG. 7E-21 shows representative data of carotid blood flow during manual compressions where blood flow is generated exclusively by chest compressions and not by the heart. The waveform 1507 includes a peak feature 1570 due to manual compression-induced blood flow. This compression peak 1570 occurs at a compression period 1575 that corresponds to a manual chest compression rate. When chest compressions are not being performed during cardiac arrest, there is substantially zero blood flow, as shown, for example, by the waveform 1507 in FIG. 7F. This waveform is substantially flat and devoid of features indicative of blood flow.

The shapes of the periodic features in FIGS. 7B-1-7E-2 are due to the underlying physical mechanisms producing blood flow and, in the case of FIGS. 7B-1 and 7B-2 waveform interference due to the presence of two physical mechanisms. Because these shape details depend upon the underlying physical mechanisms, an analysis of these details by a caregiver and/or by the processor 350 enables, at least in part, a distinction between features due to heart-induced flow and compression-induced flow. Thus these features enhance the specificity of the Doppler shift waveform with regard to detecting heart-induced blood flow and distinguishing this flow from compression-induced blood flow. Furthermore, these features enable a distinction between features due to automated compressions and manual compressions.

The heart-induced blood flow detected at, for example, the carotid artery, the brachial artery, the femoral artery, etc. is a peripheral pulse caused by a pressure wave of blood moving away from the heart following a systolic ejection and reaching vessels in these extremities. The heart-induced blood flow underlying the Doppler shift waveform is a pulse waveform characterized by a peak blood flow from a systolic contraction of the heart followed by a downward sloping plateau. The peak blood flow distends the arteries and as that distention releases, it somewhat sustains the systolic wave. Shape details of the waveform produced by heart-induced blood flow may vary with the particular physiology and pathology of individual hearts and cardiovascular systems.

The compression-induced blood flow, also detected at, for example, the carotid artery, the brachial artery, the femoral artery, etc. is a peripheral pulse caused by a pressure wave of blood moving away from the heart following an externally applied compression of the chest and reaching vessels in these extremities. Shape details of the waveform produced by compression-induced blood flow may vary with the particular type of chest compressions applied, manual or automated, along with the particular physiology and pathology of individual hearts and cardiovascular systems. The shape details for manual compressions will depend on the compression mechanics as applied using the hands of a rescuer such as force, velocity, depth, rate, and hold time at any portion of the compression. As discussed above, rescuer controlled chest compressions (e.g., mechanically unassisted manual chest compressions or mechanically assisted ACD compressions) are subject to variability in compression parameters (e.g., compression rate, periodicity, compression depth, release velocity, and other compression waveform characteristics) due to variations in human performance (e.g., due to rescuer inconsistencies, fatigue, etc.). For example, the rate and/or the depth of compressions may vary by 15%-50%. Manual chest compressions also typically vary substantially from rescuer to rescuer. For example, if first rescuer holds the compression at its deepest point longer than a second rescuer, the waveforms produced for these compressions will differ. The pattern of blood flow and the hemodynamics associated with that flow will depend in part on the details of the individual rescuer's administration mechanics for chest compressions controlled by the rescuer's body. Therefore, the waveforms produced by manual compressions will exhibit variability within a waveform and not all of the peak features will have a same shape as a result. For automated compressions, the mechanics of the compressions are substantially uniform within a set of compressions and between automated compression devices. Unlike the rescuer controlled chest compressions, the automated chest compressions exhibit significantly lower variation in rate and depth. For example, the variability of the compression rate may be within +/−2-6% of a target compression rate. Force, velocity, depth, rate, and hold time at any portion of the compression will affect the shape of the waveform in a reproducible manner from peak-to-peak and from one set of waveforms to another.

In the case of automated compressions, the automated compression device may be programmed to deliver compressions according to a particular waveform profile for applied force (or depth) over time. As an example, the waveform 1506 shown in FIG. 7E-1 was generated for automated compressions where the automated compressor is programmed to deliver the compressions according to a trapezoidal waveform profile that includes a brief pause of approximately 100 msec at the bottom of the compression. The peaks in FIG. 7E-1 reflect this with a sharp rise 1562 characterized by a first slope, an initial drop 1564 characterized by a second slope that is lower than the first slope due to the hold in the compression, and then a shoulder feature 1566 preceding a drop 1568 with a third slope that is higher than the second slope and corresponds to the release of the automated compression.

In contrast to the automated compressions, manual compressions typically lack the granular control of the force or depth profile over the course of a compression that is available with an automated compression device. Thus the trace 1507 lacks characteristics like those associated with a trapezoidal waveform (1564, 1566, 1568), for example, as shown in FIG. 7E-1. Rather, the manual compressions exhibit a more sinusoidal profile with a sharp rise 1576 when the rescuer pushes down on the patient's chest to exert a downward force and a sharp fall 1577 when the rescuer lifts their body to remove or significantly reduce the downward force. In both automated and manual compressions, there are indicators of positive flow between compressions (e.g., the features 1569 and 1579). These features are due to residual blood flow between compressions.

Referring to FIGS. 7G-1 and 7G-2, examples of spectrograms representative of a frequency domain analysis of Doppler shift waveforms for automated chest compressions are shown. Similarly, referring to FIGS. 7H-1 and 7H-2, examples of spectrograms representative of a frequency domain analysis of Doppler shift waveforms for manual chest compressions are shown. FIG. 7I shows an example of a heartbeat spectrogram used for the frequency domain analysis of the Doppler shift waveforms for automated chest compressions and/or manual chest compressions. The heartbeat spectrogram 799*e* is used together with the spectrograms in FIGS. 7G-1 and 7G-2 to analyze automated chest compressions. The heartbeat spectrogram 799*e* is used together with the spectrograms in FIGS. 7H-1 and 7H-2 to analyze manual chest compressions. The Doppler shift waveform evaluation engine 358 may apply a filter such as a notch filter and/or a band pass filter to isolate and/or remove various frequency components for the frequency analyses described herein.

Each of the spectrograms is a grayscale map of the frequency content in hertz of the Doppler shift waveform as a function of time in seconds for blood flow in the carotid artery. The amplitude plot to the right of each spectrogram show a time slice amplitude as measured at a time of approximately 36 seconds, as indicated by the dotted line 798. These spectrograms further demonstrate the specificity of the Doppler shift waveform analysis in identifying and distinguishing the source of blood flow. Even with a compression rate that is approximately equal to a heart rate, the frequency profiles and peak shapes associated with the Doppler shift waveforms differ between these sources owing to differences in the blood flow induced by a heartbeat as compared to an automated chest compression or a manual chest compression. Thus sensitivity to variations in blood flow and specificity with regard to the source of the blood flow enables Doppler shift waveform analysis to provide physiological monitoring and diagnostic analysis unavailable through a more traditional method such as manual palpation for a pulse. However, the use of the wearable ultrasound sensor combined with the analytical advantages and resulting caregiver guidance provided by a defibrillator or patient monitor provides a tool for identifying heart-induced blood flow and the end of cardiac arrest that is compatible with the environment and personnel typical of an emergency resuscitation.

The spectrogram 799*a* in FIG. 7G-1 shows the frequency content for a Doppler shift waveform produced by automated compression-induced blood flow without any underlying heart beat (e.g., no pulsatile flow). Such a frequency content would be expected for a patient in cardiac arrest (e.g., VF, VT, and PEA) and receiving automated chest compressions. This spectrogram shows a dark band 781 at approximately 1.6 Hz that corresponds to automated chest compressions delivered at 100 compressions per minute with harmonics 782 and 783 appearing at approximately 3.2 Hz and 4.8 Hz. Because there is only one waveform due to automated compression-induced blood flow, the shape of the frequency band is unaffected by interference and reflects the underlying physical mechanism generating blood flow. In this example, the underlying physical mechanism is an automated compression device that generates a substantially uniform compression profile for the duration of the compressions. Additionally, the peak 784 is characterized by a similar shoulder feature and trapezoidal profile as described above in regard to FIG. 7E-1. As discussed below in regard to FIGS. 7H-1 and 7H-2, spectrograms for manual compressions would show more variation in the band at the compression frequency with weaker or fewer harmonics depending on the relative uniformity of the manual compressions. Overall, manual compressions are less uniform than automated chest compressions due to the variability naturally introduced by human delivery (e.g., as opposed to delivery by an automated mechanical compression device) and the frequency domain is not as well-defined as with automated compressions.

The spectrogram 799*b* in FIG. 7G-2 shows the frequency content of combined Doppler shift data signals from automated compression-induced blood flow and heart-induced blood flow. The grayscale variation in the compression frequency band 741 changes over time indicating a change in intensity in this frequency band due to differences in phase between automated compressions and heartbeats. Here the heartbeat is approximately 100 bpm giving rise to a high amplitude peak 744 (e.g., higher amplitude than the peak 784 in FIG. 7G-1) resulting from the interference between the automated compression-induced blood flow waveform and the heart-induced blood flow waveform. Along with the amplitude, the shape of peak 744 also differs from that of peak 784 due to interference changing the shape of the peak envelope and the width. The spectrogram shows harmonics associated with both waveforms. Thus the frequencies noted in the spectral analysis along with the shapes and characteristics of the frequency bands demonstrate differences with FIG. 7G-1 that enable a detection of heart-induced blood flow in the presence of on-going automated chest compressions. The engine 358 may thus analyze the frequency and amplitude of the Doppler shift waveform as a function of time to identify heart-induced blood flow in the presence of automated compression-induced blood flow.

The spectrogram 799*c* in FIG. 7H-1 shows the frequency content for a Doppler shift waveform produced by manual compression-induced blood flow without any underlying heart beat (e.g., no pulsatile flow). Such a frequency content would be expected for a patient in cardiac arrest (e.g., VF, VT, and PEA) and receiving manual chest compressions. This spectrogram shows a dark band 781 at approximately 1.9 Hz that corresponds to compressions delivered at approximately 114 compressions per minute with a harmonic 786 appearing at approximately 3.8 Hz. A comparison of FIG. 7H-1 with FIG. 7G-1 shows a significantly wider gray area around the frequency peaks in FIG. 7H-1 than FIG. 7G-1. This is due to the higher variability in compression rate for manual chest compressions as compared to automated mechanical chest compressions. Because there is only one waveform due to manual compression-induced blood flow, the shape of the frequency band is unaffected by interference and reflects the underlying physical mechanism generating blood flow. In this example, the underlying physical mechanism is manual chest compressions that generates a fairly uniform compression profile for the duration of the compressions, albeit less uniform than the automated mechanical chest compressions. Additionally, the peak 788 is characterized by a similar shoulder feature and trapezoidal profile as described above in regard to FIG. 7E-1.

The spectrogram 799*d* in FIG. 7H-2 shows the frequency content of combined Doppler shift data signals from manual compression-induced blood flow and heart-induced blood flow. The grayscale variation in the compression frequency band 746 changes over time indicating a change in intensity in this frequency band due to differences in phase between manual compressions and heartbeats. The faint grayscale frequency band 747 is a harmonic. Here the heartbeat is approximately 100 bpm which is slightly slower than the manual compressions giving rise to a peak 748 that is wider and has a different peak envelope shape than the peak 788. This is due to the interference between the manual compression-induced blood flow waveform and the heart-induced blood flow waveform. The spectrogram shows harmonics associated with both waveforms. The ripples 749 are due to frequency content attributable to the heartbeat. Thus the frequencies noted in the spectral analysis along with the shapes and characteristics of the frequency bands demonstrate differences with FIG. 7H-1 that enable a detection of heart-induced blood flow in the presence of on-going manual chest compressions. The engine 358 may thus analyze the frequency and amplitude of the Doppler shift waveform as a function of time to identify heart-induced blood flow in the presence of manual compression-induced blood flow.

The ability to detect the heart-induced blood flow during the ongoing chest compressions, either automated or manual, decreases chest compression pauses (i.e., increases the chest compression fraction) which improves the patient survival rate and viability. As discussed below with regard to FIGS. 12 and 13, the ability to detect ROSC during ongoing chest compressions is particularly advantageous when ROSC occurs as a delayed physiologic response after a defibrillation shock as it minimizes the risk of re-arrest. As discussed below with regard to FIGS. 14A and 14B, the ability to detect pseudo-PEA during ongoing chest compressions is particularly advantageous in distinguishing pseudo-PEA from PEA and thereby providing the most efficacious care for each of these cardiac states.

The spectrogram 799*e* in FIG. 7I shows frequency content of Doppler shift data signals from heart-induced blood flow only. The grayscale variation in the frequency band 731 along with the harmonic 732 indicates inherent variations in blood flow produced by the heart, particularly in comparison with the uniform appearance of the frequency band 781 produced by an automated compression device. Further, the appearance of these bands along with the shape of the peak 734 differ from both the bands and peaks shown in FIGS. 7G-1, 7G-2, 7H-1, and 7H-2. Therefore, each configuration of compression-induced blood flow, heart-induced blood flow, and the combination of thereof produces a frequency profile that can be readily differentiated from each other configuration.

Figure 7J:
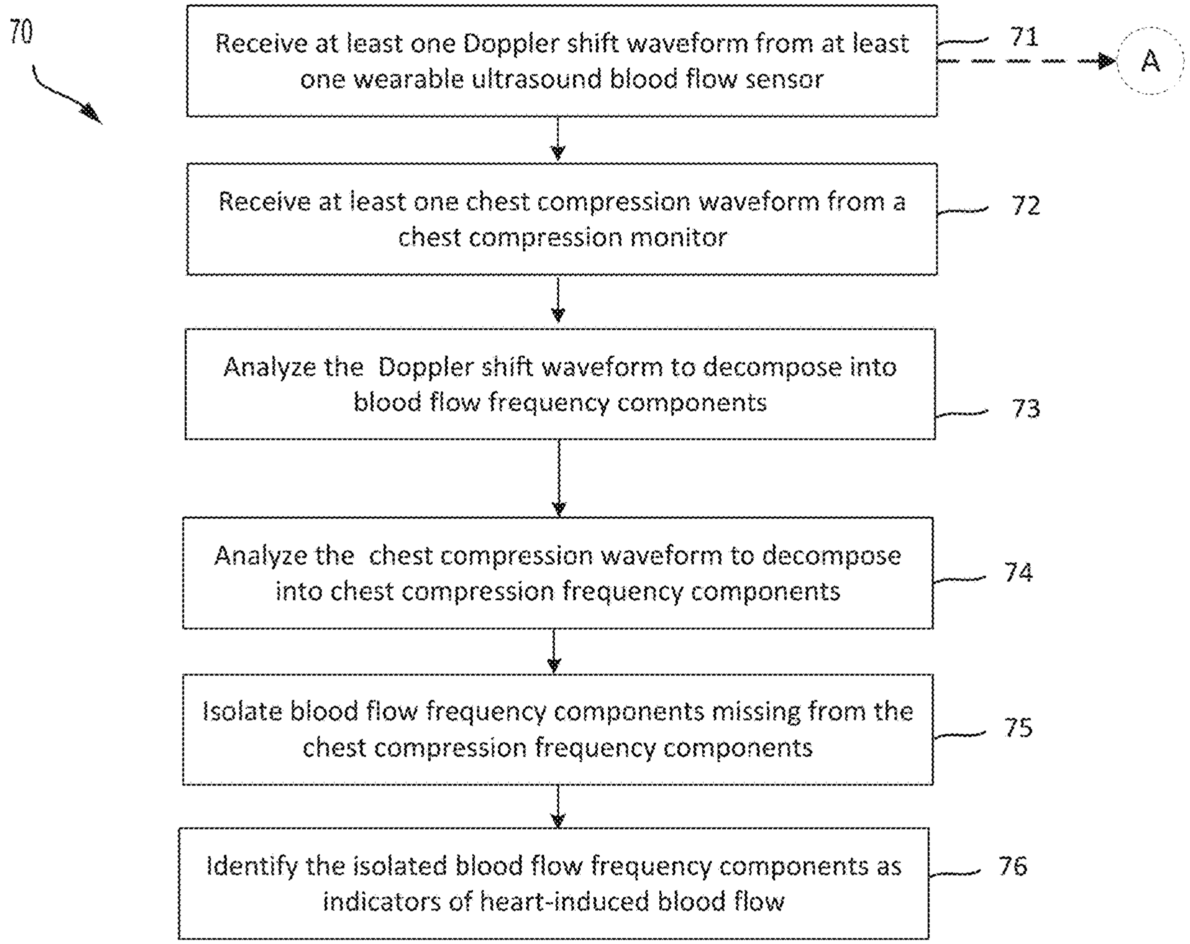
FIG. 7J shows an example of a frequency domain analysis method for a Doppler shift waveform during manual or automated compressions.

Referring to FIG. 7J, an example of a frequency domain analysis method for a Doppler shift waveform during automated or manual compressions is shown. For example, the Doppler shift waveform evaluation engine 358 may perform a frequency domain analysis 70 of the Doppler shift waveform at the stage 772. The steps shown in the analysis method 70 are examples only and not limiting of the disclosure. Additionally, the sequence of steps can be altered, e.g., by having stages added, removed, rearranged, combined, and/or performed concurrently. As demonstrated in FIGS. 7G-1 and 7G-2, the engine 358 may detect the heart-induced blood flow with the frequency domain analysis of the Doppler shift waveform during the ongoing chest compressions.

At the stage 71, the Doppler shift waveform evaluation engine 358 may receive the at least one Doppler shift waveform 310 from the wearable ultrasound blood flow sensor(s) 110. At the stage 72, the chest compression waveform evaluation engine 356 may receive the chest compression waveform 309 from the chest compression monitor 109. The Doppler shift waveform 310 may be a time domain waveform and, at the stage 73, the Doppler shift waveform evaluation engine 358 may transform the time domain waveform to a frequency domain waveform and decompose the frequency domain waveform into frequency components associated with blood flow. Similarly, the chest compression waveform 309 may be a time domain waveform. At the stage 74, the chest compression waveform evaluation engine 356 may transform the time domain waveform to a frequency domain waveform and decompose the frequency domain waveform into frequency components associated with chest compressions. The chest compression waveform evaluation engine 356 may provide the chest compression frequency components to the Doppler shift waveform evaluation engine 358. At the stage 74, the engine 358 may isolate or identify blood flow frequency components that are missing from the chest compression frequency components. These isolated or identified blood flow frequency components may be associated with blood flow patterns that originate from the heart and that are not triggered by chest compressions. Therefore, at the stage 76, the engine 358 may identify these components as indicators of heart-induced blood flow. In other words, the engine 358 may detect the heart-induced blood flow based on these isolated frequency components.

In an implementation, using multiple sensors 110 may enable the engine 358 to distinguish between compression-induced blood flow and heart-induced blood flow. For example, the multiple sensors 110 may include two wearable ultrasound blood flow sensors 110 where a first sensor 110 is positioned to detect arterial blood flow and a second sensor 110 is positioned to detect venous blood flow. The first sensor 110 may be positioned at the carotid artery and the second sensor 110 may be positioned at the jugular vein. As another example, the first and second sensors 110 may be positioned, respectively, at the femoral artery and the femoral vein or at the radial artery and the cephalic vein. These sensor positions away from the chest may better isolate the Doppler shift waveform from chest compression induced noise artifacts. The engine 358 may transform and decompose into frequency components a first Doppler shift waveform from a first sensor 110 and a second Doppler shift waveform from a second sensor 110. The engine may compare the frequency components from the two sensors and identify correlated frequency components and uncorrelated frequency components. In the absence of uncorrelated frequency components, the engine 358 would not detect heart-induced blood flow. However, in the presence of uncorrelated frequency components, the engine 358 would detect heart-induced blood flow. The correlated frequency components are associated with compression-induced blood flow and the uncorrelated frequency components are associated with spontaneous heartbeats.

Referring back to FIGS. 6 and 7A, in the absence of detected heart-induced blood flow at either stage 670 or 772, the ECG signal evaluation engine 354 repeats the heart rhythm analysis to determine if the patient's heart is in a shockable or non-shockable rhythm associated with the cardiac arrest indicated by the absence of heart-induced blood flow. In protocol 600, in the absence of heart-induced blood flow, the chest compressions that were paused at the stage 665 are resumed at the stage 675. In an implementation, the ECG analysis 680 may occur during these resumed compressions. Alternatively, the ECG analysis 680 may require a pause in chest compressions 677 during the ECG analysis. Following the ECG analysis at the stage 680, the defibrillator may discriminate between a shockable and non-shockable rhythm at the stage 685. If the rhythm is shockable, the protocol 600 returns to the stage 645 and if the rhythm is non-shockable, the protocol returns to the stage 640.

The protocol 700 follows a similar flow with an ECG analysis at the stage 780, as similarly described for the stage 680, and a distinction between shockable and non-shockable rhythms at the stage 785, as similarly described for the stage 685. Following the stage 785, the protocol 700 returns to the stage 745 for the shockable rhythm and returns to the stage 740 for the non-shockable rhythm. In an implementation, the protocol 700 may include a pause in chest compressions at the stage 777 prior to the ECG analysis 780.

In both protocols 600 and 700, in the presence of detected heart-induced blood flow, the cardiac arrest protocol ends at the stage 694 or 794 followed by a provision of advanced circulatory care at the stage 696 or 796. The advanced circulatory care may depend on the nature of the cardiac arrest and the heart-induced blood flow and is discussed in more detail with regard to FIGS. 8-14B.

In an implementation, the protocol 700 may include a pause in compressions 790 and a verification of the detection of heart-induced blood flow 792. For example, the rescuer or the automated compression device pauses compressions in order to verify the detection of heart-induced blood flow as indicated by the Doppler shift waveform. The pause may correspond to the rescuer 103 abstaining from manual chest compressions. For example, based on the detection of the heart-induced blood flow by the engine 358, the processor 350 may generate a caregiver instruction provided at the output device(s) 360 to pause chest compressions for a verification of heart-induced blood flow. Alternatively, the automated compression device 210 or 250 may pause delivery of chest compressions based on a signal from the engine 358.

The pause in compressions 790 removes any compression-induced blood flow from the Doppler waveform signal and enables the Doppler shift waveform evaluation engine 358 to analyze the signal in the absence of these contributions to verify that the engine 358 did not erroneously identify compression-induced blood flow as heart-induced blood flow. In an implementation, the Doppler shift waveform evaluation engine 358 may evaluate the Doppler shift waveform in the absence of the chest compressions (e.g., the waveform 1502 in FIG. 7C, the waveform 1504 in FIG. 7D, or a frequency content of the Doppler shift waveform as shown in the spectrogram 799*e* in FIG. 7I) against one or more pre-determined criteria to verify the detection. For example, the pre-determined criteria may include a certain number of pulse peaks (e.g., 2-5 pulse peaks), a particular intensity threshold, a particular frequency distribution, or combinations thereof.

If the engine 358 verifies the detection of heart-induced blood flow at the stage 792, the protocol 700 proceeds to the stage 794 described above. If the engine 358 does not verify the detection of heart-induced blood flow, the protocol 700 proceeds to the stage 793 to resume chest compressions paused at 790. For example, the processor 350 may generate a caregiver instruction provided at the output device(s) 360 to resume chest compressions. Alternatively, the automated compression device 210 or 250 may resume delivery of chest compressions based on a signal from the engine 358. Following the resumption of chest compressions, the protocol 700 may then proceed to the optional pause 777 followed by ECG analysis at the stage 780.

Figure 7K:
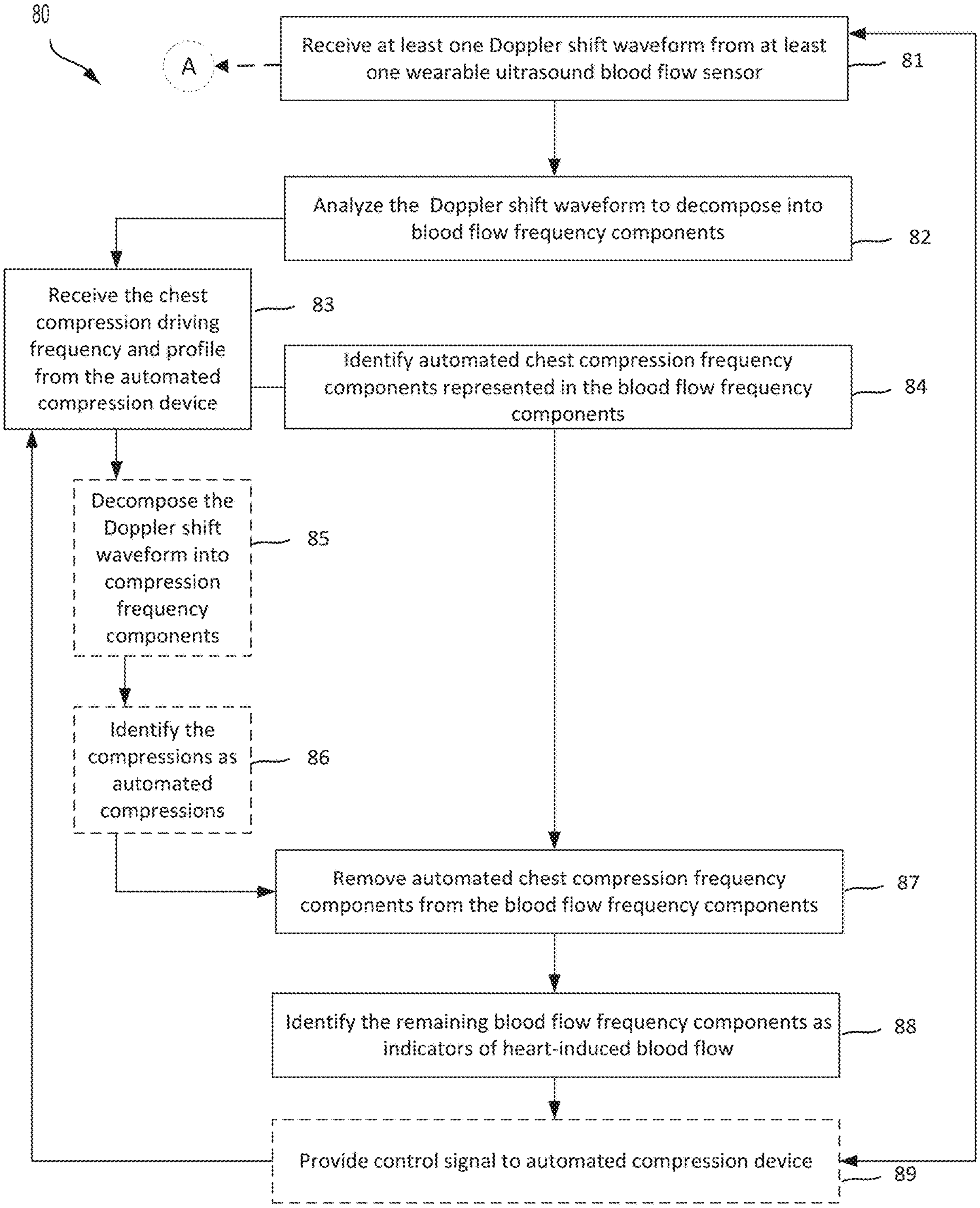
FIG. 7K shows an example of a frequency domain analysis method for a Doppler shift waveform during automated compressions.

FIG. 7K shows an example of a frequency domain analysis method for a Doppler shift waveform during automated compressions. For example, the Doppler shift waveform evaluation engine 358 may perform a frequency domain analysis 80 of the Doppler shift waveform at the stage 772. The steps shown in the analysis method 80 are examples only and not limiting of the disclosure. Additionally, the sequence of steps can be altered, e.g., by having stages added, removed, rearranged, combined, and/or performed concurrently. As demonstrated in FIGS. 7G-1 and 7G-2, the engine 358 may detect the heart-induced blood flow with the frequency domain analysis of the Doppler shift waveform during the ongoing chest compressions.

At the stage 81, the Doppler shift waveform evaluation engine 358 may receive the at least one Doppler shift waveform 310 from the wearable ultrasound blood flow sensor(s) 110. The Doppler shift waveform 310 may be a time domain waveform and, at the stage 82, the Doppler shift waveform evaluation engine 358 may transform the time domain waveform to a frequency domain waveform and decompose the frequency domain waveform into frequency components associated with blood flow.

At the stage 83, the Doppler shift waveform evaluation engine may receive the chest compression driving frequency and a profile from the automated compression device. At the stage 84, the Doppler shift waveform evaluation engine 358 may identify automated chest compression frequency components represented in the blood flow frequency components. As shown schematically in FIGS. 3A-3D, the automated compression device (e.g., 210 and/or 250) may include or be communicatively coupled to a processor that includes the Doppler shift waveform evaluation engine 358. Therefore, in an implementation, the automated compression device (e.g., 210 and/or 250) may provide its programmed compression waveform (i.e., the driving frequency for the automated compression delivery mechanism) to the Doppler shift waveform evaluation engine 358. In such an implementation, frequency analysis of the Doppler shift waveform may not require an analysis of the Doppler shift waveform to decompose into chest compression frequency components as in the analysis method 70 at the stage 74. Rather, the frequency components are known and the Doppler shift waveform evaluation engine may identify these known components and remove them at the stage 87. Alternatively or additionally, the method 80 may include the decomposition stage 85 in order to verify at the stage 86 that the compressions are in fact automated (i.e., use this decomposition to confirm and/or identify a distinction between manual and automated compressions).

At the stage 88, the Doppler shift waveform evaluation engine 358 may identify any remaining blood flow frequency components as indicators of heart-induced blood flow. Thus, the waveform analysis may be simplified when a programmed waveform from an automated compression device is available to the Doppler shift waveform evaluation engine 358.

As discussed above with regard to FIG. 3E, the communication between the automated compression device and the Doppler shift waveform evaluation engine 358 enables closed loop control of the automated compression device. For example, in an implementation, the method 80 may include the stage 89. At the stage 89, the Doppler shift waveform evaluation engine 358 may provide a control signal to the automated compression device (e.g., 210 and/or 250). The method may return to the stages 81 and 83 to receive the chest compression driving frequency and profile back from the automated compression device and the Doppler shift waveform as part of the control loop 2700 shown in FIG. 3E.

Figure 7L:
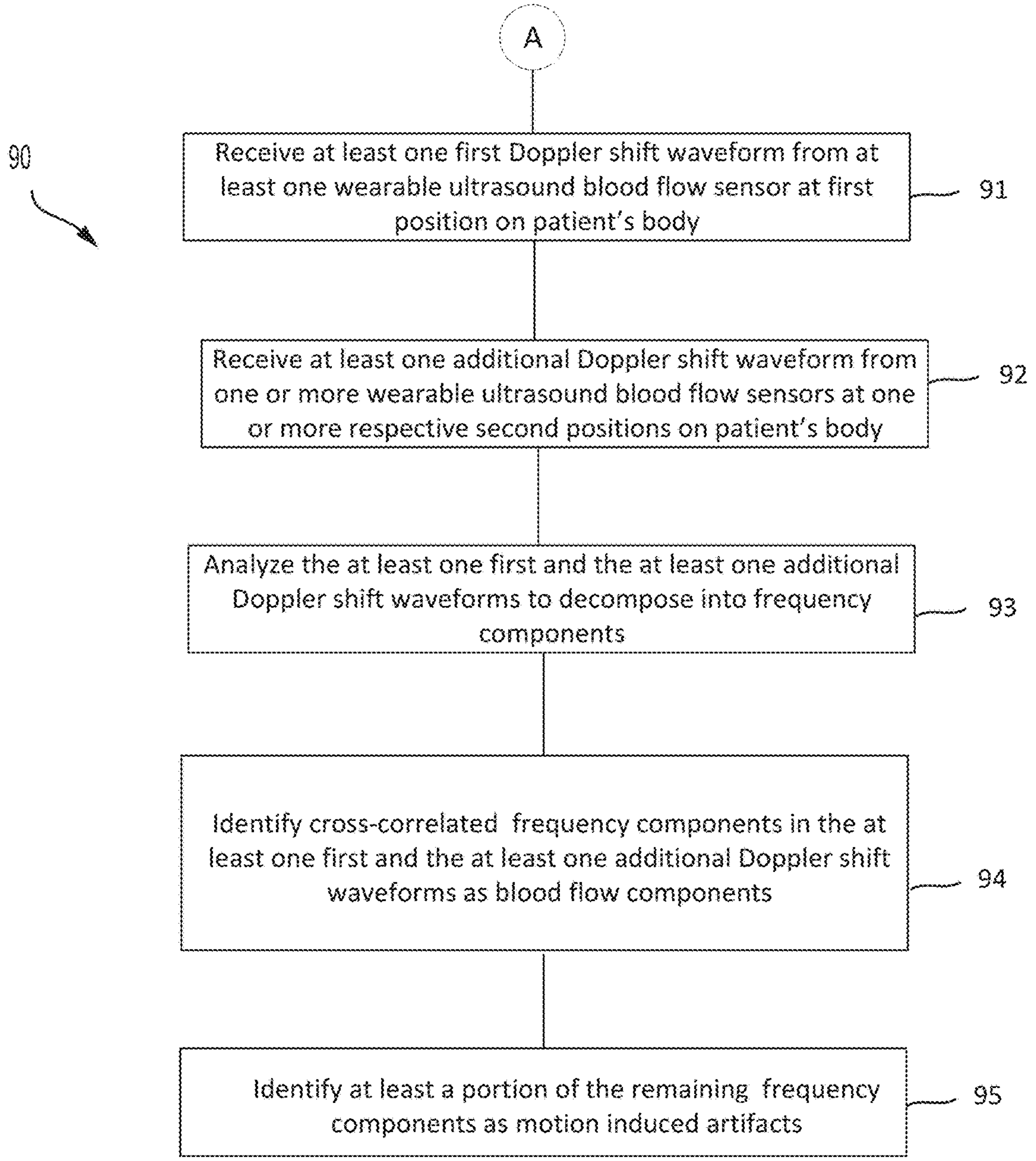
FIG. 7L shows an example of a frequency domain analysis method for a Doppler shift waveform to identify motion artifacts.

FIG. 7L shows an example of a frequency domain analysis method for a Doppler shift waveform to identify motion artifacts. For example, the Doppler shift waveform evaluation engine 358 may perform a frequency domain analysis 90 of the Doppler shift waveform. The steps shown in the analysis method 90 are examples only and not limiting of the disclosure. Additionally, the sequence of steps can be altered, e.g., by having stages added, removed, rearranged, combined, and/or performed concurrently. As demonstrated in FIGS. 7G-1 and 7G-2, the engine 358 may detect the heart-induced blood flow with the frequency domain analysis of the Doppler shift waveform during the ongoing chest compressions. Optionally, the method 90 may be incorporated into and/or combined with the method 70 or the method 80 as indicated by the arrow to the "A" link in FIGS. 7J and 7K.

As shown in FIG. 1, the caregiver may apply more than one wearable ultrasound blood flow sensor 110. These sensors may be at different parts of the body, for example, a first sensor at the carotid artery along with one or more additional sensors at the brachial artery and/or the femoral artery. The action of chest compressions, whether manual or automated, introduces noise, or motion-induced artifacts, into measured signals such as ECG and Doppler shift waveforms. Additionally, a patient may receive CPR on a gurney and/or within a moving ambulance or other vehicle. These transport tools also introduce motion-induced artifacts. One source of these artifacts in the Doppler shift waveform is due to the motion of body tissues relative to one another and relative to the wearable ultrasound blood flow sensor.

As illustrated in FIG. 4A, the motion of blood as blood flow 498 through a blood vessel 499 introduces a frequency shift between the transmitted ultrasound wave 488 and the reflected ultrasound wave 489. Motion of the tissue in which the blood vessel exists may also cause or contribute to a frequency shift between the transmitted and reflected waves. Body tissues may move during motion of a patient in a manner roughly analogous to the jiggling of gelatin within a container when the container is in motion. Additionally, while a very top surface of skin tissue may be adhered to the wearable ultrasound sensor, the tissues below this top layer may move relative to the top surface and, therefore, relative to the wearable ultrasound sensor. The tissue response to the motion is not uniform and is not the same at different parts of the body. Thus, the motion-induced artifacts in the Doppler shift waveform will vary between waveforms generated at different parts of the body.

In an implementation, the Doppler shift waveform evaluation engine 358 may perform the method 90 to identify and remove motion-induced artifact from the Doppler shift waveform signal and thereby isolate and/or identify the frequency components due to blood flow. At the stage 91, the engine 358 may receive at least one first Doppler shift waveform from at least one wearable ultrasound blood flow sensor 110 at a first position on the patient's body (e.g., a sensor located at one of the carotid artery, the brachial artery, or the femoral artery). At the stage 92, the engine 358 may receive at least one additional Doppler shift waveform from one or more wearable ultrasound blood flow sensors at one or more respective second positions on the patient's body. The second position is different than the first position. For example, if the first sensor is located at the carotid artery, then the second sensor is located at the brachial artery or the femoral artery.

At the stage 93, the engine 358 may analyze the Doppler shift waveforms from the at least two sensors located at different parts of the patient's body and decompose these waveforms into frequency components. At the stage 94, the engine 358 may identify cross-correlated frequency components in the at least one first and the at least one additional Doppler shift waveforms as blood flow components. At the stage 95, the engine 358 may identify at least a portion of the remaining frequency components as motion-induced artifacts. In an implementation, the engine 358 may filter the motion-induced artifacts and reconstruct the Doppler shift waveform without frequency components due to motion-induced artifacts. In an implementation, the engine 358 may cause the CPU 402 to adjust the selection of TX/RX pairs based on the detected motion-induced artifacts in order to select the pairs that produce the weakest motion-induced artifacts relative to the blood flow signal. In other words, the CPU 402 may adjust the selection of TX/RX pairs to maximize the signal to noise ratio for blood flow components. The selected TX/RX pairs may depend on the orientation of the wearable ultrasound blood flow sensor relative the skin and/or the artery and/or may depend on the proximity to the adhesive of the tissue generating noise and/or containing the blood flow.

Figure 8:
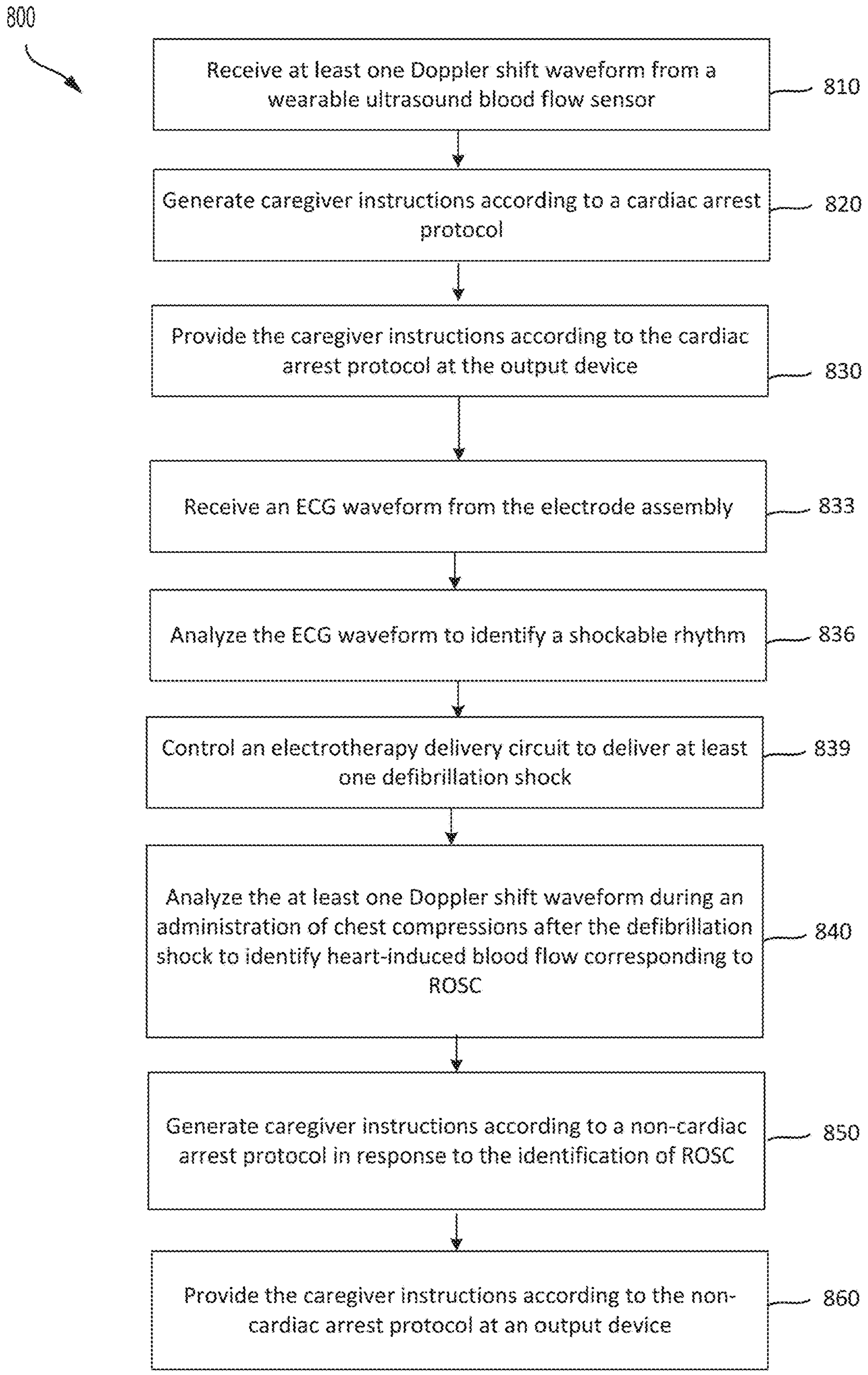
FIG. 8 shows an example of a method of identifying ROSC with a wearable ultrasound blood flow sensor.

Referring to FIG. 8, an example of a method of identifying ROSC with a wearable ultrasound blood flow sensor is shown. The steps shown in the method 800 are examples only and not limiting of the disclosure. Additionally, the sequence of steps can be altered, e.g., by having stages added, removed, rearranged, combined, and/or performed concurrently. The method 800 follows the portions of the protocol 700 in FIG. 7A that are applicable to arrhythmogenic cardiac arrest.

At the stage 810, as similarly described in regard to the stage 510 of FIG. 5, the Doppler shift waveform evaluation engine 358 may receive at least one Doppler shift waveform 310 from the wearable ultrasound blood flow sensor(s) 110. Once the Doppler shift waveform evaluation engine 358 receives the waveform 310, the engine 358 may analyze the waveform 310 to monitor chest compression-induced blood flow and to detect heart-induced blood flow. This monitoring and analysis may operate in the background of other medical device functions, such as ECG analysis and shock delivery, and continue substantially uninterrupted in a manner similar to the monitoring of other physiological parameters of the patient, such as pulse oximetry or capnography.

At the stage 820, as similarly described in regard to the stage 520 of FIG. 5, the processor 350 may generate caregiver instructions according to a cardiac arrest protocol. At the stage 830, as similarly described in regard to the stage 530 of FIG. 5, the output device(s) 360 may provide these generated instructions.

At the stage 833, the ECG signal evaluation engine 354 may receive an ECG waveform 308 from the electrodes 107 and 108. The ECG signal evaluation engine 354 may analyze the ECG waveform at the stage 836 in order to determine if the ECG waveform indicates a shockable rhythm and, if so, identify the ECG rhythm as shockable, as opposed to non-shockable. In response to the identification of the shockable rhythm, the processor 350 may control an electrotherapy delivery circuit 340 at the stage 839 to deliver at least one defibrillation shock to the victim 101 via the electrodes 107 and 108.

Following the shock administration, the Doppler shift waveform evaluation engine 358 may analyze the Doppler shift waveform(s) 310 to identify heart-induced blood flow corresponding to ROSC at the stage 840. As described in more detail below with regard to FIGS. 10A and 10B, the analysis may be ongoing during the administration of the chest compressions and ventilations or may occur during the ventilations. Either of these provides an improved chest compression fraction over compression/ventilation cycles interrupted for pulse check pauses as discussed below in regard to FIG. 11.

In an implementation, the Doppler shift waveform evaluation engine 358 may analyze the Doppler shift waveform(s) 310 to identify heart-induced blood flow during ongoing chest compressions. The analysis is not limited or confined to periods of time in which chest compressions are not administered to the patient. Examples of Doppler shift waveforms indicative of ROSC are discussed above with regard to FIGS. 7B-1 and 7B-2. The software, hardware and/or firmware of the Doppler shift waveform evaluation engine 358 may enable the engine 358 to identify the heart-induced blood flow in the presence of contributions from chest compression-induced blood flow to the Doppler shift waveform(s) 310.

At the stage 850, in response to the identification of ROSC, the processor 350 may generate caregiver instructions for interventions according to a non-cardiac arrest protocol. The output device(s) 360 may provide the caregiver instructions for the rescuer at the stage 860. Examples of interventions for advanced circulatory care during ROSC according to the non-cardiac arrest protocol are provided in Table 1. The interventions listed in Table 1 are examples only and not limiting of the disclosure and other interventions may be provided.

TABLE 1

| ROSC interventions |
| --- |
| Airway management with endotracheal tube and 10 breaths per minute |
| Provide oxygen to maintain SpO2 at 92-98% |
| Titrate oxygen to maintain PETCO2 of 35-40 mm Hg |
| Insert intravenous port |
| Provide saline, epinephrine, dopamine, or norepinephrine to maintain systolic blood pressure >90 mm Hg |
| Obtain 12-lead ECG |
| Treat myocardial infarction with a percutaneous coronary intervention |
| Provide glucose |
| Treat non-convulsive seizures indicated by electroencephalogram |
| Provide body temperature management |

ROSC indicates that the victim is no longer in cardiac arrest. Once the victim exhibits ROSC, providing interventions such as immediate transport to a medical facility, administration of medications, and other elements advanced circulatory care may be critical for patient survival and recovery without significant neurological or other physical impairment. Although ROSC indicates the resumption of a productive heart rhythm, the patient is still in a significantly weakened physiological state, likely with weak blood flow. However, the chest compressions and ventilations according to the cardiac arrest protocol are no longer of benefit to the patient post-cardiac arrest. In some cases, as discussed further below in regard to FIGS. 12, 13, 14A, and 14B continuing chest compressions post-cardiac arrest may delay other interventions and may cause a deterioration in a victim's health.

Figure 9:
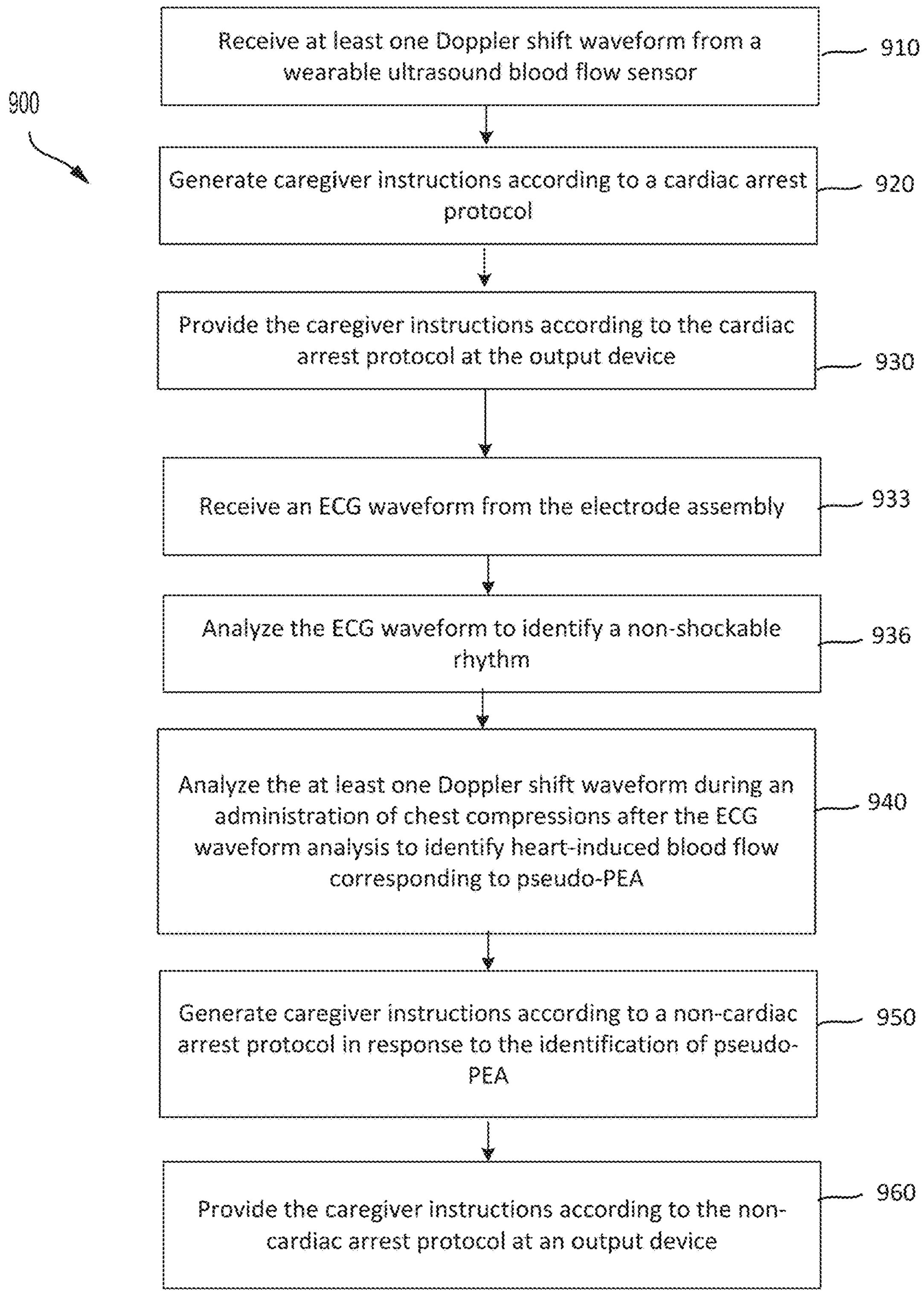
FIG. 9 shows an example of a method of identifying pseudo-PEA with a wearable ultrasound blood flow sensor.

Referring to FIG. 9, an example of a method of identifying pseudo-PEA with a wearable ultrasound blood flow sensor is shown. The steps shown in the method 900 are examples only and not limiting of the disclosure. Additionally, the sequence of steps can be altered, e.g., by having stages added, removed, rearranged, combined, and/or performed concurrently. The method 900 follows the portions of the protocol 700 in FIG. 7A that are applicable to non-arrhythmogenic cardiac arrest.

At the stage 910, as similarly described in regard to the stage 510 of FIG. 5, the Doppler shift waveform evaluation engine 358 may receive at least one Doppler shift waveform 310 from the wearable ultrasound blood flow sensor(s) 110. Once the Doppler shift waveform evaluation engine 358 receives the waveform 310, the engine 358 may analyze the waveform 310 to monitor chest compression-induced blood flow and to detect heart-induced blood flow. This monitoring and analysis may operate in the background of other medical device functions, such as ECG analysis and shock delivery, and continue substantially uninterrupted in a manner similar to the monitoring of other physiological parameters of the patient, such as pulse oximetry or capnography.

At the stage 920, as similarly described in regard to the stage 520 of FIG. 5, the processor 350 may generate caregiver instructions according to a cardiac arrest protocol. At the stage 930, as similarly described in regard to the stage 530 of FIG. 5, the output device(s) 360 may provide these generated instructions.

At the stage 933, the ECG signal evaluation engine 354 may receive an ECG waveform 308 from the electrodes 107 and 108. The ECG signal evaluation engine 354 may analyze the ECG waveform at the stage 936 in order to determine if the ECG waveform indicates a non-shockable rhythm and, if so, identify the ECG rhythm as non-shockable, as opposed to non-shockable.

At the stage 940, the Doppler shift waveform evaluation engine 358 may continue to analyze the Doppler shift waveform(s) 310 to identify heart-induced blood flow corresponding to pseudo-PEA. As described in more detail below with regard to FIGS. 10A and 10B, the analysis may be ongoing during the administration of the chest compressions and ventilations or may occur during the ventilations. Either of these provides an improved chest compression fraction over compression/ventilation cycles interrupted for pulse check pauses as discussed below in regard to FIG. 11.

In an implementation, the Doppler shift waveform evaluation engine 358 may analyze the Doppler shift waveform(s) 310 to identify heart-induced blood flow during ongoing chest compressions. The analysis is not limited or confined to periods of time in which chest compressions are not administered to the patient. Examples of Doppler shift waveforms that indicate pulsatile blood flow due to pseudo-PEA are discussed above in regard to FIG. 7D. The software, hardware and/or firmware of the Doppler shift waveform evaluation engine 358 may enable the engine 358 to identify the heart-induced blood flow in the presence of contributions from chest compression-induced blood flow to the Doppler shift waveform(s) 310.

At the stage 950, in response to the identification of pseudo-PEA, the processor 350 may generate caregiver instructions according to a non-cardiac arrest protocol. The output device(s) 360 may provide the caregiver instructions for the rescuer at the stage 960. Examples of interventions for advanced circulatory care during pseudo-PEA according to the non-cardiac arrest protocol are provided in Table 2. The interventions listed in Table 2 are examples only and not limiting of the disclosure and other interventions may be provided. In some cases, the cause of a non-arrhythmogenic heart rhythm may be trauma (e.g., blunt force trauma, penetrating trauma, etc.) and the interventions provided may correspond to trauma interventions.

TABLE 2

| pseudo-PEA interventions |
|---|
| Antibiotics or other medications for infection control |
| Blood replacement |
| Fluid replacement (e.g., saline) |
| Anti-convulsive therapy |
| Transport to a trauma center |
| Application of a tourniquet or other hemorrhage control |
| Decompression of a pneumothorax |
| Temperature management |
| Administration of tranexamic acid |
| Delivery of 100% oxygen via bag-valve mask or non-rebreather mask |
| Pain management medications |
| Ultrasound imaging to look for internal bleeding |
| Monitor lactic acid with point-of-care lactate meter |
| Electrolyte corrections |
| Extracorporeal membrane oxygenation (ECMO) |

Pseudo-PEA indicates that the victim is no longer in cardiac arrest. Once the victim exhibits pseudo-PEA, providing interventions such as immediate transport to a medical facility, administration of medications, and other elements advanced circulatory care may be critical for patient survival and recovery without significant neurological or other physical impairment. Although pseudo-PEA indicates the resumption of a pulsatile blood flow, the patient is still in a significantly weakened physiological state, likely with weak blood flow. However, the chest compressions and ventilations according to the cardiac arrest protocol are no longer of benefit to the patient post-cardiac arrest. In some cases, as discussed further below in regard to FIGS. 12, 13, 14A and 14B, continuing chest compressions post-cardiac arrest may delay other interventions and may cause a deterioration in a victim's health.

Figure 10A:
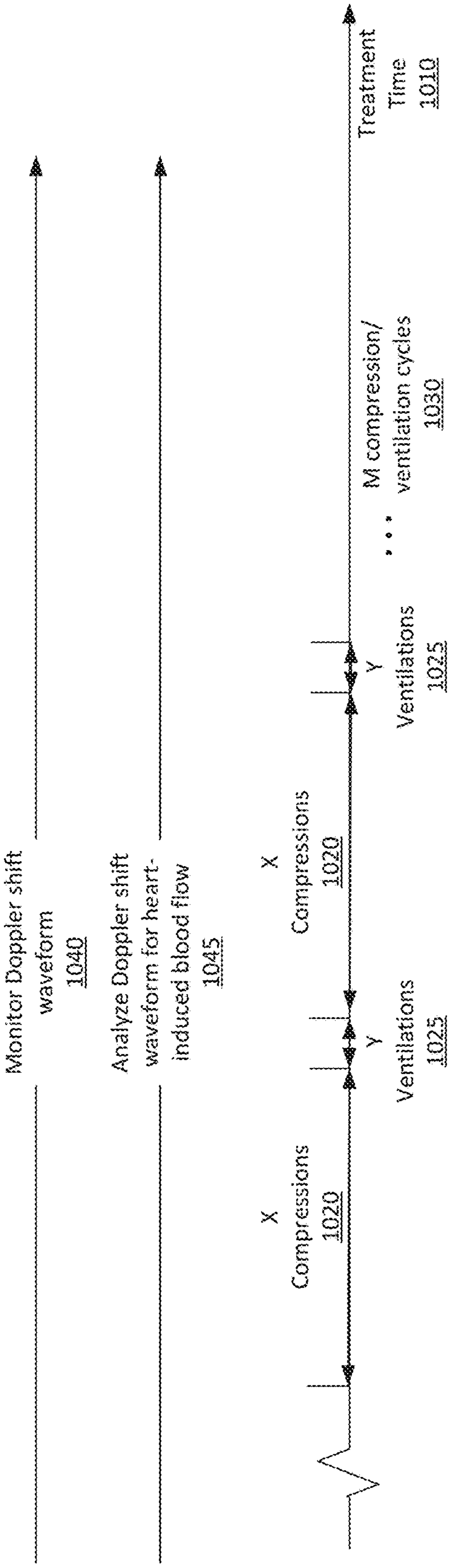
FIG. 10A shows an example of ongoing Doppler shift waveform analysis during chest compressions and ventilations.
Figure 10B:
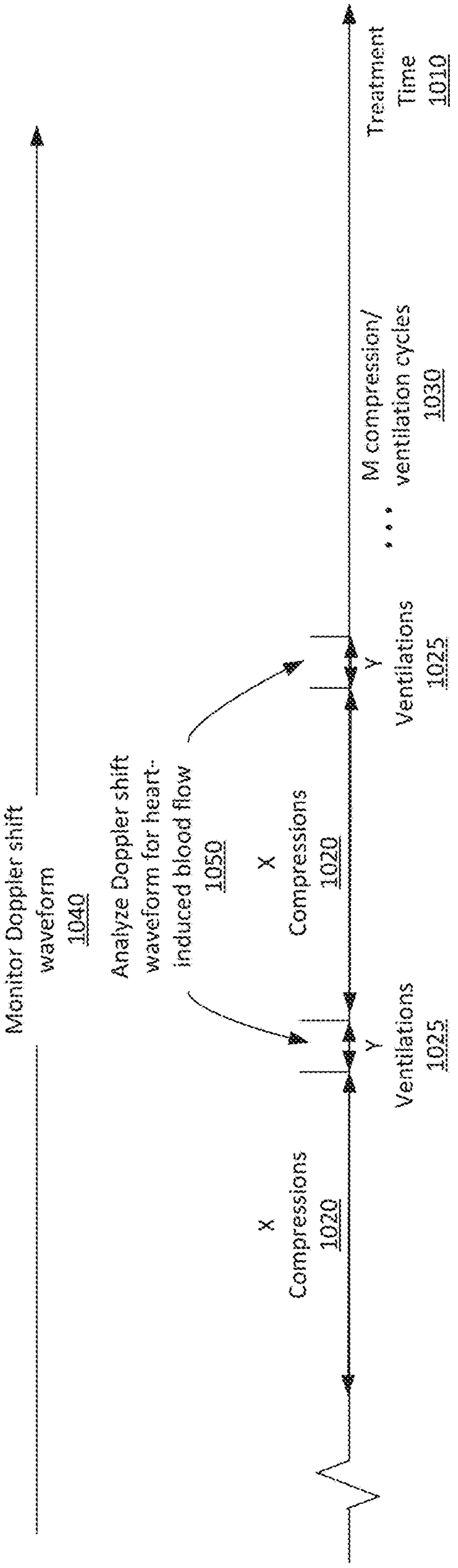
FIG. 10B shows an example of Doppler shift waveform monitoring during ventilation cycles.
Figure 11:
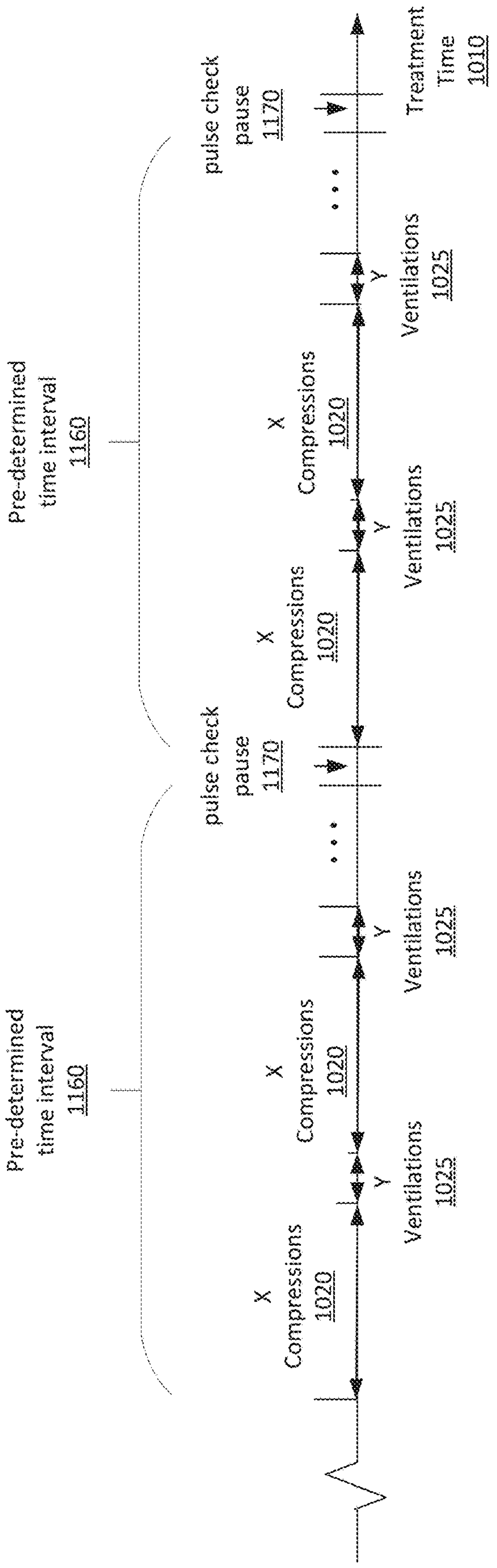
FIG. 11 shows an example of chest compressions and ventilations with pauses for pulse checks.

FIGS. 10A, 10B, and 11 exemplify an advantage of detecting heart-induced blood flow with the sensor 110 as compared with a manual palpation. As discussed above, the use of the wearable ultrasound blood flow sensor may provide an advantage of eliminating a pause in chest compressions for the purpose of detecting and identifying heart-induced blood flow. The elimination of a pause in chest compressions, even a short pause of 1-5 seconds, is of significant physiological benefit to the cardiac arrest victim. For tissue oxygenation at a level sufficient to sustain live tissue and prevent tissue damage, the interruptions in chest compressions must be minimized in order to maximize the amount of time that the compressions generate blood flow. For example, rates of survival from cardiac arrest may drop by approximately 18% with even five seconds of interruption in chest compressions.

Referring to FIG. 10A, an example of ongoing Doppler shift waveform analysis during chest compressions and ventilations is shown. The treatment of the victim occurs over a treatment time 1010 as exemplified by the timeline in FIG. 10A. Chest compressions may be delivered in a predetermined ratio with ventilations. For example, a cardiac arrest protocol may specify that a compression/ventilation cycle include a series of X chest compressions 1020 followed by a series of Y ventilations 1025. The ratio X:Y is the guideline promulgated by a resuscitative care organization like the American Heart Association. The ratio may be, for example, 15:2 for pediatric patients and 30:2 for adult patients. As shown in FIG. 10A, with the wearable ultrasound blood flow sensor 110, this cycle may be repeated for M compression/ventilation cycles 1030. The M compression/ventilation cycles 1030 may continue either until the sensor 110 detects heart-induced blood flow or for the duration of a cardiac arrest protocol implementation. As shown in FIG. 10A, the wearable ultrasound blood flow sensor 110 may monitor 1040 the Doppler shift waveform and analyze 1045 the monitored waveform for heart-induced blood flow 1045 substantially continuously during the M compression/ventilation cycles 1030.

Referring to FIG. 10B, an example of Doppler shift waveform monitoring during ventilation cycles is shown. The treatment of the victim occurs over a treatment time 1010 as exemplified by the timeline in FIG. 10B. In order to eliminate contributions to the Doppler shift waveform signal from chest compressions, the Doppler shift waveform evaluation engine 358 may analyze the Doppler shift waveform 1050 during the ventilation periods when chest compressions are not occurring.

In order to confine the Doppler shift waveform analysis to the ventilation periods, the chest compression waveform evaluation engine 356 may identify the ventilation periods. For example, the chest compression waveform evaluation engine 356 may identify the ventilations based on an absence of chest compressions as indicated by the chest compression waveform 309. Additionally or alternatively, the ventilation metrics engine 390 may identify ventilation periods based on ventilation data from the ventilation and/or respiration sensors 395. For example, changes in pulse oximetry, capnography, airflow, spirometry etc. may correspond to the administration of ventilations to the victim. The chest compression waveform evaluation engine 356 and/or the ventilation metrics engine 390 may provide a first signal, flag, or other indication to the Doppler shift waveform evaluation engine 358 to identify the beginning of the ventilation periods. In response, the Doppler shift waveform evaluation engine 358 may initiate analysis of the Doppler shift waveform in response to the first signal, flag, or other indication. In an implementation, the Doppler shift waveform evaluation engine 358 may cease analysis after a pre-determined time interval corresponding to an expected length of the ventilation period. Alternatively, the chest compression waveform evaluation engine 356 and/or the ventilation metrics engine 390 may provide a second signal, flag, or other indication to the Doppler shift waveform evaluation engine 358 to identify the end of the ventilation periods and/or the resumption of chest compressions. The Doppler shift waveform evaluation engine 358 may cease analysis in response to the second signal, flag, or other indication.

Figure 10C:
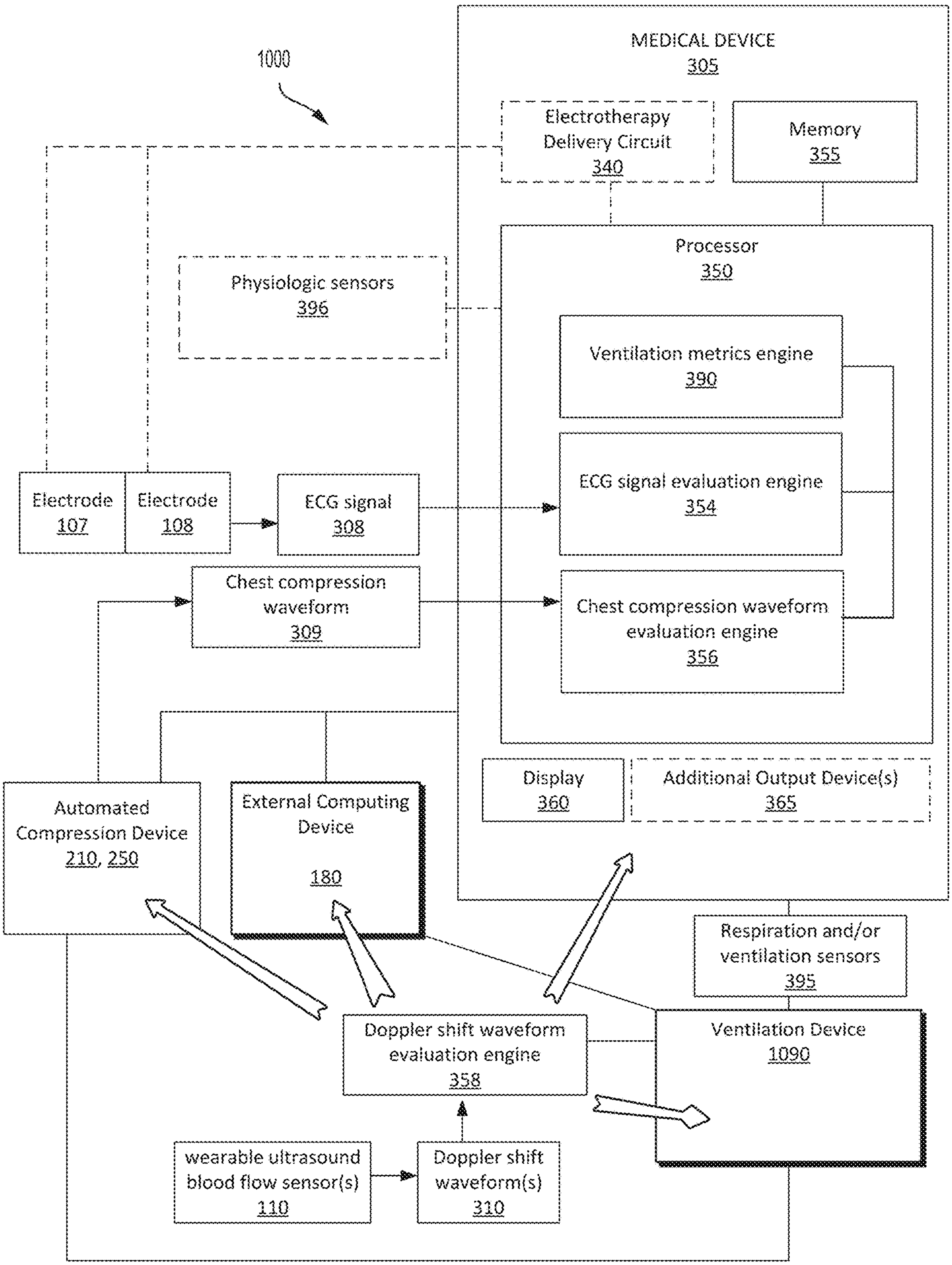
FIG. 10C is a schematic diagram of a system configured for detection of blood flow with a wearable ultrasound blood flow sensor that includes an automated compression device and a ventilation device.

Referring to FIG. 10C, an example of a system configured for detection of blood flow with a wearable ultrasound blood flow sensor that includes an automated compression device and a ventilation device. A quantity of each component in the hardware system 1000 of FIG. 10C is an example only and other quantities of each, or any, component could be used. An automated ventilation device 1090 generally provides a faster transition in and out of the ventilation pauses shown in FIG. 10A than ventilations provided by a caregiver. Additionally, the ventilation therapy provided is generally more efficient from an efficacy perspective. In an implementation the ventilation device 1090 is communicatively coupled to the Doppler shift waveform evaluation engine 358 to signal the engine 358 to perform analysis during pauses in the ventilation therapy provided by the ventilation device 1090. In an implementation, the Doppler shift waveform evaluation engine 358 may be configured to receive start and stop indications for a ventilation cycle from the ventilation device and analyze the at least one Doppler shift waveform during the ventilation cycle in response to the start and stop indications. In this manner, the evaluation may be contained within the pauses while still maintaining pauses that are as brief as possible within the constraints of providing appropriate therapies. As illustrated in FIG. 10C, the Doppler shift waveform evaluation engine 358 may be disposed in the automated compression device (e.g., 210 and/or 250), the external computing device 180, the medical device 305, or the ventilation device 1090 or is a distributed resource in two or more of these devices. The ventilation device 1090 may be further coupled to the medical device 305, the automated compression device (e.g., 210 and/or 250), and/or the external computing device 180 in order to coordinate therapies and analysis amongst these devices.

Referring to FIG. 11, an example of chest compressions and ventilations with pauses for pulse checks is shown. In comparison with FIGS. 10A and 10B, FIG. 11 illustrates the additional pauses introduced for pulse checks, for example manual palpations. Without the wearable ultrasound blood flow sensor 110, the compression/ventilation cycles are repeated for a pre-determined time interval 1160, such as 2 minutes, with a pause 1170 in compressions/ventilations for a pulse check at the end of the pre-determined time interval 1160. The entire sequence of the compression/ventilation cycle with the pulse check pause is repeated times during the treatment time either until a pulse is detected during the pause 1170 or for the duration of a cardiac arrest protocol implementation.

As demonstrated by FIGS. 10A, 10B, and 11, both the continuous analysis of the Doppler shift waveform without pauses as shown in FIG. 10A and the analysis of the Doppler shift waveform during ventilations as shown in FIG. 10B increase the fraction of time that chest compressions are applied during the cardiac arrest intervention as compared with manual pulse checks by eliminating the extra pauses for the manual palpation. As discussed above, it is critical for patient recovery to maximize the compression time and minimize pauses in compressions. The ventilations are also critical to survival and therefore are a necessary pause in compressions. Additionally, continuous analysis or analysis during the ventilation periods provide more granularity for detecting the heart-induced blood flow than the manual pulse checks. The ventilation periods occur after every X compressions (e.g., 15 or 30 compressions). At a compression rate of 100 compressions/minute, the ventilation periods occur approximately every 9-16B seconds. This interval is significantly lower than the manual pulse checks introduced every two minutes, and, therefore, provides more granularity for detecting the heart-induced blood flow than the manual pulse checks. As discussed below in more detail in regard to FIGS. 12 and 13, this increased granularity may be critical in avoiding re-arrest induced by chest compressions in the presence of heart-induced blood flow.

Figure 12:
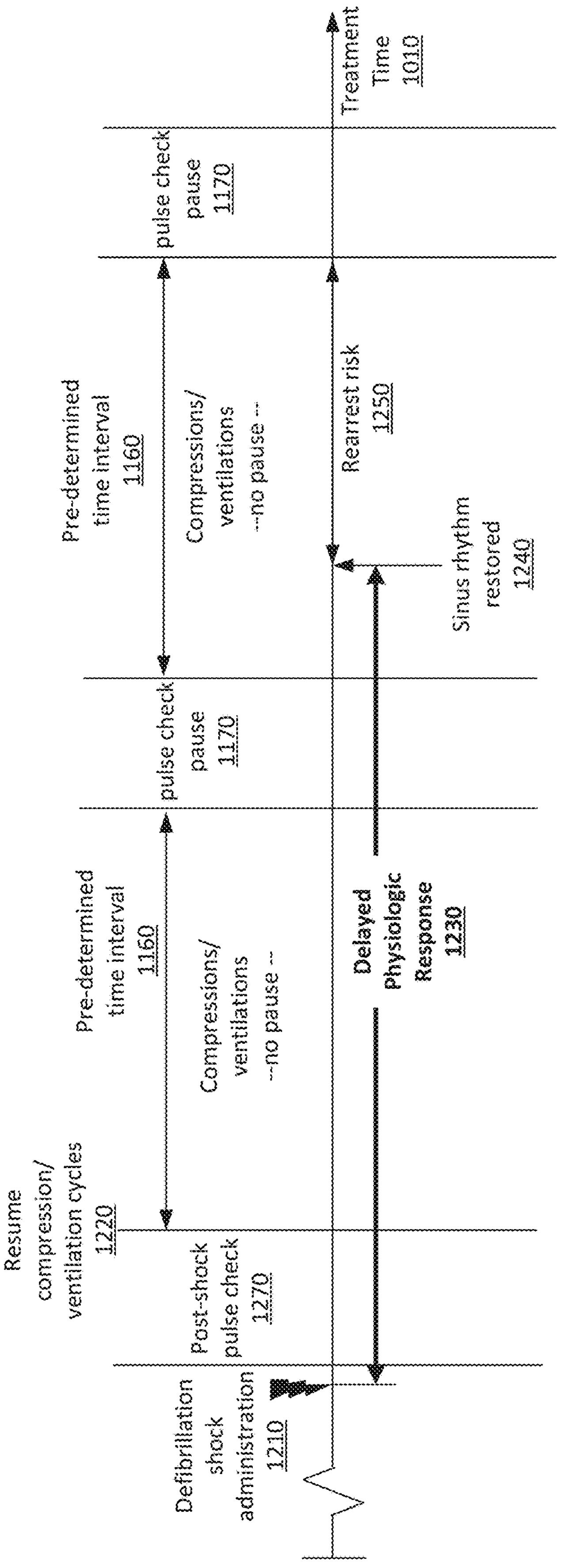
FIG. 12 schematically illustrates the risk of re-arrest risk during chest compressions without a wearable ultrasound blood flow sensor.

Referring to FIG. 12, the risk of re-arrest during chest compressions without a wearable ultrasound blood flow sensor is illustrated schematically. For an arrhythmogenic cardiac arrest, immediately following the shock administration 1210, the rescuer administers a post-shock pulse check 1270 prior to the resumption of compression/ventilation cycles 1220. The electromechanical response of the heart to the defibrillation shock is not instantaneous. In some cases, it may take up to 30 seconds for the heart to resume a sinus rhythm that induces blood flow (e.g., the sinus rhythm restoration 1240). Thus, there may be a delayed physiologic response 1230 of the heart to the defibrillation shock. When this delayed response 1230 exceeds the 2-3 second duration of the post-shock pulse check 1270, no sinus rhythm is detected during this pulse check 1270. When no pulse is detected at the pulse check 1270, the rescuer resumes 1220 the compression/ventilation cycles for the pre-determined time interval 1160. As similarly discussed in regard to FIG. 11, in the absence of the wearable ultrasound blood flow sensor, the rescuer provides compressions/ventilations in an X:Y ratio for a pre-determined time interval 1160 followed by a pause 1170 for a pulse check. The pre-determined time interval 1160 is typically about 2 minutes. The pause 1170 in compression/ventilation cycles is typically about 2-3 seconds. The sinus rhythm restoration 1240 is shown during a second compression/ventilation cycle as an example only. This restoration 1240 and the accompanying ROSC may occur at any point in the treatment time 1010 after the defibrillation shock administration 1240. Because the pulse check pauses 1270 are necessarily brief to maximize chest compression-induced blood flow and occur at pre-determined time intervals in order to ensure steady and reliable compression delivery by the rescuer, it is likely that the delayed sinus rhythm restoration 1240 does not coincide with the pulse check pauses 1170 and likely that this rhythm restoration occurs during the ongoing compressions/ventilations. Unfortunately, compressions administered to a heart in a normal sinus rhythm can cause re-fibrillation. This is known to one of skill in the art as re-arrest. Thus, if the sinus rhythm is restored and compressions are delivered, there is a re-arrest risk 1250.

Figure 13:
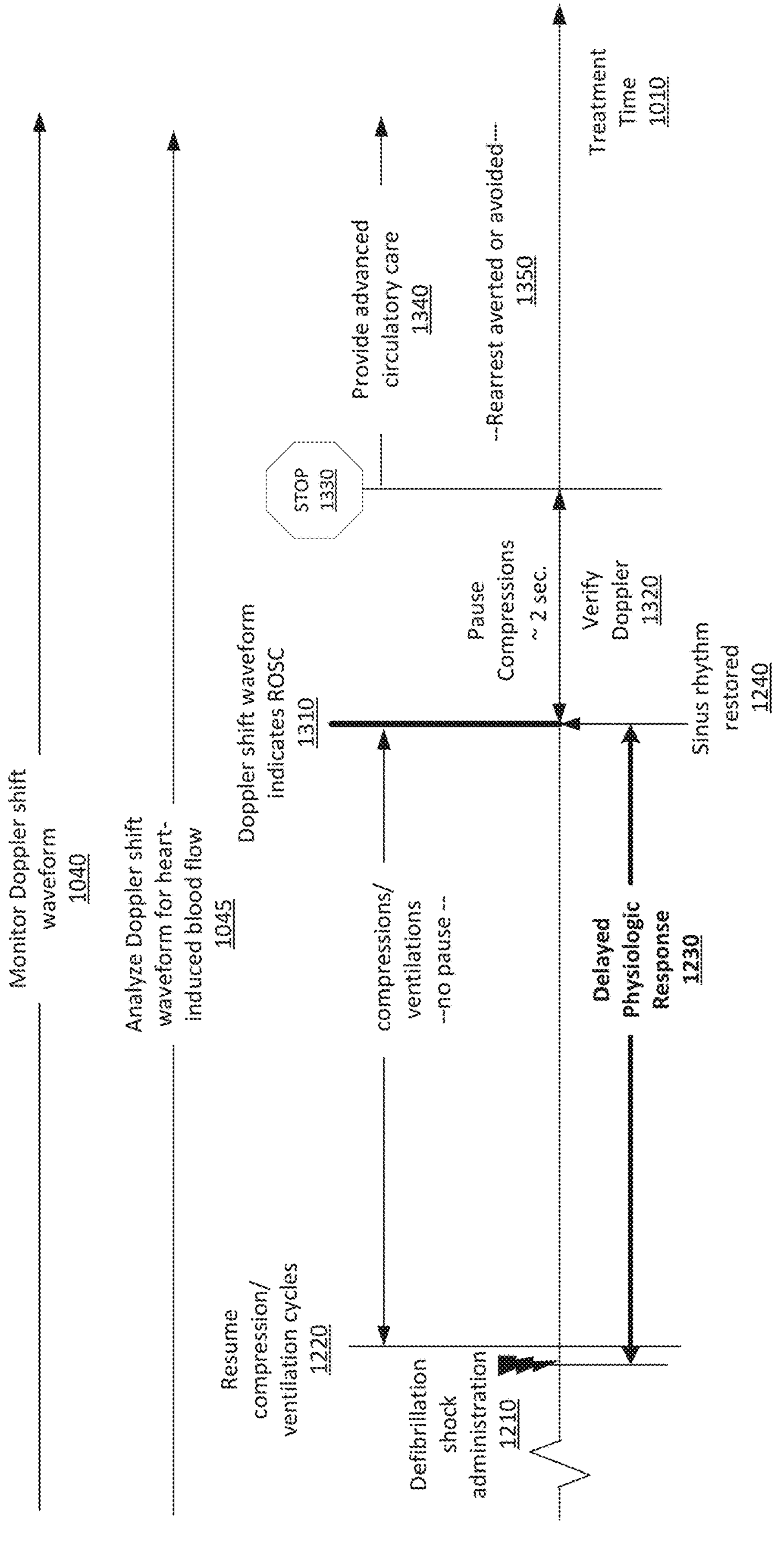
FIG. 13 schematically illustrates avoiding re-arrest during chest compressions with a wearable ultrasound blood flow sensor.

Referring to FIG. 13, avoiding re-arrest during chest compressions with a wearable ultrasound blood flow sensor is illustrated schematically. The Doppler shift waveform evaluation engine 358 may substantially continuously monitor 1040 the Doppler shift waveform from the wearable ultrasound blood flow sensor 110. Additionally, in an implementation, the Doppler shift waveform evaluation engine 358 may substantially continuously analyze 1045 the Doppler shift waveform for heart-induced blood flow. As illustrated in FIG. 13, this ongoing Doppler shift waveform analysis 1045 may occur during ongoing compression/ventilation cycles without any pauses to check for a pulse. Further, the ongoing Doppler shift waveform analysis 1045 may enable the rescuer to resume the compression/ventilation cycles 1220 immediately after the defibrillation shock administration 1210 without a delay to check for a pulse (e.g., without the post-shock pulse check 1270 that delays the resumption of compression/ventilation cycles as shown in FIG. 12). The sinus rhythm restoration 1240 may occur at any time after the defibrillation shock administration 1210 and the Doppler shift waveform evaluation engine 358 may detect ROSC based on the Doppler shift waveform analysis 1045. In response to this ROSC detection, the rescuer can pause compressions (e.g., a 1-3 second pause) to verify 1320 the Doppler waveform analysis, as similarly described above with regard to the stage 790 and 792 in FIG. 7A. In response to the verification 1320, the engine 358 can generate a caregiver instruction to stop chest compressions (e.g., the stop 1330 in FIG. 13) and the output device(s) 360 can provide the caregiver instruction to stop chest compression. In this manner, the compression time is maximized by eliminating pulse check pauses. Additionally, compressions are not delivered once the sinus rhythm is restored and the patient is in ROSC thus averting or avoiding re-arrest. The rescuer can immediately proceed to provide advanced circulatory care 1340 to treat the patient that is in ROSC and is no longer in cardiac arrest. This care may include one or more of the interventions listed in Table 1.

Figure 14A:
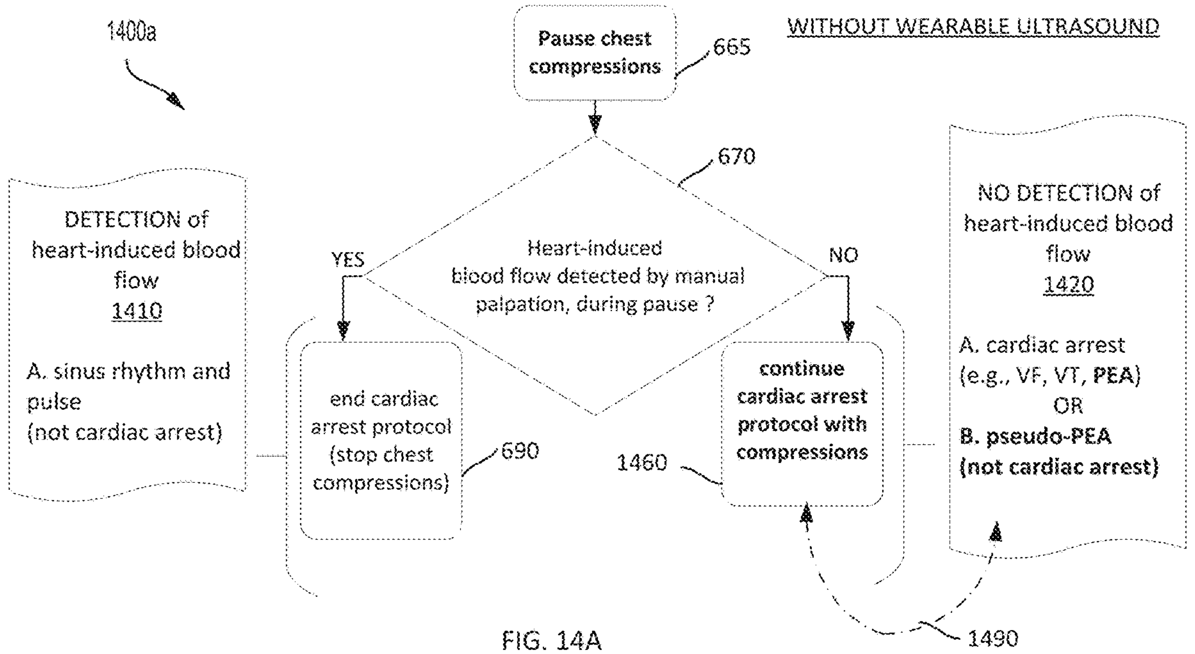
FIGS. 14A and 14B schematically illustrate distinguishing between PEA and pseudo-PEA with a wearable ultrasound blood flow sensor.
Figure 14B:
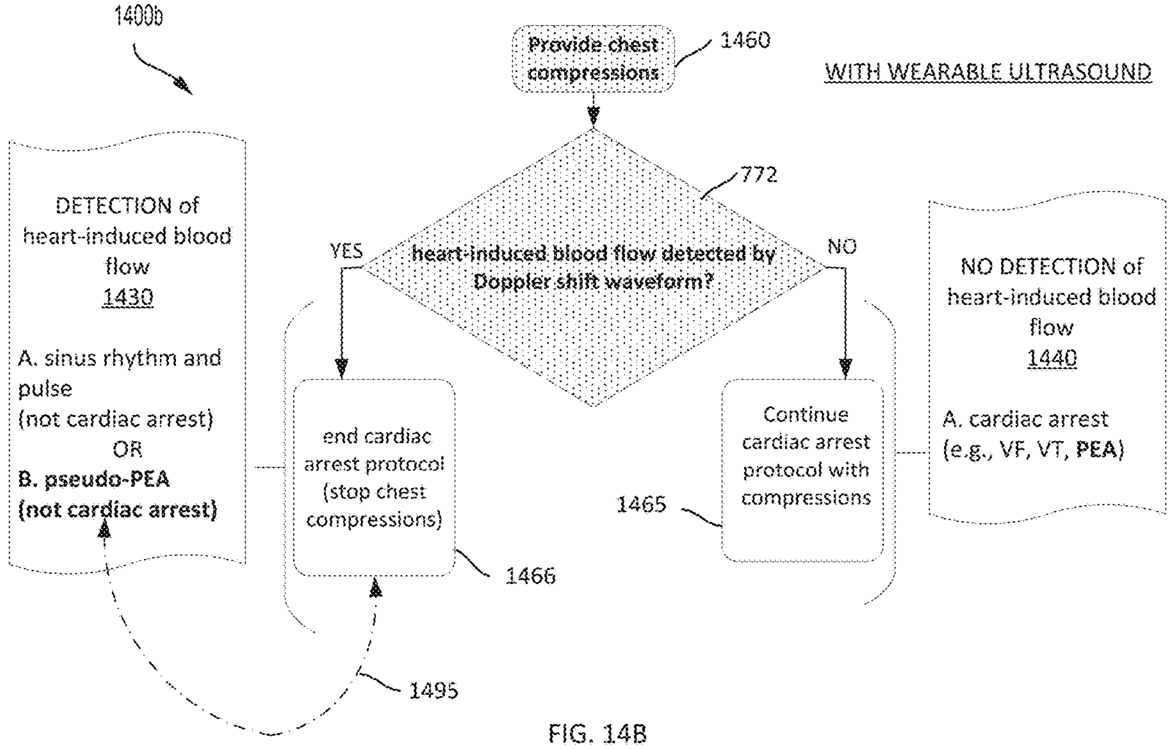
Figure 15A:
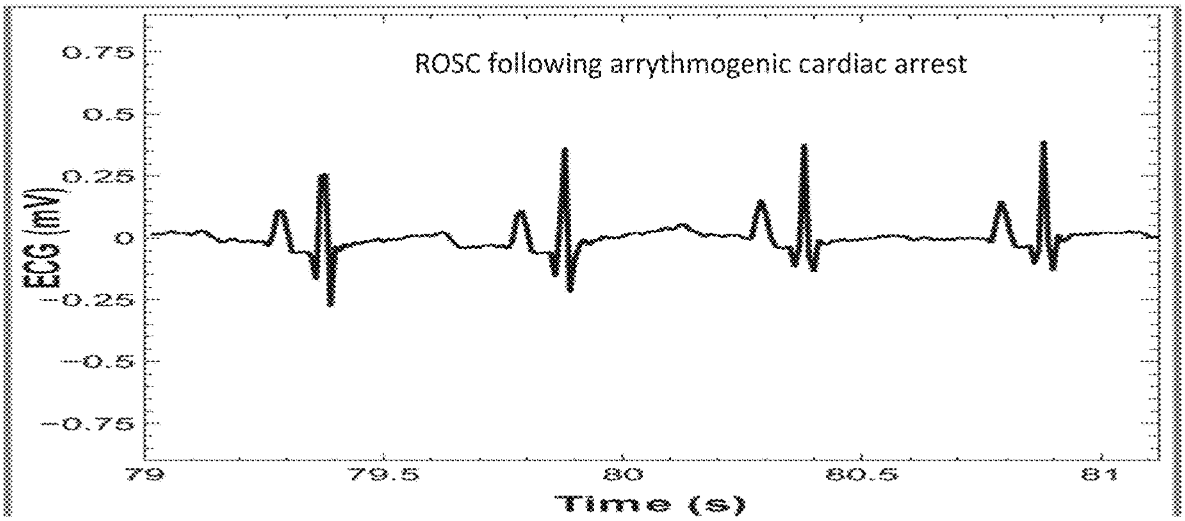
FIG. 15A shows an example of an ECG characteristic of ROSC.
Figure 15B:
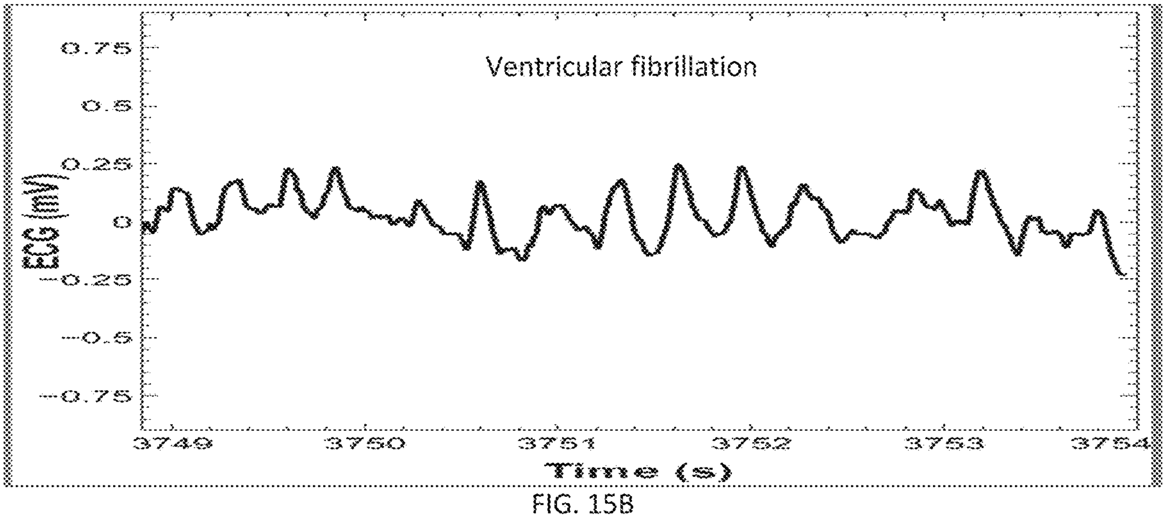
FIG. 15B shows an example of an ECG corresponding to VF.
Figure 15C:
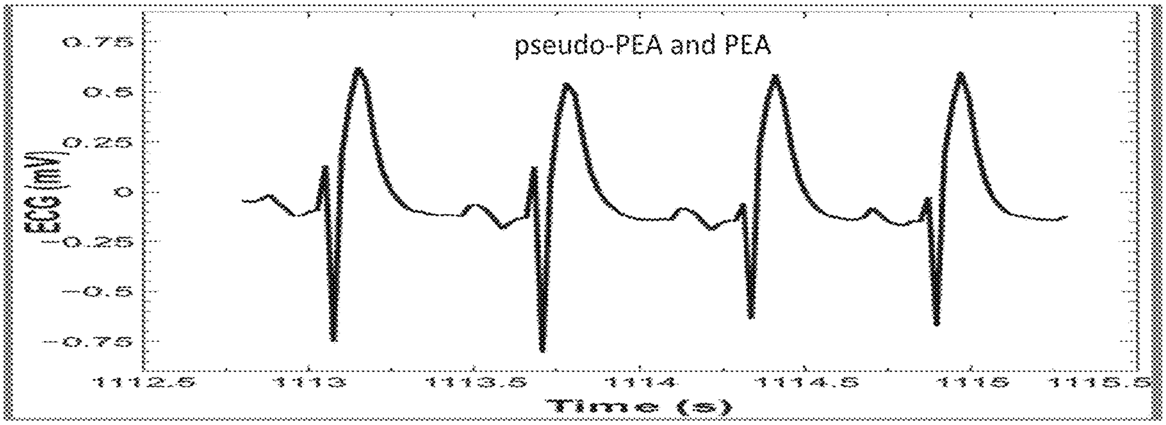
FIG. 15C shows an example of an ECG corresponding to PEA and to pseudo-PEA.

Referring to FIGS. 14A and 14B, distinguishing between PEA and pseudo-PEA with a wearable ultrasound blood flow sensor is illustrated schematically. These figures includes two flow charts. Flow chart 1400*a* in FIG. 14A corresponds to patient care without a wearable ultrasound blood flow sensor with reference to FIG. 6. Flow chart 1400*b* in FIG. 14B corresponds to patient care with a wearable ultrasound blood flow sensor with reference to FIG. 7A.

Looking at the flow chart 1400*a*, the caregiver may pause chest compressions at the stage 665 in order to check for heart-induced blood flow via manual palpation during the pause at the stage 670 and as similarly described in regard to FIG. 6. If the rescuer detects a pulse by manual palpation the stage 670, then the rescuer stops chest compressions and ends the cardiac arrest protocol at the stage 690 as similarly described in regard to FIG. 6. If the rescuer does not detect a pulse by manual palpation at the stage 670, then the rescuer resumes chest compressions and continues the cardiac arrest protocol as similarly described in regard to FIG. 6.

The stage 690 is associated with the detection state 1410. As shown in FIG. 14A, the detection state 1410 is characterized by a sinus rhythm associated with a pulse and the patient is not in cardiac arrest. The sinus rhythm associated with a pulse, as opposed to pulseless electrical activity (PEA), accompanies ROSC and an example of such an ECG is shown in FIG. 15A. The sinus rhythm in ROSC may not correspond to that of a healthy heart as the victim's heart may be damaged by the cardiac arrest and/or damage to the heart may have caused the cardiac arrest. For example, the volume of blood flow in ROSC after a cardiac arrest may be lower, than in the absence of a cardiac arrest. In the case of an arrhythmogenic cardiac arrest, the defibrillation shock may end the fibrillation activity but the ECG generally exhibits nonspecific changes in response to the shock and typically does not return, at least, over a time frame of minutes, to a sinus rhythm associated with a healthy heart. As discussed above, in the absence of a patient regaining consciousness, for example, it is not obvious that heart-induced blood flow has resumed during a resuscitation effort and rescuers do not rely on ECG as a sole indicator of blood flow.

In contrast, the stage 1460 is associated with the detection state 1420. The stage 1460 includes a resumption of chest compressions (e.g., the stage 675 in FIG. 6) and ECG analysis for shockable or non-shockable rhythm (e.g., the stages 680 and 685 in FIG. 6) with an optional pause in compressions prior to the ECG analysis (e.g., the stage 677 in FIG. 6). As shown in FIG. 14A, the detection state 1420, is characterized by a fibrillation heart rhythm (e.g., VF, VT) or by a PEA heart rhythm or by a pseudo-PEA heart rhythm. FIG. 15B shows an example of an ECG corresponding to VF. FIG. 15C shows an example of an ECG corresponding to PEA and to pseudo-PEA. For all of these, the rescuer will not detect a pulse via manual palpation. In the case of fibrillation or PEA, the rescuer will not detect the pulse because there is no heart-induced pulsatile flow. However, in the case of pseudo-PEA, there is heart-induced pulsatile flow but the pulse is too weak for detection via manual palpation. Additionally, as shown in FIG. 15C, the ECG cannot distinguish between PEA and pseudo-PEA. Therefore, in the absence of the wearable ultrasound, pseudo-PEA may be indistinguishable from PEA. The stage 1460 may also correspond to asystole as indicated by a flat-line ECG which is readily distinguished from both VF, PEA, and pseudo-PEA.

With VF or PEA, the patient is in cardiac arrest and should continue to receive chest compressions according to a cardiac arrest treatment protocol. However, as highlighted by the arrow 1490, although the patient is no longer in cardiac arrest with pseudo-PEA, in the absence of the wearable ultrasound, the patient continues to receive chest compressions according to the cardiac arrest protocol. The ECG and manual palpation cannot detect pseudo-PEA. Therefore, based on these measures, the rescuer 103 and the ECG signal evaluation engine 354 will be unaware that the patient's heart is in a state of pseudo-PEA and no longer in cardiac arrest.

There are several dangers posed to the patient as a result of this lack of detection of pseudo-PEA. First, as discussed in regard to FIG. 13, the continuance of chest compressions may cause re-arrest. Additionally, in order to minimize interruptions to chest compressions because interruptions threaten patient survival, a rescuer may continue administering chest compressions on-scene without transporting the patient. However, once the patient no longer requires chest compressions, then immediate transport to a medical facility provides the best chance for patient surviving and remaining neurologically intact. Finally, the best chance for patient surviving and remaining neurologically intact also requires that the patient receive interventions like those shown in Table 2 above that are specifically directed at pseudo-PEA. However, working under an assumption of cardiac arrest, the rescuer will not divert time and attention to these measures as they would not be efficacious procedures for cardiac arrest.

As shown in FIG. 14B, the wearable ultrasound blood flow sensor 110 provides a solution to the problem described with regard to FIG. 14A. As a more sensitive external measure than a manual palpation, the Doppler shift waveform may detect the heart-induced pulsatile flow that is characteristic of pseudo-PEA. Thus, the Doppler shift waveform evaluation engine 358 may detect pseudo-PEA and can distinguish between PEA and pseudo-PEA based on the Doppler shift waveform and the ECG. The ECG signal evaluation engine 354 may analyze the ECG waveform to identify the non-shockable rhythm as shown for example in FIG. 15C. The Doppler shift waveform evaluation engine 358 may analyze the at least one Doppler shift waveform to detect heart-induced blood flow. Based on the ECG waveform and the detected heart-induced blood flow, the processor 350 may identify the detected heart-induced blood flow as pseudo-PEA.

The detection state 1430 corresponds to a detection of heart-induced blood flow associated with either the sinus rhythm exemplified in FIG. 15A or the pseudo-PEA rhythm exemplified in FIG. 15C. As neither of these are cardiac arrest, the detection stage 1430 is associated with the stage 1466 to end the cardiac arrest protocol. The stage 1466 includes the stages 794 and 796 in FIG. 7A to change the intervention protocol and optionally the stages 790 and 792 to verify the pseudo-PEA detection. As highlighted by the arrow 1495, the analysis of the Doppler shift waveform enables the Doppler shift waveform evaluation engine 358 to distinguish between PEA and pseudo-PEA. The combination of the ECG characteristic of both PEA and pseudo-PEA with pulsatile heart-induced blood flow as detected in the Doppler shift waveform enables this distinction. Thus, with the use of the wearable ultrasound blood flow sensor 110, the processor 350 may accurately identify pseudo-PEA and provide appropriate caregiver instructions at the stage 1466.

In contrast, the detection state 1440 corresponds to no detection of heart-induced blood flow. Here, the ECG rhythm may be the VF rhythm exemplified in FIG. 15B or the PEA rhythm exemplified in FIG. 15C. As is appropriate for these physiologic cardiac states, the rescuer continues to provide interventions according to the cardiac arrest protocol at the stage 1465. This stage includes ECG analysis for shockable or non-shockable rhythm (e.g., the stages 680 and 685 in FIG. 6) with an optional pause in compressions prior to the ECG analysis (e.g., the stage 677 in FIG. 6) along with a resumption or continuation of chest compressions at the stage 745 or 740, depending on the nature of the heart rhythm.

Figure 16A:
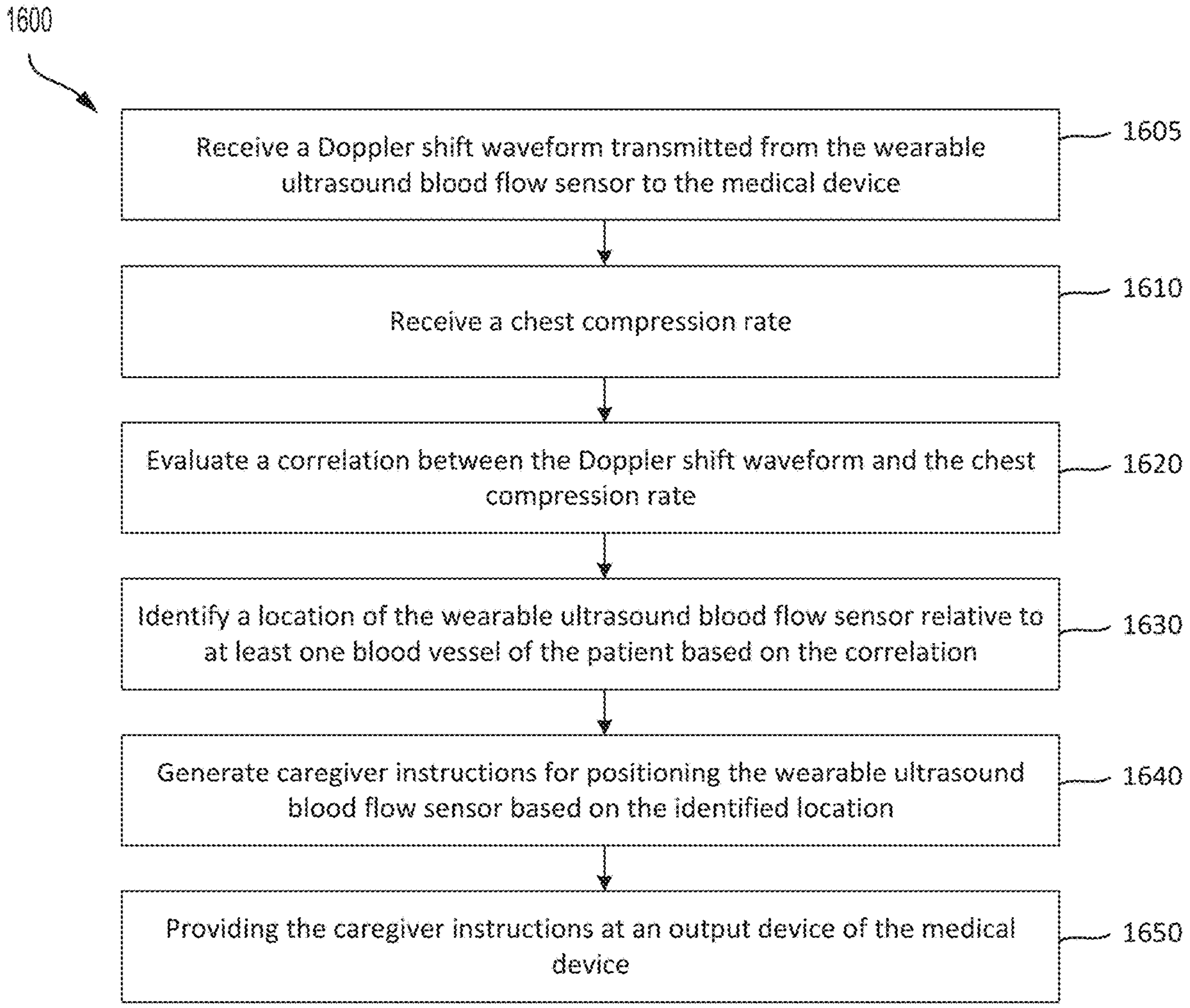
FIG. 16A shows an example of a method of positioning a wearable ultrasound blood flow sensor on a patient.

Referring to FIG. 16A, an example of a method of positioning a wearable ultrasound blood flow sensor on a patient is shown. The steps shown in the method 1600 are examples only and not limiting of the disclosure. Additionally, the sequence of steps can be altered, e.g., by having stages added, removed, rearranged, combined, and/or performed concurrently.

At the stage 1605, the medical device 305 or the external computing device 180 may receive data signals representing the Doppler shift waveform 310 transmitted from a wearable ultrasound blood flow sensor 110. For example, the Doppler shift waveform evaluation engine 358 may receive the data signals representing the Doppler shift waveform 310.

At the stage 1610, the Doppler shift waveform evaluation engine 358 may receive a chest compression rate from the chest compression waveform evaluation engine 356. As described in more detail below with regard to FIGS. 18 and 19, the chest compression rate may be a rate determined from a chest compression waveform transmitted by a chest compression monitor 109 and received at the medical device 305 (e.g., the chest compression waveform 309 received at the chest compression waveform evaluation engine 356). The chest compression monitor 109 may detect and measure manual compressions or automated compressions. As shown in FIG. 19, the chest compression waveform may be an acceleration waveform 1760, for example, from a chest compression monitor 109 that includes an accelerometer. The chest compression waveform evaluation engine 356 may integrate the acceleration waveform 1760 to derive a velocity waveform and/or may doubly integrate the acceleration waveform 1760 to derive a displacement waveform 1780. The compression rate (e.g., compressions per unit time) corresponds to a period 1785 associated with the displacement waveform.

Alternatively, and as described in more detail below with regard to FIG. 22, the chest compression rate may be a compression rate for an automated compression device (e.g., the device 210 or 250 as shown in FIG. 2). The automated compression device may be programmed to provide compressions at a particular rate that may correspond to a rate specified or recommended in a cardiopulmonary resuscitation (CPR) protocol. The automated compression device may provide the chest compression waveform 309 to the engine 356.

In an implementation, the chest compression rate may be a predetermined rate based on a cardiopulmonary resuscitation protocol. For example, the memory 355 may include a stored value for the chest compression rate and the engine 358 may retrieve this compression rate value from the memory 355.

At the stage 1620, the engine 358 may evaluate a correlation between the Doppler shift waveform 310 and a chest compression rate. The engine 358 may receive the chest compression waveform and/or a compression rate derived therefrom from the engine 356 (e.g., based on the compression waveform 309 from either the chest compression monitor 109 in the case of manual compressions or from the automated compression device 210 or 250 in the case of automated compressions). The engine 358 may evaluate this correlation based on an identification of periodic features in the Doppler shift waveform 310 that are indicative of the chest compression rate. For example, these features may be compression peaks 1510*a*, 1510*b*, 1510*c*, and 1510*d* as shown in FIG. 7B-1 or, similarly compression feature 1560 as shown in FIG. 7E-1. As another example, these features may be frequency components corresponding to compressions as shown in FIG. 7G-1. The period of the peaks or the frequency components may correspond to the compression period indicated by the compression waveform (e.g., the compression period 1785 in FIG. 19) or the pre-determined compression period, or rate, for the automated compression device. The periodic features in the Doppler shift waveform may exhibit an expected phase relationship with the chest compression waveform. The chest compressions initiate blood flow at the chest and the wearable ultrasound blood flow sensor 110 detects blood flow at a location on the victim that is remote from the chest (e.g., the neck, the upper arm, the groin). Therefore, there is a time lag between the provided chest compression and the resulting throb of blood flow at the location of the sensor 110. The expected phase relationship may be, for example, 100-305 milliseconds.

At the stage 1630, the engine 358 may identify a location of the wearable ultrasound blood flow sensor 110 relative to a blood vessel of the patient based on the correlation between the periodic features in the Doppler shift waveform 310 and the compression period or rate. For example, a presence of the periodic features indicative of the chest compression rate in the at least one Doppler shift waveform (i.e., periodic features in the Doppler shift waveform that are correlated with the compression rate), may indicate that the sensor 110 is positioned in a location corresponding to a blood vessel of the patient. If the sensor 110 detects the periodic blood flow triggered by the chest compressions, then this blood flow will manifest itself as peaks or frequency components in the Doppler shift waveform. In this case, the location of the sensor 110 is sufficiently close to the blood vessel for the transducer array 420 to receive reflected ultrasound signals 489 from the red blood cells in the blood vessel. Alternatively, an absence of the periodic features indicative of the chest compression rate in the at least one Doppler shift waveform (i.e., periodic features in the Doppler shift waveform that are correlated with the compression rate), may indicate that the sensor 110 is not positioned in a location corresponding to a blood vessel of the patient. If the sensor 110 does not detect the periodic blood flow triggered by the chest compressions, then this blood flow will not manifest itself as peaks or frequency components in the Doppler shift waveform. In this case, the location of the sensor 110 may be insufficiently close to the blood vessel for the transducer array 420 to receive reflected ultrasound signals 489 from the red blood cells in the blood vessel. The coupling between the chest compression waveform evaluation engine 356 and the Doppler shift waveform evaluation engine 358 enables the engine 358 to identify the location of the sensor 110 relative to the blood vessel and thereby aid in proper positioning of the sensor 110.

During cardiac arrest the heart ceases its pumping function. Therefore, there is no blood flow through the blood vessels and, accordingly, a signal from the sensor 110 would show no frequency shift due to blood flow. However, even in the presence of blood flow, the signal from the sensor 110 would also show no frequency shift due to blood flow if the sensor 110 is not positioned in sufficient proximity to a vessel such that the blood flow can cause this shift. Therefore, lack of frequency shift of the received ultrasound wave 489 relative to the transmitted wave 488 may result from a lack of blood flow and/or a sensor 110 that is improperly positioned over a blood vessel 499. Given the critically time-sensitive nature of cardiac arrest interventions, effective care for the patient based on the continuous monitoring afforded by the sensor 110 relies upon a fast, efficient, and repeatable method of properly locating the sensor 110 on the victim. Ideally, this method should require minimal training and expertise because often the first rescuer at a scene is a layperson or a rescuer with basic training like a firefighter or an emergency medical technician (e.g., as opposed to a physician, a medic, a paramedic, or a nurse). For any of these personnel, chest compressions are one of the first steps in resuscitating the cardiac arrest victim. The chest compressions create blood flow that is detectable by the sensor 110. Therefore, a system that integrates Doppler shift waveform analysis with automated chest compression recognition and waveform analysis, like that discussed herein (and illustrated, for example, in FIG. 3A) enables a rescuer to properly position the sensor 110 based on frequency shift caused by compression-induced blood flow. If the sensor 110 is properly positioned relative to a blood vessel, the sensor 110 will detect the blood flow due to chest compressions. In the absence of a Doppler shift waveform signal from the sensor 110, there may be no heart-induced pulse and/or the sensor 110 may be in the wrong place on the victim relative to the blood vessel. However, if the sensor 110 provides a Doppler shift waveform signal during chest compressions, then the sensor 110 is properly positioned on the victim relative to the blood vessel. Once this proper position is verified based on the Doppler shift waveform signal from chest compressions, then the sensor 110 is properly positioned to detect heart-induced blood flow. Thus a lack of a signal corresponding to heart-induced blood flow indicates a lack of such flow rather than an improperly positioned sensor 110. The integrated system discussed herein can recognize this proper positioning and, given the automated nature of this recognition, can generate rescuer instructions and feedback regarding this proper positioning. As such, a layperson or rescuer with basic training using an AED and/or a rescuer with more advanced training using a defibrillator in BLS or ALS mode may quickly, efficiently, and repeatably position the sensor 110. Additionally, this integrated system enables the engine 358 to analyze the Doppler shift waveform and distinguish between contributions to this waveform from heart-induced blood flow and from compression-induced blood flow. This provides a specificity that allows the engine 358 to identify heart-induced blood flow during ongoing chest compressions.

At the stage 1640, the ultrasound sensor positioning engine 352 may generate caregiver instructions for positioning the wearable ultrasound blood flow sensor 110 based on the identified location relative to the blood vessel. Examples of the caregiver instructions are discussed in more detail below with regard to FIGS. 16B-21. At the stage 1650, the output device(s) 360 may provide the caregiver instructions for the caregiver.

Figure 16B:
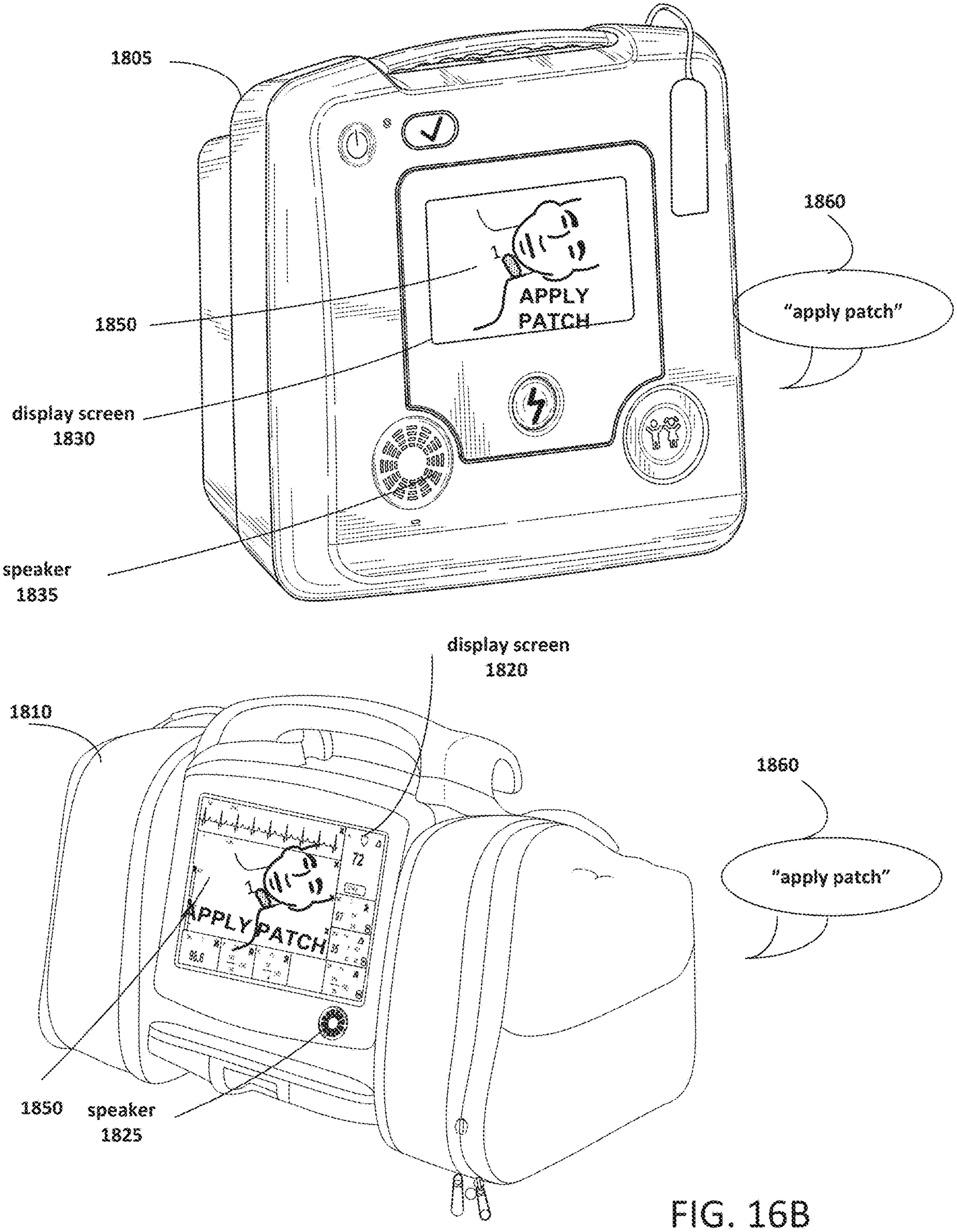
FIG. 16B shows examples of various defibrillator devices configured for use with the wearable ultrasound transducer array.

Referring to FIG. 16B, examples of various defibrillator devices configured for use with the wearable ultrasound transducer array are shown. Optionally, prior to or in conjunction with the stage 1605 the processor 350 may generate a visual and/or audible caregiver instructions to attach the wearable ultrasound sensor 110 to the patient. The output device(s) 360 may provide this caregiver instruction. Examples of the visual caregiver instruction 1850 and the audible caregiver instruction 1860 are shown in FIG. 16B. As shown in FIG. 16B, the medical device 305 may be a defibrillator 105 and the defibrillator 105 may be an automated external defibrillator (AED) 1805 designed for use by a layperson or medical professional. The output device(s) 360 for the AED 1805 may include a display screen 1830 and/or a speaker 1835. Alternatively, the defibrillator 105 may be a combination external defibrillator and patient monitor 1810 designed for use by medical professionals in a basic life support (BLS) or advanced life support (ALS) mode. The output device(s) 360 for the external defibrillator and patient monitor 1810 may include a display screen 1820 and a speaker 1825.

Figure 17:
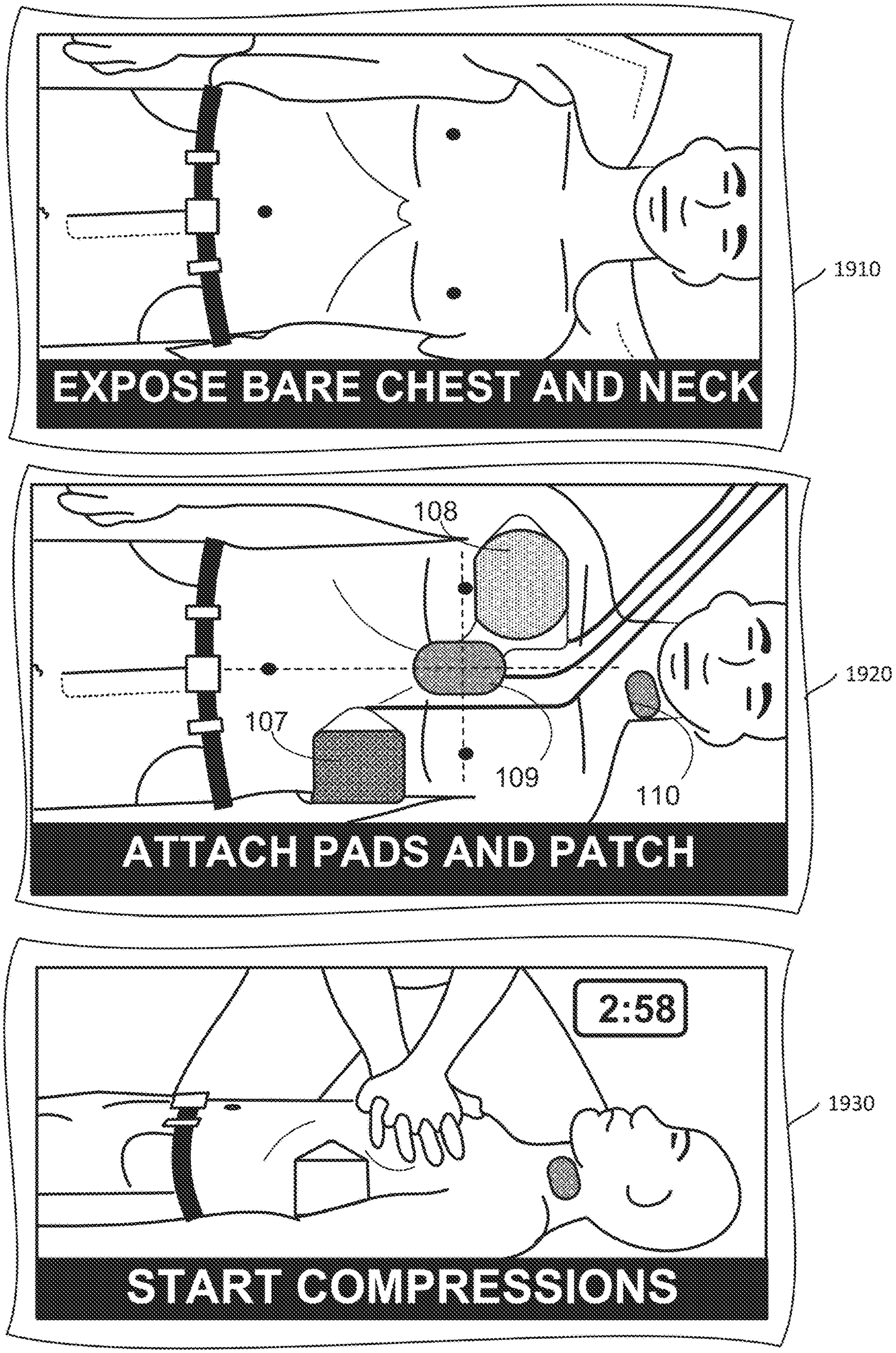
FIG. 17 shows examples of caregiver instructions for initiating chest compressions with a wearable ultrasound transducer array.

Referring to FIG. 17, examples of caregiver instructions for initiating chest compressions with a wearable ultrasound transducer array are shown. A quantity of each component in FIG. 17 is an example only and other quantities of each, or any, component could be used. In an implementation, the output device(s) 360 may provide instructions to attach or couple the wearable ultrasound sensor 110 to the patient concurrently with electrode application instructions as combined instructions for a wearable ultrasound sensor 110 and for the electrode pads 107 and 108. The output device(s) 360 may provide these instructions as visible displayed instructions and/or audible instructions. For example, the combined instructions may include an instruction 1910 to expose the bare chest of the patient. This instruction may also include instructions to expose one or more of a bare neck, a bare arm, a bare leg, a bare groin region and/or another region of the patient's body corresponding to a blood vessel that may be monitored for blood flow with the sensor 110. The combined instructions may further include an instruction 1920 to attach the electrode pads 107 and 108 and the sensor 110. The instruction 1920 may include a diagram of a patient with anatomical reference points for proper placement of the electrodes and the sensor 110. In the example of FIG. 17, the sensor 110 is in the form of a patch adhered to the neck of the patient. This is an example only and other coupling mechanisms for the sensor 110 and other locations on the patient, including multiple locations for multiple sensors 110 are within the scope of the disclosure. In an implementation, the instruction 1920 may include placement instructions for a chest compression monitor 109. In an implementation, the combined instructions may include an instruction 1930 to begin chest compressions according to a cardiac arrest protocol with the sensor 110 in place on the patient.

Figure 18:
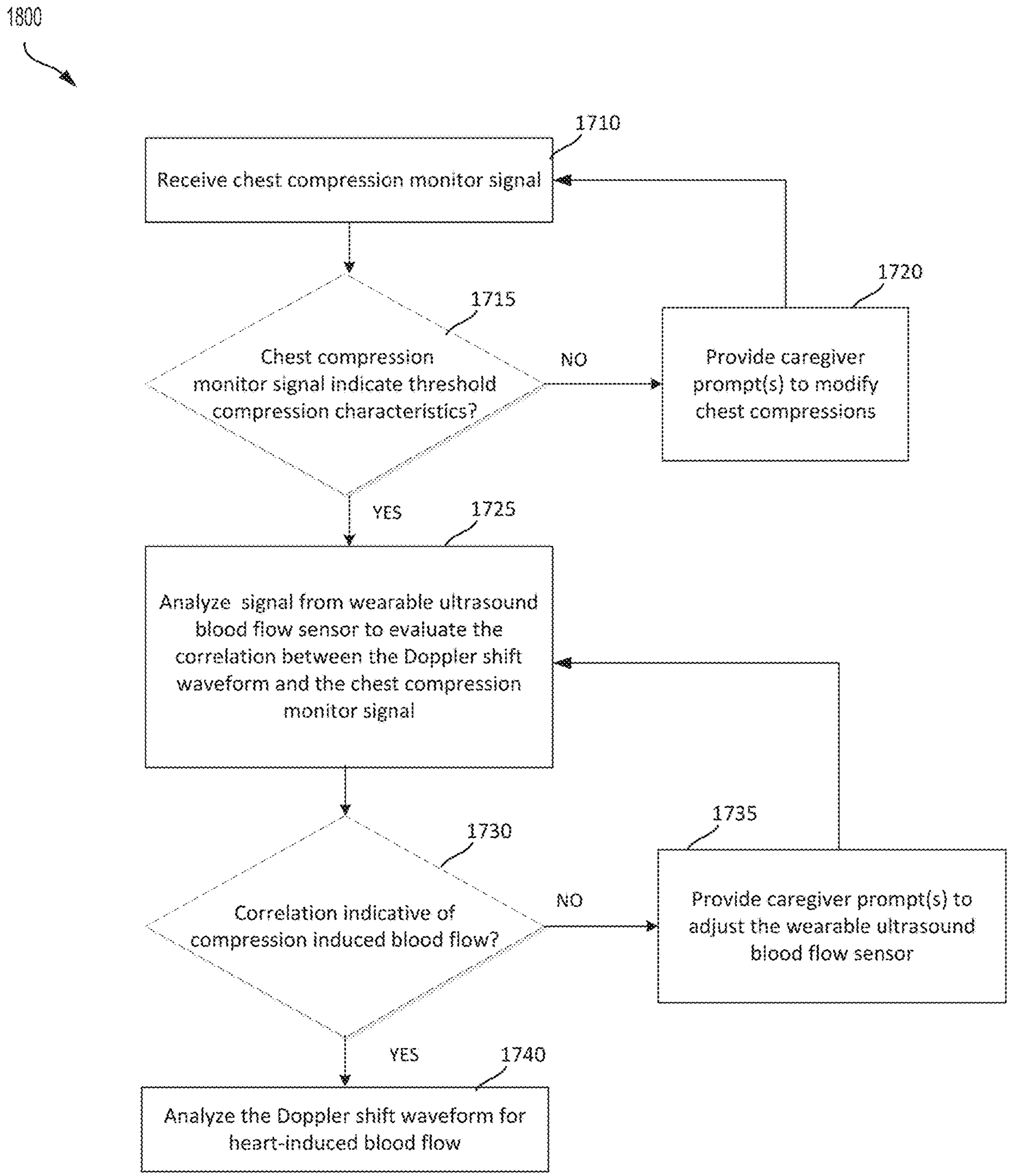
FIG. 18 shows an example of a method for positioning a wearable ultrasound blood flow sensor in conjunction with manual chest compressions.
Figure 19:
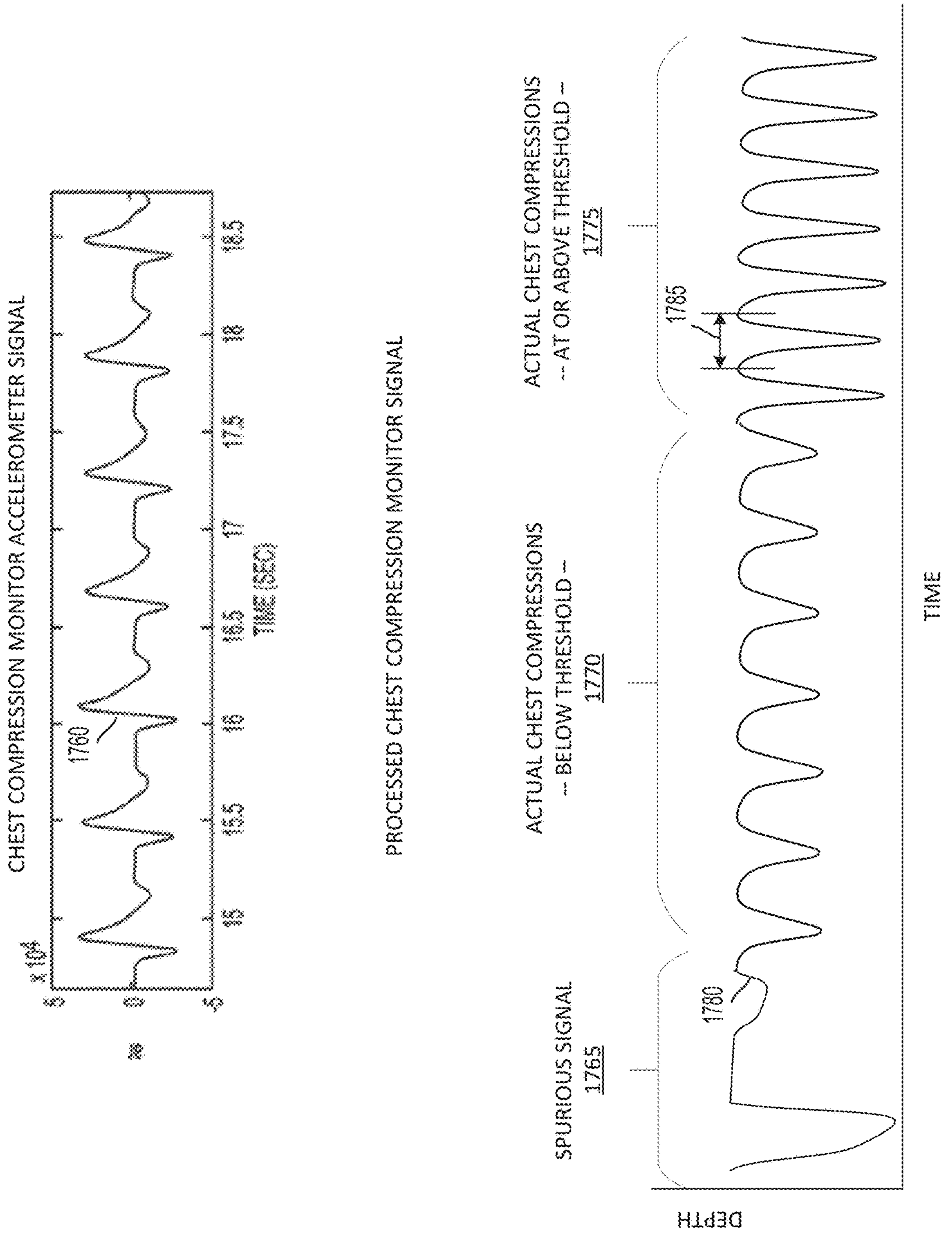
FIG. 19 shows examples of the chest compression waveforms.
Figure 20:
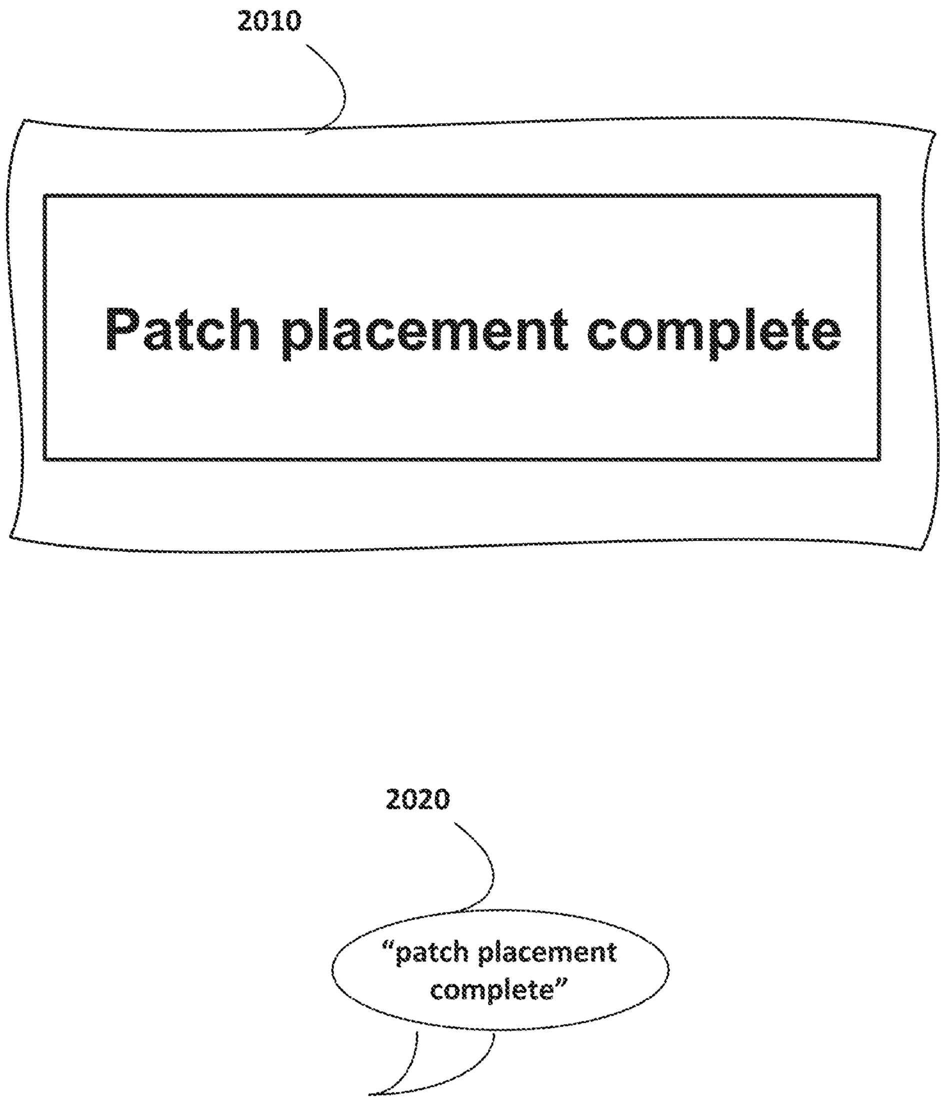
FIG. 20 shows examples of caregiver prompts for placement of the wearable ultrasound blood flow sensor.

Referring to FIG. 18, an example of a method for positioning a wearable ultrasound blood flow sensor in conjunction with manual chest compressions is shown. The steps shown in the method 1700 are examples only and not limiting of the disclosure. Additionally, the sequence of steps can be altered, e.g., by having stages added, removed, rearranged, combined, and/or performed concurrently.

At the stage 1710, the chest compression waveform evaluation engine 356 may receive the chest compression waveform 309 from the chest compression monitor 109. The chest compression waveform 309 may indicate motion detected by the chest compression monitor 109, for example, due to manual chest compressions. At the stage 1715, the engine 356 may evaluate the chest compression waveform to determine whether the signal exhibits threshold compression requirements. As explained below in conjunction with FIG. 19, these requirements verify that detected peaks or other features of the chest compression waveform 309 are actually indicative of and caused by chest compression motion from manual chest compressions as opposed to spurious motions of the monitor 109. Additionally, these requirements verify that the manual chest compressions being delivered are of a depth and rate capable of generating detectable blood flow at the location of the sensor 110.

Referring to FIG. 19, examples of the chest compression monitor data signals are shown. In these examples, the chest compression waveform 309 is an acceleration waveform 1760 (e.g., from one or more accelerometers included in the chest compression monitor 109). This is an example only as other types of data signals, such as a force signal, are within the scope of the disclosure. The chest compression waveform evaluation engine 356 may doubly integrate the acceleration waveform 1760 to derive a depth waveform 1780. Additionally, the evaluation engine 356 may implement an algorithm to analyze the acceleration waveform 1760, the depth waveform 1780, and/or a velocity waveform derived from the acceleration waveform 1760 to evaluate the chest compression waveform for indications of an administration of manual chest compressions meeting threshold compression requirements. In an implementation, the processor 350 may generate visual and/or audible caregiver instructions to modify the manual chest compressions.

An example of this algorithm may implement the following procedures. The algorithm may identify a series of chest compressions corresponding to an administration of chest compressions based on data signals from the chest compression monitor 109. The algorithm may distinguish between signal that corresponds to chest compressions (e.g., signal 1770 and 1775) and spurious signal 1765 that does not correspond to chest compressions. For example, a spurious signal may correspond to movement of the chest compression monitor 109 while the rescuer 103 is positioning the monitor on a patient and/or motion of the chest compression monitor 109 induced by ambulance and/or gurney motion. The spurious signal may resemble a signal generated during a chest compression but in fact may be due to inadvertent and transient movement of the chest compression monitor 109 rather than an intentionally performed chest compression. The algorithm may prevent the signal generated from this transient movement from being incorrectly identified as a signal corresponding to a first chest compression in a series of CPR chest compressions.

The series of actual chest compressions may be identified as a group of a minimum number of compressions occurring at a minimum rate and corresponding to a minimum depth. More than one compression is needed in order to establish a rate. For example, the minimum number of compressions may be three, the minimum rate may be 60 compressions per minute and the minimum compression depth may be 0.75 inches (1.9 cm). In other words, the series may be identified for an occurrence of at least three compressions with a compression rate (e.g., as indicated by the compression period 1785) of greater than or equal to 60 cpm and a compression depth of greater than or equal to 0.75 inches (1.9 cm). The values of three compressions, 60 cpm, and 0.75 inches (1.9 cm) are examples only and not limiting of the disclosure.

As a further example of the algorithm procedures, the algorithm may identify the pause periods. The pause period may be identified based on an absence of identified CPR chest compressions for a particular minimum time period. The particular minimum time period may be a fixed value set by the medical device 305. Alternatively, the medical device 305 may provide a default value for this time period and the default value may be user-configurable.

Once the algorithm identifies actual chest compressions, the chest compression evaluation engine 356 may evaluate whether or not the actual chest compressions are below a threshold or at or above the threshold. The threshold may be a pre-determined rate and depth expected to generate sufficient blood flow to generate a Doppler shift waveform that is above a signal noise level. In other words, if compressions are too slow and/or too shallow, these compressions may not generate significant blood flow. In this case, the system may attribute the absence of a Doppler shift waveform to a lack of compression-induced blood flow rather than, for example, an improper placement of the transducer array away from an artery and/or a transducer array improperly attached to the victim. In an implementation, the threshold may be a rate and a depth as specified by Advanced Cardiac Life Support (ACLS) guidelines. These guidelines provide compression rate and depth targets sufficient to obtain life-sustaining blood flow. For example, the ACLS guideline may specify a compression rate of 100-120 compressions per minute at a depth of 5 cm.

In the case of an automated chest compression device, the engine 356 may distinguish between signal that corresponds to chest compressions and spurious signal 1765 that does not correspond to chest compressions. However, once the algorithm identifies signal corresponding to chest compressions, the Doppler shift waveform evaluation engine 358 may evaluate the Doppler shift waveform(s) 310 without a verification of a threshold by the chest compression evaluation engine 356. This is because the automated chest compression device is pre-programmed to deliver compressions meeting the threshold and is not subject to the variability associated with manual compressions. Therefore, unless the automated chest compression device is malfunctioning, the compressions delivered by this device will automatically meet the threshold.

Referring again to FIG. 18, in an implementation, at the stage 1720, the medical device 305 may provide rescuer feedback at the output device(s) 360 to guide the rescuer in adjusting the manual chest compressions to meet the threshold corresponding to the ACLS guideline. The method 1700 may loop around the stages 1710, 1715 and 1720 until the engine 356 verifies that the chest compressions meet the threshold compression characteristics.

At the stage 1725, in response to a verification by the chest compression evaluation engine 356 that the compressions meet the threshold, the Doppler shift waveform evaluation engine 358 may analyze the Doppler shift waveform(s) 310 to evaluate the correlation between the Doppler shift waveform and the chest compression waveform. The stage 1725 is substantially as described for the stage 1620 in FIG. 16A.

In an implementation, at the stage 1710 and/or 1725, one or more of the Doppler shift waveform evaluation engine 358 and the chest compression waveform evaluation engine 356 may extract noise contributions, for example, due to motion artifacts created by gurney motion, ambulance motion, patient motion relative to a support structure, motion of the patient's head or limbs during chest compressions, etc. The engine 358 and/or the engine 356 may extract noise contributions from the Doppler shift waveform 310 and/or the chest compression waveform 309.

Once the engine 356 verifies that the compressions meet the threshold, the Doppler shift waveform 310 should include a detectable frequency contribution from compression-induced blood flow that correlates with the chest compression waveform. The engine 358 evaluates this correlation and detectability at the stage 1730.

If there are detectable features or frequency contributions in the Doppler shift waveform that correlate with the chest compression waveform, then the engine 358 may analyze the Doppler shift waveform for heart-induced blood flow at the stage 1740. The correlation with the chest compression waveform confirms that the sensor 110 is properly positioned on the patient and that analysis of the Doppler shift waveform received during ongoing patient care will indicate heart-induced blood flow when and if ROSC or pseudo-PEA occur. In an implementation, and as shown for example in FIG. 20, the positioning engine 352 may generate a visual caregiver prompt 2010 and/or an audible caregiver prompt 2020 indicating proper placement of the wearable ultrasound blood flow sensor. The output device(s) 360 (e.g., the screen 1830, the screen 1820, the speaker 1835 and/or the speaker 1825) may provide the visual prompt 2010 and/or the audible prompt 2020.

If there are no detectable features or frequency contributions in the Doppler shift waveform that correlate with the chest compression waveform, then the wearable ultrasound blood flow sensor(s) 110 may be improperly connected to the patient or to the medical device or they may be properly connected but improperly positioned on the patient. Additionally, if the signal strength of the Doppler shift waveform is below a threshold signal strength (e.g., based on a desired signal-to-noise ratio) and/or if the engine 358 does not detect a signal from the sensor(s) 110, then the sensor(s) 110 may be in an improper position relative to a blood vessel, improperly connected to the patient, malfunctioning, and/or improperly connected to the medical device 305.

At the stage 1735, the positioning engine 352 may generate one or more caregiver prompts to adjust the sensor 110. The positioning engine 352 may generate these instructions in response to the identification of the location of the wearable ultrasound blood flow sensor as the location with insufficient proximity to the at least one blood vessel to detect the blood flow of the patient. In this case, the engine may not detect a contribution to the Doppler shift waveform from the compression-induced blood flow. Alternatively or additionally, the positioning engine 352 may generate these instructions in response to an insufficient signal form the sensor(s) 110 indicative of the malfunction, the improper connection to the medical device 305, and/or the improper connection to the patient 101. In this case, the engine 358 may receive data signals representing the Doppler shift waveform that are below the threshold signal strength for analysis or the engine 358 may not receive any data signals at all. The engine 358 may determine that a received data signals representing the at least one Doppler shift waveform fail to meet a threshold signal strength. The threshold signal strength may be a signal-to-noise ratio threshold indicative of acoustic coupling between the wearable ultrasound blood flow sensor and the patient.

Figure 21:
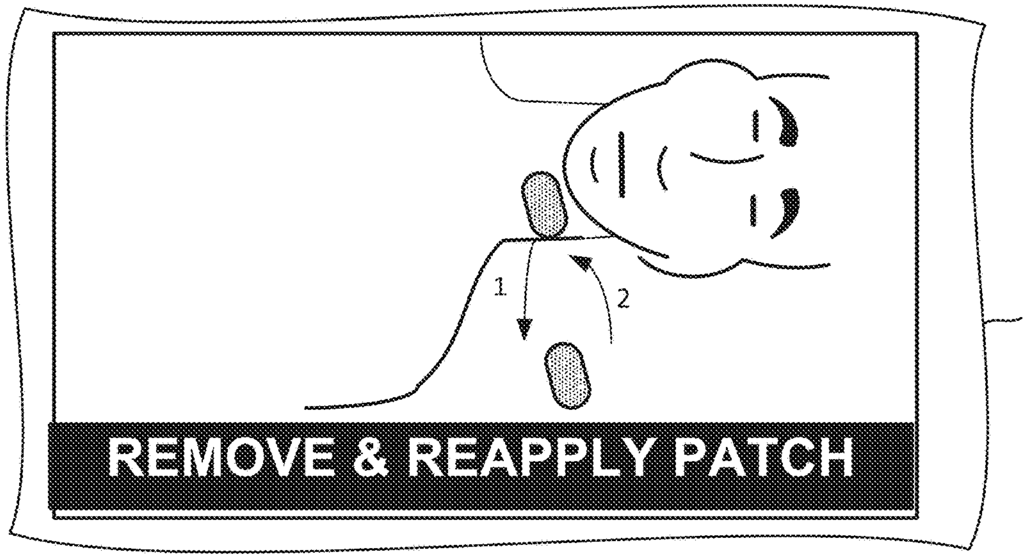
FIG. 21 shows examples of caregiver prompts to adjust the wearable ultrasound blood flow sensor.
Figure 21:
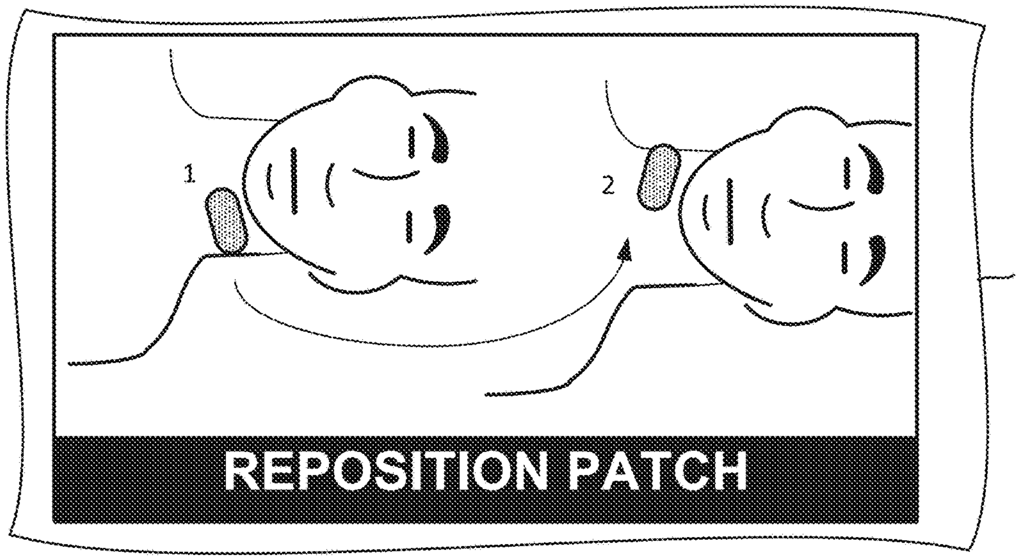
Figure 21:
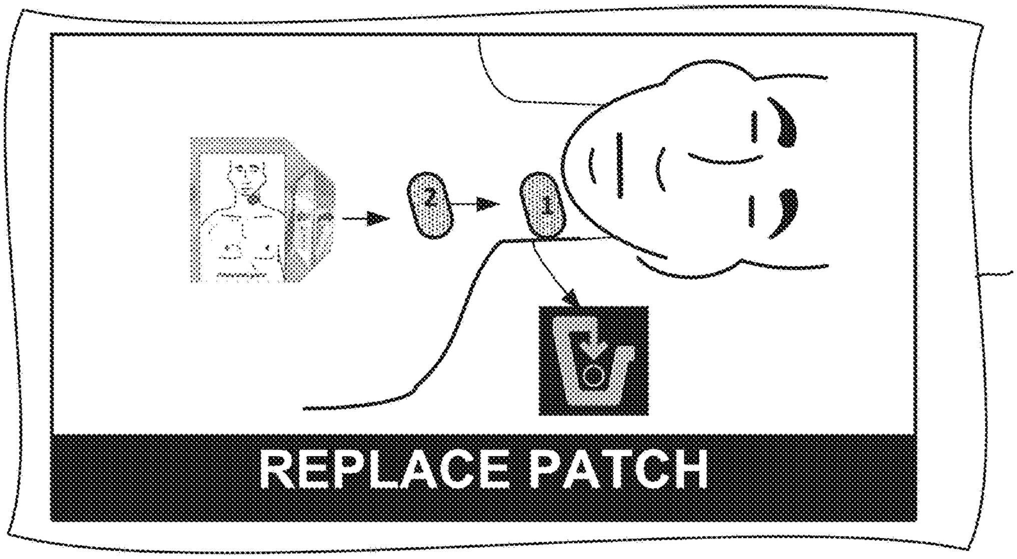

Referring to FIG. 21, examples of caregiver prompts to adjust the sensor 110 are shown. The positioning engine 352 may generate the caregiver prompts. The output device(s) 360, for example the defibrillator display 1830 and/or 1820 and/or a defibrillator speaker 1835 and/or 1825 may be configured to provide caregiver prompts to adjust the sensor 110. In an implementation, the positioning engine 352 may generate one or more of the caregiver prompts at the stage 1730 (or at the stage 2235 of the method 2200) as first caregiver prompts to adjust the sensor as described below and the engine 358 may re-check the signal at the stage 1725 (or at the stage 2225 of the method 2200). If the signal re-check does not indicate a correlation and/or fails to meet the threshold signal strength, then the positioning engine 352 may generate one or more second caregiver prompts that are different from the first caregiver prompts. The output device(s) 360 may provide the generated caregiver prompts. For example, the first caregiver prompts may include a prompt to remove and reapply the same sensor 110 and the second caregiver prompts may include a different prompt to replace the sensor 110 with a new sensor 110.

As one example, the caregiver prompts to adjust the sensor 110 may include a prompt 2110 to remove the sensor from the patient and reapply the sensor 110 to the patient in approximately the same location (i.e., proximate to a same blood vessel). As shown, for example in FIG. 21, the original position of the sensor 110 may be proximate to the right carotid artery and the caregiver may reapply the sensor 110 to a position proximate to the right carotid artery. This action may compensate for improper adhesion or location of the sensor 110 during an initial application.

As another example, the caregiver prompts to adjust the sensor 110 may include a prompt 2120 to remove the sensor from the patient and reapply the sensor 110 to the patient in a different location (i.e., proximate to a different blood vessel). The different location may be a location proximate to a same type of blood vessel on an opposite side of the patient than as originally applied relative to a sagittal plane. As shown, for example in FIG. 21, the first position of the sensor 110 may be proximate to the right carotid artery and the second and different position of the sensor 110 may be proximate to the left carotid artery. As another example, the first position of the sensor 110 may be proximate to the right carotid artery and the second and different position of the sensor may be proximate to a blood vessel in a different part of the body such as the brachial or femoral artery. This action may compensate for improper adhesion or location of the sensor 110 during an initial application and/or for a physical anomaly or characteristic of the first blood vessel and/or the patient's morphology or anatomy in the region of the first blood vessel that interferes with detection of the Doppler shift waveform signal.

As a further example, the caregiver prompts to adjust the sensor 110 may include a prompt 2130 to remove and discard the sensor 110 and replace it with a new sensor 110. The instruction may guide the caregiver in placing the new sensor at a same or different location on the patient. This action may compensate for a damaged or otherwise malfunctioning sensor 110. Additionally or alternatively, the caregiver prompts may include an instruction to confirm liner removal for the sensor 110 (e.g., removal of a peel-back liner on an adhesive configured to couple the sensor 110 to the patient 101) and/or an instruction to confirm that the sensor 110 has been placed on the patient according to placement instructions provided at one or more of the housing for the sensor 110, a packaging for the sensor 110, and/or the output device(s) 360.

Figure 22:
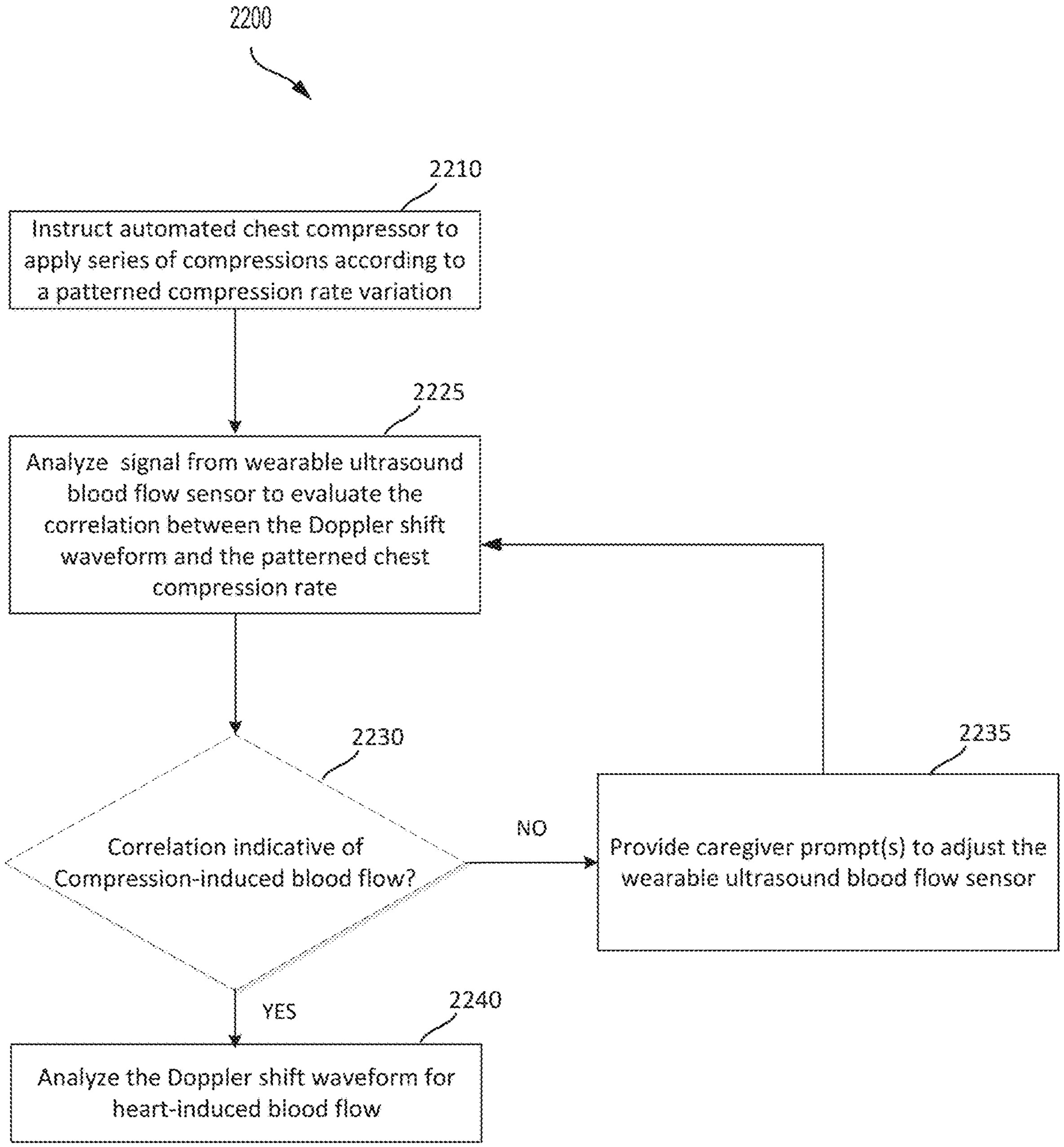
FIG. 22 shows an example of a method for positioning a wearable ultrasound blood flow sensor in conjunction with automated chest compressions.

Referring to FIG. 22, an example of a method for positioning a wearable ultrasound blood flow sensor in conjunction with automated chest compressions is shown. The steps shown in the method 2200 are examples only and not limiting of the disclosure. Additionally, the sequence of steps can be altered, e.g., by having stages added, removed, rearranged, combined, and/or performed concurrently.

At the stage 2210, the ultrasound sensor positioning engine 352 may cause or instruct the automated compression device to provide a series of chest compression according to a patterned compression rate variation. The patterned compression rate variation may cause variations in detected blood flow corresponding to the patterned compression rate variation. The patterned compression rate may include two or more different compression rates applied for groups of three or more compressions. For example, the positioning engine 352 may cause or instruct the automated compression device to provide three compressions at 80 cpm followed by three compressions at 100 cpm followed by a return to 80 cpm. As another example, the positioning engine 352 may cause or instruct the automated compression device to provide five compressions at 100 cpm followed by three compressions at 80 cpm followed by six compressions at 100 cpm and a return to 80 cpm. In general, the patterned compression rate may be J compressions at R cpm followed by K compressions at S cpm followed by a return to T cpm or one or more additional cycles of a number of compressions at a particular compression rate. J, K, R, S, and T are all integers and R, S, and T are all compression rates consistent with recognized cardiac arrest protocol compression rates.

At the stage 2225, the engine 358 may evaluate a correlation between the Doppler shift waveform 310 and the patterned chest compression rate. In order to evaluate this correlation, the engine 358 may analyze the at least one Doppler shift waveform for periodic features corresponding to the patterned compression rate variation. The engine 358 may determine the correlation between these waveforms based on an identification of periodic features in the Doppler shift waveform 310 that are indicative of the patterned chest compression rate. For example, the Doppler shift waveform 310 may include compression peaks similar to those in FIGS. 7B-1 and 7D but appearing as groups of peaks according to the patterned compression rate. As one example, if the compression rate pattern was three compressions at 80 cpm followed by three compressions at 100 cpm followed by a return to 80 cpm, the Doppler shift waveform 310 would include a first group of three peaks with a first compression period and a second group of three peaks with a second and different compression period followed by peaks at the first compression period. Other patterns would manifest themselves similarly in the Doppler shift waveform as variations in the number of peaks in a group with a compression period different from another group of peaks. In an implementation, the engine 358 may demodulate the Doppler shift waveform to extract the compression rate changes and compare the extracted compression rate changes to the patterned compression rate variation from the positioning engine 352 to evaluate the correlation.

At the stage 2230, the Doppler shift waveform 310 should include a detectable frequency contribution from compression-induced blood flow that correlates with the patterned chest compression rate. Therefore, at this stage, the engine 358 evaluates this correlation and detectability.

If there are detectable features or frequency contributions in the Doppler shift waveform that correlate with the patterned chest compression rate, then the engine 358 may analyze the Doppler shift waveform for heart-induced blood flow at the stage 2240. The correlation with the patterned chest compression rate confirms that the sensor 110 is properly positioned on the patient and that analysis of the Doppler shift waveform received during ongoing patient care will indicate heart-induced blood flow when and if ROSC or pseudo-PEA occur. In an implementation, and as shown for example in FIG. 20, the positioning engine 352 may generate a visual caregiver prompt 2010 and/or an audible caregiver prompt 2020 indicating proper placement of the wearable ultrasound blood flow sensor. The output device(s) 360 (e.g., the screen 1830, the screen 1820, the speaker 1835 and/or the speaker 1825) may provide the visual prompt 2010 and/or the audible prompt 2020.

If there are no detectable features or frequency contributions in the Doppler shift waveform that correlate with the patterned chest compression rate, then the wearable ultrasound blood flow sensor(s) 110 may be improperly connected to the patient or to the medical device or they may be properly connected but improperly positioned on the patient. An improper position is one that is not sufficiently proximate to a blood vessel so as to detect the compression-induced blood flow. In this case, at the stage 2235 and as similarly discussed above for the stages 1730 and 1735, the positioning engine 352 may generate one or more caregiver prompts to adjust the sensor 110 (e.g., the instructions discussed above in regard to FIG. 21).

Figure 23:
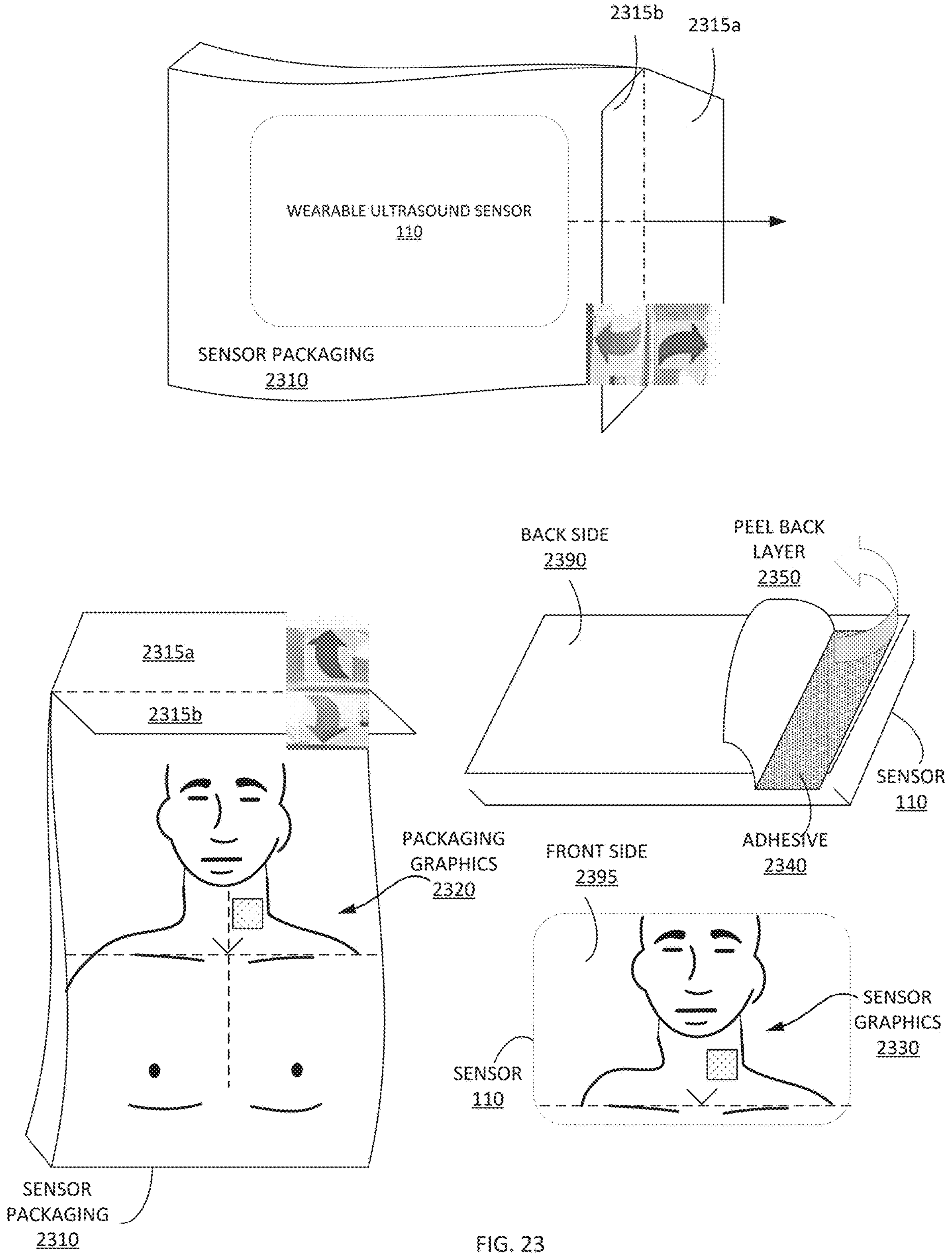
FIG. 23 shows an example of a wearable ultrasound blood flow sensor and packaging with graphic positioning instructions.

Referring to FIG. 23, an example of a wearable ultrasound blood flow sensor and packaging with graphic positioning instructions is shown. A quantity of each component in FIG. 23 is an example only and other quantities of each, or any, component could be used. In an implementation, the wearable ultrasound blood flow sensor 110 may be provided in sensor packaging 2310. The sensor packaging 2310 may open by peeling apart two separable sheets **2315*a* and 2315*b* in order to remove the sensor 110 from the packaging. As another example, the packaging 2310 may include a perforation, a line indicating a scissors path, a pull tab, an integrated and reusable sealing mechanism (e.g., a zipper strip, a slider, etc.), or other mechanism or indication that enables the caregiver to quickly open the packaging to release the sensor 110. The sensor packaging 2310 may include packaging graphics 2320 that indicate a proper placement of the sensor 110 proximate to a blood vessel. Additionally or alternatively, a front side 2395 of the sensor 110 may include sensor graphics 2330. The front side 2395 of the sensor 110 faces and/or is visible by the caregiver during placement and use while the backside 2390 of the sensor 110 is in contact, at least in part, with the patient. In an implementation, all or a portion of the backside 2390 of the sensor 110 may include a peel back layer 2350 that reveals an adhesive 2340 upon removal of the peel back layer 2350 from the sensor 110. The peel back layer 2350 may cover all or a portion of the patient pad 450 and/or the adhesive 440 discussed in regard to FIG. 4A. In an implementation, the backside 2390 may correspond to the sensor housing 430***a* discussed in regard to FIG. 4A.

Figure 24:
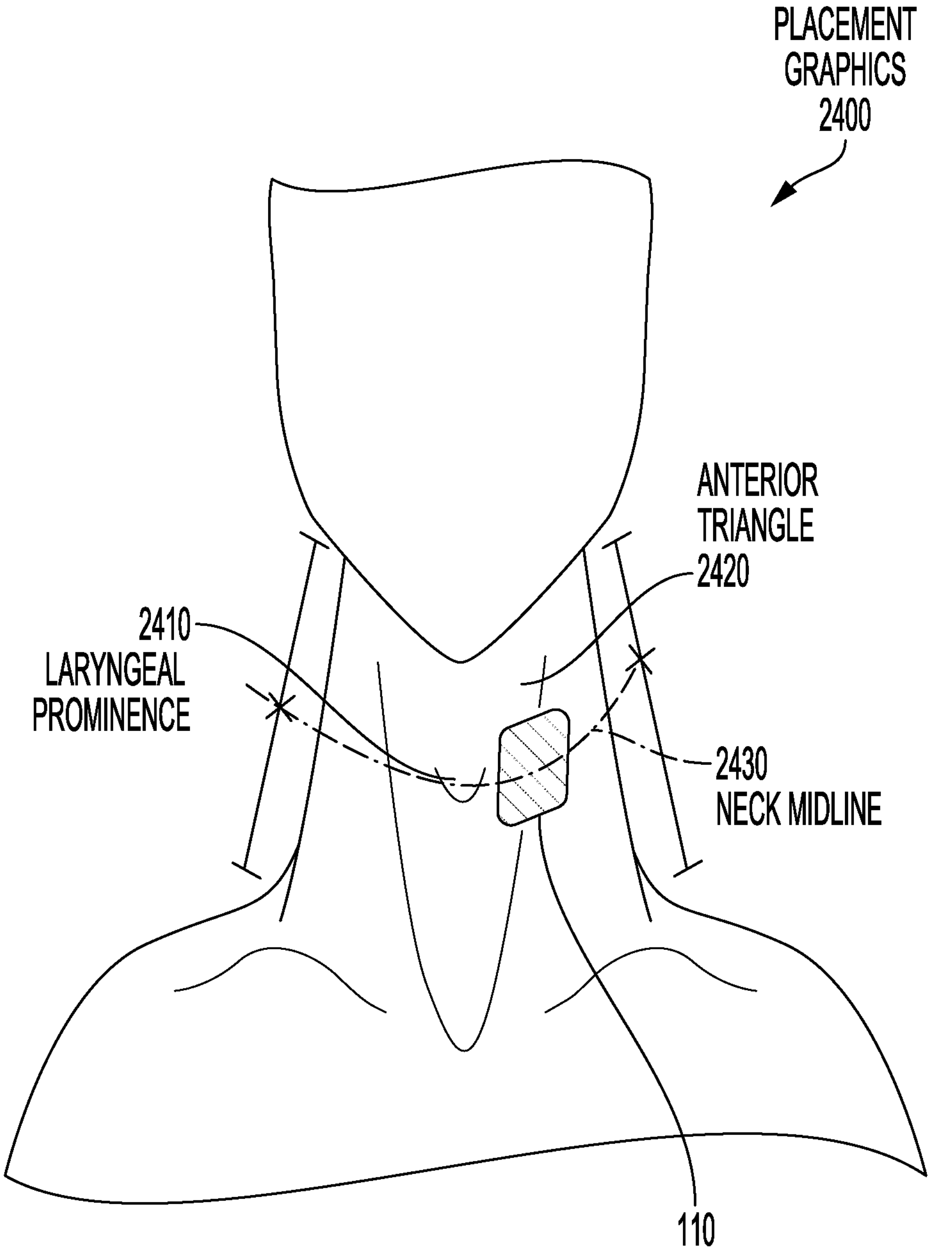
FIG. 24 shows examples of placement graphics for a wearable ultrasound blood flow sensor.

Referring to FIG. 24, examples of placement graphics for a wearable ultrasound blood flow sensor are shown. The placement graphics 2400 include anatomical reference points. Placement of the wearable ultrasound blood flow sensor 110 relative to the anatomical reference points as indicated in the graphics 2400 enable the caregiver 103 to position the sensor 110 proximate to a blood vessel corresponding to the anatomical reference points. For example, the anatomical reference points of the laryngeal prominence 2410, the anterior triangle 2420, and the neck midline 2430 enable positioning of the sensor 110 proximate to the carotid artery. In the example of FIG. 24, proper positioning of the sensor 110 is to center the sensor 110 on the neck midline 2430 and anterior triangle 2420 to the right of the laryngeal prominence 2410 for the right carotid artery or to the left of the laryngeal prominence 2410 for the left carotid artery. The anatomical reference points correspond to features that are found relatively quickly and reliably despite variations in body size, body fat, skin tone, and head or neck geometry or position. Anatomical reference points for a neck placement may also include a jawline, a collarbone, a suprasternal notch, and/or a manubrium of the sternum. These anatomical reference points for the frame are not limiting of the disclosure. In an implementation, the reference points for a neck placement may include other features of the head, neck, and/or sternum of the patient Although the placement graphics shown in the example of FIG. 24 are for a placement on the neck of a patient proximate to the carotid artery, this placement is an example only and not limiting of the disclosure. In various implementations, the placement graphics may include graphics illustrating placement proximate to one or more of the carotid artery, the brachial artery (e.g., an upper arm placement), the femoral artery (e.g., a leg/groin placement), or another blood vessel. Similarly, audible instructions descriptive of the graphics may include placements on one or more blood vessels of the patient not limited to the carotid artery of the neck.

The placement graphics 2400 may be graphics provided on the sensor (e.g., the sensor graphics 2330), on the sensor packaging (e.g., the packaging graphics 2320), on the medical device (e.g., on the display screen 1830 or on the display screen 1820), and/or on the external computing device 180. In an implementation, the output device(s) 360 may provide an audible description of the placement graphics to guide the caregiver.

Figure 25:
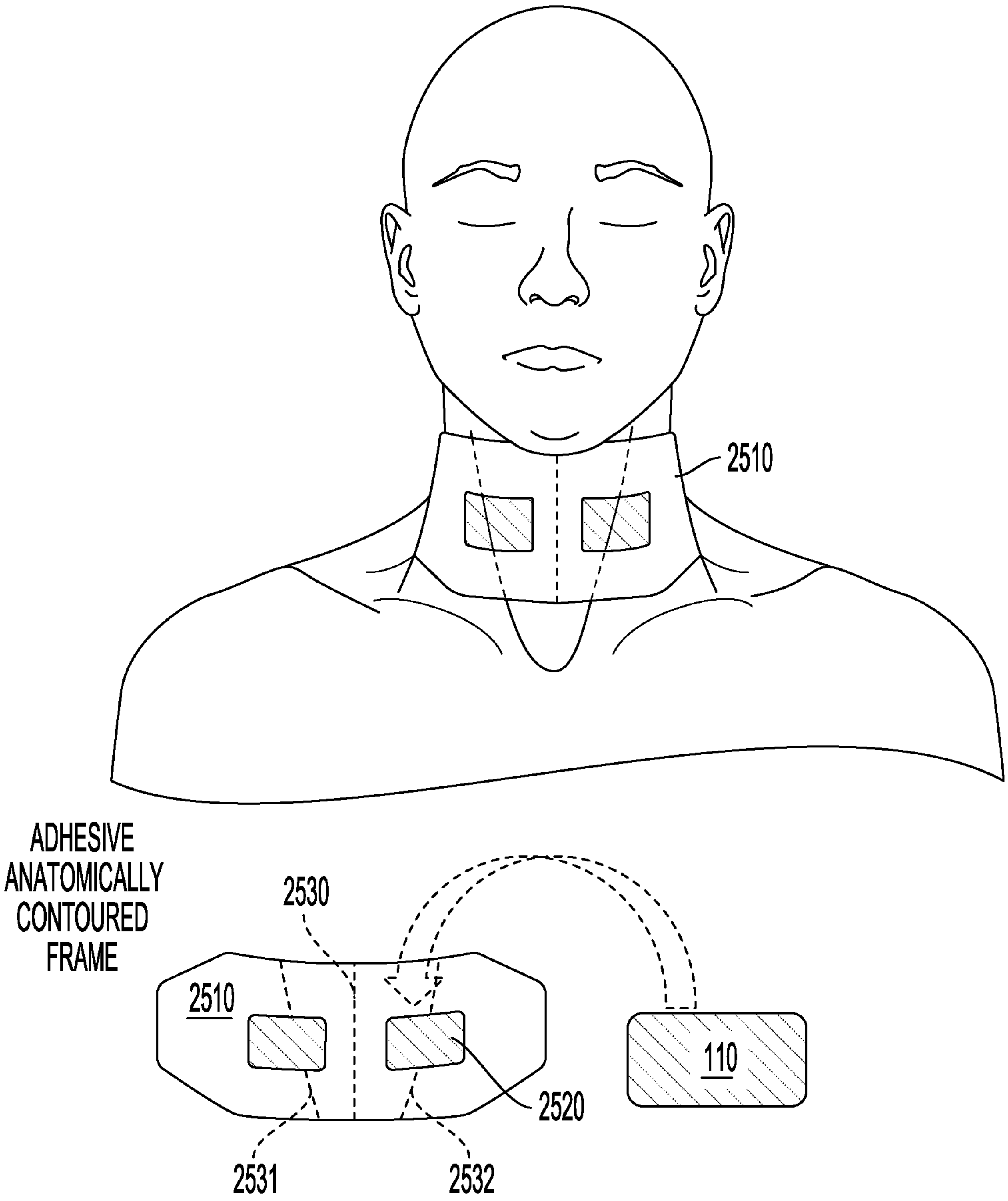
FIG. 25 shows an example of a position frame for the wearable ultrasound blood flow sensor.

Referring to FIG. 25, an example of a position frame for the wearable ultrasound blood flow sensor is shown. In an implementation, the sensor 110 may couple with the positioning frame 2510. The frame 2510 may include at least one opening configured to accept the sensor 110 and enable the sensor 110 to couple to the patient. The frame may be anatomically contoured for use on a neck with at least one opening corresponding to a location of the carotid artery, an upper arm with at least one opening corresponding to a location of a brachial artery, or a thigh with at least one opening corresponding to a location of a femoral artery. In an implementation, the frame 2510 may include two openings, as shown for example in FIG. 25, where each opening corresponds to one of two bilaterally located blood vessels (e.g., the right and left carotid arteries). In an implementation, sensor 110 may be compatible with multiple frames where each frame is configured for use on a different size patient. In an implementation, wearable ultrasound blood flow sensor 110 may be part of a sensor system that may include one or more frames. Thus, a kit available to the rescuer 103 may include the sensor 110 and multiple frames. The frames may include pre-printed sizes for quick reference by the rescuer 103. In an implementation, the frame may be adjustable for use with patients of a variety of sizes. In an implementation, a provider of the medical device 305 provides the sensor 110 and/or one or more frames 2510 with the medical device 305.

The positioning frame may include an adhesive or an external bandage to secure the frame to the patient. Securing the frame 2510 to the patient also couples the sensor 110 to the patient when the sensor is in place in the frame 2510. Further, the frame 2510 enables proper positioning of the sensor 110 relative to a blood vessel by limiting the position of the sensor 110 to one or more openings 2520 in the frame 2510. In an implementation, the sensor 110 may be disposable and the frame 2510 may be disposable or reusable. In an implementation, the frame 2510 may include anatomical reference points (e.g., the longitudinal axis 2530 and the two sides of the laryngeal triangle, 2531 and 2532. These anatomical reference points for the frame are not limiting of the disclosure. In an implementation, the reference points for a neck placement may include other features of the head, neck, and/or sternum of the patient (e.g., jawline, a collarbone, a suprasternal notch, a manubrium of the sternum, the laryngeal prominence, the neck midline, etc.

In an implementation, the frame may be self-adhesive and/or may wrap around the neck or a limb to secure the frame to the patient. The frame may be flexible and the shape of the frame may include contours that mirror human anatomy. For example, a frame for a neck may have contours that mirror the jawline and/or the collarbone so that the frame fits on the patient in one orientation to allow accurate placement of the sensor 110. In an implementation, the frame may not secure to the patient but rather may be a mat or pad that fits within various anatomical fiducials.

Although the frame shown in the example of FIG. 25 is for a placement of a sensor 110 proximate to the carotid artery, this frame is an example only and not limiting of the disclosure. In various implementations, the frame may conform to the anatomy of the upper arm or the leg/groin regions to enable placement of the sensor proximate to the brachial artery (e.g., an upper arm placement), the femoral artery (e.g., a leg/groin placement), or another blood vessel.

Referring to FIGS. 26A and 26B, an example of augmented reality (AR) glasses used as an output device for placement instructions for the wearable ultrasound blood flow sensor is shown. A quantity of each component in FIGS. 26A and 26B is an example only and other quantities of each, or any, component could be used. The output device(s) 360 may include the AR glasses 2610. As an output device, the AR glasses 2610 may provide one or more of the caregiver instructions discussed herein. The AR glasses may be communicatively coupled to the medical device 305 and the processor 350 and receive the caregiver instructions generated by the processor 350 for placement and use of the sensor 110. The AR glasses 2610 may provide the placement instructions for the sensor 110 as an image 2605 on the lens 2615 of the AR glasses 2610. Further, the placement instructions may include visible and/or audible instructions provided at the AR glasses 2610 describing placement steps and providing AR images of blood vessels superimposed on a real-time view of the patient.

The AR glasses 2610 may include a processor 2632, a memory 2631, a projector 2624, and other components configured to provide an augmented reality (AR) display image 2605 at the lens 2615 of the AR glasses 2610. In an implementation, the AR glasses 2610 may include a communications interface 2640 that enables the processor 2632 to communicatively couple to the medical device 305. In an implementation, the AR glasses 2610 may include one or more of a camera 2650, a haptic device 2678, speakers 2672, and a microphone 2674. In order to provide AR display image(s) 2605 on the lens 2615 of virtual objects within the caregiver's field of view, the AR glasses 2610 may include an optical projector 2624.

In some examples, the optical projector 2624 is configured to emit light beams in a coordinated manner to an inwardly directed surface of the lens 2615. The emitted light beams are reflected from the lens 2615 to the caregiver's eyes, causing the caregiver 103 to perceive the images of the virtual object(s) as if the virtual object(s) are present within the field of view of the caregiver 103. In an implementation, the optical projector 2624 may be positioned to project the images on or through the lens 2615 to be viewed by the caregiver 103, such that the caregiver 103 perceives the images as virtual three-dimensional objects in interactive combination with physical objects in a mixed reality environment. In some examples, the optical lens 2615 is positioned over the caregiver's eyes such that when the optical projector 2624 is not emitting virtual images, the caregiver 103 perceives a substantially unobstructed view of surrounding objects.

In addition to the processor(s) 2632 and memory 2631, the AR glasses 2610 may include one or more of an information and/or image-processing module 2634 for two-dimensional and/or three-dimensional information and/or image processing, the camera 2650, a gesture recognition module 2638, and a user position module 2642 in communication with the optical projector 2624. The image-processing module 2634 may receive and process three-dimensional information about the rescue scene, for example, to help identify one or more resuscitation activities being performed by the caregiver 103. For instance, a three-dimensional sensor may provide information about the positioning and size of objects relative to one another, though, images recorded by a digital camera may provide more definitive information for identifying particular objects, such as a medical device and/or other treatment equipment and devices, a rescuer, patient, etc. The image processing module 2634 may also receive and process two-dimensional images of the rescue scene obtained by the camera 2650 and/or another optical sensor to extract and/or interpret image information and/or refine an accuracy or specificity of physical objects identified based on the three dimensional information.

The camera 2650 may include one or more of a digital camera, RGB camera, digital video camera, red-green-blue sensor, and/or depth sensor for capturing visual information and static or video images of the rescue scene. The camera 2650 may be positioned to substantially correspond to the caregiver's field of view. In an implementation, the AR glasses 2610 may include multiple cameras, such as a camera positioned adjacent to each of the caregiver's eyes to generate a stereo-image, which substantially corresponds to the caregiver's field of view. The processor 2632 and/or the image-processing module 2634 may process the stereo-image to determine depth information for objects in the rescue scene. In an implementation, one or more cameras may face to the side (e.g., to the right or left of the caregiver's field of view) to, for example, capture a 260 degree or larger view of the rescue scene. Another camera may obtain images of the caregiver's eyes to detect, for example, when the caregiver's gaze changes direction and/or moves from one object to a different object. Although designs differ from different vendors, as is known in the art, a camera usually comprises a charge-coupled device (CCD) or complementary metal-oxide-semiconductor (CMOS) imaging sensor, a lens, a multifunctional video control chip, and a set of discrete components (e.g., capacitor, resistors, and connectors). The imaging sensor may record an image and the video control chip may process the image. The video control chip may provide the processed image to the image-processing module 2634 for further processing and for identifying physical objects contained in the captured images. The processing module 2634 may also prepare certain images for transmission from the AR glasses 2610 to other electronic/computing devices. In some examples, the camera 2650 may include one or more three-dimensional optical sensors for obtaining three-dimensional information about the rescue scene and/or cameras for capturing still or moving two-dimensional images of the rescue scene. Three-dimensional information may include distance or depth information about how far away physical objects are from the sensor, as well as their size/dimensions. The processor 2632 may process three-dimensional information and/or images from the optical sensors to produce a three-dimensional representation of the rescue scene. The three-dimensional representation may be useful for the identification of the patient's anatomy, for example, in identifying a proper a placement location for the sensor 110. The image-processing module 2634 may be configured to perform processing routines on the collected three-dimensional information and images to assist with operation of the AR glasses 2610 and, in particular, with positioning and/or movement of images of virtual objects as the caregiver 103 changes position. In some examples, the AR glasses 2610 may also be configured to apply spatially sensitive rules for generated virtual objects in the three-dimensional representation based on a position of identified physical objects. The spatially sensitive rules may provide a contextual basis for displaying images of the virtual object to the caregiver 103. For example, the processor 2632 may identify a position of the patient in captured images. Any images of virtual objects displayed on the visual display of the AR device in the caregiver's field of view may be positioned so as not to obscure the view of the patient. Other images of virtual objects may be projected on the visual display of the AR device to appear to rest on the patient. For example, placement instructions, either textual 2611*a*, 2611*b*, 2611*c* or graphical 2612 may displayed as resting on the patient's body. In addition, anatomical fiducials 2613 or blood vessel locations 2614 may also be displayed as resting on the patient's body.

The processor 2632 and/or the image processor 2634 may be configured to apply a variety of known image processing algorithms for identifying objects in captured images including based on color (e.g., pixel color) of certain portions of captured images. In other examples, shape recognition algorithms may be applied to captured images to identify shapes of different objects. For example, the processor 2632 and/or the image processor 2634 may recognize a caregiver's hand and/or a portion of the patient's body (e.g., head, neck, arm, leg, etc.) based on a combination of recognition of skin tones in the captured image and identification of shapes of the fingers and palm in the captured image.

The user position module 2642 may generate and provide one or more spatially sensitive rules. The AR glasses 2610 may be configured to display images of the virtual three-dimensional objects projected or otherwise provided by the optical projector 2624 in accordance with and/or to abide by the one or more spatially sensitive rules. For example, the spatially sensitive rules may comprise instructions linking a position or orientation of physical objects or environmental conditions with types of information to be displayed to the caregiver 103 through virtual images. In a similar manner, the instructions may tailor the information displayed at the lens 2615 to particular activities or actions (e.g., resuscitation activities) performed by the caregiver 103 wearing the AR glasses 2610. Spatially sensitive rules may further comprise instructions for positioning images of the three-dimensional virtual objects in relation to the physical objects within the caregiver's field of view. For example, the spatially sensitive rules may require that images of visual objects be projected over (e.g., appear to be on top of) certain physical objects within the caregiver's field of view. As discussed herein, the images of the visual objects may be modified as the caregiver manipulates physical object(s).

The AR glasses 2610 may further include AR components that supplement and/or enhance visual feedback projected or displayed within the caregiver's field of view. For example, the AR glasses 2610 may include the speaker(s) 2672 for providing caregiver prompts and/or other audible indicators to the caregiver 103 and audio input components, such as the microphone 2674, for recording sound. In an implementation, the caregiver 103 may receive assistance in positioning the sensor 110 from another rescuer on site or a remote rescuer via the images, camera, speaker, and microphone of the AR glasses 2610. In some examples, the AR glasses 2610 may include the haptic device(s) 2678 (e.g., a vibration motor) configured to provide vibration feedback to the caregiver 103.

The AR glasses 2610 may further include a communications interface 2640, such as a wireless transceiver, configured to communicatively couple the AR glasses 2610 with one or more of the medical device 305, the external computing device 180, the automated compression device 210 or 250, and/or another medical or computing device either on scene or remotely located but communicatively coupled to the AR glasses 2610. The communications interface 2640 may include short range or long range data communications features, such as a wireless data transceiver, for wireless communication between the AR glasses 2610 and other electronic devices located at, or remote from, the rescue scene. The communication protocol may include Bluetooth®, Zigbee, Wi-Fi, and/or an 802.2626 data transmission protocol. In some examples, the communications interface may transmit including images captured by the camera 2650. In some examples, images may be transmitted to the remote electronic device in substantially real-time. In other examples, obtained images may be stored locally on the AR glasses 2610, for example in the computer readable memory 2631. The stored images may be transmitted by the communications interface 2640 to the remote electronic device as a batch download at predetermined intervals. The communications interface 2640 may also be configured to receive information, such as instructions to provide feedback to the caregiver 103 from the medical device 305. In some examples, the AR glasses 2610 may be in communication with other devices (e.g., medical device, defibrillator, patient monitor, sensors, communications device, smartwatch, wearable device, etc.) connected to, or associated with, the caregiver 103 to form a personal area network (PAN). Information and instructions may be shared between the different devices so that feedback may be provided to the caregiver 103. In some examples, the AR glasses 2610 may serve as a front end (e.g., a remote display) for a separate medical device, system, or network. For example, the AR glasses 2610 may be configured to display information generated by the medical device 305 to inform the caregiver 103 about the status of the device.

In some examples, the communications interface 2640 may be configured to transmit data to an intermediate device having long-range data transmission capabilities. The intermediate device (e.g., a smartphone, tablet, laptop computer, or PDA) may receive and, in some cases, perform additional processing on the received data. The communications interface 2640 may transmit additionally processed data to an external electronic device, computer network, or database using the long-range data transmission capabilities of the intermediate device.

In some further examples, the communications interface 2640 may comprise circuitry for long-range data transmission directly from the device 2610 itself. Long-range data transmission may be performed by a long-range data transmitter or transceiver, for example a Wi-Fi transmitter or a cellular transmitter (e.g., 3G, 4G, or 5G enabled systems). Data collected by the device 2610 may be sent to external sources by the long-range data transmitter or transceiver. The long-range communications may be via a cellular and/or a computer network.

The gesture recognition module 2638 may be configured to identify the caregiver's hands within images obtained by the AR glasses 2610 and, based on the position, orientation, and movement of the hands, may identify gestures performed by the caregiver 103 for the purpose of controlling operation of the AR glasses 2610 and/or for manipulating a virtual touchpad and/or other display features provided to the caregiver 103 by the optical projector 2624 at the lens 2615.

The AR glasses 2610 may further comprise a number of sensors 2652 (e.g., motion sensors, accelerometers, light sensors, capacitive sensors, proximity sensors, etc.) for measuring additional information about the wearer's field of view and the surrounding environment. For example, the sensor 2652 of the AR glasses 2610 may determine the caregiver's position relative to other objects and/or determine when the caregiver's position and/or field of view changes (e.g., when the caregiver 103 moves his or her head or to identify detected physical objects in the field of view).

In some examples, the AR glasses 2610 further comprise a timer 2658, for tracking passage of time (e.g., during a resuscitation activity) and/or for determining a current time. For example, the timer 2658 may measure an amount of time for a chest compression pause or an interval between pauses.

Reference has been made to illustrations representing methods and systems according to implementations of this disclosure. Aspects thereof may be implemented by computer program instructions. These computer program instructions may be provided to a processor of a general-purpose computer, special purpose computer, a medical device (e.g., a device that provides and/or controls therapeutic interventions or treatments for a patient and/or that receives, monitors, and/or analyzes physiologic data for patient as collected by one or more sensors coupled to the medical device), or other programmable data processing apparatus and/or distributed processing systems having processing circuitry, such that the instructions, which execute via the processor of the computer or other programmable data processing apparatus, create means for implementing the functions/operations specified in the illustrations.

One or more processors can be utilized to implement various functions and/or algorithms described herein. Additionally, any functions and/or algorithms described herein can be performed upon one or more virtual processors. The virtual processors, for example, may be part of one or more physical computing systems such as a computer farm or a cloud drive.

Aspects of the present disclosure may be implemented by software logic, including machine-readable instructions or commands for execution via processing circuitry. The software logic may also be referred to, in some examples, as machine-readable code, software code, or programming instructions. The software logic, in certain embodiments, may be coded in runtime-executable commands and/or compiled as a machine-executable program or file. The software logic may be programmed in and/or compiled into a variety of coding languages or formats.

Aspects of the present disclosure may be implemented by hardware logic (where hardware logic naturally also includes any necessary signal wiring, memory elements and such), with such hardware logic able to operate without active software involvement beyond initial system configuration and any subsequent system reconfigurations (e.g., for different object schema dimensions). The hardware logic may be synthesized on a reprogrammable computing chip such as a field programmable gate array (FPGA) or other reconfigurable logic device. In addition, the hardware logic may be hard coded onto a custom microchip, such as an application-specific integrated circuit (ASIC). In other embodiments, software, stored as instructions to a non-transitory computer-readable medium such as a memory device, on-chip integrated memory unit, or other non-transitory computer-readable storage, may be used to perform at least portions of the herein described functionality.

Various aspects of the embodiments disclosed herein are performed on one or more medical devices, such as an external defibrillator, a patient monitor, a combined patient monitor-external defibrillator, a ventilation device, a wearable ultrasound blood flow sensor, or an automated compression device, and/or on one or more computing devices, such as a laptop computer, tablet computer, mobile phone, wearable device (e.g., watch, glasses), or other handheld computing device, or one or more servers. Such medical devices and computing devices include processing circuitry embodied in one or more processors or logic chips, such as a central processing unit (CPU), graphics processing unit (GPU), field programmable gate array (FPGA), application-specific integrated circuit (ASIC), or programmable logic device (PLD). Further, the processing circuitry may be implemented as multiple processors cooperatively working in concert (e.g., in parallel) to perform the instructions of the inventive processes described above.

The process data and instructions used to perform various methods and algorithms derived herein may be stored in non-transitory (i.e., non-volatile) computer-readable medium or memory. The claimed advancements are not limited by the form of the computer-readable media on which the instructions of the inventive processes are stored. For example, the instructions may be stored on CDs, DVDs, in FLASH memory, RAM, ROM, PROM, EPROM, EEPROM, hard disk or any other information processing device with which the computing device and/or medical device communicates, such as a server or computer. The processing circuitry and stored instructions may enable the computing device and/or medical device to perform all or a portion of, in some examples, the method 500 of FIG. 5, the method 600 of FIG. 6, the method 700 of FIG. 7A, the method 70 of FIG. 7J, the method 800 of FIG. 8, the method 900 of FIG. 9, the processes of FIGS. 10A, 10B, and 13, the method 1400*a* of FIG. 14A, the method 1400*b* of FIG. 14B, the method 1600 of FIG. 16A, and the method 1700 of FIG. 18.

These computer program instructions can direct a computing device, medical device, or other programmable data processing apparatus to function in a particular manner, such that the instructions stored in the computer-readable medium produce an article of manufacture including instruction means which implement the function/operation specified in the illustrated process flows.

Embodiments of the present description rely on network communications. As can be appreciated, the network can be a public network, such as the Internet, or a private network such as a local area network (LAN) or wide area network (WAN) network, or any combination thereof and can also include PSTN or ISDN sub-networks. The network can also be wired, such as an Ethernet network, and/or can be wireless such as a cellular network including EDGE, 3G, 4G, and 5G wireless cellular systems. The wireless network can also include Wi-Fi®, Bluetooth®, Zigbee®, or another wireless form of communication. The network, in some examples, may support communications between the medical device 305 and one or more of the ventilation and/or respiration sensors 395, the automated compression device 210 or 250, the chest compression monitor 109, the wearable ultrasound blood flow sensor 110, the external computing device(s) 180, and the output device(s) 360. The network, in some examples, may further support communications between a remote computing device and one or more of the medical device 305, the ventilation and/or respiration sensors 395, the automated compression device 210 or 250, the chest compression monitor 109, the wearable ultrasound blood flow sensor 110, the external computing device(s) 180, and the output device(s) 360. The wired communications links may include a wired electrically coupling, an optical coupling via an optical cable, etc. The wireless communications link may include coupling via a radio frequency or other transmission media. The network may include a satellite network. The communications link may include near field communications which may be implemented via a communications RFID tag. In various implementations, the communicative couplings described herein may provide secure and/or authenticated communications channels. In an implementation, the devices described herein may encrypt and/or decrypt the data transmitted and/or received via the communicative couplings. Communicatively coupled components described herein may be coupled directly and/or indirectly for uni-directional or bi-directional communications, in various implementations.

The computing device and/or medical device, in some embodiments, further includes a display controller for interfacing with a display, such as a built-in display or LCD monitor. A general-purpose I/O interface of the computing device and/or medical device may interface with a keyboard, a hand-manipulated movement tracked I/O device (e.g., mouse, virtual reality glove, trackball, joystick, etc.), and/or touch screen panel or touch pad on or separate from the display.

Moreover, the present disclosure is not limited to the specific circuit elements described herein, nor is the present disclosure limited to the specific sizing and classification of these elements. For example, the skilled artisan will appreciate that the circuitry described herein may be adapted based on changes in battery sizing and chemistry or based on the requirements of the intended back-up load to be powered.

The functions and features described herein may also be executed by various distributed components of a system. For example, one or more processors may execute these system functions, where the processors are distributed across multiple components communicating in a network. The distributed components may include one or more client and server machines, which may share processing, in addition to various human interface and communication devices (e.g., display monitors, smart phones, tablets, personal digital assistants (PDAs)). The network may be a private network, such as a LAN or WAN, or may be a public network, such as the Internet. Input to the system, in some examples, may be received via direct user input and/or received remotely either in real-time or as a batch process.

Although provided for context, in other implementations, methods and logic flows described herein may be performed on modules or hardware not identical to those described. Accordingly, other implementations are within the scope that may be claimed.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A system for providing patient care guidance to a caregiver based on ultrasound detection of blood flow, the system comprising:

- a defibrillator comprising an electrode assembly and a first output device; and
- a portable computing device communicatively coupled to the defibrillator and comprising a second output device;
- a Doppler shift waveform evaluation engine disposed at one or more of the defibrillator and the portable computing device; and
- a chest compression evaluation engine configured to receive data signals representing a chest compression waveform and identify chest compression frequency components;
- at least one wearable ultrasound blood flow sensor configured to couple to the Doppler shift waveform evaluation engine and to a patient,
- wherein the Doppler shift waveform evaluation engine is configured to:
- receive data signals representing at least one Doppler shift waveform from the at least one wearable ultrasound blood flow sensor,
- analyze the at least one Doppler shift waveform to identify blood flow frequency components,
- isolate a subset of the blood flow frequency components that are absent from the chest compression frequency components,
- identify the isolated subset of the blood flow frequency components as frequency components associated with heart-induced blood flow, and
- generate caregiver instructions with at least one of the first output device and the second output device according to a cardiac arrest protocol, and according to a non-cardiac arrest protocol in response to the identified heart-induced blood flow.

2. The system of claim 1, wherein the Doppler shift waveform evaluation engine is configured to analyze the at least one Doppler shift waveform during ongoing chest compression and ventilation cycles according to the cardiac arrest protocol.

3. The system of claim 2, wherein the Doppler shift waveform evaluation engine is configured to analyze the data signals representing the at least one Doppler shift waveform during an administration of chest compressions, wherein the ongoing chest compression and ventilation cycles alternate between chest compressions and ventilations according to a predetermined X:Y ratio of X chest compressions and Y ventilations.

4. The system of claim 3, wherein the Doppler shift waveform evaluation engine is configured to identify return of spontaneous circulation (ROSC) based at least in part on the analysis of the at least one Doppler shift waveform.

5. The system of claim 4, wherein the Doppler shift waveform evaluation engine is configured to identify re-arrest subsequent to ROSC based at least in part on the analysis of the at least one Doppler shift waveform.

6. The system of claim 3, wherein the Doppler shift waveform evaluation engine is configured to identify pseudo-pulseless electrical activity (pseudo-PEA) based at least in part on the analysis of the at least one Doppler shift waveform.

7. The system of claim 6, wherein the Doppler shift waveform evaluation engine is configured to detect the heart-induced blood flow associated with a manually impalpable pulse based on the at least one Doppler shift waveform.

8. The system of claim 7, wherein the Doppler shift waveform evaluation engine is configured to detect the heart-induced blood flow at a blood pressure below approximately 60-80 systolic.

9. The system of claim 6, wherein the Doppler shift waveform evaluation engine is configured to distinguish between PEA and pseudo-PEA based at least in part on the analysis of the at least one Doppler shift waveform.

10. The system of claim 6, wherein the Doppler shift waveform evaluation engine is configured to distinguish between ROSC and pseudo-PEA based at least in part on the analysis of the at least one Doppler shift waveform.

11. The system of claim 6, wherein the Doppler shift waveform evaluation engine is configured to identify pseudo-PEA as distinguished from ROSC based on an absence of an indication of positive blood flow between peaks in the at least one Doppler shift waveform.

12. The system of claim 2, wherein the Doppler shift waveform evaluation engine is configured to analyze the data signals representing the at least one Doppler shift waveform during an administration of ventilations, wherein the ongoing chest compression and ventilation cycles alternate between chest compressions and ventilations according to a predetermined X:Y ratio of X chest compressions and Y ventilations.

13. The system of claim 1, wherein the Doppler shift waveform evaluation engine is configured to analyze the at least one Doppler shift waveform to identify the heart-induced blood flow in a presence of compression-induced blood flow based on an analysis of peaks in the at least one Doppler shift waveform, wherein the at least one Doppler shift waveform indicates blood flow volume per unit time as a function of time.

14. The system of claim 13, wherein the Doppler shift waveform evaluation engine is configured to distinguish between peaks due to compression-induced blood flow and the heart-induced blood flow based on one or more of a peak shape, a period or frequency associated with the peaks, and a phase shift between the peaks due to the compression-induced blood flow and the heart-induced blood flow.

15. The system of claim 13, wherein the Doppler shift waveform evaluation engine is configured to perform a spectral analysis of the at least one Doppler shift waveform to identify the heart-induced blood flow in the presence of compression-induced blood flow wherein the spectral analysis comprises an analysis of frequency and amplitude of the at least one Doppler shift waveform as a function of time.

16. The system of claim 1, wherein the defibrillator is configured to:

receive an ECG waveform from the electrode assembly, and wherein the Doppler shift waveform evaluation engine is configured to:

analyze the ECG waveform to identify the ECG waveform as representing a shockable heart rhythm or a non-shockable heart rhythm, and provide the caregiver instructions according to the cardiac arrest protocol based on the ECG waveform analysis and on the at least one Doppler shift waveform analysis.

17. The system of claim 16, wherein the defibrillator is configured to:

analyze the ECG waveform to identify the shockable heart rhythm, control a defibrillation shock circuit to deliver at least one defibrillation shock, and wherein the Doppler shift waveform evaluation engine is configured to:

analyze the data signals representing the at least one Doppler shift waveform during ongoing chest compressions after the at least one defibrillation shock, identify the heart-induced blood flow corresponding to ROSC, and generate the caregiver instructions according to the non-cardiac arrest protocol, wherein the non-cardiac arrest protocol includes ROSC interventions.

18. The system of claim 16, wherein the defibrillator is configured to analyze the ECG waveform to identify a non-shockable rhythm, and wherein the Doppler shift waveform evaluation engine is configured to:

analyze the data signals representing the at least one Doppler shift waveform during ongoing chest compressions, identify the heart-induced blood flow corresponding to pseudo-PEA, and generate the caregiver instructions according to the non-cardiac arrest protocol, wherein the non-cardiac arrest protocol includes pseudo-PEA interventions.

19. The system of claim 1, wherein the chest compression evaluation engine is communicatively coupled to the Doppler shift waveform evaluation engine.

20. The system of claim 19, wherein the chest compression evaluation engine is configured to receive the data signals representing the chest compression waveform from a chest compression monitor configured for use during manual chest compressions.

21. The system of claim 1, wherein the Doppler shift waveform evaluation engine is configured to:

generate the caregiver instructions to pause chest compressions in response to the identification of the heart-induced blood flow based on the at least one Doppler shift waveform analysis, verify the heart-induced blood flow identification during the paused chest compressions, and generate the caregiver instructions to cease the chest compressions in response to the verification.

22. The system of claim 1, wherein the at least one Doppler shift waveform is first physiologic data and the system comprises one or more physiologic sensors configured to provide one or more types of second physiologic data other than blood flow data based on the at least one Doppler shift waveform, and wherein the Doppler shift waveform evaluation engine is configured to:

analyze the one or more types of second physiologic data together with the at least one Doppler shift waveform to generate a cumulative blood flow score, and automatically detect heart-induced blood flow based on the cumulative blood flow score.

23. The system of claim 1 comprising an automated chest compression device communicatively coupled to at least one of the defibrillator and the portable computing device, wherein the Doppler shift waveform evaluation engine is configured to:

receive a chest compression driving frequency from the automated chest compression device, and identify automated chest compression frequency components represented in the at least one Doppler shift waveform;

receive the identified automated chest compression frequency components from the chest compression waveform evaluation engine, remove the automated chest compression frequency components from the at least one Doppler shift waveform; and identify remaining blood flow frequency components as indicators of heart-induced blood flow.

24. The system of claim 23, wherein the Doppler shift waveform evaluation engine is configured to provide a control signal to the automated chest compression device based on the blood flow frequency components, and wherein the control signal and the at least one Doppler shift waveform enable closed loop control of the automated chest compression device by the defibrillator.

25. The system of claim 24, wherein the control signal controls one or more compression delivery parameters for the automated chest compression device based on the blood flow frequency components of the at least one Doppler shift waveform.

26. The system of claim 25, wherein the one or more compression delivery parameters comprise one of more of compression rate, compression depth, compression driving frequency, and a compression waveform envelope.

27. The system of claim 24, wherein the defibrillator is configured to:

receive an ECG waveform from the electrode assembly, and provide the ECG waveform to the Doppler shift waveform evaluation engine, and wherein the Doppler shift waveform evaluation engine is configured to:

determine a phase of automated compressions delivered by the automated chest compression device that is synchronous with a repetitive feature of the ECG waveform, control the automated chest compression device to deliver compressions according to the determined phase via the control signal.

28. The system of claim 1, wherein the first and second output devices comprise one or more of a touchscreen, an audio device, a haptic device, and a wearable device comprising one or more of a watch and glasses.

* * * * *